US012459932B2

(12) United States Patent
Tamayo et al.

(10) Patent No.: US 12,459,932 B2
(45) Date of Patent: Nov. 4, 2025

(54) KIF18A INHIBITORS

(71) Applicant: AMGEN INC., Thousand Oaks, CA (US)

(72) Inventors: Nuria A Tamayo, Newbury Park, CA (US); Abhisek Banerjee, Karnataka (IN); James Alexander Brown, Moorpark, CA (US); Michael J Frohn, Thousand Oaks, CA (US); Jian Jeffrey Chen, San Diego, CA (US); Kexue Li, Newbury Park, CA (US); Qingyian Liu, Camarillo, CA (US); Jonathan Dante Low, Reseda, CA (US); Vu Ma, Oak Park, CA (US); Liping H Pettus, Thousand Oaks, CA (US); Mary Catherine Walton Cabrera, Camarillo, CA (US); Ana Minatti, Los Angeles, CA (US); Matthew Paul Bourbeau, Woodland Hills, CA (US); Lei Jia, San Diego, CA (US); Thomas T Nguyen, Newbury Park, CA (US); Nobuko Nishimura, West Hills, CA (US); Qiufen May Xue, Thousand Oaks, CA (US); John Gordon Allen, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 869 days.

(21) Appl. No.: 17/416,411

(22) PCT Filed: Dec. 20, 2019

(86) PCT No.: PCT/US2019/068172

§ 371 (c)(1),
(2) Date: Jun. 18, 2021

(87) PCT Pub. No.: WO2020/132651

PCT Pub. Date: Jun. 25, 2020

(65) Prior Publication Data

US 2022/0073504 A1 Mar. 10, 2022

Related U.S. Application Data

(60) Provisional application No. 62/783,069, filed on Dec. 20, 2018.

(51) Int. Cl.

| | |
|---|---|
| ***C07D 413/14*** | (2006.01) |
| ***C07D 401/12*** | (2006.01) |
| ***C07D 401/14*** | (2006.01) |
| ***C07D 405/14*** | (2006.01) |

(52) U.S. Cl.

CPC ......... *C07D 413/14* (2013.01); *C07D 401/12* (2013.01); *C07D 401/14* (2013.01); *C07D 405/14* (2013.01)

(58) Field of Classification Search

CPC .. C07D 413/14; C07D 401/12; C07D 401/14; C07D 405/14

See application file for complete search history.

(56) References Cited

U.S. PATENT DOCUMENTS

| | | | |
|---|---|---|---|
| 5,100,883 | A | 3/1992 | Schiehser |
| 5,118,677 | A | 6/1992 | Caufield |
| 5,118,678 | A | 6/1992 | Kao |
| 5,120,842 | A | 6/1992 | Failli |
| 5,151,413 | A | 9/1992 | Caufield |
| 5,256,790 | A | 10/1993 | Nelson |
| 5,258,389 | A | 11/1993 | Goulet |
| 5,521,184 | A | 5/1996 | Zimmermann |
| 5,650,415 | A | 7/1997 | Tang |
| 5,656,643 | A | 8/1997 | Spada |
| 5,728,813 | A | 3/1998 | Lyman |
| 5,747,498 | A | 5/1998 | Schnur |
| 5,770,599 | A | 6/1998 | Gibson |
| 5,789,427 | A | 8/1998 | Chen |
| 5,861,510 | A | 1/1999 | Piscopio |
| 5,863,949 | A | 1/1999 | Robinson |
| 5,969,110 | A | 10/1999 | Beckmann |
| 5,981,245 | A | 11/1999 | Fox |
| 5,990,141 | A | 11/1999 | Hirth |

(Continued)

FOREIGN PATENT DOCUMENTS

| | | | |
|---|---|---|---|
| DE | 19629652 | A1 | 1/1998 |
| EP | 039051 | A | 11/1981 |

(Continued)

OTHER PUBLICATIONS

"3-Pyridinecarboxamide, 2-(4,4-difluoro-1-piperidinyl)-N-(1,2-dihydro-4-methyl-2-oxo-6-quinolinyl)- (ACI)," SciFinder, CAS Registry No. 1870849-76-5, 1 page. (2016).
"3-Pyridinecarboxamide, N-(phenyl-t)- (9CI)," SciFinder, CAS Registry No. 74804-46-9, 1 page. (1984).
"4-Pyridinecarboxamide, 2-ethoxy-N-[2-(1-pyrrolidinyl)-3-pyridinyl]- (ACI)," SciFinder, CAS Registry No. 1385383-83-4, 1 page. (2012).
"4-Pyridinecarboxamide, N-[4-(1-piperidinyl)-3-pyridinyl]-2-(1H-1,2,4-triazol-1-yl)- (ACI)," SciFinder, CAS Registry No. 1385284-78-5, 1 page. (2012).
"4-Pyrimidinecarboxamide, 2,6-dimethyl-N-[2-(1-piperidinyl)phenyl]- (ACI)," SciFinder, CAS Registry No. 2178899-05-01, 1 page. (Feb. 22, 2018).

(Continued)

*Primary Examiner* — Joseph K McKane
*Assistant Examiner* — Quincy McKoy
(74) *Attorney, Agent, or Firm* — Elsa D. Lemoine

(57) ABSTRACT

Compounds of formula (I): (I), as defined herein, and synthetic intermediates thereof, which are capable of modulating KIF18A protein thereby influencing the process of cell cycle and cell proliferation to treat cancer and cancer-related diseases. The invention also includes pharmaceutical compositions, including the compounds, and methods of treating disease states related to the activity of KIF18A.

34 Claims, No Drawings

(56) References Cited

U.S. PATENT DOCUMENTS

| | | | |
|---|---|---|---|
| 6,057,124 | A | 5/2000 | Bartley |
| 6,111,090 | A | 8/2000 | Gorman |
| 6,232,447 | B1 | 5/2001 | Cerretti |
| 6,235,764 | B1 | 5/2001 | Larson |
| 6,258,812 | B1 | 7/2001 | Bold |
| 6,413,932 | B1 | 7/2002 | Cerretti |
| 6,515,004 | B1 | 2/2003 | Misra |
| 6,596,852 | B2 | 7/2003 | Cerretti |
| 6,630,500 | B2 | 10/2003 | Gingrich |
| 6,656,963 | B2 | 12/2003 | Firestone |
| 6,713,485 | B2 | 3/2004 | Carter |
| 6,727,225 | B2 | 4/2004 | Wiley |
| 7,025,962 | B1 | 4/2006 | Gorman |
| 7,618,632 | B2 | 11/2009 | Collins |
| 7,776,869 | B2 | 8/2010 | Chaffee |
| 7,812,135 | B2 | 10/2010 | Smith |
| 8,388,967 | B2 | 3/2013 | Smith |
| 8,586,023 | B2 | 11/2013 | Shiku |
| 8,591,886 | B2 | 11/2013 | Ponath |
| 9,630,976 | B2 | 4/2017 | Ishida |
| 9,815,846 | B2 | 11/2017 | Mitchell |
| 10,590,121 | B2 | 3/2020 | Taylor |
| 10,752,609 | B2 | 8/2020 | Hartz |
| 11,377,438 | B2 | 7/2022 | Arasappan |
| 2002/0042368 | A1 | 4/2002 | William, III |
| 2003/0105091 | A1 | 6/2003 | Riedl |
| 2003/0162712 | A1 | 8/2003 | Cerretti |
| 2009/0012085 | A1 | 1/2009 | Baum |
| 2010/0168084 | A1 | 7/2010 | Huber |
| 2020/0239441 | A1 | 7/2020 | Tamayo |
| 2022/0073504 | A1 | 3/2022 | Tamayo |
| 2022/0119363 | A1 | 4/2022 | Breslin |
| 2023/0151432 | A1* | 5/2023 | Payton ............... A61K 31/5377 435/6.14 |

FOREIGN PATENT DOCUMENTS

| | | | |
|---|---|---|---|
| EP | 0090505 | A | 10/1983 |
| EP | 520722 | A | 12/1992 |
| EP | 566226 | A | 10/1993 |
| EP | 606046 | A | 7/1994 |
| EP | 0682027 | A | 11/1995 |
| EP | 0787772 | A2 | 8/1997 |
| EP | 0818442 | A2 | 1/1998 |
| EP | 0837063 | A | 4/1998 |
| EP | 931788 | A | 7/1999 |
| EP | 0780386 | B1 | 10/2002 |
| EP | 1181017 | B1 | 4/2003 |
| EP | 1004578 | B1 | 2/2004 |
| EP | 1786785 | B9 | 5/2013 |
| EP | 1947183 | B1 | 7/2013 |
| EP | 1866339 | B2 | 9/2021 |
| JP | 2000256358 | A | 9/2000 |
| JP | 2016535755 | A | 11/2016 |
| MX | 2020008656 | A | 12/2020 |
| WO | 9005719 | W | 5/1990 |
| WO | 9205179 | W | 4/1992 |
| WO | 9220642 | W | 11/1992 |
| WO | 9311130 | W | 6/1993 |
| WO | 9402136 | W | 2/1994 |
| WO | 9402485 | W | 2/1994 |
| WO | 9409010 | W | 4/1994 |
| WO | 9509847 | W | 4/1995 |
| WO | 9514023 | W | 5/1995 |
| WO | 9516691 | W | 6/1995 |
| WO | 9519774 | W | 7/1995 |
| WO | 9519970 | W | 7/1995 |
| WO | 9627583 | W | 9/1996 |
| WO | 9630347 | W | 10/1996 |
| WO | 9631510 | W | 10/1996 |
| WO | 9633172 | W | 10/1996 |
| WO | 9633980 | W | 10/1996 |
| WO | 9641807 | W | 12/1996 |
| WO | 9702266 | W | 1/1997 |
| WO | 9713771 | W | 4/1997 |
| WO | 9719065 | W | 5/1997 |
| WO | 9727199 | W | 7/1997 |
| WO | 9730034 | W | 8/1997 |
| WO | 9730044 | W | 8/1997 |
| WO | 9732880 | W | 9/1997 |
| WO | 9732881 | W | 9/1997 |
| WO | 9734895 | W | 9/1997 |
| WO | 9738983 | W | 10/1997 |
| WO | 9738994 | W | 10/1997 |
| WO | 9749688 | W | 12/1997 |
| WO | 9802434 | W | 1/1998 |
| WO | 9802437 | W | 1/1998 |
| WO | 9802438 | W | 1/1998 |
| WO | 9802441 | W | 1/1998 |
| WO | 9803516 | W | 1/1998 |
| WO | 9807697 | W | 2/1998 |
| WO | 9807726 | W | 2/1998 |
| WO | 9814449 | W | 4/1998 |
| WO | 9814450 | W | 4/1998 |
| WO | 9814451 | W | 4/1998 |
| WO | 9817662 | W | 4/1998 |
| WO | 9830566 | W | 7/1998 |
| WO | 9833768 | W | 8/1998 |
| WO | 9833798 | W | 8/1998 |
| WO | 9834915 | W | 8/1998 |
| WO | 9834918 | W | 8/1998 |
| WO | 9907701 | W | 2/1999 |
| WO | 1999007675 | A1 | 2/1999 |
| WO | 9920758 | W | 4/1999 |
| WO | 9929667 | W | 6/1999 |
| WO | 9935132 | W | 7/1999 |
| WO | 9935146 | W | 7/1999 |
| WO | 9940196 | W | 8/1999 |
| WO | 9945009 | W | 9/1999 |
| WO | 9952889 | W | 10/1999 |
| WO | 9952910 | W | 10/1999 |
| WO | 9961422 | W | 12/1999 |
| WO | 0002871 | W | 1/2000 |
| WO | 0012089 | W | 3/2000 |
| WO | 0059509 | W | 10/2000 |
| WO | 200103720 | W | 1/2001 |
| WO | 0114387 | W | 3/2001 |
| WO | 0132651 | W | 5/2001 |
| WO | 0137820 | W | 5/2001 |
| WO | 0255501 | W | 7/2002 |
| WO | 0259110 | W | 8/2002 |
| WO | 0266470 | W | 8/2002 |
| WO | 0268406 | W | 9/2002 |
| WO | 0405279 | W | 1/2004 |
| WO | 0407458 | W | 1/2004 |
| WO | 0407481 | W | 1/2004 |
| WO | 0409784 | W | 1/2004 |
| WO | 2004005281 | A1 | 1/2004 |
| WO | 2004039795 | A2 | 5/2004 |
| WO | 2005007190 | A1 | 1/2005 |
| WO | 05011700 | W | 2/2005 |
| WO | 2005055808 | A2 | 6/2005 |
| WO | 2005115451 | A2 | 12/2005 |
| WO | 06044453 | W | 4/2006 |
| WO | 2006083289 | A2 | 8/2006 |
| WO | 06122806 | W | 11/2006 |
| WO | 2006121168 | A1 | 11/2006 |
| WO | 2007133822 | A1 | 11/2007 |
| WO | 2008070740 | A1 | 6/2008 |
| WO | 2008106692 | A1 | 9/2008 |
| WO | 2008133274 | A1 | 11/2008 |
| WO | 09036082 | W | 3/2009 |
| WO | 09055730 | W | 4/2009 |
| WO | 2010003118 | A1 | 1/2010 |
| WO | 2011028683 | A1 | 3/2011 |
| WO | 2011051726 | A2 | 5/2011 |
| WO | 2011084985 | A1 | 7/2011 |
| WO | 2011085261 | A1 | 7/2011 |
| WO | 2011090754 | A1 | 7/2011 |
| WO | 2013039954 | A1 | 3/2013 |
| WO | 2015021936 | A1 | 2/2015 |
| WO | 2015069594 | A1 | 5/2015 |
| WO | 2016016316 | A1 | 2/2016 |

(56) References Cited

FOREIGN PATENT DOCUMENTS

| | | | |
|---|---|---|---|
| WO | 2018098412 | A1 | 5/2018 |
| WO | 2019006126 | A1 | 1/2019 |
| WO | 2019123378 | A1 | 6/2019 |
| WO | 2019164846 | A1 | 8/2019 |
| WO | 2020006075 | A1 | 1/2020 |
| WO | 2020092187 | A1 | 5/2020 |
| WO | 2020092667 | A1 | 5/2020 |
| WO | 2020132649 | A1 | 6/2020 |
| WO | 2020132653 | A1 | 6/2020 |

OTHER PUBLICATIONS

"4-Pyrimidinecarboxamide, 5-chloro-2-(1-methylethyl)-N-[2-(1-piperidinyl)phenyl]- (ACI)," SciFinder, CAS Registry No. 2192384-26-0, 1 page. (Mar. 16, 2018).

"4-Pyrimidinecarboxamide, N-[2-fluoro-6-(1-pyrrolidinyl)phenyl]-2,6-dimethyl- (ACI)," SciFinder, CAS Registry No. 2210084-28-7, 1 page.(Apr. 11, 2018).

"Benzamide, 5-chloro-2-methyl-N-[3-(1-methylethyl)-2-pyrazinyl]- (ACI)," SciFinder, CAS Registry No. 2320884-81-7, 1 page. (May 30, 2019).

Anand et al., "Palladium-Silver Cooperativity in an Aryl Amination Reaction through C-H Functionalization," ACS Catalysis, vol. 6(2), pp. 696-708 (2016).

Barillari et al., "Classical Bioisosteres," Bioisosteres in Medicinal Chemistry, pp. 15-29 (2012).

Barnett et al., "Identification and characterization of pleckstrin-homology-domain-dependent and isoenzyme-specific Akt inhibitors," Biochem. J., vol. 385 (Pt. 2), pp. 399-408 (2005).

Berge et al., "Pharmaceutical Salts", Journal of Pharmaceutical Sciences, vol. 66 (1), pp. 1-19 (Jan. 1977).

Braun et al., "Synthesis and Biological Evaluation of Optimized Inhibitors of the Mitotic Kinesin Kif18A", Acs Chemical Biology, vol. 10, pp. 554-560 (2014).

Bundgaard et al., "A novel solution-stable, water-soluble prodrug type for drugs containing a hydroxyl or an NH- acidic group", J Med Chem., vol. 32 (12), pp. 2503-2507 (1989).

Bundgaard, "Design of prodrugs", Elsevier Science Publishers B.V., Netherlands, 2 pages (1985) (Table of Contents Only).

Dasmahapatra et al. "In vitro combination treatment with perifosine and UCN-01 demonstrates synergism against prostate (PC-3) and lung (A549) epithelial adenocarcinoma cell lines," Clin. Cancer Res., vol. 10(15), pp. 5242-5252 (2004).

Gangarapu et al., "Design, Synthesis, and Biological Evaluation of 3,5-Disubstituted 2-Pyrazineamide Derivatives as Antitubercular Agents," Journal of Heterocyclic Chemistry, vol. 56(3), pp. 1115-1126 (2019).

Gangarapu et al., "NMI/MsCI-Mediated Amide Bond Formation of Aminopyrazines and Aryl/Heteroaryl Carboxylic Acids: Synthesis of Biologically Relevant Pyrazine Carboxamides," ChemistrySelect, vol. 2(25), pp. 7706-7710 (2017).

Gennaro et al., "Pharmaceutical Sciences", Remington's, 18th Edition, 13 pages (1990) (Table of Contents Only).

Gills et al., "The development of phosphatidylinositol ether lipid analogues as inhibitors of the serine/threonine kinase, Akt," Expert. Opin. Investig. Drugs, vol. 13, pp. 787-797 (2004).

Girgis et al., "Novel synthesis of nicotinamide derivatives of cytotoxic properties," Bioorg. Med. Chem., vol. 14, pp. 4466-4476 (2006).

Goldberg et al., "Role of PD-1 and its ligand, B7-H1, in early fate decisions of CD8 T cells," Blood, vol. 110(1), pp. 186-192 (2007).

Goldstein et al., "Biological efficacy of a chimeric antibody to the epidermal growth factor receptor in a human tumor xenograft model," Clin Cancer Res, vol. 1(11), pp. 1311-1318 (1995).

Huang et al., "Epidermal growth factor receptor blockade with C225 modulates proliferation, apoptosis, and radiosensitivity in squamous cell carcinomas of the head and neck," Cancer Res., vol. 59(8), pp. 1935-1940 (1999).

Jin et al., "Inhibition of AKT survival pathway by a small molecule inhibitor in human endometrial cancer cells," Br. J. Cancer, vol. 91, pp. 1808-1812 (2004).

Mayr et al., "The Human Kinesin Kif18A Is a Motile Microtubule Depolymerase Essential for Chromosome Congression," Current Biology, vol. 17, pp. 488-498 (2007).

Modjtahedi et al., "Immunotherapy of human tumor xenografts overexpressing the EGF receptor with rat antibodies that block growth factor-receptor interaction," Br. J. Cancer, vol. 67(2), pp. 254-261 (1993).

Nagahara et al., "Kinesin 18A expression: Clinical relevance to colorectal cancer progression," International Journal of Cancer, vol. 129, pp. 2543-2552 (2011).

Paez et al., "EGFR Mutations In Lung Cancer Correlation With Clinical Response To Gefitinib Therapy," Science, vol. 304(5676), pp. 1497-1500 (2004).

Rath et al., "Kinesins and cancer," Cancer, vol. 12, pp. 527-539 (2012).

Sarkar et al., "Indole-3-carbinol and prostate cancer," J Nutr., vol. 134(12 Suppl), p. 3493S-3498S (2004).

Siqueira et al., "Trifluoromethyl arylamides with antileukemia effect and intracellular inhibitory activity over serine/ arginine-rich protein kinases (SRPKs)," European Journal of Medicinal Chemistry, vol. 134, pp. 97-109 (2017).

Svensson et al., "The Design And Bioactivation of Presystemically Stable Prodrugs", Drug Metab Rev., vol. 19 (2), pp. 165-194 (1988).

Teramoto et al., "Inhibitory Effect of Anti-Epidermal Growth Factor Receptor Antibody on a Human Gastric Cancer," Cancer, vol. 77(8), pp. 1639-1645 (1996).

The Human Protein Atlas, "Expression of Kif 18A in cancer," Retrieved from Internet at <https://www.proteinatlas.org/ENSG00000121621-KIF18A/cancer>, (2025).

Thompson et al., "PD-1 is expressed by tumor-infiltrating immune cells and is associated with poor outcome for patients with renal cell carcinoma," Clin. Cancer Res., vol. 13(6), pp. 1757-1761 (2007).

Traxler, "Tyrosine kinase inhibitors in cancer treatment (Part II)," Exp. Opin. Ther. Patents, vol. 8(12), pp. 1599-1625 (1998).

Wang et al., "Ligand-Promoted Rhodium(III)-Catalyzed ortho-C-H Amination with Free Amines," Angewandte Chemie International Edition, vol. 56(26), pp. 7449-7453 (2017).

Yan et al., "Pharmacogenics and pharmacogenomics in oncology therapeutic antibody development," BioTechniques, vol. 39, pp. 565-568 (2005).

Yang et al., "Akt/Protein Kinase B Signaling Inhibitor-2, a Selective Small Molecule Inhibitor of Akt Signaling with Antitumor Activity in Cancer Cells Overexpressing Akt", Cancer Res., vol. 64 (13), pp. 4394-4399 (2004).

Yang et al., "Eradication of established tumors by a fully human monoclonal antibody to the epidermal growth factor receptor without concomitant chemotherapy," Cancer Res., vol. 59, pp. 1236-1243 (1999).

Yu et al., "The role of kinesin family proteins in tumorigenesis and progression," Cancer, vol. 116(22), pp. 5150-5160 (2010).

Zhang et al., "Kif18A is involved in human breast carcinogenesis," Carcinogenesis, vol. 31(9), pp. 1676-1684 (2010).

Zhao et al., "Discovery of 2-(pyridin-2-yl)aniline as a directing group for the sp2 C-H bond amination mediated by cupric acetate," Org. Biomol. Chem, vol. 15, pp. 6622-6631 (2017).

* cited by examiner

KIF18A INHIBITORS

CROSS REFERENCES TO RELATED APPLICATIONS

This application is a National Stage Application under 35 U.S.C. § 371 of International Application No. PCT/US2019/068172, having an international filing date of Dec. 20, 2019, which is published on Jun. 25, 2020, as WO 2020/132651, which is claiming priority from U.S. Provisional Application No. 62/783,069, having a filing date of Dec. 20, 2018.

The invention relates to the field of pharmaceutical agents and, more specifically, is directed to compounds and compositions useful for modulating KIF18A, and to uses and methods for managing cell proliferation and for treating cancer.

BACKGROUND OF THE INVENTION

Cancer is one of the most widespread diseases afflicting mankind and a major cause of death worldwide. In an effort to find an effective treatment or a cure for one or more of the many different cancers, over the last couple of decades, numerous groups have invested a tremendous amount of time, effort and financial resources. However, to date, of the available cancer treatments and therapies, only a few offer any considerable degree of success.

Cancer is often characterized by unregulated cell proliferation. Damage to one or more genes, responsible for the cellular pathways, which control progress of proliferation through the cell cycle and centrosome cycle, can cause the loss of normal regulation of cell proliferation. These deregulated genes can code for various tumor suppressor or oncogene proteins, which participate in a cascade of events, leading to unchecked cell-cycling progression and cell proliferation. Various kinase and kinesin proteins have been identified, which play key roles in cell cycle and mitotic regulation and progression of normal dividing cells and cancer cells.

Kinesins are molecular motors that play important roles in cell division and intracellular vesicle and organelle transport. Mitotic kinesin plays roles in several aspects of spindle assembly, chromosome segregation, centrosome separation and dynamics (reviewed in O. Rath and F. Kozielski, *Nature Review Cancer,* 12:527-39, 2012). Human kinesins are categorized into 14 subfamilies based on sequence homology within the so called "motor domain", this domains ATPase activity drives unidirectional movement along microtubules (MTs). The non-motor domain of these proteins is responsible for cargo attachment; a "cargo" can include any one of a variety of different membranous organelles, signal transduction scaffolding systems, and chromosomes. Kinesins use the energy of ATP hydrolysis to move cargo along polarized microtubules. Thus, kinesins are often called "plus-end" or "minus-end" directed motors.

KIF18A gene belongs to Kinesin-8 subfamily and is a plus-end-directed motor. KIF18A is believed to influence dynamics at the plus end of kinetochore microtubules to control correct chromosome positioning and spindle tension. Depletion of human KIF18A leads to longer spindles, increased chromosome oscillation at metaphase, and activation of the mitotic spindle assembly checkpoint in HeLa cervical cancer cells (MI Mayr et al, *Current Biology* 17, 488-98, 2007). KIF18A appears to be viable target for the treatment of cancer. KIF18A is overexpressed in various types of cancers, including but not limited to colon, breast, lung, pancreas, prostate, bladder, head, neck, cervix, and ovarian cancers. Further, genetic deletion or knockdown, or inhibition of KIF18A effects mitotic spindle apparatus in cancer cell lines. Particularly, inhibition of KIF18A has been found to induce mitotic cell arrest, a known vulnerability that can promote cell death in mitosis via apoptosis, mitotic catastrophe, or multipolarity driven lethality or death after mitotic slippage in interphase. Accordingly, there has been a strong interest in finding inhibitors of KIF18A proteins.

Thus, the inhibition of KIF18A ATPase activity is a promising approach for the development of novel anti-cancer agents.

SUMMARY OF THE INVENTION

The present invention provides a new class of compounds useful for modulating KIF18A protein alone or in a bound complex with microtubules for treating KIF18A-mediated conditions and/or diseases, including cancer, inflammation, or ciliopathologies.

The compounds provided by the invention have MT-based KIF18A modulatory activity and, in particular, KIF18A inhibitory activity. To this end, the invention also provides the use of these compounds, as well as pharmaceutically acceptable salts thereof, in the preparation and manufacture of a pharmaceutical composition or medicament for therapeutic, prophylactic, acute or chronic treatment of KIF18A mediated diseases and disorders, including without limitation, cancer. Thus, the compounds of the invention are useful in the manufacture of anti-cancer medicaments. The invention also provides processes for making compounds of Formula I, as well as intermediates useful in such processes.

In embodiment 1, the present invention provides a compound of Formula (I), A compound of formula I:

(I)

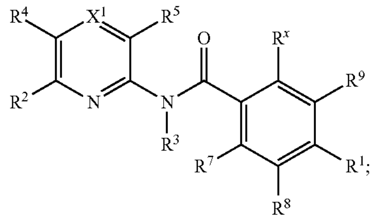

or any pharmaceutically-acceptable salt thereof, wherein:

X is N or $-CR^6$;

$R^1$ is a group $-Z-R^2$ wherein Z is $-C_{0-4}$alk-, $-NR^{11}-$, $-NR^{11}SO_2-C_{0-4}$alk-, $-SO_2NR^{11}-C_{0-4}$alk-, $-NR^{11}SO_2NR^{11}-$, $-NR^{11}SO_2NR^{11}-C(=O)-O-$, $-C_{0-4}$alk-S(=O)(=NH)$-$, $C_{0-4}$alk-$NR^{11}-$S(=O)(=NH), $-C_{0-4}$alk-S$-$, $-C_{0-4}$alk-S(=O)$-$, $-C_{0-4}$alk-$SO_2-$, $C_{0-4}$alk-O$-$, $-P-$, $-P(=O)$, $-P(=O)_2$, $-(C=O)-$, $-(C=O)NR^{11}-$, $-C=N(OH)-$, or $-NR^{11}(C=O)$; or the group $-Z-R^{12}$ is $-N=S(=O)-(R^{12})_2$, wherein the two $R^{12}$ pair can alternatively combine with the sulfur atom attached to each of them to form a saturated or partially-saturated 3, 4-, 5-, or 6-membered monocyclic ring containing 0, 1, 2 or 3 N atoms and 0, 1, or 2 atoms selected from O and S;

$R^2$ is halo or a group $-Y-R^{13}$, wherein Y is $-C_{0-4}$alk-, $-N(C_{0-1}$alk)-$C_{0-4}$alk-, $-C(=O)NR^aR^a(C_{1-4}$alk)-, $-O-C_{0-4}$alk-, $-S-$, $-S=O$, $-S(=O)_2-$, —$SO_2N(C_{0-1}alk)$-$C_{0-4}alk$-, —$N(C_{0-1}alk)$-$SO_2$—$C_{0-4}$ alk-, —$C_{0-4}alk$-S(═O)(═NH)—, —(C═O)—, —$C_{0-4}$ alk-(C═O)—O—; or the group —Y—$R^{13}$ is —N═S(═O)—$(R^{13})_2$, wherein the two $R^3$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S;

$R^3$ is H, methyl, or ethyl;

$R^4$ is H, halo, CN, $C_{1-4}alk$, or $C_{1-4}haloalk$;

$R^5$ is H, halo, $C_{1-5}alk$, or $C_{1-4}haloalk$;

$R^6$ is H, halo, CN, $C_{1-8}alk$, $C_{1-4}haloalk$, —O—$C_{0-6}alk$-, or $R^{6a}$;

$R^7$ is H, halo, $C_{1-8}alk$, or $C_{1-4}haloalk$;

$R^8$ is H, halo, $C_{1-8}alk$, or $C_{1-4}haloalk$;

$R^9$ is H, halo, $C_{1-8}alk$, or $C_{1-4}haloalk$;

$R^x$ is selected from the group consisting of

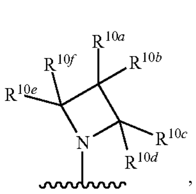
,
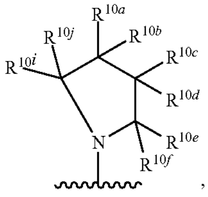
,
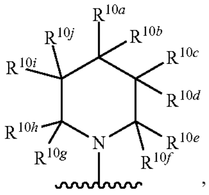
, and
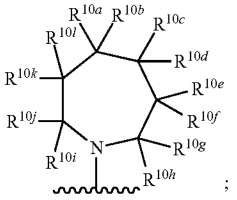
;

Each of $R^{10a}$, $R^{10b}$, $R^{10c}$, $R^{10d}$, $R^{10f}$, $R^{10g}$, $R^{10i}$, and $R^{10j}$ is H, halo, $R^{10k}$, or $R^{10l}$; or alternatively, each of $R^{10a}$ and $R^{10b}$ pair, $R^{10c}$ and $R^{10d}$ pair, $R^{10e}$ and $R^{10f}$ pair, $R^{10g}$ and $R^{10h}$ pair, or $R^{10i}$ and $R^{10j}$ pair, independently, can combine with the carbon atom attached to each of them to form a saturated or partially-saturated 3-, 4-, 5-, 6-membered monocyclic ring spiro to the $R^x$ ring; wherein said 3-, 4-, 5-, 6-membered monocyclic ring contains 0, 1, 2 or 3 N atoms and 0, 1, or 2 atoms selected from 0 and S, and further wherein said 3-, 4-, 5-, 6-membered monocyclic ring is substituted by 0, 1, 2 or 3 group(s) selected from F, Cl, Br, $C_{1-6}alk$, $C_{1-4}haloalk$, —$OR^a$, —$OC_{1-4}haloalk$, CN, —$NR^aR^a$, or oxo;

$R^{11}$ is H or $C_{1-8}alk$;

$R^{12}$ is H, $R^{12a}$, or $R^{12b}$;

$R^{13}$ is $R^{13a}$ or $R^{13b}$;

$R^{6a}$, $R^{10k}$, $R^{12a}$, and $R^{13a}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from O and S, which is substituted by 0, 1, 2 or 3 group(s) selected from F, Cl, Br, $C_{1-6}alk$, $C_{1-4}haloalk$, —$OR^a$, —$OC_{1-4}$ haloalk, CN, —C(═O)$R^b$, —C(═O)$OR^a$, —C(═O)$NR^aR^a$, —C(═$NR^a$)$NR^aR^a$, —OC(═O)$R^b$, —OC(═O)$NR^aR^a$, —$OC_{2-6}alkNR^aR^a$, —$OC_{2-6}alkOR^a$, —$SR^a$, —S(═O)$R^b$, —$S(═O)_2R^b$, —$S(═O)_2NR^aR^a$, —$NR^aR^a$, —$N(R^a)$C(═O)$R^b$, —$N(R^a)$C(═O)OR, —$N(R^a)$C(═O)$NR^aR^a$, —$N(R^a)$C(═$NR^a$)$NR^aR^a$, —$N(R^a)S(═O)_2R^b$, —$N(R^a)S(═O)_2NR^aR^a$, —$NR^aC_{2-6}alkNR^aR^a$, —$NR^aC_{2-6}alkOR^a$, —$C_{1-6}alkN$-$R^aR^a$, —$C_{1-6}alkOR^a$, —$C_{1-6}alkN(R^a)$C(═O)$R^{11}$, —$C_{1-6}alkOC$(═O)$R^b$, —$C_{1-6}alkC$(═O)$NR^aR^a$, —$C_{1-6}$ alkC(═O)$OR^a$, $R^{14}$, and oxo;

$R^{10l}$, $R^{12b}$, and $R^{13b}$ is independently, at each instance, selected from the group consisting of $C_{1-6}alk$ substituted by 0, 1, 2, 3, 4, or 5 group(s) selected from F, Cl, Br, —C(═O)$OR^a$, —$OR^a$, —$C_{1-2}haloalk$, —$OC_{1-4}$haloalk, CN, $NH_2$, $NH(CH_3)$, or $N(CH_3)_2$;

$R^{14}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from O and S, which is substituted by 0, 1, 2 or 3 group(s) selected from F, Cl, Br, $C_{1-6}alk$, $C_{1-4}$haloalk, —$OR^a$, —$OC_{1-4}haloalk$, CN, —C(═O)$R^b$, —C(═O)$OR^a$, —C(═O)$NR^aR^a$, —C(═$NR^a$)$NR^aR^a$, —OC(═O)$R^b$, —OC(═O)$NR^aR^a$, —$OC_{2-6}alkNR^a$ $R^a$, —$OC_{2-6}alkOR^a$, —$SR^a$, —S(═O)$R^b$, —$S(═O)_2$ R, —$S(═O)_2NR^aR^a$, —$NR^aR^a$, —$N(R^a)$C(═O)R, —$N(R^a)$C(═O)OR, —$N(R^a)$C(═O)$NR^aR^a$, —$N(R^a)$ C(═$NR^a$)$NR^aR^a$, —$N(R^a)S(═O)_2R^b$, —$N(R^a)$S (═O)$_2NR^aR^a$, —$NR^aC_{2-6}alkNR^aR^a$, —$NR^aC_{2-6}$ alk$OR^a$, —$C_{1-6}alkNR^aR^a$, —$C_{1-6}alkOR^a$, —$C_{1-6}alkN$ $(R^a)$C(═O)R, —$C_{1-6}alkOC$(═O)$R^x$, —$C_{1-6}alkC$ (═O)$NR^aR^a$, —$C_{1-6}alkC$(═O)$OR^a$, and oxo;

$R^a$ is independently, at each instance, H or $R^b$; and $R^b$ is independently, at each instance, $C_{1-6}alk$, phenyl, or benzyl, wherein the $C_{1-6}alk$ is being substituted by 0, 1, 2 or 3 substituents selected from halo, —OH, —$OC_{1-4}$ alk, —$NH_2$, —$NHC_{1-4}alk$, —OC(═O)$C_{1-4}alk$, or —$N(C_{1-4}alk)C_{1-4}alk$; and the phenyl or benzyl is being substituted by 0, 1, 2 or 3 substituents selected from halo, $C_{1-4}alk$, $C_{1-3}haloalk$, —OH, —$OC_{1-4}alk$, —$NH_2$, —$NHC_{1-4}alk$, —OC(═O)$C_{1-4}alk$, or —$N(C_{1-4}alk)$ $C_{1-4}$ alk.

In embodiment 2, the present invention provides compounds wherein $R^x$ is

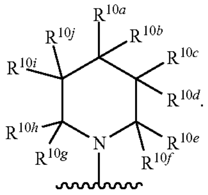

In embodiment 3, the present invention provides compounds wherein $X^1$ is —$CR^6$; having the formula (Ia):

(Ia)

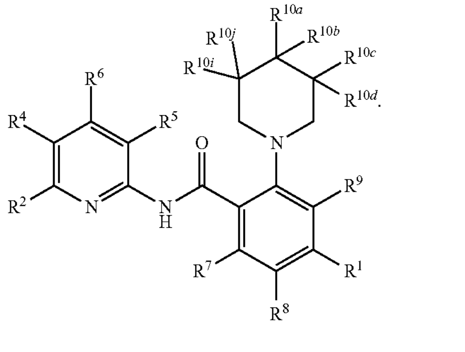

In embodiment 4, the present invention provides compounds wherein $X^1$ is N; having the formula (Ib):

(Ib)

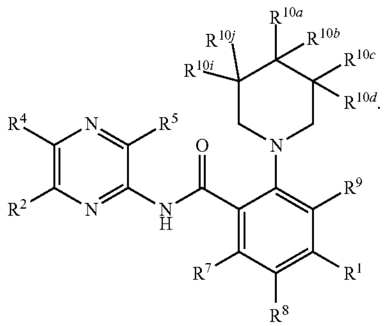

In embodiment 5, the present invention provides compounds in accordance with any of the above embodiments, or pharmaceutically acceptable salts thereof, wherein $R^3$ is H or methyl.

In embodiment 6, the present invention provides compounds in accordance with any of the above embodiments, or pharmaceutically acceptable salts thereof, wherein each of $R^{10c}$, $R^{10d}$, $R^{10e}$, $R^{10f}$, $R^{10g}$, $R^{10h}$, $R^{10i}$, and $R^{10j}$ is H, halo, $C_{1-6}$alk, or $C_{1-4}$haloalk; and each of $R^{10a}$ and $R^{10b}$ pair combine with the carbon atom attached to each of them form a saturated 3-, 4-, or 5-membered monocyclic ring spiro to the $R^x$ ring; wherein said ring contains 0, 1, 2 or 3 N atoms and 0 or 1 atoms selected from O and S.

In embodiment 7, the present invention provides compounds in accordance with any of the above embodiments, or pharmaceutically acceptable salts thereof, wherein each of $R^{10c}$, $R^{10d}$, $R^{10e}$, $R^{10f}$, $R^{10g}$, $R^{10h}$, $R^{10i}$, and $R^{10j}$ is H, methyl, or ethyl; and each of $R^{10a}$ and $R^{10b}$ pair combine with the carbon atom attached to each of them form a cyclopropyl, cyclobutyl, or cyclopentyl ring spiro to the R ring.

In embodiment 8, the present invention provides compounds in accordance with any of the above embodiments, or pharmaceutically acceptable salts thereof, wherein R is selected from:

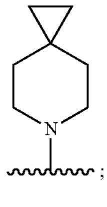 ; 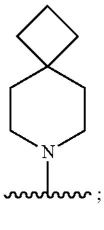 ; 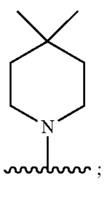 ; or 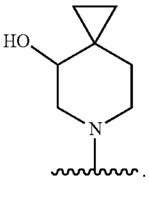 .

In embodiment 9, the present invention provides compounds in accordance with any of the above embodiments, or pharmaceutically acceptable salts thereof, wherein $R^x$ is

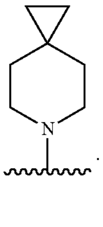 .

In embodiment 10, the present invention provides compounds in accordance with any of the above embodiments, or pharmaceutically acceptable salts thereof, wherein Z is absent, NH—, —$NHSO_2$—$(CH_2)_{0-4}$—, —$N(CH_3)$—$SO_2$—$(CH_2)_{0-4}$—, —$NCH_3SO_2NH$, —$NHSO_2NH$—C(═O)—O—, —$SO_2NH$—$(CH_2)_{0-4}$—, —$(CH_2)_{0-2}$—S(═O)(═NH)—, —$(CH_2)_{0-2}$—S—, —$(CH_2)_{0-2}$—S(═O)—, $(CH_3CH)$—S(═O)—, —$(CH_2)_{0-2}$—$SO_2$—, —O—, —P(═O), —(C═O)—, or —NH(C═O)—.

In embodiment 11, the present invention provides compounds in accordance with any of the above embodiments, or pharmaceutically acceptable salts thereof, wherein the group —Z—$R^{12}$ is —N═S(═O)—$(R^{12})_2$, wherein the two $R^{12}$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S; which is selected from:

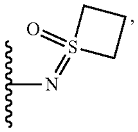 , 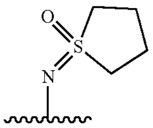 , or 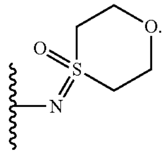

In embodiment 12, the present invention provides compounds in accordance with any of the above embodiments, or pharmaceutically acceptable salts thereof, wherein $R^1$ is —Z—$R^{12}$, wherein Z is absent, NH—, —$NHSO_2$—$(CH_2)_{0-4}$—, —$N(CH_3)$—$SO_2$—$(CH_2)_{0-4}$—, —$NCH_3SO_2NH$, —$NHSO_2NH$—C(═O)—O—, —$SO_2NH$—$(CH_2)_{0-4}$—, —$(CH_2)_{0-2}$—S(═O)(═NH)—, —$(CH_2)_{0-2}$—S—, —$(CH_2)_{0-2}$—S(═O)—, $(CH_3CH)$—S(═O)—, —$(CH_2)_{0-2}$—$SO_2$—, —O—, —P(═O), —(C═O)—, or —NH(C═O); and $R^{12}$ is selected from:

(a) H;

(b) cyclopropyl, cyclobutyl, cyclopentyl, cyclohexyl, oxiranyl, oxetanyl, tetrahydrofuranyl, azetidinyl, imidazolyl, morpholinyl, pyrrolidinyl, piperazinyl,

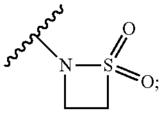 ; 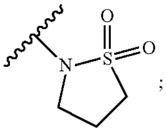 ; 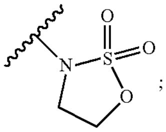 ;

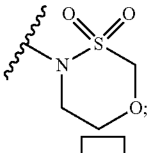 ; 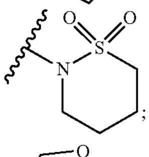 ; 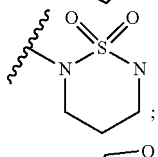 ;

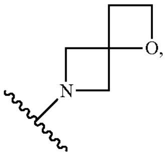 , 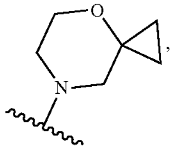 , or 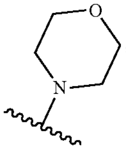 ;

wherein each said ring is substituted by 0, 1, 2 or 3 group(s) selected from wherein each ring is substituted by 0, 1, 2 or 3 OH, F, methyl, —$CH_2OH$, —C(═O)$OCH_3$, —C(═O)OC$(CH_3)_3$, $NH_2$, CN, and oxo; or $C_{1-6}$alk substituted by 0, 1, 2 or 3 OH, F, —C(═O)$OCH_3$, —$NH_2$, —$NH(CH_3)$, or —$N(CH_3)_2$.

In embodiment 13, the present invention provides compounds in accordance with any of the above embodiments, or pharmaceutically acceptable salts thereof, wherein $R^1$ is a group —Z—$R^{12}$, wherein Z is —$NHSO_2$— or —$SO_2NH$—; and $R^{12}$ is oxetanyl, cyclopropyl, or $R^{12}$ is $C_{1-6}$alk substituted by 0, 1, 2 or 3 OH group(s).

In embodiment 14, the present invention provides compounds in accordance with any of the above embodiments, or pharmaceutically acceptable salts thereof, wherein $R^1$ is a group —Z—$R^{12}$, wherein Z is —$NHSO_2$— and $R^{12}$ is —$CH_2$—$CH_2$—OH.

In embodiment 15, the present invention provides compounds in accordance with any of the above embodiments, or pharmaceutically acceptable salts thereof, wherein $R^2$ is halo or a group —Y—$R^{13}$, wherein Y is absent, —$SO_2NH$—$(CH_2)_{0-4}$—, NH—, —NH—$SO_2$—$(CH)_2)_{0-4}$—, —O—$(CH_2)_{0-4}$, —O—(CH($CH_3$))—, —$(CH_2)_{0-4}$—S(═O)(═NH)—, —(C═O)—, —$(CH_2)_{0-4}$—(C═O)—O—, or —$(CH_2)_{1-4}$;

$R^{13}$ is a saturated, partially-saturated or unsaturated 3-, 4-, 5-, 6-, or 7-membered monocyclic or 8-9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —OH, —$OC_{1-4}$haloalk, CN, $R^{14}$, and oxo; or; $R^1$ is $C_{1-6}$alk substituted by 0, 1, 2, 3, 4, or 5 group(s) selected from F, Cl, Br, —OH, —$OC_{1-4}$haloalk, or CN.

In embodiment 16, the present invention provides compounds in accordance with any of the above embodiments, or pharmaceutically acceptable salts thereof, wherein $R^2$ is a saturated 5- or 6-membered monocyclic ring wherein each said ring contains 0, 1, or 2 N atoms and 0 or 1 O atom, and wherein each said ring is substituted by 0, 1, 2 or 3 group(s) selected from F, Cl, Br, $C_{1-6}$alk, $C_{1-4}$haloalk, —OH, —$OCH_3$, —$OC_{1-4}$haloalk, CN, $R^4$, and oxo.

In embodiment 17, the present invention provides compounds in accordance with any of the above embodiments, or pharmaceutically acceptable salts thereof, wherein $R^2$ is:

(a) F, Br;

(b) a group —Y—$R^{13}$, wherein Y is absent; and $R^{13}$ is morpholinyl, piperidinyl, azetidinyl, pyrrolidinyl, cyclopropyl, cyclobutyl, cyclopentyl, cyclohexyl, piperazinyl, tetrahydrofuranyl, tetrahydropyranyl, pyridinyl, pyrimidinyl, 3,6-dihydro-2H-pyranyl,

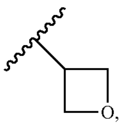, 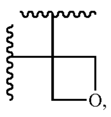, 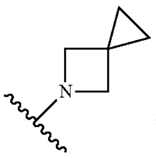, 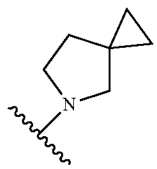,

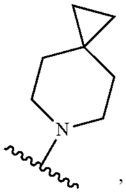, 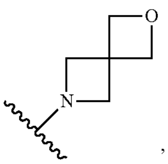, 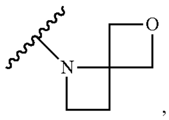,

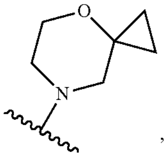, 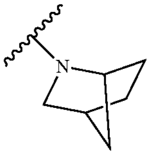, 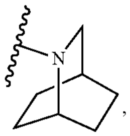,

-continued

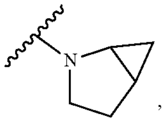, 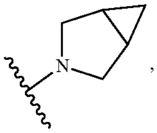, 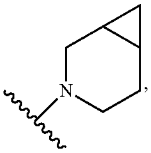,

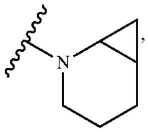, 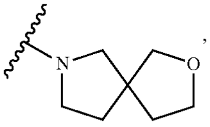, 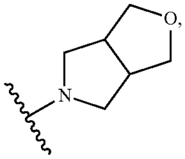

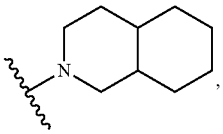, 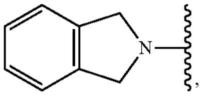,

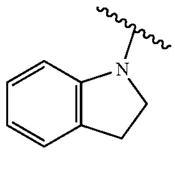, or 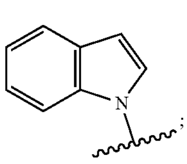;

wherein each said ring is substituted by 0, 1, 2 or 3 group(s) selected from F, Cl, Br, methyl, $CF_3$, $CH_2OH$, $CH(CH_3)OH$, $C(CH_3)_2OH$, —OH, —$OCHF_2$, CN, oxo, or cyclopropyl; or (c) a group —Y—$R^3$, wherein Y is absent, —$SO_2NH$—, NH, —O—, S(═O)(═NH)—, —O—$(CH_2)$, —O—(CH($CH_3$))—, C(═O)—, C(═O)—O—, —$CH_2C$(═O)—O—, or —CH—; and wherein $R^{13}$ is

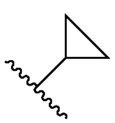, 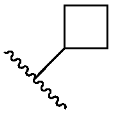, 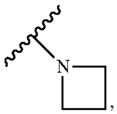, 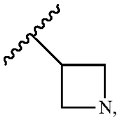

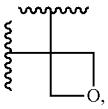, 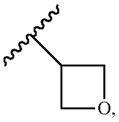, 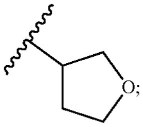;

wherein each ring is substituted by 0, 1, 2, 3, 4, or 5 group(s) selected from F, Cl, Br, methyl, $CF_3$, —OH, or CN; or $R^3$ is H or $C_{1-6}$alk substituted by 0, 1, 2, 3, 4, or 5 group(s) selected from F, Cl, Br, methyl, $CF_3$, —OH, or CN.

In embodiment 18, the present invention provides compounds in accordance with embodiments 1-17, or pharmaceutically acceptable salts thereof, wherein $R^2$ is (a) halo; (b) a group —Y—$R^{13}$, wherein Y is absent; and $R^{13}$ is morpholinyl, piperidinyl, azetidinyl, pyrrolidinyl, cyclopropyl, cyclobutyl, cyclopentyl, cyclohexyl, piperazinyl, tetrahydrofuranyl,

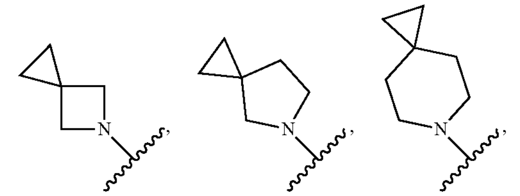

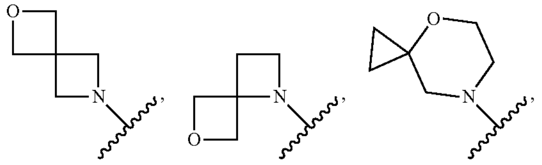

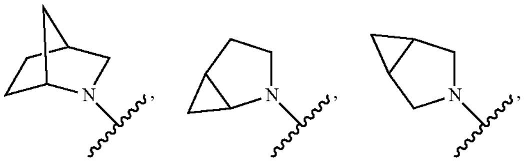

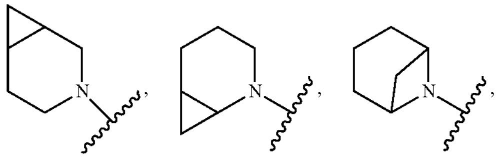

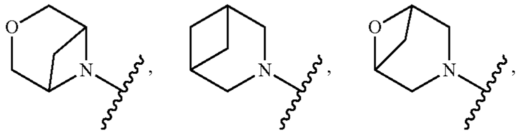

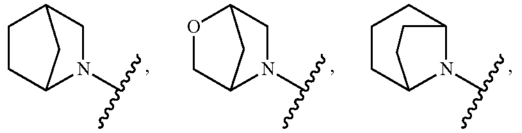

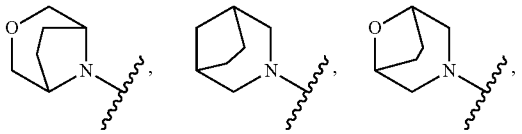

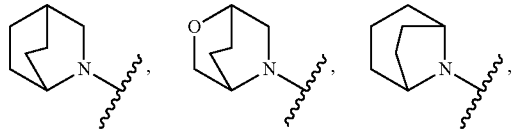

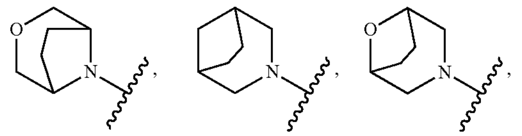

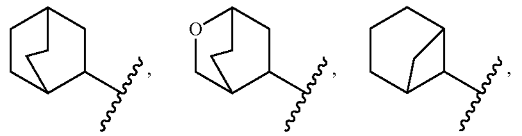

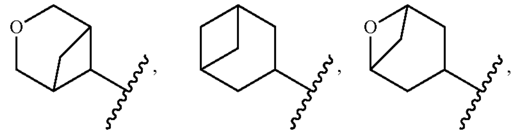

-continued

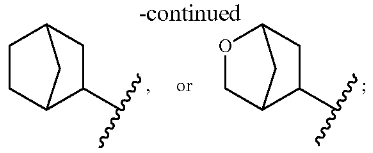

wherein each said ring is substituted by 0, 1, 2 or 3 group(s) selected from F, Cl, Br, methyl, $CF_3$, —OH, —$OCHF_2$, CN, and oxo; or (c) a group —Y—$R^{13}$, wherein Y is NH, —O—, —O—($CH_2$)—, —O—($CH_2$)—($CH_2$)—, or —O—($CH_2$)—($CH_2$)—($CH_2$)—, and wherein $R^{13}$ is

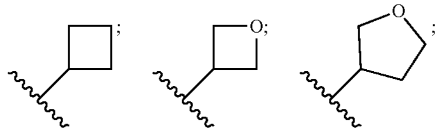

or $R^{13}$ is $C_{1-6}$alk substituted by 0, 1, 2, 3, 4, or 5 group(s) selected from F, Cl, Br, methyl, $CF_3$, —OH, or CN.

In embodiment 19, the present invention provides compounds in accordance with any of the above embodiments, or pharmaceutically acceptable salts thereof, wherein $R^2$ is

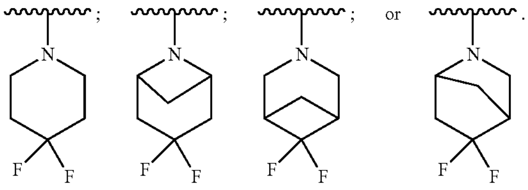

In embodiment 20, the present invention provides compounds in accordance with any of the above embodiments, or pharmaceutically acceptable salts thereof, wherein $R^2$ is morpholinyl or piperidinyl substituted by 0, 1, 2 or 3 group(s) selected from F, Cl, Br, methyl, $CF_3$, —OH, —$OCHF_2$, CN, or oxo.

In embodiment 21, the present invention provides compounds in accordance with any of the above embodiments, or pharmaceutically acceptable salts thereof, wherein $R^2$ is morpholinyl substituted by 1, 2 or 3 methyl group(s).

In embodiment 22, the present invention provides compounds in accordance with any of the above embodiments, or pharmaceutically acceptable salts thereof, wherein $R^4$ is selected from H, F, methyl, CN, or Br.

In embodiment 23, the present invention provides compounds in accordance with any of the above embodiments, or pharmaceutically acceptable salts thereof, wherein $R^4$ is H.

In embodiment 24, the present invention provides compounds in accordance with any of the above embodiments, or pharmaceutically acceptable salts thereof, wherein $R^5$ is H.

In embodiment 25, the present invention provides compounds in accordance with any of the above embodiments, or pharmaceutically acceptable salts thereof, wherein $R^6$ is H, methyl, cyclopropyl, CN, $CF_3$, or azetidinyl.

In embodiment 26, the present invention provides compounds in accordance with any of the above embodiments, or pharmaceutically acceptable salts thereof, wherein $R^7$ is H.

In embodiment 27, the present invention provides compounds in accordance with any of the above embodiments, or pharmaceutically acceptable salts thereof, wherein $R^8$ is H or F.

In embodiment 28, the present invention provides compounds in accordance with any of the above embodiments, or pharmaceutically acceptable salts thereof wherein $R^9$ is H or F.

In embodiment 29, the present invention provides a compound, or pharmaceutically acceptable salts thereof, selected from:

| Ex. # | Chemical Structure | Name |
|---|---|---|
| 1 | 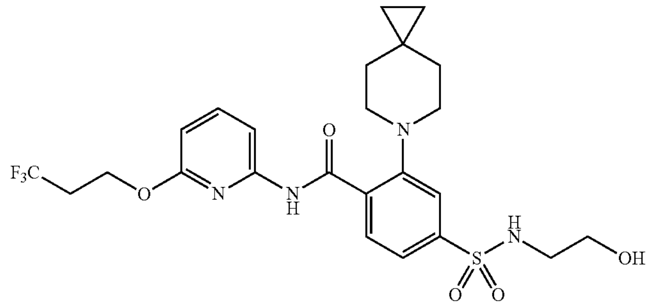 [SMILES: O=C(Nc1cccc(OCCC(F)(F)F)n1)c1ccc(S(=O)(=O)NCCO)cc1N1CCC2(CC1)CC2] | 4-(N-(2-Hydroxyethyl)sulfamoyl)-2-(6-azaspiro[2.5]octan-6-yl)-N-(6-(3,3,3-trifluoropropoxy)pyridin-2-yl)benzamide |
| 1-1 | 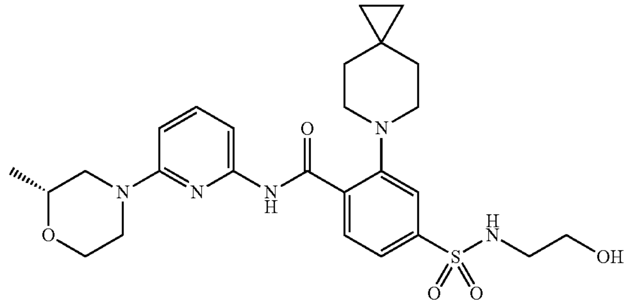 [SMILES: C[C@@H]1CN(c2cccc(NC(=O)c3ccc(S(=O)(=O)NCCO)cc3N3CCC4(CC3)CC4)n2)CCO1] | (R)-4-(N-(2-Hydroxyethyl)sulfamoyl)-N-(6-(2-methylmorpholino)pyridin-2-yl)-2-(6-azaspiro[2.5]octan-6-yl)benzamide |
| 1-2 | 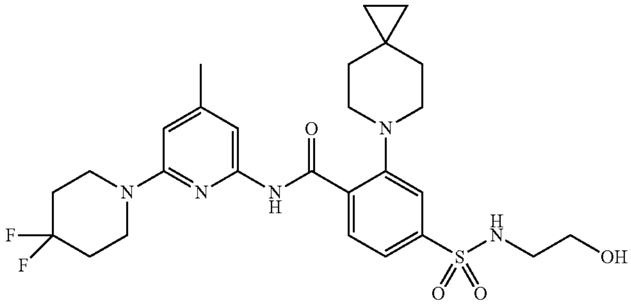 [SMILES: Cc1cc(NC(=O)c2ccc(S(=O)(=O)NCCO)cc2N2CCC3(CC2)CC3)nc(N2CCC(F)(F)CC2)c1] | N-(6-(4,4-Difluoropiperidin-1-yl)-4-methylpyridin-2-yl)-4-(N-(2-hydroxyethyl)sulfamoyl)-2-(6-azaspiro[2.5]octan-6-yl)benzamide |
| 2 | 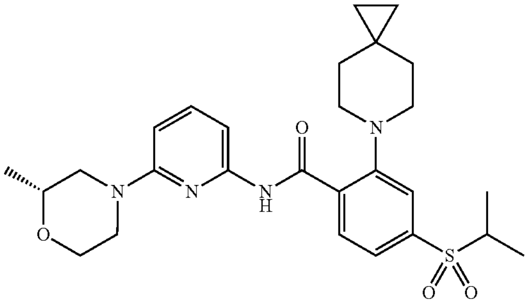 [SMILES: CC(C)S(=O)(=O)c1ccc(C(=O)Nc2cccc(N3CCO[C@H](C)C3)n2)c(N2CCC3(CC2)CC3)c1] | (R)-4-(Isopropylsulfonyl)-N-(6-(2-methylmorpholino)pyridin-2-yl)-2-(6-azaspiro[2.5]octan-6-yl)benzamide |

-continued

| Ex. # | Chemical Structure | Name |
|---|---|---|
| 2-7 | 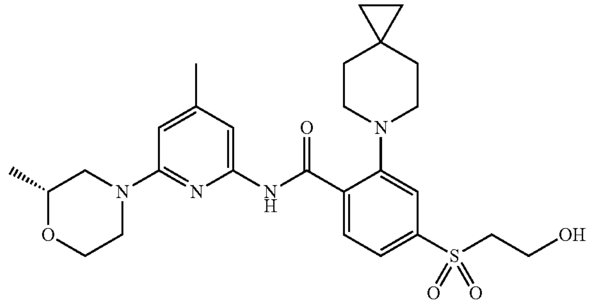 [SMILES: Cc1cc(NC(=O)c2ccc(S(=O)(=O)CCO)cc2N2CCC3(CC2)CC3)nc(N2CCO[C@H](C)C2)c1] | (R)-4-((2-Hydroxyethyl)sulfonyl)-N-(4-methyl-6-(2-methylmorpholino)pyridin-2-yl)-2-(6-azaspiro[2.5]octan-6-yl)benzamide |
| 3 | 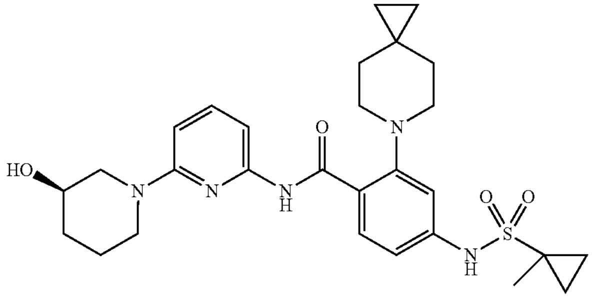 [SMILES: CC1(S(=O)(=O)Nc2ccc(C(=O)Nc3cccc(N4CCC[C@@H](O)C4)n3)c(N3CCC4(CC3)CC4)c2)CC1] | (R)-N-(6-(3-Hydroxypiperidin-1-yl)pyridin-2-yl)-4-((1-methylcyclopropane)-1-sulfonamido)-2-(6-azaspiro[2.5]octan-6-yl)benzamide |
| 4 | 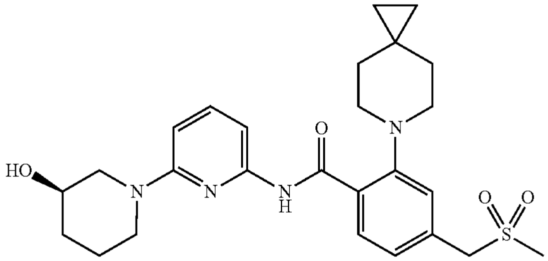 [SMILES: CS(=O)(=O)Cc1ccc(C(=O)Nc2cccc(N3CCC[C@@H](O)C3)n2)c(N2CCC3(CC2)CC3)c1] | (R)-N-(6-(3-hydroxypiperidin-1-yl)pyridin-2-yl)-4-((methylsulfonyl)methyl)-2-(6-azaspiro[2.5]octan-6-yl)benzamide |
| 5 | 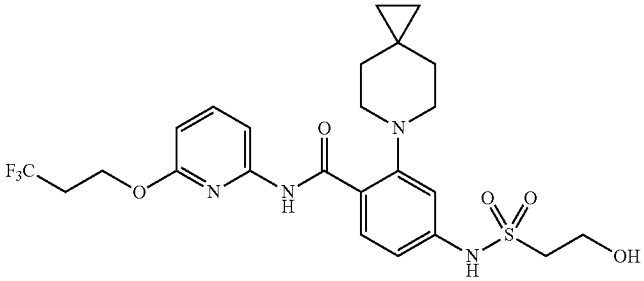 [SMILES: O=C(Nc1cccc(OCCC(F)(F)F)n1)c1ccc(NS(=O)(=O)CCO)cc1N1CCC2(CC1)CC2] | 4-((2-Hydroxyethyl)sulfonamido)-2-(6-azaspiro[2.5]octan-6-yl)-N-(6-(3,3,3-trifluoropropoxy)pyridin-2-yl)benzamide |
| 6 | 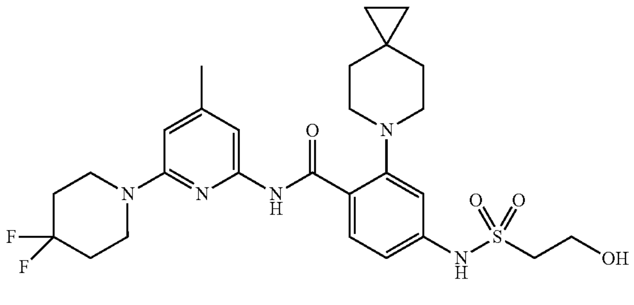 | N-(6-(4,4-Difluoropiperidin-1-yl)-4-methylpyridin-2-yl)-4-((2-hydroxyethyl)sulfonamido)-2-(6-azaspiro[2.5]octan-6-yl)benzamide |

-continued

| Ex. # | Chemical Structure | Name |
|---|---|---|
| 7-1 | 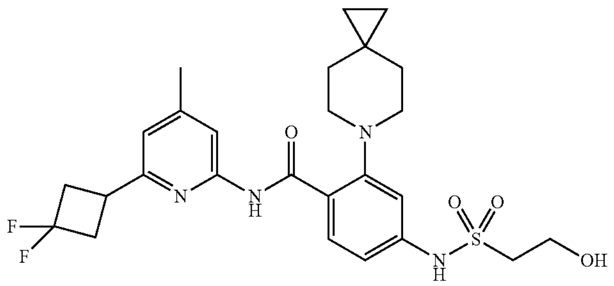 [SMILES: Cc1cc(NC(=O)c2ccc(NS(=O)(=O)CCO)cc2N2CCC3(CC2)CC3)nc(C2CC(F)(F)C2)c1] | N-(6-(3,3-Difluorocyclobutyl)-4-methylpyridin-2-yl)-4-((2-hydroxyethyl)sulfonamido)-2-(6-azaspiro[2.5]octan-6-yl)benzamide |
| 7-12 | 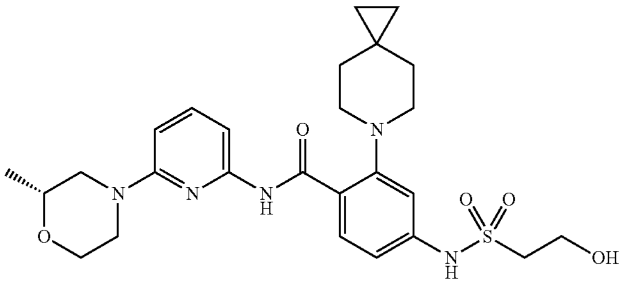 [SMILES: C[C@@H]1CN(c2cccc(NC(=O)c3ccc(NS(=O)(=O)CCO)cc3N3CCC4(CC3)CC4)n2)CCO1] | (R)-4-((2-Hydroxyethyl)sulfonamido)-N-(6-(2-methylmorpholino)pyridin-2-yl)-2-(6-azaspiro[2.5]octan-6-yl)benzamide |
| 7-33 | 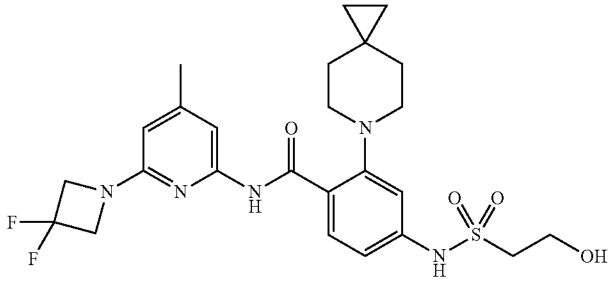 [SMILES: Cc1cc(NC(=O)c2ccc(NS(=O)(=O)CCO)cc2N2CCC3(CC2)CC3)nc(N2CC(F)(F)C2)c1] | N-(6-(3,3-Difluoroazetidin-1-yl)-4-methylpyridin-2-yl)-4-((2-hydroxyethyl)sulfonamido)-2-(6-azaspiro[2.5]octan-6-yl)benzamide |
| 7-44 | 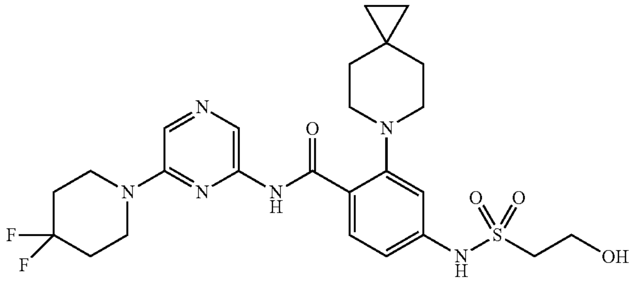 [SMILES: O=C(Nc1cncc(N2CCC(F)(F)CC2)n1)c1ccc(NS(=O)(=O)CCO)cc1N1CCC2(CC1)CC2] | N-(6-(4,4-Difluoropiperidin-1-yl)pyrazin-2-yl)-4-((2-hydroxyethyl)sulfonamido)-2-(6-azaspiro[2.5]octan-6-yl)benzamide |
| 8-1 | 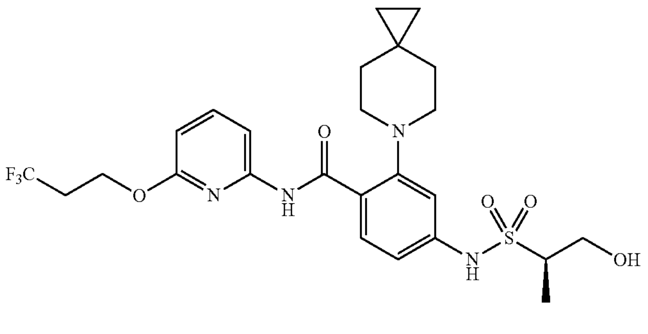 [SMILES: C[C@H](CO)S(=O)(=O)Nc1ccc(C(=O)Nc2cccc(OCCC(F)(F)F)n2)c(N2CCC3(CC2)CC3)c1] | (R)-4-((2-Hydroxy-1-methylethyl)sulfonamido)-2-(6-azaspiro[2.5]octan-6-yl)-N-(6-(3,3,3-trifluoropropoxy)pyridin-2-yl)benzamide |

-continued

| Ex. # | Chemical Structure | Name |
|---|---|---|
| 8-2 | 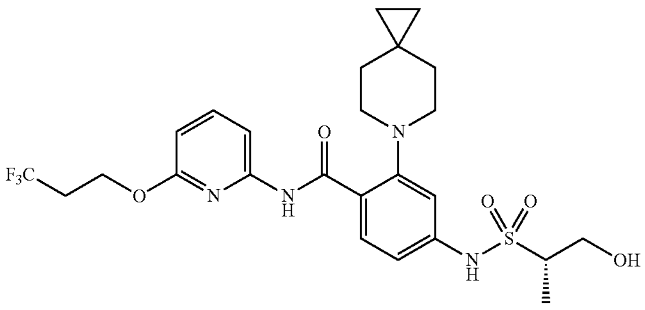 [SMILES: C[C@@H](CO)S(=O)(=O)Nc1ccc(C(=O)Nc2cccc(OCCC(F)(F)F)n2)c(N2CCC3(CC2)CC3)c1] | (S)-4-((2-Hydroxy-1-methylethyl)sulfonamido)-2-(6-azaspiro[2.5]octan-6-yl)-N-(6-(3,3,3-trifluoropropoxy)pyridin-2-yl)benzamide |
| 9-7 | 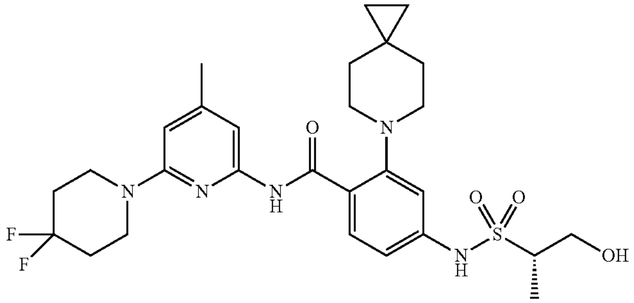 [SMILES: Cc1cc(NC(=O)c2ccc(NS(=O)(=O)[C@@H](C)CO)cc2N2CCC3(CC2)CC3)nc(N2CCC(F)(F)CC2)c1] | (S)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide |
| 9-8 | 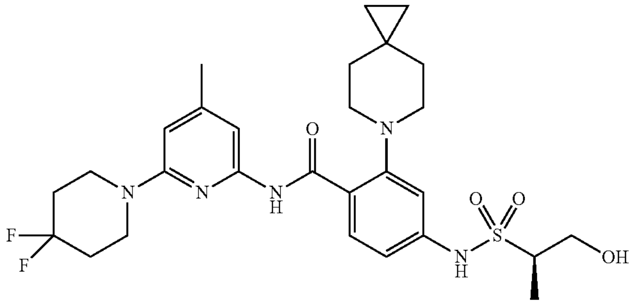 [SMILES: Cc1cc(NC(=O)c2ccc(NS(=O)(=O)[C@H](C)CO)cc2N2CCC3(CC2)CC3)nc(N2CCC(F)(F)CC2)c1] | (R)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide |
| 10 | 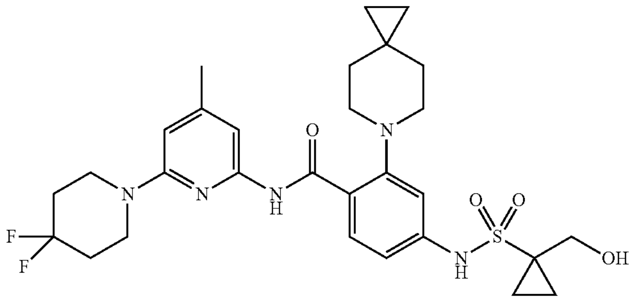 [SMILES: Cc1cc(NC(=O)c2ccc(NS(=O)(=O)C3(CO)CC3)cc2N2CCC3(CC2)CC3)nc(N2CCC(F)(F)CC2)c1] | N-(6-(4,4-Difluoropiperidin-1-yl)-4-methylpyridin-2-yl)-4-((1-(hydroxymethyl)cyclopropane)-1-sulfonamido)-2-(6-azaspiro[2.5]octan-6-yl)benzamide |
| 11 | 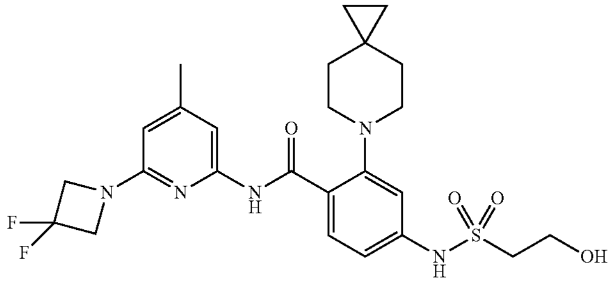 [SMILES: Cc1cc(NC(=O)c2ccc(NS(=O)(=O)CCO)cc2N2CCC3(CC2)CC3)nc(N2CC(F)(F)C2)c1] | N-(6-(3,3-Difluoroazetidin-1-yl)-4-methylpyridin-2-yl)-4-((2-hydroxyethyl)sulfonamido)-2-(6-azaspiro[2.5]octan-6-yl)benzamide |

-continued

| Ex. # | Chemical Structure | Name |
|---|---|---|
| 14 | 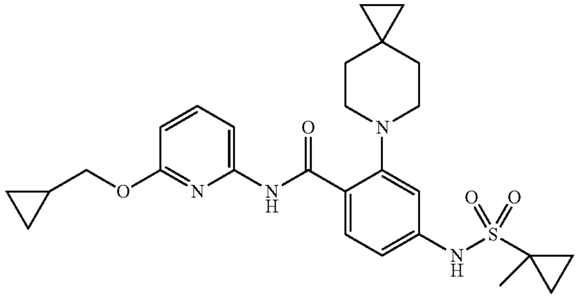 [SMILES: CC1(S(=O)(=O)Nc2ccc(C(=O)Nc3cccc(OCC4CC4)n3)c(N3CCC4(CC3)CC4)c2)CC1] | N-(6-(Cyclopropylmethoxy)pyridin-2-yl)-4-((1-methylcyclopropane)-1-sulfonamido)-2-(6-azaspiro[2.5]octan-6-yl)benzamide |
| 16 | 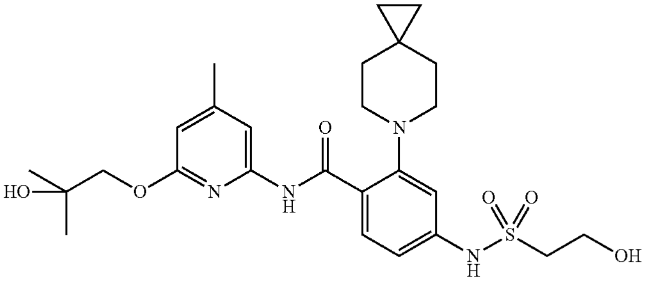 [SMILES: Cc1cc(NC(=O)c2ccc(NS(=O)(=O)CCO)cc2N2CCC3(CC2)CC3)nc(OCC(C)(C)O)c1] | N-(6-(2-Hydroxy-2-methylpropoxy)-4-methylpyridin-2-yl)-4-((2-hydroxyethyl)sulfonamido)-2-(6-azaspiro[2.5]octan-6-yl)benzamide |
| 17 | 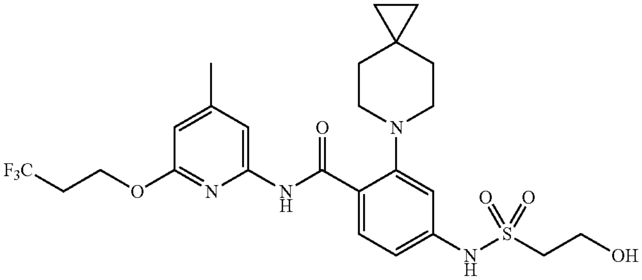 [SMILES: Cc1cc(NC(=O)c2ccc(NS(=O)(=O)CCO)cc2N2CCC3(CC2)CC3)nc(OCCC(F)(F)F)c1] | 4-((2-Hydroxyethyl)sulfonamido)-N-(4-methyl-6-(3,3,3-trifluoropropoxy)pyridin-2-yl)-2-(6-azaspiro[2.5]octan-6-yl)benzamide |
| 21 | 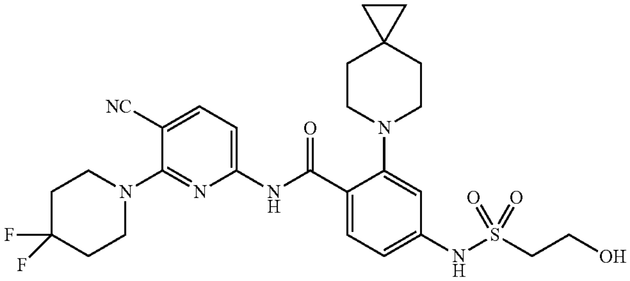 [SMILES: N#Cc1ccc(NC(=O)c2ccc(NS(=O)(=O)CCO)cc2N2CCC3(CC2)CC3)nc1N1CCC(F)(F)CC1] | N-(5-Cyano-6-(4,4-difluoropiperidin-1-yl)pyridin-2-yl)-4-((2-hydroxyethyl)sulfonamido)-2-(6-azaspiro[2.5]octan-6-yl)benzamide |
| 22 | 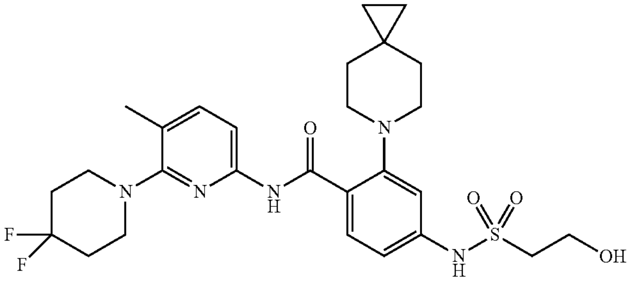 [SMILES: Cc1ccc(NC(=O)c2ccc(NS(=O)(=O)CCO)cc2N2CCC3(CC2)CC3)nc1N1CCC(F)(F)CC1] | N-(6-(4,4-Difluoropiperidin-1-yl)-5-methylpyridin-2-yl)-4-((2-hydroxyethyl)sulfonamido)-2-(6-azaspiro[2.5]octan-6-yl)benzamide |

-continued

| Ex. # | Chemical Structure | Name |
|---|---|---|
| 23 | 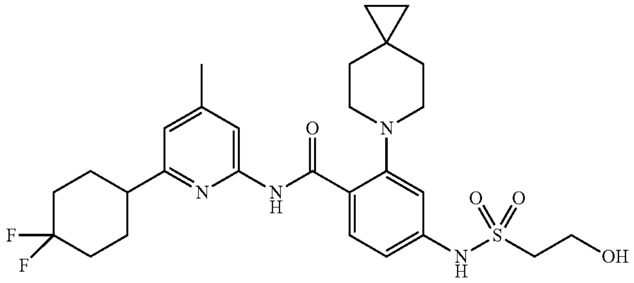 [SMILES: Cc1cc(NC(=O)c2ccc(NS(=O)(=O)CCO)cc2N2CCC3(CC2)CC3)nc(C2CCC(F)(F)CC2)c1] | N-(6-(4,4-difluorocyclohexyl)-4-methylpyridin-2-yl)-4-((2-hydroxyethyl)sulfonamido)-2-(6-azaspiro[2.5]octan-6-yl)benzamide |
| 24 | 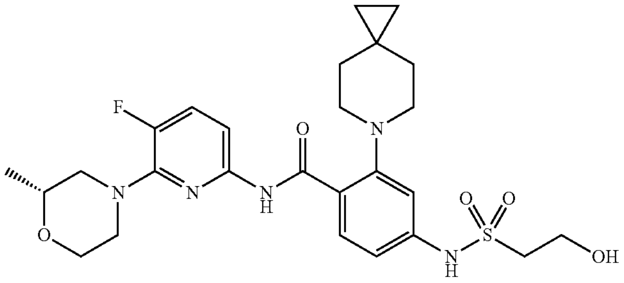 [SMILES: C[C@@H]1CN(c2nc(NC(=O)c3ccc(NS(=O)(=O)CCO)cc3N3CCC4(CC3)CC4)ccc2F)CCO1] | (R)-N-(5-Fluoro-6-(2-methylmorpholino)pyridin-2-yl)-4-((2-hydroxyethyl)sulfonamido)-2-(6-azaspiro[2.5]octan-6-yl)benzamide |
| 25 | 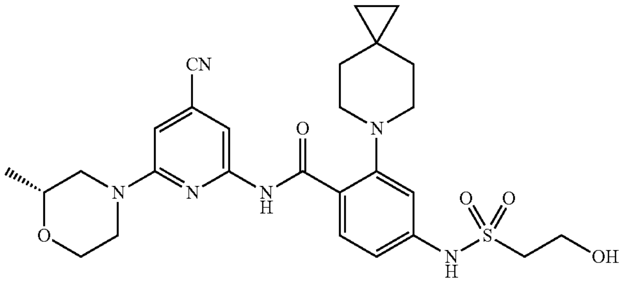 [SMILES: C[C@@H]1CN(c2cc(C#N)cc(NC(=O)c3ccc(NS(=O)(=O)CCO)cc3N3CCC4(CC3)CC4)n2)CCO1] | (R)-N-(4-Cyano-6-(2-methylmorpholino)pyridin-2-yl)-4-((2-hydroxyethyl)sulfonamido)-2-(6-azaspiro[2.5]octan-6-yl)benzamide |
| 27-1 | 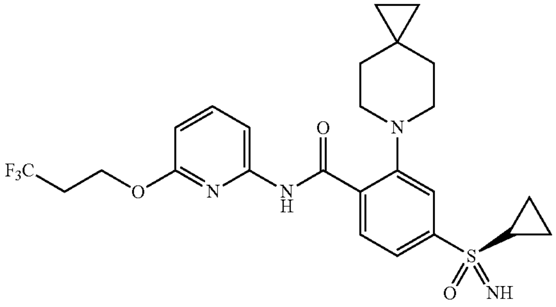 [SMILES: N=[S@](=O)(c1ccc(C(=O)Nc2cccc(OCCC(F)(F)F)n2)c(N2CCC3(CC2)CC3)c1)C1CC1] | 2-(6-Azaspiro[2.5]octan-6-yl)-4-(S-cyclopropylsulfonimidoyl)-N-(6-(3,3,3-trifluoropropoxy)-2-pyridinyl)benzamide |
| 27-2 | 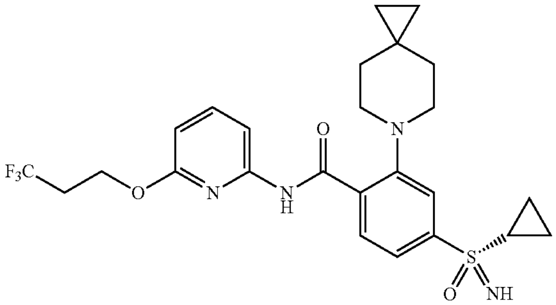 [SMILES: N=[S@@](=O)(c1ccc(C(=O)Nc2cccc(OCCC(F)(F)F)n2)c(N2CCC3(CC2)CC3)c1)C1CC1] | 2-(6-Azaspiro[2.5]octan-6-yl)-4-(R-cyclopropylsulfonimidoyl)-N-(6-(3,3,3-trifluoropropoxy)-2-pyridinyl)benzamide |

or any pharmaceutically-acceptable salt thereof.

In embodiment 30, the present invention provides pharmaceutical compositions comprising a compound, or pharmaceutically acceptable salts thereof, in accordance with any one of embodiments 1-29, and a pharmaceutically acceptable diluent or carrier.

In embodiment 31, the present invention provides a method of treating a condition that may be treated with KIF18a inhibitors, the method comprising administering to a patient in need thereof a therapeutically effective amount of the compound in accordance with embodiments 1-29, or the composition according to embodiment 30.

In embodiment 32, the present invention provides the method of embodiment 31, wherein said condition is cancer selected from the group consisting of (a) a solid or hematologically derived tumor selected from cancer of the cancer of the bladder, endometrial, lung squamous cell, breast, colon, kidney, liver, lung, small cell lung cancer, esophagus, gall-bladder, brain, head and neck, ovary, pancreas, stomach, cervix, thyroid, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, or (f) a melanoma, seminoma, teratocarcinoma, osteosarcoma, xenoderoma pigmentosum, keratoctanthoma, thyroid follicular cancer or Kaposi's sarcoma.

In a sub-embodiment 32a, the present invention provides the method of embodiment 31, wherein said condition is cancer selected from the group consisting of melanoma, prostate cancer, cervical cancer, breast cancer, colon cancer, sarcoma, or leukemia. See: Zhang C. et. al., "Kif18A is involved in human breast carcinogenesis", Carcinogenesis, 2010 September; 31(9):1676-84. doi: 10.1093/carcin/bgql34. Epub 2010 Jul. 1. See also: (1) https://www.proteinatlas.org/ENSG00000121621-KIF18A/pathology; (2) Nagahara, M. et. al., "Kinesin 18A expression: clinical relevance to colorectal cancer progression", *Int. J. Cancer:* 129, 2543-2552 (2011) VC 2011 UIC; and (3) Yu, Y. et. al., "The Role of Kinesin Family Proteins in Tumorigenesis and Progression—Potential Biomarkers and Molecular Targets for Cancer Therapy", *Cancer* 2010; 116:5150-60. VC 2010 American Cancer Society.

In embodiment 33, the present invention provides a method of reducing the size of a solid tumor in a subject, the method comprising administering to the subject in need thereof a therapeutically effective amount of the compound in accordance with embodiments 1-29, or the composition according to embodiment 30.

In embodiment 34, the present invention provides a method of treating a cell proliferation disorder in a subject, the method comprising administering to the subject in need thereof a therapeutically effective amount of the compound in accordance with embodiments embodiments 1-29, or the composition according to embodiment 30.

In embodiment 35, the present invention provides a method of inhibiting KIF18A in a cell, comprising contacting the cell with a compound, or pharmaceutically acceptable salts thereof, in accordance with embodiments embodiments 1-29, or the composition according to embodiment 30.

In embodiment 36, the invention provides a method of preparing a compound of Formula (I) as described herein.

In embodiment 37, the invention provides an intermediate compound used in the method of preparing a compound of Formula (I) as described herein.

DETAILED DESCRIPTION OF THE INVENTION

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^{2}H$ and $^{3}H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{3}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof.

Unless otherwise specified, the following definitions apply to terms found in the specification and claims:

"$C_{\alpha-\beta}$alk" means an alkyl group comprising a minimum of α and a maximum of β carbon atoms in a branched or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

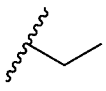 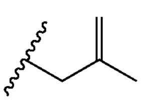 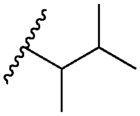 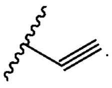.

"Benzo group", alone or in combination, means the divalent radical $C_4H_4=$, one representation of which is $-CH=CH-CH=CH-$, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atom selected from F, Cl, Br and I.

"$C_{\alpha-\beta}$haloalk" means an alk group, as described above, wherein any number—at least one—of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

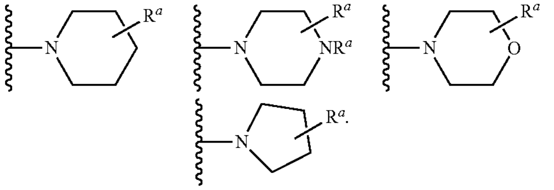

The group $N(C_{\alpha-\beta}alk)\ C_{\alpha-\beta}alk$, wherein $\alpha$ and $\beta$ are as defined above, include substituents where the two $C_{\alpha-\beta}alk$ groups together form a ring, optionally including a N, O or S atom, and include groups such as:

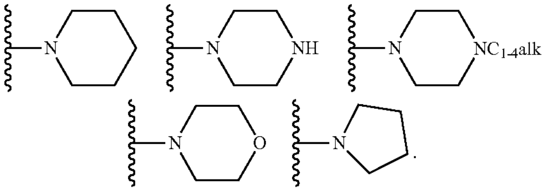

"Bicyclic ring" means a group that features two joined rings. A bicyclic ring can be carbocyclic (all of the ring atoms are carbons), or heterocyclic (the rings atoms consist, for example, 1, 2 or 3 heteroatoms, such as N, O, or S, in addition to carbon atoms). The two rings can both be aliphatic (e.g. decalin and norbornane), or can be aromatic (e.g. naphthalene), or a combination of aliphatic and aromatic (e.g. tetralin). Bicyclic rings include (a) spirocyclic compounds, wherein the two rings share only one single atom, the spiro atom, which is usually a quaternary carbon. Examples of spirocyclic compound include, but are not limited to:

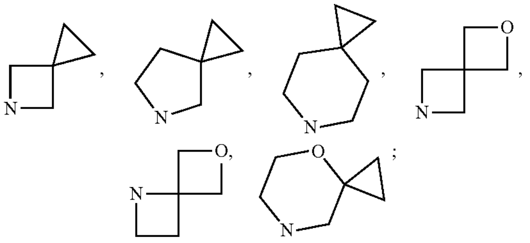

(b) fused bicyclic compounds, wherein two rings share two adjacent atoms. In other words, the rings share one covalent bond, i.e. the bridgehead atoms are directly connected (e.g. α-thujene and decalin), Examples of fused bicyclic rings include, but are not limited to:

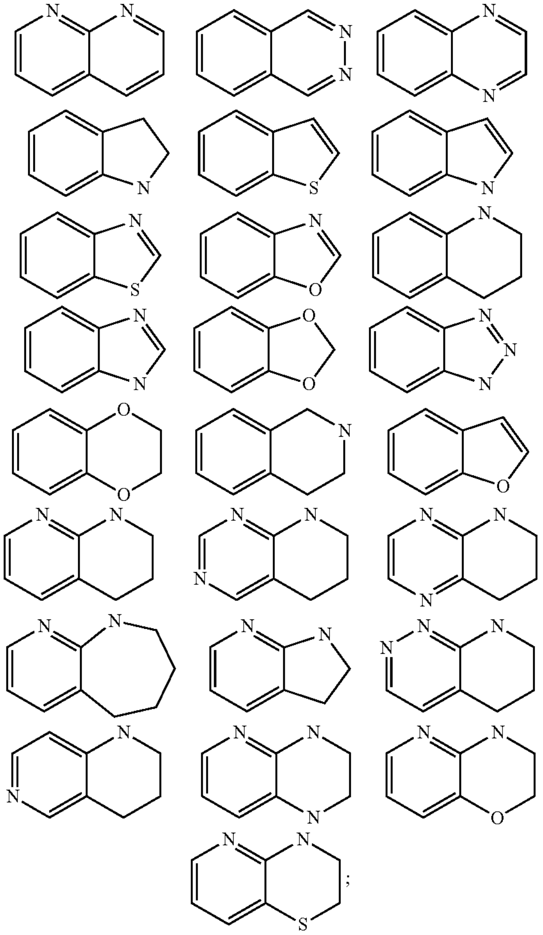

and (c) bridged bicyclic compounds, wherein the two rings share three or more atoms, separating the two bridgehead atoms by a bridge containing at least one atom. For example, norbornane, also known as bicyclo[2.2.1]heptane, can be thought of as a pair of cyclopentane rings each sharing three of their five carbon atoms. Examples of bridged bicyclic rings include, but are not limited to:

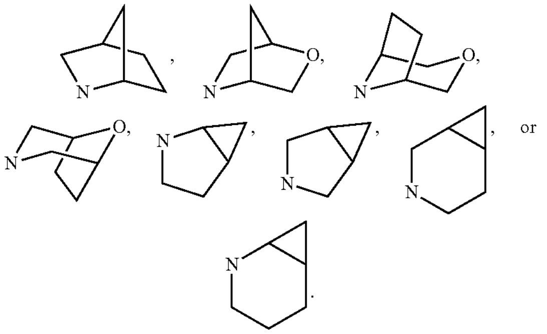

or

"Carbocycle" or "Carbocyclic" means a ring comprising by itself or in combination with other terms, represents, unless otherwise stated, cyclic version of "$C_{\alpha\text{-}\beta}$alk". Examples of carbocycle include cyclopentyl, cyclohexyl, 1-cyclohexenyl, 3-cyclohexenyl, cycloheptyl, cyclobutylene, cyclohexylene and the like.

"Heterocycle" or "Heterocyclic" means a ring comprising at least one carbon atom and at least one other atom selected from N, O and S. Examples of heterocycles that may be found in the claims include, but are not limited to, the following:

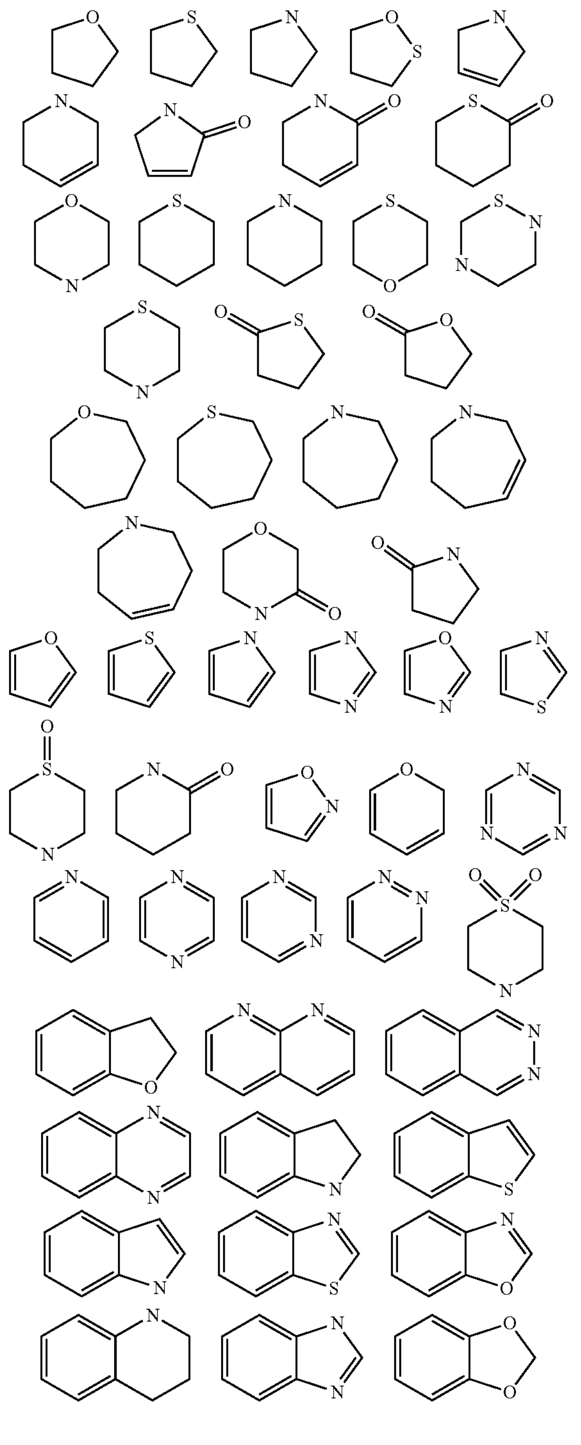

-continued

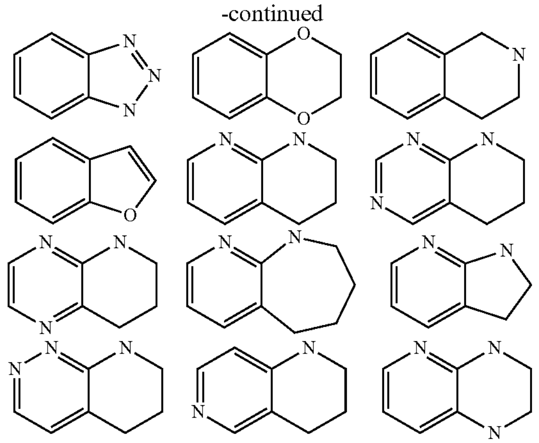

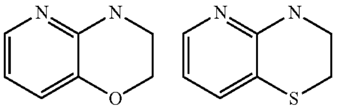

and

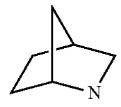

.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine. a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'═O, S, NR), and the like, which are illustrated in the following examples:

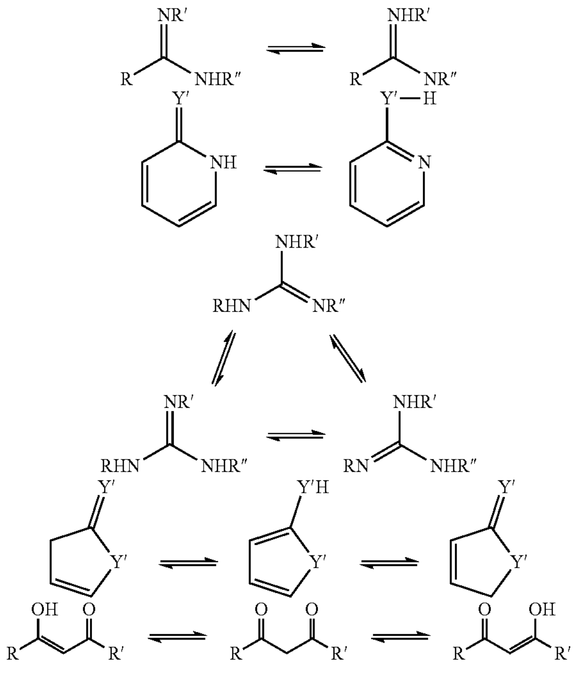

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard *J. Med. Chem.* 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, 4/11/81) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pennsylvania, 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable e" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise com syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores.

Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KIF18A-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KIF18A activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. While individual needs vary, determination of optimal ranges of effective amounts of the compound is within the skill of the art. Such doses may be administered in a single dose or it may be divided into multiple doses.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer, ovarian cancer, and endometrial cancer. While the term "cancer" as used herein is not limited to any one specific form of the disease, it is believed that the methods of the invention will be particularly effective for cancers which are found to be accompanied by unregulated levels of KIF18A or dependent on KIF18A for proper chromosome segregation and survival in the mammal.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "patient", "subject", or "mammal" as used herein refers to any "patient", "subject", or "mammal" including humans, cows, horses, dogs and cats. In one embodiment of the invention, the mammal is a human.

The term "comprising" is meant to be open ended, including the indicated component(s) but not excluding other elements.

The terms "Formula I" include any sub formulas.

METHODS OF USING KIF18A INHIBITORS

The present disclosure provides compounds having MT-based KIF18A modulatory activity in general, and inhibitory activity in particular. In one embodiment of the invention, there is provided a method of modulating KIF18A protein in a subject, the method comprising administering to the subject an effective dosage amount of a compound of Formulas L As such, the compounds of the invention may be used to treat cellular proliferation disorders, including uncontrolled cell growth, aberrant cell cycle regulation, centrosome abnormalities (structural and or numeric, fragmentation). Other diseases or disorders associated with the accumulation of extra centrosomes (>2) include human papillomavirus (HPV) infection, including HPV-associated neoplasias. The compounds are also useful for cilia-related diseases as well as ablating haploid germ cell population which could be used as a male contraceptive.

In addition, compounds of the invention are useful for, but not limited to, the prevention or treatment of cancer and other KIF18A-mediated diseases or disorders. For example, compounds of the invention would be useful for the treatment of various solid and hematologically derived tumors, such as carcinomas, including, without limitation, cancer of the bladder, breast, colon, kidney, liver, lung (including squamous cell and small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

Based on the ability to modulate kinesin impacting angiogenesis, the compounds of the invention are also useful in treatment and therapy of proliferative diseases. Particularly, these compounds can be used for the treatment of an inflammatory disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

COMBINATIONS

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy, small molecule targeted agents (e.g. PARP inhibitors, kinase inhibitors), therapeutic antibodies (e.g. naked and drug-conjugate) immunotherapy antibodies (checkpoint inhibitors, bi-specific T-cell engagers) with neoplastic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

There are large numbers of anticancer agents available in commercial use, in clinical evaluation and in pre-clinical development, which would be selected for treatment of neoplasia by combination drug chemotherapy. Such agents fall into several major categories such as antibiotic-type agents, alkylating and alkylating-like agents, antimitotic agents, targeted small molecule agents, antimetabolite agents, hormonal agents, immunological agents, anti-angiogenic agents, interferon-type agents and a category of miscellaneous agents.

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, targeted small molecule agents, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of antimitotic agents, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel, Nab-paclitaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin, oxaliplatin, carboplatin; etoposide (VP-16); ifosfamide; mitomycin C; mitoxantrone; vinblastine vincristine; vinorelbine; navelbine; novantrone; teniposide; daunomycin; aminopterin; xeloda; ibandronate; topotecan; camptothecin-11 (CPT-11); topoisomerase inhibitor RFS 2000; difluoromethylornithine (DMFO), Where desired, the compounds or pharmaceutical composition of the present disclosure can be used in combination with commonly prescribed anti-cancer drugs such as Herceptin®, Avastin®, Erbitux®, Rituxan®, Taxol®, Abraxane, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Talazoparib, Niraparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl) amine, Troxacitabine, Uramustine, Vadimezan, Vinflunine, ZD6126 or Zosuquidar, CDK4/6 inhibitors (Palbociclib. Ibrance; Ribociclib, Kisqali; Abemaciclib, Verzenio).

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No. EP1181017, United States Publication No. US20090012085, United States Publication U.S. Pat. No. 5,863,949, United States Publication U.S. Pat. No. 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxombicin, bromocriptine, carmustine, cytarabine, fluorouracil, HIT diclofenac, interferon alfa, daunorubicin, doxorubicin, tretinoin, edelfosine, edrecolomab, eflomithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fe MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof Δn agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aetema, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as *vinca* alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RG13286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237, AMG 900, AZD-1152), cell surface monoclonal antibodies (e.g., anti-CD38 (HUMAX-CD38), anti-CS1 (e.g., elotuzumab), HSP90 inhibitors (e.g., 17 AAG and KOS 953), P13K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., INK128), kinase inhibitor (e.g., GS-1101), ER/UPRtargeting agent (e.g., MKC-3946), cFMS inhibitor (e.g., ARRY-382), JAK1/2 inhibitor (e.g., CYT387), PARP inhibitor (e.g., olaparib, Talazoparib, Niraparib veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds or pharmaceutical compositions of the disclosure can also be used in combination with an amount of one or more substances selected from EGFR inhibitors, MEK inhibitors, PI3K inhibitors, AKT inhibitors, TOR inhibitors, and immune therapies, including anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., Pharmacogenetics and Pharmacogenomics In Oncology Therapeutic Antibody Development, BioTechniques 2005; 39(4): 565-8, and Paez J G, et. al., EGFR Mutations In Lung Cancer Correlation With Clinical Response To Gefitinib Therapy, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published January 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12):1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, *Cancer Res.* 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INKJ117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) Biochem. J., 385 (Pt. 2), 399-408); Akt-1-1,2 (inhibits Akl and 2) (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin.

Investig. Drugs 13, 787-97); and triciribine (TCN or API-2 or NCI identifier: NSC 154020; Yang et al. (2004) *Cancer Res.* 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, orAP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

Immune therapies include, but are not limited to, anti-PD-1 agents, anti-PDL-1 agents, anti-CTLA-4 agents, anti-LAG1 agents, and anti-OX40 agents. Exemplary anti-PD-1 antibodies and methods for their use are described by Goldberg et al., Blood 110(1):186-192 (2007), Thompson et al., Clin. Cancer Res. 13(6):1757-1761 (2007), and Korman et al., International Application No. PCT/JP2006/309606 (publication no. WO 2006/121168 A1), each of which are expressly incorporated by reference herein. include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXPERIMENTAL

Abbreviations: The following abbreviations may be used herein:

| | |
|---|---|
| ACN or MeCH | acetonitrile |
| AcOH | acetic acid |
| aq or aq. | aqueous |
| BOC or Boc | tert-butyloxycarbonyl |
| BrettPhos | 2-(dicyclohexylphosphino)3,6-dimethoxy-2',4',6'-triisopropyl-1,1'-biphenyl |
| cataCXium ® A | rac-((3R,5R,7R)-adamantan-1-yl)((35,5S,7S)-adamantan-1-yl)(butyl)phosphane |
| DABSO | 1,4-diazabicyclo[2.2.2]octane bis(sulfur dioxide) adduct |
| DCE | 1,2-dichloroethane |

-continued

| | |
|---|---|
| DCM | dichloromethane |
| DMAP | 4-dimethylaminopyridine |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | Equivalent |
| ESI or ES | electrospray ionization |
| Et | Ethyl |
| $Et_2O$ | diethyl ether |
| EtOH | ethyl alcohol |
| EtOAc | ethyl acetate |
| g | grams |
| h | hour |
| HATU | 1-[bis(dimethylamino)methylene]-1H-1,2,3-triazolo[4,5-b]pyridinium 3-oxid hexafluorophosphate |
| HPLC | high pressure liquid chromatography |
| IPA | isopropanol |
| iPr | Isopropyl |
| $iPr_2NEt$ or DIPEA | N-ethyl diisopropylamine (Hunig's base) |
| KOAc | potassium acetate |
| LDA | Lithium diisopropylamide |
| LC MS, LCMS, LC-MS or LC/MS | liquid chromatography mass spectroscopy |
| LG | leaving group (e.g., halogen, mesylate, triflate) |
| LHMDS | lithium bis(trimethylsilyl)amide |
| m/z | mass divided by charge |
| mCPBA or MCPBA | meta-chloroperoxybenzoic acid |
| Me | methyl |
| MeOH | methanol |
| Met | metal species for cross-coupling (e.g., MgX, ZnX, $SnR_3$, $SiR_3$, $B(OR)_2$) |
| Mg | milligrams |
| Min | minutes |
| mL | milliliters |
| MS | mass spectra |
| MsCl | methanesulfonyl chloride |
| MTBE | tert-butyl methyl ether |
| NMP | 1-methyl-2-pyrrolidine |
| n-BuLi | n-butyllithium |
| NMR | nuclear magnetic resonance |
| $Pd_2(dba)_3$ | tris(dibenzylideneacetone)dipalladium(0) |
| $Pd(dppf)Cl_2$•DCM | [1,1'-bis(diphenylphosphino)ferrocene]dichloropalladium(II), complex with dichloromethane |
| $Pd(PPh_3)_4$ | tetrakis(triphenylphosphine)palladium(0) |
| Ph | phenyl |
| Phen | 1,10-phenanthroline |
| PR or PG or Prot. group | protecting group |
| rbf | round-bottom flask |
| RP-HPLC | reverse phase high pressure liquid chromatography |
| RT or rt | room temperature |
| sat. or satd. | saturated |
| SFC | supercritical fluid chromatography |
| SPhos Pd G3 or SPhos G3 | (2-dicyclohexylphosphino-2',6'-dimethoxybiphenyl) [2-(2'-amino-1,1'-biphenyl)]palladium(II) methanesulfonate |
| TBAF | tetra-n-butylammonium fluoride |
| t-BuOH | tert-butanol |
| TATU | O-(7-azabenzotriazolyl)-tetramethyluronium tetrafluorobor |
| TEA or $Et_3N$ | trimethylamine |
| TFA | trifluoroacetic acid |
| THF | tetrahydrofuran |
| TLC | thin layer chromatography |
| $T_3P$ | 2,4,6-tripropyl-1,3,5,2,4,6-trioxatriphosphinane 2,4,6-trioxide |
| UV | ultraviolet |
| Xantphos | 4,5-bis(diphenylphosphino)-9,9-dimethylxanthene |
| XtalFluor-M | difluoro(morpholino)sulfonium tetrafluoroborate |

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 μm, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, CA). Silica gel chromatography was generally performed with prepacked silica gel cartridges (Biotage, Uppsala, Sweden or Teledyne-Isco, Lincoln, NE). $^1H$ NMR spectra were recorded on a Bruker AV-400 (400 MHz) spectrometer (Bruker Corporation, Madison, WI) or a Varian (Agilent Technologies, Santa Clara, CA) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, CA) LC/MS with UV detection at 254 nm and 215 nm and a low resonance electrospray mode (ESI).

For the purpose of clarity in this general synthesis section, Compounds of Formula (I) as defined in the summary of the inventions can be schematically drawn to contain Ring $Ar^1$ and Ring $Ar^2$ as follows:

(I)

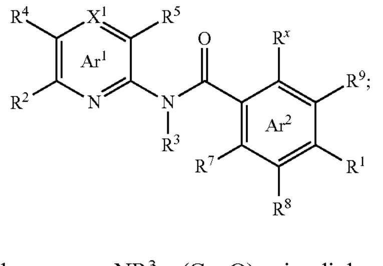

wherein the group —$NR^3$—(C═O)— is a linker, ring $Ar^1$ is located to the left of the linker, and ring $Ar^2$ is located to the right of linker. Generally, compounds of Formula (I), can be synthesized via three general steps as follows:

Step 1: Preparation of Ring $Ar^1$ compound.

Step 2: Preparation of Ring $Ar^2$ compound.

Step 3: Coupling of Ring $Ar^1$ compound to Ring $Ar^2$ compound.

The generic Schemes A-E below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

Scheme A

According to Scheme A, in one embodiment a compound of Formula (I) as disclosed herein can be synthesized as follows:

Step 1a: Preparation of Ring $Ar^1$ Compound:

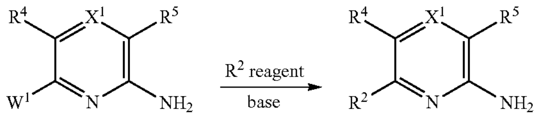

A-1 A-2

Step 1a: Preparation of Ring $Ar^1$ compound:: Compound A-1, wherein $W^1$ is a halogen, for example fluoro, chloro, or bromo can be reacted with an $R^2$ group containing agent in the presence of a suitable base, in a suitable organic solvent such as NMP, dioxane, acetonitrile, tetrahydrofuran, DMF, methylene chloride, and the like, to form compound A-2. Compound A-1 is commercially available or can be synthesized by known methods by those skilled in the art. Examples of compound A-1 include, but are not limited to, 6-fluoropyridin-2-amine, 6-fluoro-4-methylpyridin-2-amine, 6-chloro-5-methylpyridin-2-amine, 6-bromo-5-methylpyridin-2-amine, or 6-chloropyrazin-2-amine. Examples of $R^2$ reagents include, but not limited to (1) (R)-2-methylmorpholine, (2) 4,4-difluoropiperidine hydrochloride, (3) 3,3-difluoroazetidine hydrochloride, or (4) 3,3,3-trifluoropropan-1-ol. Examples of bases include, but are not limited to diisopropylethyl amine, potassium carbonate, or sodium hydride.

Step 1b: Preparation of Ring $Ar^1$ Compound:

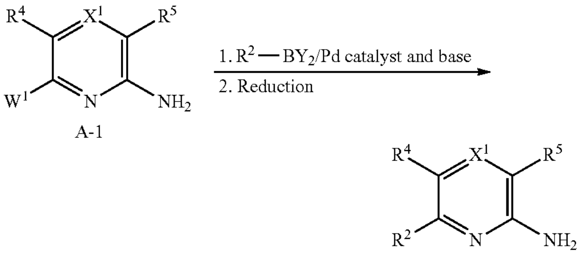

A-1

A-2

Alternatively, compound A-1 as defined in step 1a, can be converted to compound A-2, as defined in step 1a, via Suzuki cross coupling reaction with a suitable organoboron $R^2$ reagent ($R^2$—$BY_2$, wherein Y is an organic functional group) such as 2-(4,4-difluorocyclohex-1-en-1-yl)-4,4,5,5-tetramethyl-1,3,2-dioxaborolane or 2-(4-fluorocyclopent-1-en-1-yl)-4,4,5,5-tetramethyl-1,3,2-dioxaborolane, and a suitable palladium catalyst and a base, such as $PdCl_2$(dppf)-DCM adduct and potassium phosphate tribasic. This step is followed by a reduction with a suitable palladium catalyst and a hydrogen source, such as Pd/C in the presence of hydrogen gas, to form compound A-2. This alternative Suzuki reaction can be used when the group $R^2$ is linked to the $Ar^1$ ring via a carbon-carbon bond.

Step 2a: Preparation of Ring $Ar^2$ Compound:

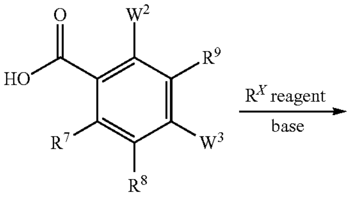

A-3

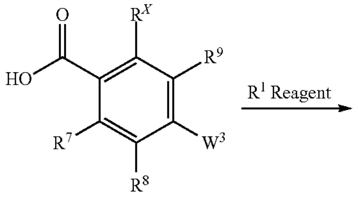

A-4

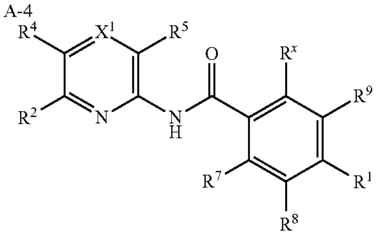

(I)

In Step 2a, Compound A-3, wherein each of $W^2$ and $W^3$ is independently a halogen, for example fluoro, chloro, bromo, or iodo, can be reacted with an $R^x$ reagent, such as (1) 6-azaspiro[2.5]octane hydrochloride, (2) 4,4-dimethylpiperidine hydrochloride, (3) 3,4,4-trimethylpiperidine hydrochloride, (4) 4-methyl-6-azaspiro[2.5]octane hydrochloride, or (5) 7-azaspiro[3.5]nonane hydrochloride, in a suitable organic solvent such as NMP, acetonitrile, tetrahydrofuran, DMF, methylene chloride, DMSO, and the like, to form Compound A-4.

Step 3a: Coupling of Ring $Ar^1$ Compound to Ring $Ar^2$ Compound Followed by Introduction of $R^1$:

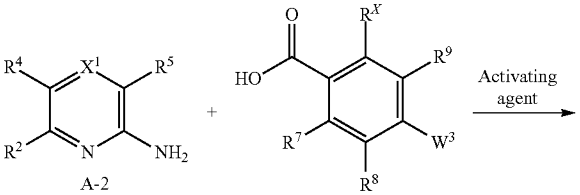

A-2

A-4

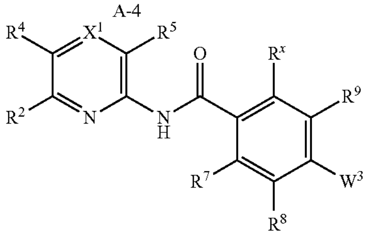

A-5

In Step 3a, compound A-4, which was obtained from Step 2a, can be reacted with an activating agent such as acid chloride $(COCl)_2$ or $SOCl_2$, in a suitable organic solvent such as tetrahydrofuran, methylene chloride, and the like, to form an acid chloride derivative, which can then react with compound A-2 to form compound A-5. Alternatively, compound A-2 can be directly coupled with compound A-4, which was obtained from Step 2a, in a suitable organic solvent such as acetonitrile, tetrahydrofuran, DMF, methylene chloride, and the like, in the presence of a coupling reagent, such as N,N'-diisopropylcarbodiimide, N-(3-dimethylaminopropyl)-N'-ethylcarbodiimide, benzotriazol-1-yl-oxytripyrrolidinophosphonium hexafluorophosphate, O-(benzotriazol-1-yl)-N,N,N',N'-tetramethyluronium hexafluorophosphate, carbonyl diimidazole, and polyphosphonic anhydride. Those ordinary skilled synthetic chemists will readily understand that other coupling agents can be used. Further manipulation of halogen group $W^3$ by transformation reactions such as, metal-catalyzed sulfoamidation, sulfination, or sulfonylation, in a suitable organic solvent such as DMSO, acetonitrile, tetrahydrofuran, DMF, methylene chloride, and the like, in the presence of a metal catalyst and an $R^1$ reagent, such as (1) 1-methylcyclopropane-1-sulfonamide, (2) 3-methyloxetan-3-amine, (3) tert-butyl 3-mercaptoazetidine-1-carboxylate, (4) ethyl 2-sulfamoylpropanoate, (5) 2-hydroxypropane-1-sulfonamide, (6) 2-hydroxyethane-1-sulfonamide, (7) ethyl iodoacetate, (8) 2-mercaptopropan-1-ol, (9) 2-mercapto-2-methylpropan-1-ol, (10) 2-aminoethan-1-ol, or (11) cyclopropanethiol can be used to form Compound (I). Those ordinary skilled chemists will readily understand that coupling reaction such as shown in Step 3a can be performed under various known conditions.

Scheme B

Step 1a or 1b: Preparation of Ring $Ar^1$ Compound: See SCHEME a Above

Step 2b: Preparation of Ring $Ar^2$ Compound:

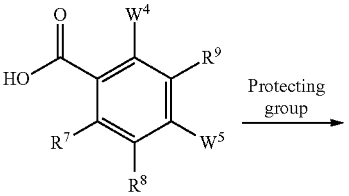

B-1

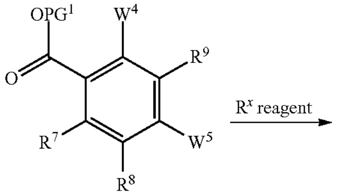

B-2

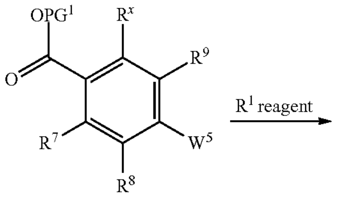

B-3

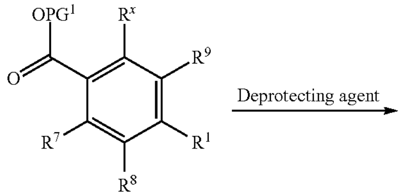

B-4

-continued

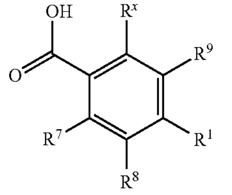

B-5

Scheme B provides an alternative method for formation of compounds of Formula (I) as disclosed herein. After Step 1a or Step 1b as described in Scheme A, the group $R^1$ can alternatively be introduced to Ring $Ar^2$ in Step 2b rather that in Step 3a as in Scheme A. According to Step 2b, compound B-1, wherein each of $W^4$ and $W^5$ is independently a halogen, for example fluoro, chloro, bromo, or iodo, can be reacted with an appropriate carboxylic acid protecting group ($PG_1$ reagent), such as methyl iodide in the presence of a base such as potassium carbonate, to form a methyl ester, or other appropriate protecting group to form other ester such as benzyl ester, in a suitable organic solvent such as NMP, acetonitrile, tetrahydrofuran, DMF, methylene chloride and the like, to form compound B-2, wherein each of $W^4$ and $W^5$ are as defined in compound B-1. Compound B-2 can then be reacted with an $R^x$ reagent, such as 6-azaspiro[2.5]octane, in a suitable organic solvent such as NMP, acetonitrile, tetrahydrofuran, DMF, methylene chloride, DMSO, and the like, to form compound B-3, wherein $W^5$ is as defined in compound B-1. Compound B-3 can then be reacted with an $R^1$ reagent by a transformation reaction such as, metal-catalyzed sulfoamidation, sulfination, or sulfonylation, in a suitable organic solvent such as DMSO, acetonitrile, tetrahydrofuran, DMF, and the like, in the presence of a metal catalyst, such as copper iodide, $Pd_2(dba)_3$ to form compound B-4, which can then be reacted further with an appropriate carboxylic acid deprotecting agent to form compound B-5. Appropriate carboxylic acid protecting groups and deprotection agents are known to those skilled in the art, e.g., as discussed in Greene's Protective Groups in Organic Synthesis.

Step 3b: Coupling of Ring $Ar^1$ compound to Ring $Ar^2$ compound:

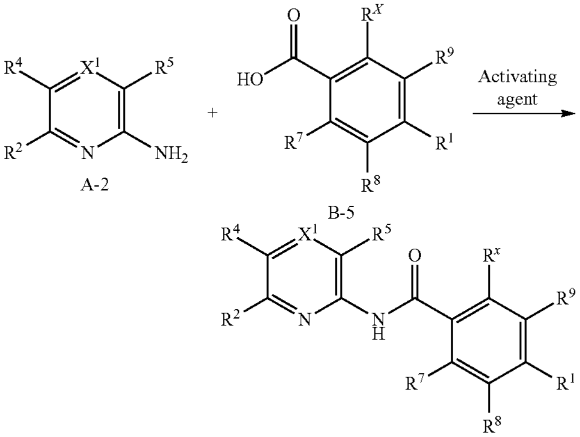

A-2

B-5

(I)

Step 3b is similar to the coupling reaction as described above in Step 3a.

Scheme C

Scheme C provides yet another alternative method for formation of compounds of Formula (I) as disclosed herein. According to Scheme C, Step 1a can be performed as described in Scheme A, followed by Step 2b as described in Scheme B.

Step 3c: Coupling of Ring $Ar^1$ Compound to Ring $Ar^2$ Compound:

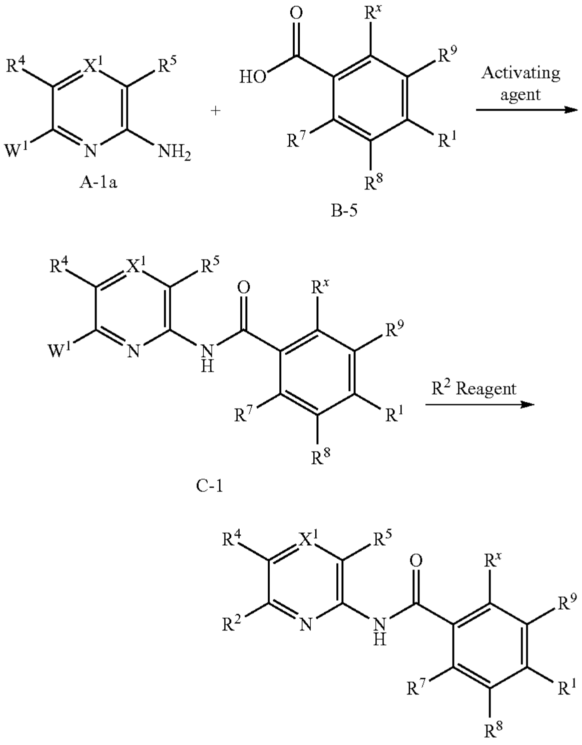

A-1a

B-5

C-1

(I)

In Step 3c, compound A-1a, which is compound A-1 of Scheme A, wherein $X^1$ is N or $CR^6$ and $W^1$ is a halogen, for example fluoro or chloro, can be reacted with compound B-5 obtained from step 2b of scheme B, in the presence of an activating agents under conditions similar to step 3a and 3b above, to form compound C-1, wherein $W^1$ is as defined in compound A-1a, which then can be reacted with an $R^2$ group containing agent, such as (1) (R)-2-methylmorpholine, (2) 4,4-difluoropiperidine hydrochloride, (3) 3,3-difluoroazetidine hydrochloride, or (4) 3,3,3-trifluoropropan-1-ol, in the presence of a suitable base, such as diisopropylethyl amine, potassium carbonate, or sodium hydride, in a suitable organic solvent such as NMP, dioxane, acetonitrile, tetrahydrofuran, DMF, methylene chloride, and the like, to form compound of formula (I).

Scheme D

Scheme D provides yet another alternative method for formation of compounds of Formula (I) as disclosed herein. According to Scheme D, Step 1a or 1b can be performed as described in Scheme A, followed by Step 2b as described in Scheme B.

Step 3d: Coupling of Ring $Ar^1$ compound to Ring $Ar^2$ Compound:

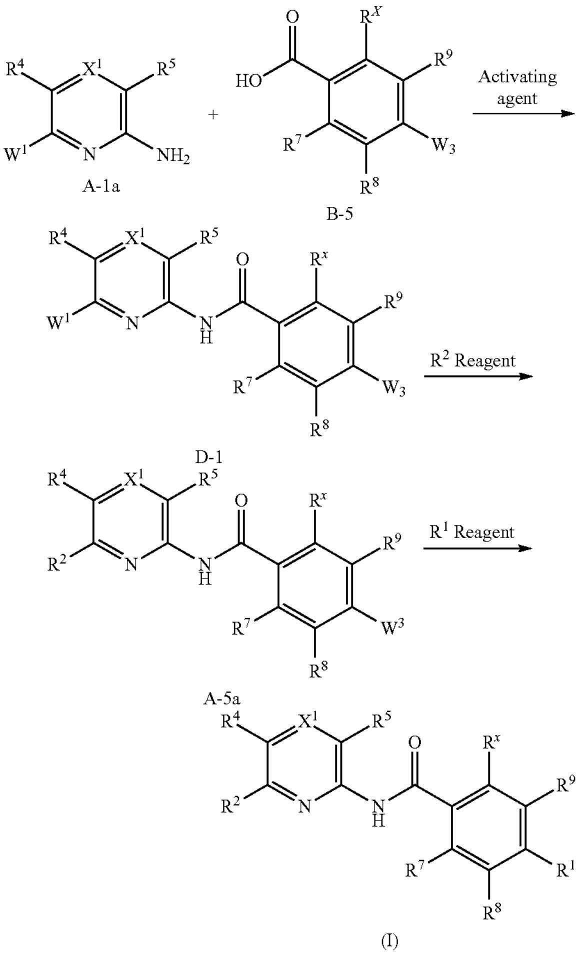

A-1a
B-5
D-1
A-5a
(I)

In Step 3d, compound A-1a, which is compound A-1 of Scheme A, wherein $X^1$ is N or $CR^6$ and $W^1$ is a halogen, for example fluoro or chloro, can be reacted with compound B-5 obtained from step 2a of scheme A, in the presence of a activating agent under conditions similar to step 3a and 3b above, to form compound D-1, wherein $W^1$ is as defined in compound A-1a and $W^3$ is as defined in compound B-5, which then can be reacted with an $R^2$ group containing agent, such as (1) (R)-2-methylmorpholine, (2) 4,4-difluoropiperidine hydrochloride, (3) 3,3-difluoroazetidine hydrochloride, or (4) 3,3,3-trifluoropropan-1-ol, optionally in the presence of a suitable base, such as diisopropylethyl amine, potassium carbonate, or sodium hydride, in a suitable organic solvent such as NMP, dioxane, acetonitrile, tetrahydrofuran, DMF, and the like, to form compound A-5a, which is compound A-5, wherein $X^1$ is N and $W^3$ is as defined in compound B-5, which can then be reacted with an $R^1$ group containing agent by a transformation reaction such as, metal-catalyzed sulfoamidation, sulfination, or sulfonylation, in a suitable organic solvent such as DMSO, dioxane, acetonitrile, tetrahydrofuran, DMF, and the like, in the presence of a metal catalyst, to form compound formula (I).

Scheme E

Scheme E provides yet another alternative method for formation of compounds of Formula (I) as disclosed herein.

According to Scheme E, Step 1a or 1b can be performed as described in Scheme A to prepare compound A-2. Compound E-1, wherein $W^6$ is a halogen, for example fluoro or chloro, which includes but is not limited to 2-fluoro-4-nitrobenzoic acid, 2,5-difluoro-4-nitrobenzoic acid, or 2,6-difluoro-4-nitrobenzoic acid, is commercially available or can be synthesized according to known methods by those skilled in the art.

Step 3e: Coupling of Ring $Ar^1$ Compound to Ring $Ar^2$ Compound

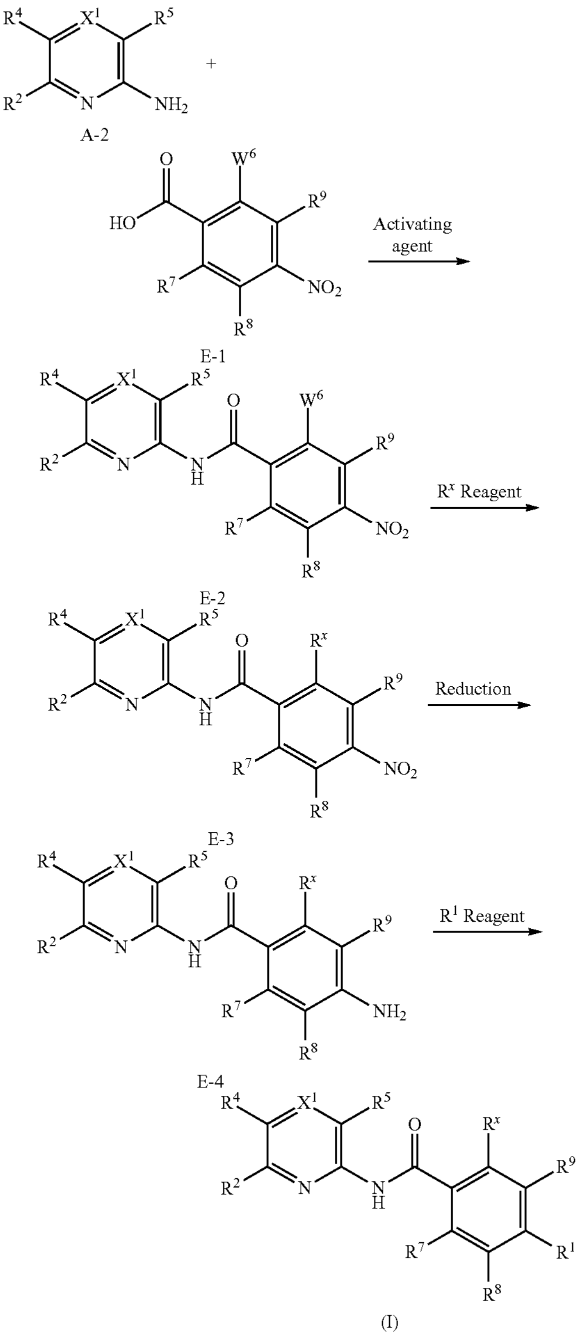

A-2
E-1
E-2
E-3
E-4
(I)

In step 3e, compound A-2 can be reacted with compound E-1, the presence of an activation reagent under conditions similar to step 3a and 3b above, to form compound E-2, which then can be reacted with an $R^x$ reagent in a similar way as described in Step 2a to form compound E-3. The nitro group on compound E-4 can then be converted into an amino group by reacting with a reducing agent, which includes but is not limited to palladium on carbon and hydrogen gas, to form compound E-4, which can then be reacted with an $R^1$ reagent, such as (1) 1-methylcyclopropane-1-sulfonamide, (2) 3-methyloxetan-3-amine, (3) tert-butyl 3-mercaptoazetidine-1-carboxylate, (4) ethyl 2-sulfamoylpropanoate, (5) 2-hydroxypropane-1-sulfonamide, (6) 2-hydroxyethane-1-sulfonamide, (7) ethyl iodoacetate, (8) 2-mercaptopropan-1-ol, (9) 2-mercapto-2-methylpropan-1-ol, (10) 2-aminoethan-1-ol, or (11) cyclopropanethiol, by a transformation reaction such as, metal-catalyzed sulfoamidation, sulfination, or sulfonylation, in a suitable organic solvent such as DMSO, dioxane, -acetonitrile, tetrahydrofuran, DMF, and the like, in the presence of a metal catalyst, to form compound (I).

EXAMPLES

Preparation of Synthetic Intermediates

Ring Ar[1] Intermediates

Intermediate 1: 6-Amino-N-(tert-butyl)pyridine-2-sulfonamide

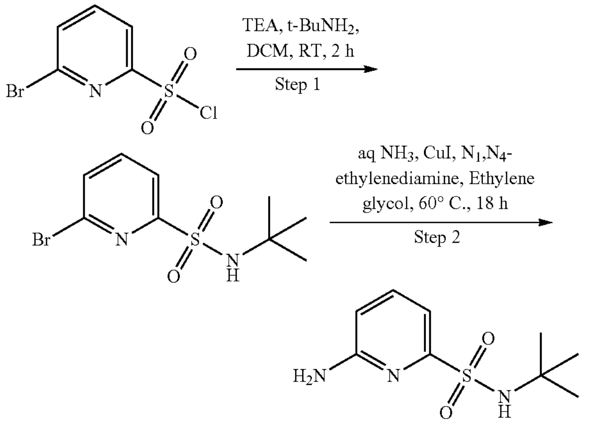

Intermediate 1

Step 1: To an ice-cold solution of 6-bromopyridine-2-sulfonyl chloride (0.50 g, 1.9 mmol, Suzhou sibian, China) in dichloromethane (10 mL), triethylamine (0.543 mL, 3.90 mmol) and tert-butylamine (0.310 mL, 2.92 mmol) were successively added under nitrogen atmosphere. The reaction mixture was stirred at room temperature for 1.5 h. After completion, reaction mixture was quenched with water (10 mL) and the bi-phasic mixture was extracted with dichloromethane (3×15 mL). The combined organic extracts were washed with saturated brine solution (15 mL) and dried over anhydrous $Na_2SO_4$. The solution was filtered and concentrated under reduced pressure to give the crude material as a light-yellow oil. The crude material was absorbed onto a plug of silica gel and purified by Isolera-Biotage, eluted with 17% to 22% ethyl acetate in petroleum ether, to provide 6-bromo-N-(tert-butyl)pyridine-2-sulfonamide (0.35 g, 1.19 mmol, 61% yield) as an off white solid. $^1$H NMR (400 MHz, Chloroform-d) δ 7.98 (dd, J=7.6, 0.9 Hz, 1H), 7.75 (t, J=7.8 Hz, 1H), 7.65 (dd, J=8.0, 0.9 Hz, 1H), 4.96 (s, 1H), and 1.27 (s, 9H).

Step 2: In a 500 mL sealed tube, a mixture of 6-bromo-N-(tert-butyl)pyridine-2-sulfonamide (14.5 g, 49.5 mmol), N1,N2-dimethylethane-1,2-diamine (0.436 g, 4.95 mmol), $K_2CO_3$ (1.367 g, 9.89 mmol), and copper(I) iodide (0.471 g, 2.47 mmol) were taken up in aqueous ammonia (21%, 100 mL, 970 mmol) and ethylene glycol (100 mL). The tube was sealed with a screw cap under nitrogen atmosphere. The resulting reaction mixture was stirred at 60° C. for 18 h. The reaction mixture was allowed to cool to room temperature, diluted with water (150 mL) and extracted with EtOAc (3×100 mL). The combined organic extracts were washed with saturated brine solution (50 mL) and dried over anhydrous Na2SO4. The solution was filtered and concentrated under reduced pressure to give the crude material as a light-yellow oil. The crude material was absorbed onto a plug of silica gel and purified by Isolera-Biotage, eluting with 5% to 6% methanol in chloroform, to provide 6-amino-N-(tert-butyl)pyridine-2-sulfonamide (6.94 g, 30.3 mmol, 61% yield) as an off white solid. $^1$H NMR (400 MHz, DMSO-$d_6$) δ 7.54 (ddd, J=8.4, 7.2, 1.3 Hz, 1H), 7.21 (s, 1H), 7.03 (dt, J=7.3, 0.9 Hz, 1H), 6.59 (dt, J=8.4, 1.0 Hz, 1H), 6.33 (s, 2H), and 1.12 (d, J=1.3 Hz, 9H). m/z (ESI): 230.1 $(M+H)^+$.

Intermediate 2: 4-Methyl-6-morpholinopyridin-2-amine

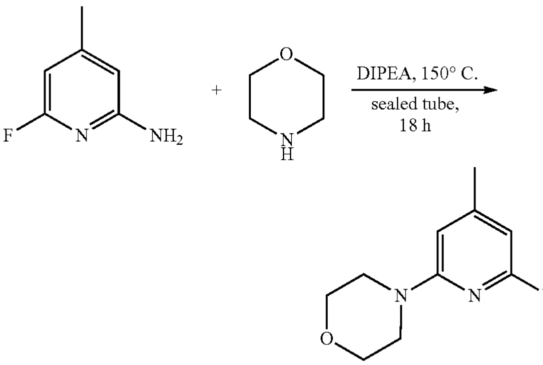

Intermediate 2

To a 250-mL pressure tube were added 6-fluoro-4-methylpyridin-2-amine (10.0 g, 79 mmol, Sibian chemicals, China), morpholine (8.29 g, 95 mmol), and DIPEA (41.5 mL, 238 mmol). The mixture was heated at 150° C. for 18 h. The reaction mixture was quenched with water (100 mL) and extracted with EtOAc (2×250 mL). The combined organic extracts were washed with brine (200 mL), dried over anhydrous $Na_2SO_4$, filtered, and concentrated under reduced pressure. The crude residue was absorbed onto a plug of silica gel and purified by flash chromatography through a Redi-Sep pre-packed silica gel column (40 g), eluting with a gradient of 1% to 15% EtOAc in hexanes, to give the title compound (8.5 g, 44.0 mmol, 56% yield) as a brown semisolid. $^1$H NMR (400 MHz, DMSO-$d_6$) δ 5.75 (s, 1H), 5.67 (s, 1H), 5.44 (s, 2H), 3.65 (t, J=8.4 Hz, 4H), 3.30 (t, J=8.4 Hz, 4H), 2.06 (s, 3H). m/z (ESI): 194.2 (M+H)+.

Intermediate 3: (R)-6-(2-Methylmorpholino)pyridin-2-amine

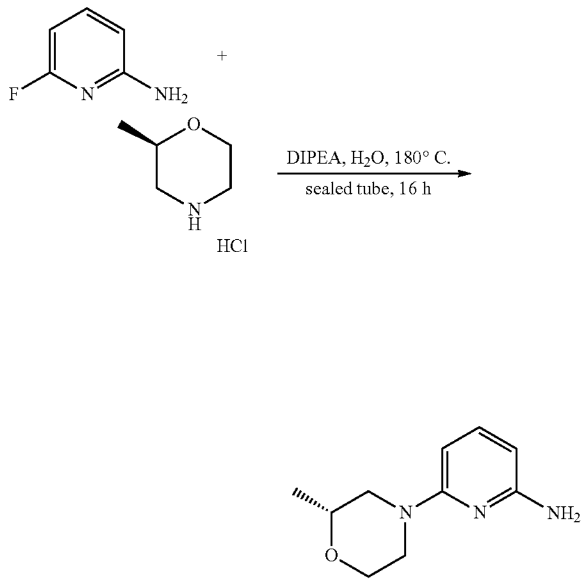

Intermediate 3

To a 500-mL pressure tube were added 6-fluoropyridin-2-amine (30.0 g, 268 mmol, Combi-Blocks, San Diego, CA), (R)-2-methylmorpholine hydrochloride (44.2 g, 321 mmol, F chemicals, China) and DIPEA (140 mL, 803 mmol) in water (60 mL). The mixture was heated at 180° C. for 18 h. The reaction mixture was cooled to room temperature and diluted with water (100 mL). The mixture was extracted with EtOAc (2×250 mL) and washed with brine (200 mL). The combined organic extracts were dried over anhydrous $Na_2SO_4$, filtered, and concentrated under reduced pressure. The crude residue was absorbed onto a plug of silica gel and purified by flash chromatography through a Redi-Sep pre-packed silica gel column (330 g), eluting with a gradient of 1% to 20% EtOAc in hexanes, to give the title compound (38.0 g, 197 mmol, 74% yield) as a yellow solid. $^1H$ NMR (400 MHz, DMSO-$d_6$): δ 7.20-7.14 (m, 1H), 5.89 (d, J=8.0 Hz, 1H), 5.79 (d, J=7.8 Hz, 1H), 5.53 (s, 2H), 4.07-3.97 (m, 1H), 3.98-3.82 (m, 2H), 3.55-3.45 (m, 2H), 2.71-2.58 (m, 1H), 2.35-2.29 (m, 1H), 1.13 (d, J=6.2 Hz, 3H). m/z (ESI): 194.2 $(M+H)^+$.

Intermediate 4: (R)-4-Methyl-6-(2-methylmorpholino)pyridin-2-amine

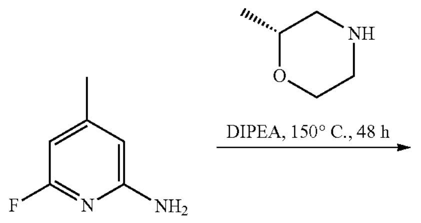

-continued

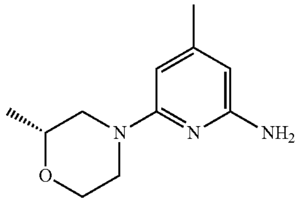

Intermediate 4

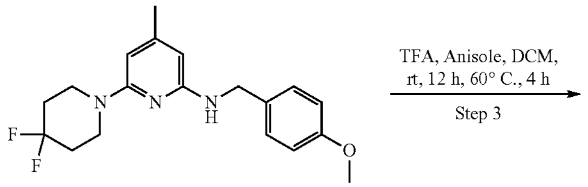

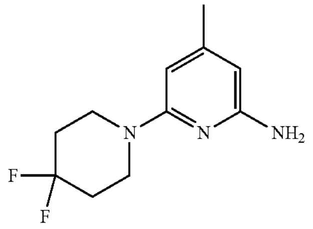

Intermediate 5

A mixture of 6-fluoro-4-methylpyridin-2-amine (75.0 g, 595 mmol), and (R)-2-methylmorpholine hydrochloride (84 g, 832 mmol) in DIPEA (312 mL, 11.78 mol) was heated 150° C. in an autoclave (600 mL) for 48 h. The reaction mixture was quenched with water (1000 mL) and extracted with EtOAc (2×2500 mL). The combined organic layers were washed with brine solution (1000 mL), dried ($Na_2SO_4$), filtered, and concentrated under reduced pressure. The crude residue was purified by column chromatography over silica gel (60-120 mesh) using 30 to 100% ethyl acetate in hexanes to give the title compound (62 g, 50% yield) as an off-white solid. $^1H$ NMR (300 MHz, DMSO-$d_6$): δ 5.74 (s, JH), 5.63 (s, 1H), 5.43 (s, 2H), 3.98 (dt, J=12.8, 2.5 Hz, 1H), 3.90-3.80 (m, 2H), 3.53-3.44 (m, 2H), 2.62 (ddd, J=15.9, 8.0, 3.7 Hz, 1H), 2.29 (ddd, J=13.4, 10.5, 3.1 Hz, 1H), 2.04 (s, 3H), 1.11 (d, J=6.3 Hz 3H). m/z (ESI): 208.1 $(M+H)^+$.

TABLE 1

| The intermediates below were prepared following similar procedures for Intermediates 2-4: | | | |
|---|---|---|---|
| Int. # | Chemical Structure | Name | LRMS: (ESI + ve ion) m/z |
| 4-1 | 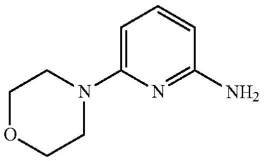 [SMILES: Nc1cccc(N2CCOCC2)n1] | 6-Morpholinopyridin-2-amine | 180.2 |
| 4-2 | 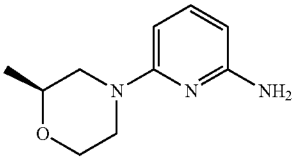 | (S)-6-(2-Methylmorpholino)pyridin-2-amine | 194.2 |
| 4-3 | 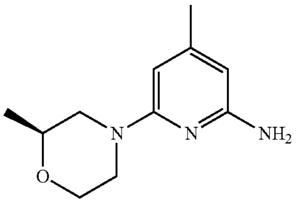 | (S)-4-Methyl-6-(2-methylmorpholino)pyridin-2-amine | 208.1 |
| 4-4 | 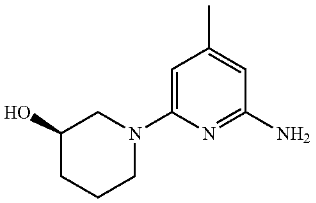 | (R)-1-(6-Amino-4-methylpyridin-2-yl)piperidin-3-ol | 208.1 |
| 4-5 | 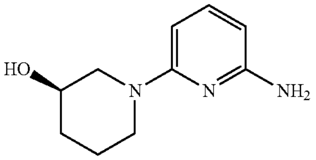 [SMILES: Nc1cccc(N2CCC[C@@H](O)C2)n1] | (R)-1-(6-Aminopyridin-2-yl)piperidin-3-ol | 194.1 |
| 4-6 | 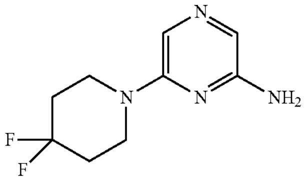 [SMILES: Nc1cncc(N2CCC(F)(F)CC2)n1] | 6-(4,4-Difluoropiperidin-1-yl)pyrazin-2-amine | 215.1 |

Intermediate 5: 6-(4,4-Difluoropiperidin-1-yl)-4-methylpyridin-2-amine

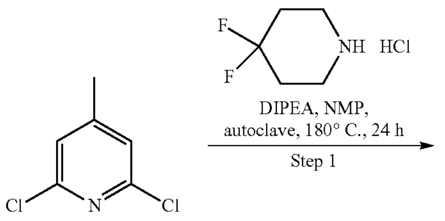

-continued

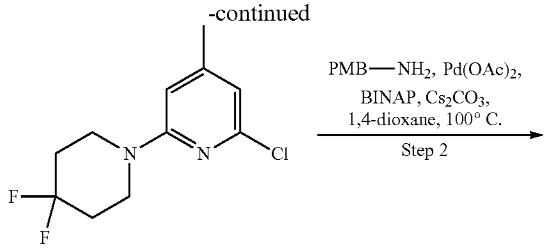

Step 1: To an autoclave was added 2,6-dichloro-4-methylpyridine (80 g, 490 mmol), 4,4-difluoropiperidine hydrochloride (86 g, 540 mmol), and DIPEA (342 mL, 1980 mmol) in NMP (800 mL). The reaction mixture was heated at 180° C. for 24 h. The reaction mixture was cooled to room temperature and basified to pH-9 using 10% aqueous $NaHCO_3$ solution. The reaction mixture was extracted with ethyl acetate (2×1500 mL), washed with water (1500 mL), dried ($Na_2SO_4$), filtered, and concentrated under reduced pressure. The crude material was purified by column chromatography over silica gel (60-120 mesh) using 5-10% ethyl acetate in hexanes to give the mixture of 2,6-dichloro-4-methylpyridine and 2-chloro-6-(4,4-difluoropiperidin-1-yl)-4-methylpyridine in 1:3 ratio (102 g) as a pale brown oil. This mixture (102 g) was further purified by reverse phase chromatography using 60% acetonitrile in water as an eluent to give 2-chloro-6-(4,4-difluoropiperidin-1-yl)-4-methylpyridine (70 g, 58% yield) as a pale brown liquid. $^1$H NMR (400 MHz, DMSO-$d_6$): δ 6.76 (s, 1H), 6.57 (s, 1H), 3.66 (t, J=5.6 Hz, 4H), 2.22 (s, 3H), 2.03-1.91 (m, 4H). m/z (ESI): 247.1 $(M+H)^+$.

Step-2: To a solution of 2-chloro-6-(4,4-difluoropiperidin-1-yl)-4-methylpyridine (30.0 g, 122 mmol) in 1,4-dioxane (300 mL) were added (4-methoxyphenyl)methanamine (23.8 mL, 182 mmol) and $Cs_2CO_3$ (79 g, 240 mmol). The reaction mixture was degassed and purged with nitrogen for 30 min. BINAP (7.57 g, 12.2 mmol) and palladium(II)acetate (2.73 g, 12.2 mmol), were added to the reaction mixture and stirred at 100° C. for 16 h. The reaction mixture was cooled to room temperature, filtered through a CELITE® bed, and washed with ethyl acetate (100 mL). The filtrate was concentrated under reduced pressure. The residue was extracted with EtOAc (2×500 mL), washed with water (500 mL) followed by brine (500 mL). The combined organic extracts were dried ($Na_2SO_4$), filtered, and concentrated under reduced pressure. The crude residue was purified by column chromatography over silica gel (60-120 mesh) using 5-8% ethyl acetate in hexanes to give 6-(4,4-difluoropiperidin-1-yl)-N-(4-methoxybenzyl)-4-methylpyridin-2-amine (48 g, 76% yield) as a yellow oil. $^1$H NMR (400 MHz, DMSO-$d_6$): δ 7.22 (d, J=7.2 Hz, 2H), 6.85 (d, J=7.2 Hz, 2H), 6.64 (t, J=6.0 Hz, 1H), 5.84 (s, 1H), 5.68 (s, 1H), 4.31 (d, J=6.0 Hz, 2H), 3.71 (s, 3H), 3.56 (t, J=5.6 Hz, 4H), 2.05 (s, 3H), 1.90-1.80 (m, 4H). m/z (ESI): 348.1 $(M+H)^+$.

Step-3: To a solution of 6-(4,4-difluoropiperidin-1-yl)-N-(4-methoxybenzyl)-4-methylpyridin-2-amine (48.0 g, 138 mmol) in dry dichloromethane (480 mL) were added anisole (30.2 mL, 276 mmol) and TFA (240 mL, 3120 mmol). The reaction mixture was stirred at 55° C. for 4 h and concentrated under reduced pressure. The residue was dissolved in water (200 mL) and basified with 10% aqueous sodium bicarbonate solution to pH~8 and extracted with ethyl acetate (2×500 mL). The combined organic layers were washed with water (200 mL) followed by brine (200 mL), dried ($Na_2SO_4$), filtered, and concentrated under reduced pressure. The crude residue was purified by column chromatography over silica gel using 25% to 35% ethyl acetate in hexanes to give 6-(4,4-difluoropiperidin-1-yl)-4-methylpyridin-2-amine (LCMS ~85%) as a brown oil. This material was further purified by reverse phase chromatography using 50-60% acetonitrile in water to give 6-(4,4-difluoropiperidin-1-yl)-4-methylpyridin-2-amine (16.5 g, 72 mmol, 53% yield) as a brown oil. $^1$H NMR (400 MHz, DMSO-$d_6$): δ 5.86 (s, 1H), 5.65 (s, 1H), 5.48 (s, 2H), 3.56 (t, J=5.2 Hz, 4H), 2.06 (s, 3H), 1.96-1.87 (m, 4H). m/z (ESI): 228.2 $(M+H)^+$.

TABLE 2

The intermediates below were prepared following a similar procedure for Intermediate 5:

| Int. # | Chemical Structure | Name | LRMS: (ESI + ve ion) m/z |
|---|---|---|---|
| 5-1 | 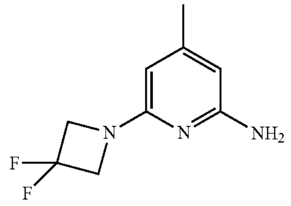 | 6-(3,3-Difluoroazetidin-1-yl)-4-methylpyridin-2-amine | 200.1 |

Intermediate 6: 6-(3,3,3-Trifluoropropoxy)pyridin-2-amine

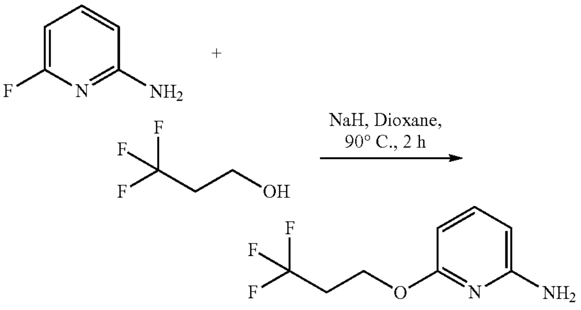

Intermediate 6

To a solution of 6-fluoropyridin-2-amine (50 g, 450 mmol, Combi-Blocks) in 1,4-dioxane (500 mL) was added 3,3,3-trifluoropropan-1-ol (102 g, 892 mmol, Apollo) under nitrogen atmosphere and the reaction was cooled to 0° C. NaH (60% in mineral oil, 42.8 g, 1780 mmol) was added to the reaction mixture at 0° C. and the resulting mixture was stirred at 90° C. for 2 h. The reaction mixture was quenched with cold water (500 mL) and extracted with ethyl acetate (2×1000 mL). The combined organic extracts were dried ($Na_2SO_4$), filtered, and concentrated under reduced pressure. The crude residue was purified by column chromatography over silica gel (60-120 mesh) using 10% ethyl acetate in hexanes to give the title compound (45 g, 50% yield) as a pale brown oil. $^1$H NMR (400 MHz, DMSO-$d_6$): δ 7.30-7.26 (t, J=7.8 Hz, 1H), 6.02-6.00 (dd, J=7.8, 0.8 Hz, 1H), 5.89-5.86 (m, 3H), 4.36-4.33 (t, J=6.2 Hz, 2H), 2.79-2.67 (qt, J=11.5, 6.2 Hz, 2H). m/z (ESI): 207.1 $(M+H)^+$.

Intermediate 7: 6-(3,3-Difluorocyclobutyl)-4-methylpyridin-2-amine

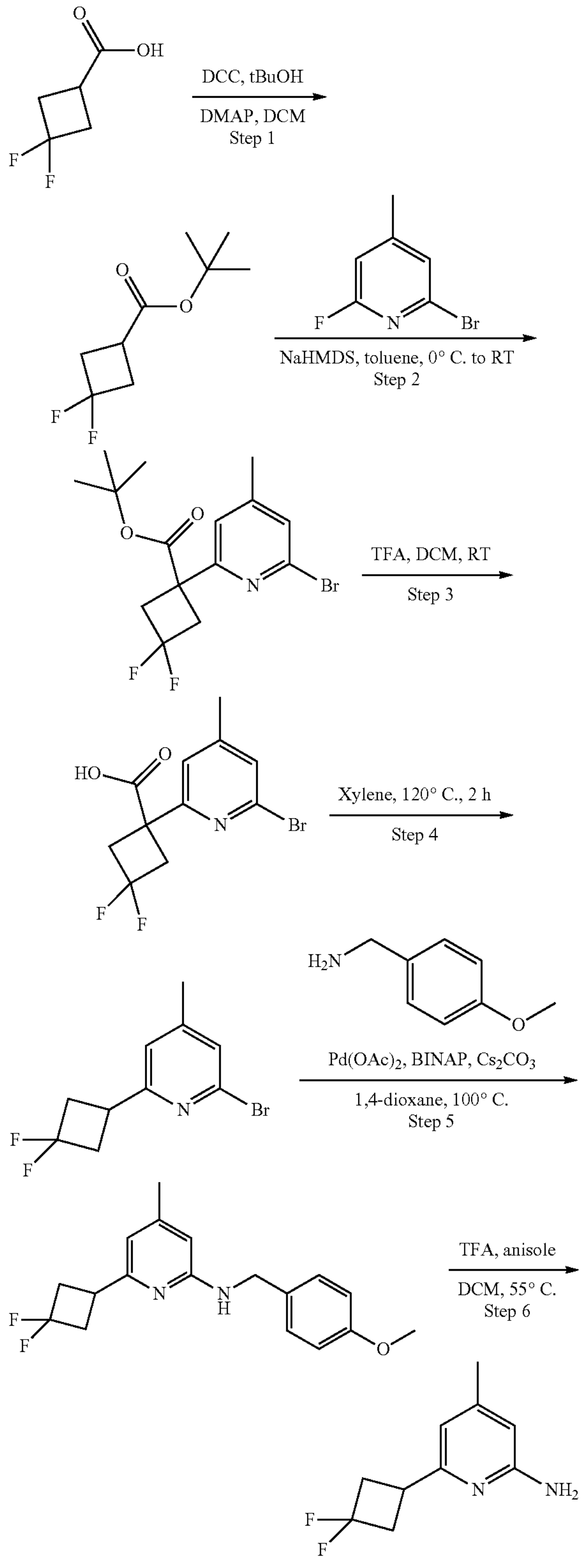

Intermediate 7

Step 1: To a solution of 3,3-difluorocyclobutane-1-carboxylic acid (3.0 g, 22. mmol, Combi-Blocks) and DMAP (0.269 g, 2.20 mmol) in dichloromethane (30 mL) were added tert-butanol (4.22 mL, 44.1 mmol) followed by dicyclohexyl carbodiimide (5.00 g, 24.2 mmol) at 0° C. The reaction mixture was stirred at RT for 18 h before diethyl ether (20 mL) was added to the reaction mixture at 0° C. The precipitated solid was filtered off, and the filtrate was washed with 1.5 N HCl (100 mL), water and brine, dried over $Na_2SO_4$ and concentrated under reduced pressure to provide tert-butyl 3,3-difluorocyclobutane-1-carboxylate (2.78 g, 14.5 mmol, 65.6% yield) as a clear oil. $^1$H NMR (300 MHz, DMSO-$d_6$): δ ppm 2.93 (dddd, J=14.8, 7.5, 3.8, 2.1 Hz, 1H), 2.63-2.87 (m, 4H), 1.42 (d, J=2.3 Hz, 9H).

Step 2: To a solution of 2-bromo-6-fluoro-4-methylpyridine (1.5 g, 7.9 mmol, TCI Chemicals) and tert-butyl 3,3-difluorocyclobutane-1-carboxylate (1.82 g, 9.47 mmol) in toluene (35 mL) was dropwise added sodium bis(trimethylsilyl)amide in THF (11.84 mL, 11.84 mmol, 1 M, Symax laboratories) at 0° C. and the reaction mixture was stirred for 20 min at 0° C. and 4 h at rt. The reaction mixture was quenched with a saturated aqueous solution of $NH_4Cl$ (50 mL) and extracted with EtOAc (2×50 mL). The combined organic extracts were washed with brine, dried over $Na_2SO_4$, filtered, and concentrated. The residue was purified by flash column chromatography using a gradient of 0% to 20%, EtOAc in petroleum ether to provide tert-butyl 1-(6-bromo-4-methylpyridin-2-yl)-3,3-difluorocyclobutane-1-carboxylate (1.6 g, 3.2 mmol, 41% yield) as a clear yellow oil. $^1$H NMR (300 MHz, DMSO-$d_6$): δ ppm 7.48 (t, J=1.0 Hz, 1H), 7.34 (t, J=1.0 Hz, 1H), 3.15-3.31 (m, 2H), 2.63-2.89 (m, 2H), 2.34 (s, 3H), 1.36 (s, 9H). m/z (ESI): 362.0 $(M+H)^+$.

Step 3: To a solution of tert-butyl 1-(6-bromo-4-methylpyridin-2-yl)-3,3-difluorocyclobutane-1-carboxylate (1.4 g, 2.8 mmol) in dichloromethane (24 mL) was added TFA (0.87 mL, 11.3 mmol) at RT. The reaction mixture was stirred for 18 h before it was concentrated to provide 1-(6-bromo-4-methylpyridin-2-yl)-3,3-difluorocyclobutane-1-carboxylic acid (0.90 g, 2.2 mmol, 77% yield) as a brown sticky liquid. $^1$H NMR (300 MHz, DMSO-$d_6$): δ ppm 7.47 (s, 1H), 7.38 (s, 1H), 3.25 (q, J=12.8 Hz, 2H), 2.66-2.85 (m, 2H), 2.33 (s, 3H). m/z (ESI): 306.0 $(M+H)^+$.

Step 4: A solution of 1-(6-bromo-4-methylpyridin-2-yl)-3,3-difluorocyclobutane-1-carboxylic acid (0.60 g, 1.4 mmol) in 2-xylene (7.0 mL) was stirred at 120° C. for 2 h. The reaction mixture was diluted with water (50 mL), extracted with EtOAc (2×50 mL), washed with water (50 mL) and brine, dried over $Na_2SO_4$, filtered, and concentrated. The concentrate was purified by flash column chromatography using a gradient of 0% to 5%, EtOAc in petroleum ether to provide 2-bromo-6-(3,3-difluorocyclobutyl)-4-methylpyridine (0.41 g, 1.2 mmol, 85% yield) as light-yellow oil. $^1$H NMR (300 MHz, DMSO-$d_6$): δ ppm 7.39 (s, 1H), 7.25 (s, 1H), 3.47 (qt, J=9.1, 4.5 Hz, 1H), 2.73-2.97 (m, 4H), 2.29 (s, 3H). m/z (ESI): 262.0 $(M+H)^+$.

Step 5: A mixture of 2-bromo-6-(3,3-difluorocyclobutyl)-4-methylpyridine (0.400 g, 1.53 mmol), (4-methoxyphenyl)methanamine (0.314 g, 2.29 mmol), $Cs_2CO_3$ (1.49 g, 4.58 mmol), BINAP (0.095 g, 0.153 mmol) and $Pd(OAc)_2$ (0.034 g, 0.15 mmol) in 1,4-dioxane (4 mL) was stirred at 100° C. for 16 h. The reaction mixture was filtered and diluted with EtOAc. The resulting solution was washed with water, and brine, dried over $Na_2SO_4$, filtered, and concentrated. The concentrate was purified by flash column chromatography using a gradient of 0% to 10% ethyl acetate in petroleum ether to afford 6-(3,3-difluorocyclobutyl)-N-(4-methoxy-benzyl)-4-methylpyridin-2-amine (0.360 g, 1.131 mmol, 74% yield) as yellow oil. $^1$H NMR (400 MHz, DMSO-$d_6$): δ ppm 7.22-7.31 (m, 2H), 6.85 (dt, J=8.5, 2.1 Hz, 2H), 6.26 (s, 1H), 6.15 (s, 1H), 4.38 (d, J=6.0 Hz, 2H), 3.71 (s, 3H), 3.14-3.22 (m, 1H), 2.71-2.86 (m, 4H), 2.09 (s, 3H). m/z (ESI): 319.1 $(M+H)^+$.

Step 6: To a mixture of 6-(3,3-difluorocyclobutyl)-N-(4-methoxybenzyl)-4-methylpyridin-2-amine (0.355 g, 1.12 mmol) and anisole (0.244 mL, 2.23 mmol) in dichloromethane (4 mL) was added trifluoroacetic acid (1.8 mL, 23 mmol) at 0° C. The reaction mixture was stirred at 55° C. for 16 h before it was concentrated and then diluted with DCM (20 mL). The organic layer was washed with a saturate aqueous solution of $NaHCO_3$ solution (3 mL), water and brine, dried over $Na_2SO_4$, filtered, and concentrated. The concentrate was purified by flash column chromatography using a gradient of 10% to 20%, EtOAc in petroleum ether to provide 6-(3,3-difluorocyclobutyl)-4-methylpyridin-2-amine (0.090 g, 0.45 mmol, 41% yield) as a light-yellow oil. $^1$H NMR (300 MHz, DMSO-$d_6$): δ ppm 6.27 (s, 1H), 6.12 (s, 1H), 3.18 (td, J=8.8, 3.1 Hz, 1H), 2.69-2.85 (m, 4H), 2.10 (d, J=2.1 Hz, 3H). m/z (ESI): 199.1 $(M+H)^+$.

Intermediate 8: 5-Methyl-6-morpholinopyridin-2-amine

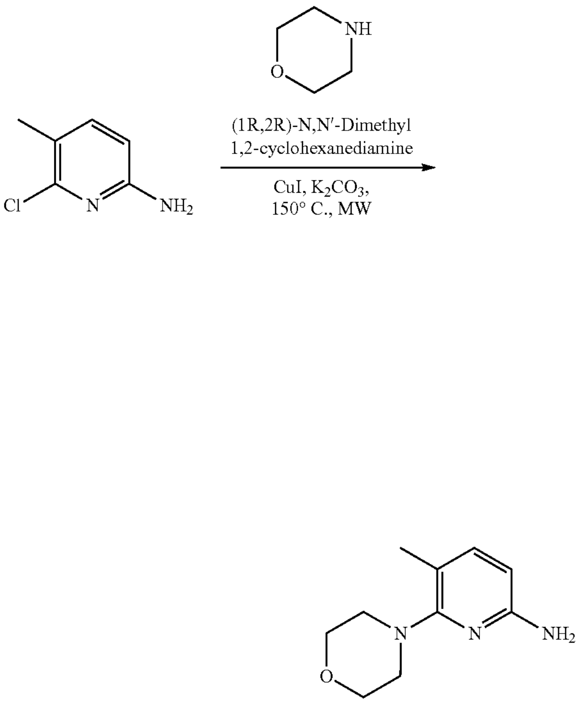

Intermediate 8

A mixture of 6-chloro-5-methylpyridin-2-amine (0.1 g, 0.70 mmol), morpholine (0.092 g, 1.05 mmol), $K_2CO_3$ (0.145 g, 1.052 mmol), copper(I) iodide (0.027 g, 0.140 mmol) and (1R,2R)—N1,N2-dimethylcyclohexane-1,2-diamine (0.020 g, 0.140 mmol) in DMF (2 mL) was heated in microwave at 150° C. for 4 h. Then the reaction mixture was filtered through a plug of celite and the filtrate was diluted with EtOAc, washed with water, brine, dried over $Na_2SO_4$, filtered, and concentrated. The concentrate was purified by flash column chromatography eluting with 15% ethyl acetate in petroleum ether to provide 5-methyl-6-morpholinopyridin-2-amine (10 mg, 0.052 mmol, 7% yield) as pale-yellow solid. m/z (ESI): 194.2 $(M+H)^+$.

Preparation of Ring $AR^2$ Intermediates

Intermediate 9: 4-Iodo-2-(6-azaspiro[2.5]octan-6-yl) benzoic acid

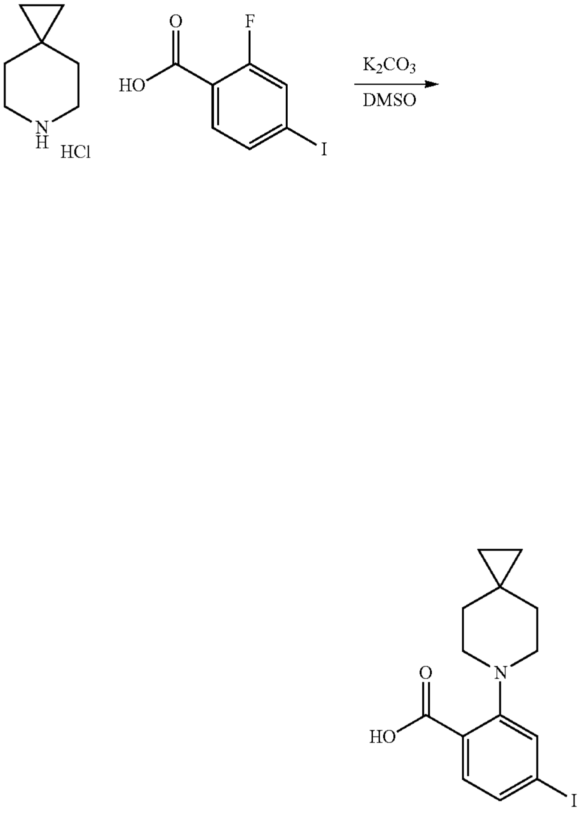

Intermediate 9

To a solution of 2-fluoro-4-iodobenzoic acid (300 g, 1.13 mol, Combi-Blocks, San Diego, CA) in DMSO (2.1 L) was added 6-azaspiro[2.5]octane hydrochloride (216 g, 1.47 mol, Wuxi AppTec) at 20° C. Then $K_2CO_3$ (468 g, 3.38 mol) was added and the reaction solution was stirred at 140° C. for 48 h under $N_2$. The reaction solution was slowly poured into ice water (4.20 L), then extracted with hexanes (2 L×3). The water phase was taken and the pH was adjusted to 6 with HCl (2.00 mol/L, aq). A precipitate was obtained and collected by filtration. The solid was washed with water (700 mL×3) and filtered. The moist solid was spread out on a large watch glass and dried in the air at 25° C. 4-Iodo-2-(6-azaspiro[2.5]octan-6-yl)benzoic acid (280 g, 777 mmol, 68.9% yield) was obtained as a light yellow solid. 400 MHz DMSO-$d_6$ δ ppm 8.07 (s, 1H), 7.76-7.66 (m, 2H), 3.10 (t, J=5.2 Hz, 4H), 1.55 (br s, 4H), 0.41 (s, 4H).

TABLE 3
| Intermediates 9-1 to 9-5 were prepared following a similar procedure for intermediate 9: | | | |
|---|---|---|---|
| Int. # | Chemical Structure | Name | LRMS: (ESI + ve ion) m/z |
| 9-1 | 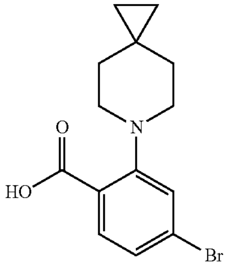 [SMILES: O=C(O)c1ccc(Br)cc1N1CCC2(CC1)CC2] | 4-Bromo-2-(6-azaspiro[2.5]octan-6-yl)benzoic acid | 310.2/312.2 |
| 9-2 | 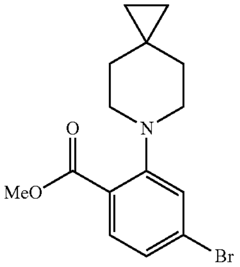 | Methyl 4-bromo-2-(6-azaspiro[2.5]octan-6-yl)benzoate | 324.1/326.1 |
| 9-3 | 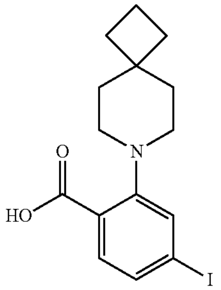 [SMILES: O=C(O)c1ccc(I)cc1N1CCC2(CCC2)CC1] | 4-Iodo-2-(7-azaspiro[3.5]nonan-7-yl)benzoic acid | 372.0 |
| 9-4 | 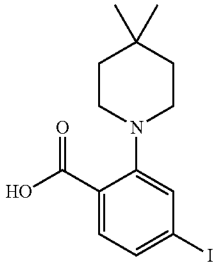 [SMILES: CC1(C)CCN(c2cc(I)ccc2C(=O)O)CC1] | 2-(4,4-Dimethylpiperidin-1-yl)-4-iodobenzoic acid | 360.0 |
| 9-5 | 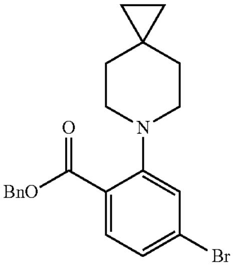 [SMILES: O=C(OCc1ccccc1)c1ccc(Br)cc1N1CCC2(CC1)CC2] | Benzyl 4-bromo-2-(6-azaspiro[2.5]octan-6-yl)benzoate | 400.1/402.1 |

Intermediate 10: 4-(Methylsulfonyl)-2-(6-azaspiro[2.5]octan-6-yl)benzoic acid

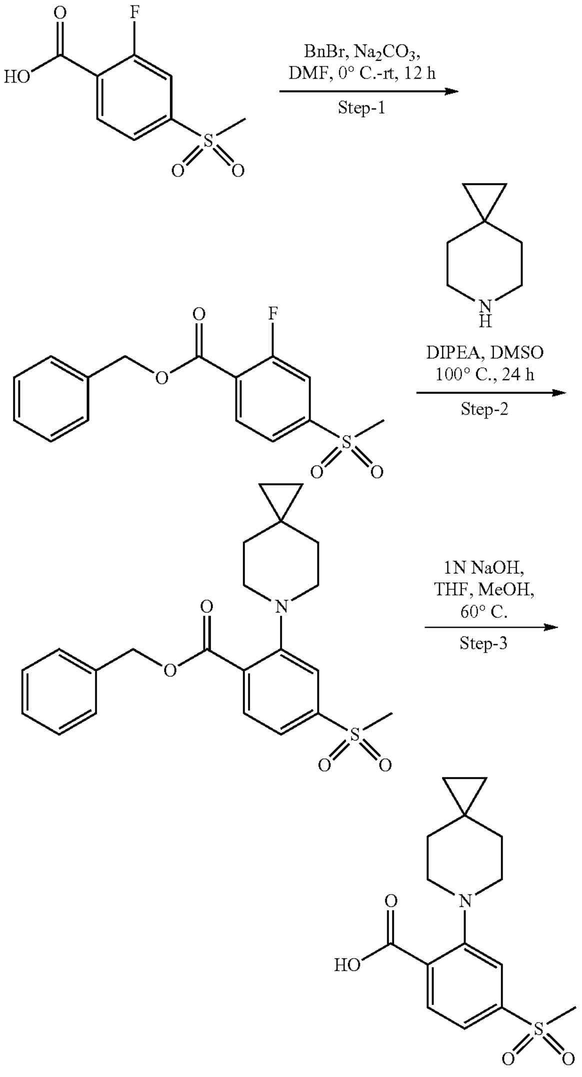

Intermediate 10

Step-1: To a solution of 2-fluoro-4-(methylsulfonyl)benzoic acid (90.0 g, 412 mmol) in DMF (1 L) was added benzyl bromide (78.1 g, 454 mmol) and sodium carbonate (52.5 g, 495 mmol) at 0° C. The reaction mixture was stirred for 12 h at room temperature. The reaction mixture was quenched with water (1 L) and extracted with MTBE (3×1 L). The combined organic extracts were washed with brine (1 L), dried over $Na_2SO_4$, filtered, and concentrated under reduced pressure. The crude residue was purified by column chromatography over silica gel (230-400 mesh) using 0 to 30% ethyl acetate in hexanes to give benzyl 2-fluoro-4-(methylsulfonyl)benzoate (100 g, 79% yield) as a white solid. $^1H$ NMR (300 MHz, DMSO-$d_6$): δ 8.16 (dd, J=8.2, 6.9 Hz, 1H), 7.98-7.86 (m, 2H), 7.48-7.31 (m, 5H), 5.40 (s, 2H), 3.33 (s, 3H).

Step-2: To a solution of benzyl 2-fluoro-4-(methylsulfonyl)benzoate (55 g, 180 mmol) in dimethyl sulfoxide (550 mL) was added DIPEA (57.6 g, 446 mmol) followed by 6-azaspiro[2.5]octane (29.8 g, 268 mmol) and the reaction mixture was stirred at 100° C. for 24 h. The reaction mixture was quenched with water (1 L) and extracted with MTBE (3×1 L). The combined organic extracts were washed with brine (1 L), dried over $Na_2SO_4$, filtered, and concentrated under reduced pressure. The crude product was purified by column chromatography over silica gel (230-400 mesh) using 0 to 10% ethyl acetate in hexanes to give benzyl 4-(methylsulfonyl)-2-(6-azaspiro[2.5]octan-6-yl)benzoate (55 g, 77% yield) as a white solid. $^1H$ NMR (400 MHz, DMSO-$d_6$): δ 7.76 (d, J=8.0 Hz, 1H), 7.52-7.45 (m, 4H), 7.43-7.35 (m, 3H), 5.35 (s, 2H), 3.25 (s, 3H), 3.05 (t, J=5.3 Hz, 4H), 1.36 (t, J=5.3 Hz, 4H), 0.30 (s, 4H). m/z (ESI): 400.1 $(M+H)^+$.

Step-3: To a solution of benzyl 4-(methylsulfonyl)-2-(6-azaspiro[2.5]octan-6-yl)benzoate (65 g, 160 mmol) in THF (108 mL) and methanol (36 mL) was added sodium hydroxide (1N, 407 mL) and the reaction mixture was stirred for 12 h at 60° C. The reaction mixture was concentrated under reduced pressure to remove THF and methanol. The remaining aqueous solution was acidified to pH ~2 with 1.5 N HCl solution. The precipitate was filtered, washed with water (200 mL) followed by hexanes (200 mL), and dried under vacuum to give 4-(methylsulfonyl)-2-(6-azaspiro[2.5]octan-6-yl)benzoic acid (42 g, 83% yield) as an off-white solid. $^1H$ NMR (400 MHz, DMSO-$d_6$): δ 16.13 (s, 1H), 8.04 (d, J=8.0 Hz, 1H), 7.99 (s, 1H), 7.75 (d, J=8.0 Hz, 1H), 3.29 (s, 3H), 3.17 (b s, 4H), 1.55 (b s, 4H), 0.41 (s, 4H). m/z (ESI): 308.1 $(M+H)^+$.

Intermediate 11: 4-((1-Methylcyclopropane)-1-sulfonamido)-2-(6-azaspiro[2.5]octan-6-yl)benzoic acid

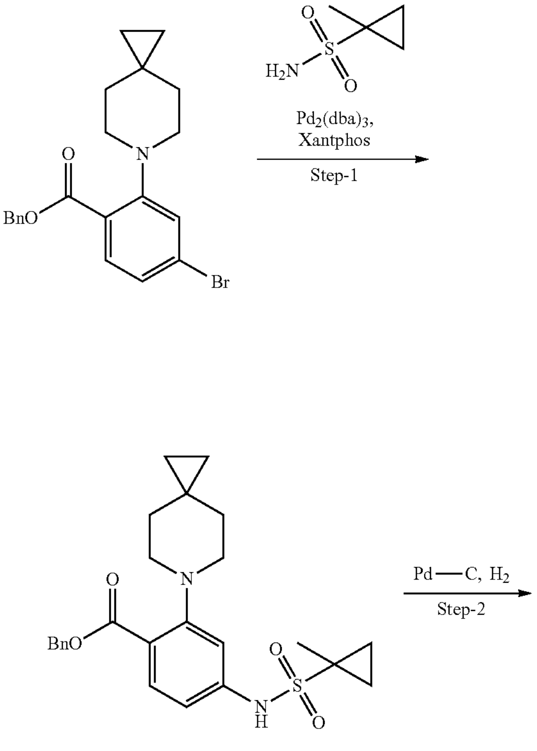

-continued

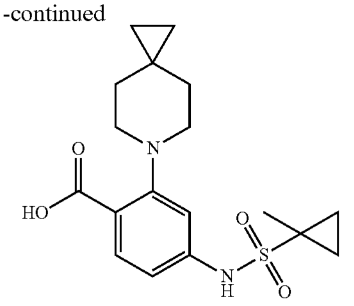

Intermediate 11

Step 1: To a 250-mL sealed tube were added benzyl 4-bromo-2-(6-azaspiro[2.5]octan-6-yl)benzoate (9 g, 22.48 mmol, kit. 9-5), 1-methylcyclopropane-1-sulfonamide (3.95 g, 29.2 mmol, Combi-Blocks, San Diego, CA) and $K_2CO_3$ (6.21 g, 45.0 mmol) in 1,4-dioxane (90 mL). The reaction was degassed and purged with nitrogen for 5 min. To this reaction mixture was added Xantphos (1.301 g, 2.248 mmol) followed by $Pd_2(dba)_3$ (1.029 g, 1.12 mmol) and the sealed tube was closed and stirred at 110° C. for 18 h. The reaction mixture was quenched with water (250 mL) and extracted with ethyl acetate (2×150 mL). The combined organic extracts were washed with water (100 mL), dried over $Na_2SO_4$, filtered, and concentrated under reduced pressure. The crude residue was purified by column chromatography over silica gel eluting with a gradient of 0% to 15% EtOAc in hexanes to give benzyl 4-((1-methylcyclopropane)-1-sulfonamido)-2-(6-azaspiro[2.5]octan-6-yl)benzoate (6.1 g, 59% yield) as an orange oil. $^1H$ NMR (400 MHz, DMSO-$d_6$): δ 10.06 (s, 1H), 7.62 (d, J=8.5 Hz, 1H), 7.48-7.31 (m, 5H), 6.98 (s, 1H), 6.81 (d, J=8.5 Hz, 1H), 5.27 (s, 2H), 2.92 (t, J=4.96 Hz, 4H), 1.40-1.30 (m, 7H), 1.16 (dd, J=6.4, 4.7 Hz, 2H), 0.81 (dd, J=6.4, 4.7 Hz, 2H), 0.28 (s, 4H). m/z (ESI): 455.2 $(M+H)^+$.

Step 2: To a solution of benzyl 4-((1-methylcyclopropane)-1-sulfonamido)-2-(6-azaspiro[2.5]octan-6-yl)benzoate (2.1 g, 4.6 mmol) in MeOH (20 mL) and ethyl acetate (10 mL) was added 10% Pd—C (1.05 g, 50% wt/wt) under nitrogen atmosphere. The reaction mixture was degassed and stirring under hydrogen (1 atm, balloon pressure) for 4 h. The reaction mixture was filtered through a celite bed and washed with methanol (20 mL). The filtrate was concentrated under reduced pressure. The residue was triturated with diethyl ether (50 mL) to give 4-((1-methylcyclopropane)-1-sulfonamido)-2-(6-azaspiro[2.5]octan-6-yl)benzoic acid (1.2 g, 71% yield) as an off white solid. $^1H$ NMR (400 MHz, DMSO-$d_6$): δ 13.20 (s, 1H), 10.33 (s, 1H), 7.95 (d, J=8.6 Hz, 1H), 7.41 (s, 1H), 7.20 (d, J=8.6 Hz, 1H), 2.99 (s, 4H), 1.56 (s, 4H), 1.39 (s, 3H), 1.18 (t, J=4.8 Hz, 2H), 0.83 (t, J=4.7 Hz, 2H), 0.42 (s, 4H). m/z (ESI): 363.2 $(M-H)^+$.

Intermediate 12: 4-(N-(3-methyloxetan-3-yl)sulfamoyl)-2-(6-azaspiro[2.5]octan-6-yl)benzoic acid

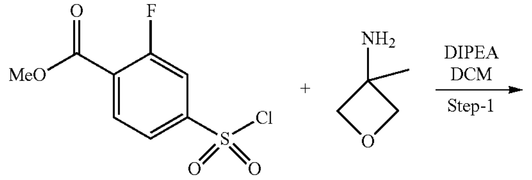

-continued

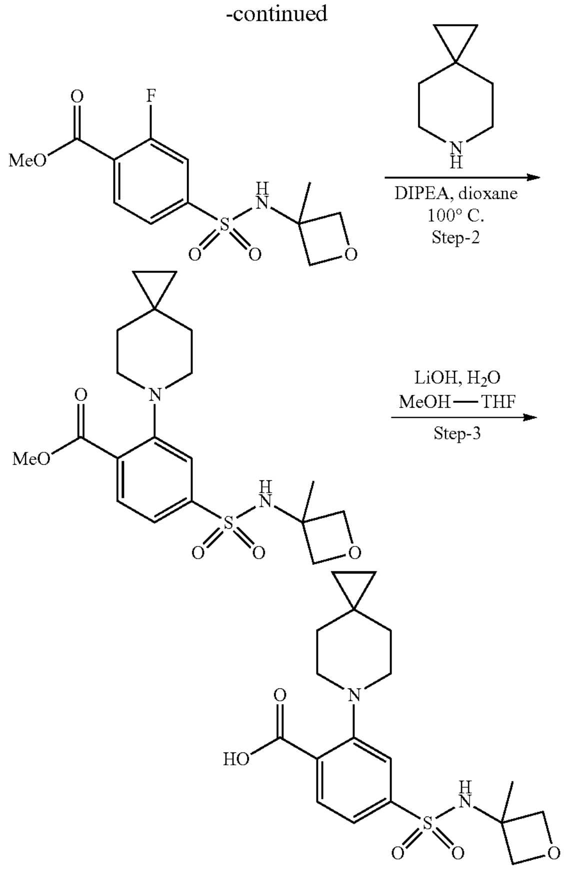

Intermediate 12

Step 1: To a solution of 3-methyl-3-oxetanamine hydrochloride (5.50 g, 44.5 mmol) and DIPEA (23.3 mL, 134 mmol) in DCM (200 mL) at 0° C., methyl 4-(chlorosulfonyl)-2-fluorobenzoate (12.4 g, 49.0 mmol) was added and the mixture stirred from 0° C. to room temperature for 1 h. The mixture was diluted with 1.0 N HCl (200 mL) and extracted with dichloromethane (150 mL×2). The combined organic layers were washed with brine, dried with anhydrous sodium sulfate, filtered, and concentrated under reduced pressure to afford crude product. The crude product was purified with Biotage SNAP 100 g column eluting with 0-30% EtOAc-EtOH (3:1) in heptane to afford methyl 2-fluoro-4-(N-(3-methyloxetan-3-yl)sulfamoyl)benzoate (13.6 g, 44.8 mmol, 100% yield) as a white solid. $^1H$ NMR (500 MHz, DMSO-d6) δ 8.67 (s, 1H), 8.11 (t, J=7.37 Hz, 1H), 7.76-7.82 (m, 1H), 7.69-7.76 (m, 1H), 4.56 (d, J=6.23 Hz, 2H), 4.18 (d, J=6.75 Hz, 2H), 3.90 (s, 3H), 1.42 (s, 3H).

Step 2: A mixture of DIPEA (16 mL, 93 mmol), 6-azaspiro[2.5]octane (6.22 g, 55.9 mmol), and methyl 2-fluoro-4-(N-(3-methyloxetan-3-yl)sulfamoyl)benzoate (14.1 g, 46.6 mmol) in anhydrous dioxane was stirred at 100° C. for 20 h. The mixture was cooled down to room temperature, quenched with water, and extracted with ethyl acetate. The combined organic extracts were washed with brine, dried, and evaporated to dryness under reduced pressure. The crude product was purified using the Biotage SNAP 340 g column eluting with 0-40% EtOAc-EtOH (3:1) in heptane to give methyl 4-(N-(3-methyloxetan-3-yl)sulfamoyl)-2-(6-azaspiro[2.5]octan-6-yl)benzoate (14.2 g, 35.9 mmol, 77% yield) as an off-white solid. $^1H$ NMR (500 MHz, DMSO-d6) δ 8.42 (s, 1H), 7.72 (d, J=8.04 Hz, 1H), 7.47 (d, J=1.56 Hz, 1H), 7.36 (dd, J=1.82, 8.04 Hz, 1H), 4.55 (d, J=5.97 Hz, 2H), 4.14 (d, J=6.49 Hz, 2H), 3.85 (s, 3H), 3.02-3.09 (m, 4H), 1.44-1.50 (m, 4H), 1.42 (s, 3H), 0.35 (s, 4H).

Step 3: A mixture of methyl 4-(N-(3-methyloxetan-3-yl) sulfamoyl)-2-(6-azaspiro[2.5]octan-6-yl)benzoate (14.2 g, 35.9 mmol) and lithium hydroxide monohydrate (22.6 g, 538 mmol) in THF-water-MeOH (1:1:1, 300 mL) was stirred at room temperature for 16 h. The mixture was concentrated under reduced pressure to partially remove the organic solvent. The solution was acidified with 2N HCl to reach pH<3. The precipitate was filtered and dried in air to give 4-(N-(3-methyloxetan-3-yl)sulfamoyl)-2-(6-azaspiro [2.5]octan-6-yl)benzoic acid (9.94 g, 26.1 mmol, 73% yield) as a white solid. $^1$H NMR (500 MHz, DMSO-d6) δ 8.51 (s, 1H), 8.04 (d, J=8.04 Hz, 1H), 7.89 (d, J=1.30 Hz, 1H), 7.66 (dd, J=1.69, 8.17 Hz, 1H), 4.55 (d, J=6.23 Hz, 2H), 4.09-4.17 (m, 2H), 3.06-3.19 (m, 4H), 1.56 (t, J=5.19 Hz, 4H), 1.40 (s, 3H), 0.36-0.46 (s, 4H).

Intermediate 13: 4-(N-(tert-Butyl)sulfamoyl)-2-(6-azaspiro[2.5]octan-6-yl)benzoic acid

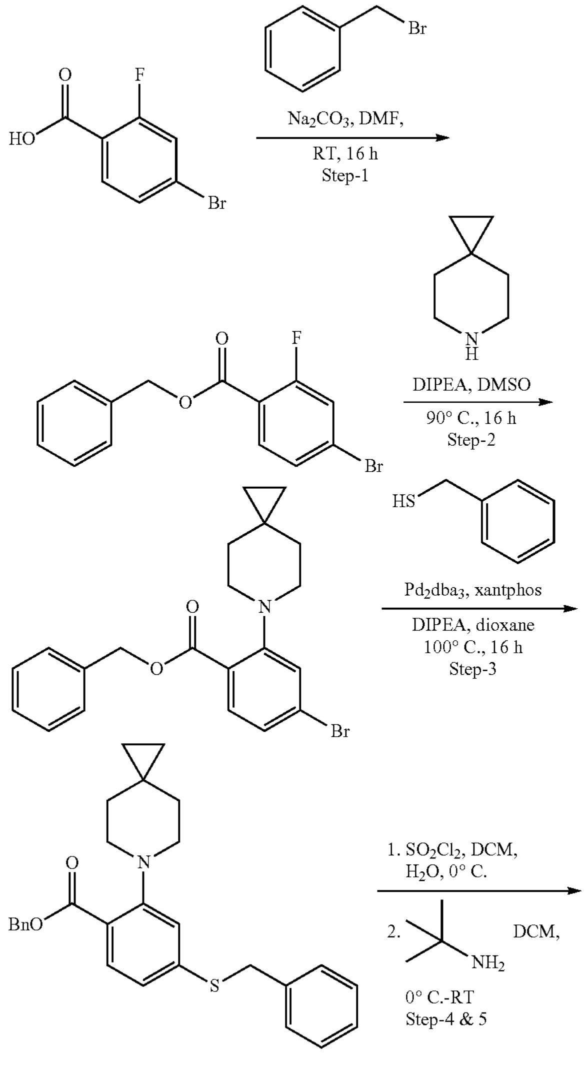

-continued

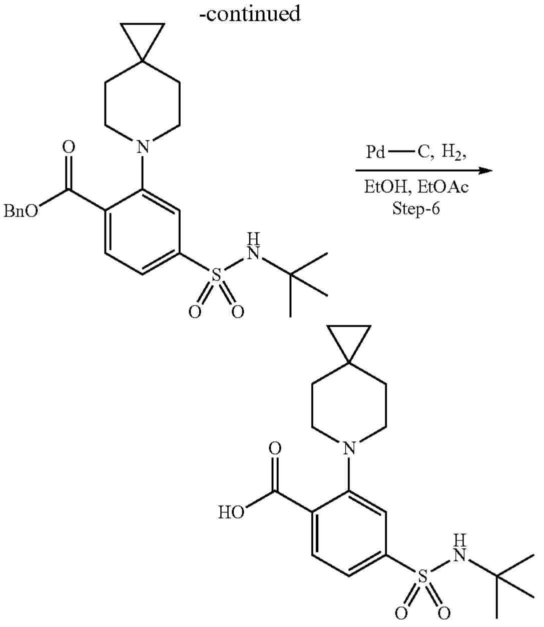

Intermediate 13

Step 1: To a solution of 4-bromo-2-fluorobenzoic acid (40 g, 180 mmol) in DMF (600 mL) were added sodium carbonate (23.2 g, 219 mmol) and benzyl bromide (22.8 mL, 192 mmol) at 0° C. The reaction mixture was stirred at room temperature for 16 h before quenched with water (1.5 L) and extracted with ethyl acetate (3×500 mL). The combined organic extracts were washed with water (1500 mL) and brine (500 mL), dried over anhydrous $Na_2SO_4$, filtered, and concentrated under reduced pressure. The crude residue was purified by column chromatography over silica gel (60-120 mesh) using 10% ethyl acetate in hexanes to give benzyl 4-bromo-2-fluorobenzoate (50 g, 89% yield) as a pale yellow liquid. $^1$H NMR (400 MHz, Chloroform-d): δ 7.86 (dd, J=8.0, 7.4 Hz, 1H), 7.50-7.35 (m, 7H), 5.40 (s, 2H).

Step 2: To a solution of benzyl 4-bromo-2-fluorobenzoate (30 g, 97 mmol) in DMSO (300 mL) were added 6-azaspiro [2.5]octane (15.1 g, 136 mmol) and DIPEA (33.9 mL, 194 mmol) at room temperature. The reaction mixture was stirred at 90° C. for 16 h. The reaction mixture was quenched with water (500 mL) and extracted with ethyl acetate (2×500 mL). The combined organic extracts were washed with brine (600 mL), dried over anhydrous $Na_2SO_4$, filtered, and concentrated under reduced pressure. The crude residue was purified by column chromatography over silica gel (60-120 mesh) using 0% to 10% of ethyl acetate in hexanes to give benzyl 4-bromo-2-(6-azaspiro[2.5]octan-6-yl)benzoate (25 g, 64% yield) as a pale-yellow oil. $^1$H NMR (400 MHz, Chloroform-d): δ 7.61 (d, J=8.4 Hz, 1H), 7.47 (d, J=8.0 Hz, 2H), 7.43-7.35 (m, 3H), 7.22 (s, 1H), 7.09 (d, J=8.4 Hz, 1H), 5.36 (s, 2H), 3.09 (t, J=5.3 Hz, 4H), 1.49 (t, J=5.3 Hz, 4H), 0.34 (s, 4H). m/z (ESI): 400.1 $(M-H)^+$.

Step 3: A solution of benzyl 4-bromo-2-(6-azaspiro[2.5] octan-6-yl)benzoate (25 g, 62 mmol), DIPEA (21.8 mL, 125 mmol), xantphos (1.81 g, 3.12 mmol), $Pd_2(dba)_3$ (1.14 g, 1.25 mmol) and benzyl mercaptan (10 g, 81 mmol) in 1,4 dioxane (250 mL) degassed and purged with nitrogen for 15 min. The reaction mixture was heated at 100° C. for 16 h in a sealed pressure vessel. The reaction mixture was quenched with water (500 mL) and extracted with ethyl acetate (2×500 mL). The combined organic extracts were dried over anhydrous $Na_2SO_4$, filtered, and concentrated under reduced pressure. The crude residue was purified by column chromatography over silica gel (60-120 mesh) using 5% to 10% of ethyl acetate in hexanes to give benzyl 4-(benzylthio)-2-(6-azaspiro[2.5]octan-6-yl)benzoate (20 g, 72% yield) as a pale yellow liquid. $^1H$ NMR (400 MHz, DMSO-$d_6$): δ 7.57-7.53 (m, 1H), 7.48-7.26 (m, 10H), 6.93-6.87 (m, 2H), 5.27 (s, 2H), 4.32 (s, 2H), 2.95-2.87 (m, 4H), 1.35 (t, J=5.3 Hz, 4H), 0.28 (s, 4H). m/z (ESI): 442.2 $(M-H)^+$.

Step 4 & 5: To a solution of benzyl 4-(benzylthio)-2-(6-azaspiro[2.5]octan-6-yl)benzoate (20 g, 45 mmol) in DCM (160 mL) and water (40 mL), was added sulfuryl chloride (18.3 mL, 225 mmol) at 0° C. The reaction mixture was stirred for 1 h before diluted with water (200 mL) and extracted with DCM (200 mL). The organic extract was dried over anhydrous $Na_2SO_4$, filtered, and cooled to 0° C. tert-Butylamine (47.8 mL, 451 mmol) was added to the above solution. The reaction mixture was stirred at room temperature for 1 h before quenched with water (200 mL) and extracted with DCM (2×100 mL). The combined organic extracts were dried over anhydrous $Na_2SO_4$, filtered, and concentrated under reduced pressure. The crude residue was purified by column chromatography over silica gel (60-120 mesh) using 15% ethyl acetate in hexanes to give benzyl 4-(N-(tert-butyl)sulfamoyl)-2-(6-azaspiro[2.5]octan-6-yl)benzoate (12 g, 61% yield) as a pale yellow solid. $^1H$ NMR (400 MHz, DMSO-$d_6$): δ 7.71 (d, J=8.0 Hz, 1H), 7.63 (s, 1H), 7.55-7.46 (m, 3H), 7.45-7.33 (m, 4H), 5.33 (s, 2H), 3.01 (b s, 4H), 1.38 (b s, 4H), 1.10 (s, 9H), 0.31 (2, 4H). m/z (ESI): 457.2 $(M-H)^+$.

Step 6: To a solution of benzyl 4-(N-(tert-butyl)sulfamoyl)-2-(6-azaspiro[2.5]octan-6-yl)benzoate (10 g, 21.9 mmol) in ethanol (50 mL) and ethyl acetate (50 mL) was added 10% palladium on carbon (4.66 g, 4.38 mmol) at room temperature under nitrogen atmosphere. The reaction mixture was degassed and stirred under hydrogen atmosphere (1 atm) at room temperature for 16 h. The reaction mixture was filtered through a celite bed and the filter bed was washed with ethyl acetate (200 mL). The filtrate was concentrated under reduced pressure. The crude residue was triturated with diethyl ether (200 mL) to give the title compound (6.0 g, 75% yield) as an off-white solid. $^1H$ NMR (400 MHz, DMSO-$d_6$): δ 8.06 (d, J=8.2 Hz, 1H), 7.98 (s, 1H), 7.73-7.68 (m, 2H), 3.12 (t, J=5.3 Hz, 4H), 1.57 (t, J=5.3 Hz, 4H), 1.10 (s, 9H), 0.43 (s, 4H). m/z (ESI): 367.2 $(M-H)^+$.

Intermediate 14: 4-((Methylsulfonyl)methyl)-2-(6-azaspiro[2.5]octan-6-yl)benzoic acid

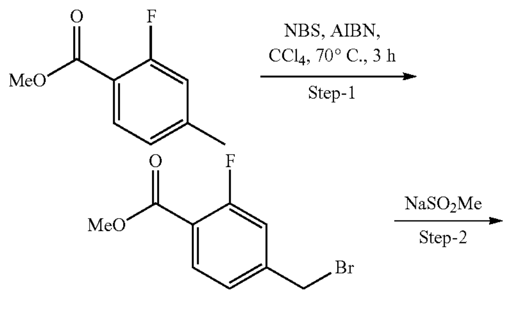

-continued

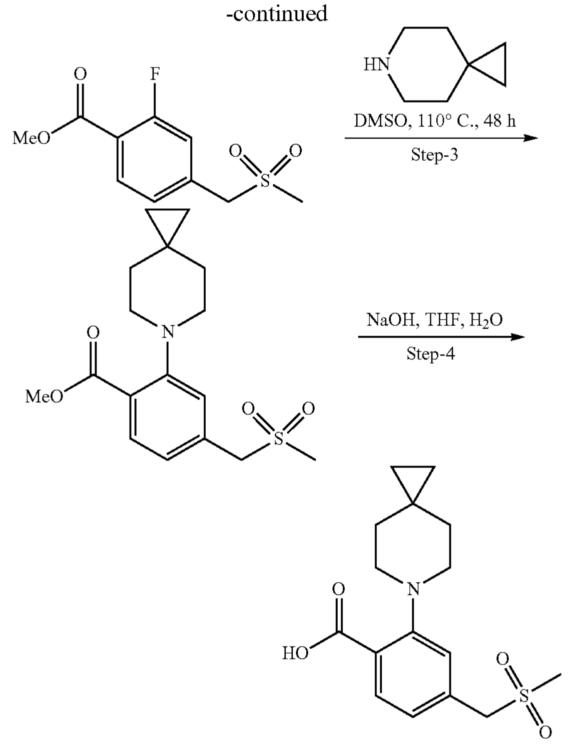

Intermediate 14

Step 1: To a solution of methyl 2-fluoro-4-methylbenzoate (10.0 g, 59.5 mmol) in carbon tetrachloride (200 mL) were added NBS (11.6 g, 65.4 mmol) and AIBN (0.976 g, 5.95 mmol) at rt. The reaction mixture was stirred at 70° C. for 3 h before quenched with water (250 mL) and extracted with dichloromethane (2×200 mL). The combined organic extracts were washed with brine (150 mL), dried over $Na_2SO_4$, filtered, and concentrated under reduced pressure to give methyl 2-fluoro-4-methylbenzoate (14.0 g, crude) as a pale yellow oil. $^1H$ NMR (400 MHz, Chloroform-d): δ 8.04-7.88 (m, 1H), 7.27-7.13 (m, 2H), 4.46 (s, 2H), 3.96 (s, 3H).

Step 2: A mixture of methyl 2-fluoro-4-methylbenzoate (14.0 g, 56.7 mmol) and sodium methanesulfinate (12.15 g, 119 mmol) in DMF (42 mL) was irradiated in a microwave oven (Biotage initiator+) at 120° C. for 30 min. The reaction mixture was quenched with water (150 mL) and extracted with ethyl acetate (2×200 mL). The combined organic extracts were washed with saturated brine solution (150 mL), dried over $Na_2SO_4$, filtered, and concentrated under reduced pressure to give methyl 2-fluoro-4-((methylsulfonyl)methyl)benzoate (6 g, crude) as an off-white solid.

Step 3: A mixture of methyl 2-fluoro-4-((methylsulfonyl)methyl)benzoate (6.0 g, 24 mmol) and 6-azaspiro[2.5]octane (2.71 g, 24.4 mmol) in DMSO (30 mL) was irradiated in a microwave oven at 150° C. for 1 h. The reaction mixture was quenched with water (50 mL) and extracted with ethyl acetate (2×50 mL). The combined organic extracts were washed with brine (50 mL), dried over $Na_2SO_4$, filtered, and concentrated under reduced pressure to give methyl 4-((methylsulfonyl)methyl)-2-(6-azaspiro[2.5]octan-6-yl) benzoate (4.0 g, crude) as an off-white solid. The material as such was taken onto the next step without any further purification. $^1H$ NMR (400 MHz, Chloroform-d) δ 7.72 (d, J=7.8 Hz, 1H), 7.11 (s, 1H), 6.96 (dd, J=7.8, 1.6 Hz, 1H), 4.24 (s, 2H), 3.93 (s, 3H), 3.12 (t, J=5.4 Hz, 4H), 2.78 (s, 3H), 1.55 (t, J=5.5 Hz, 4H), 0.37 (s, 4H). m/z (ESI): 338.1 $(M-H)^+$.

Step 4: To a solution of methyl 4-((methylsulfonyl) methyl)-2-(6-azaspiro[2.5]octan-6-yl)benzoate (2.0 g, 3.0 mmol) in THF (15 mL) was added sodium hydroxide (0.474 g, 11.8 mmol) in water (7 mL) and stirred at room temperature for 12 h. The reaction mixture was acidified with 1.5 N HCl solution to pH ~3 and extracted with ethyl acetate (5×20 mL). The combined organic extracts were washed with brine solution (20 mL), dried over $Na_2SO_4$, filtered, and concentrated under reduced pressure to give 4-((methylsulfonyl) methyl)-2-(6-azaspiro[2.5]octan-6-yl)benzoic acid (1.0 g, 10% yield over 3 steps) as a white solid. m/z (ESI): 324.1 $(M-H)^+$.

Intermediate 15: 4-((1-(tert-Butoxycarbonyl)azetidin-3-yl)sulfonyl)-2-(6-azaspiro[2.5]octan-6-yl)benzoic acid

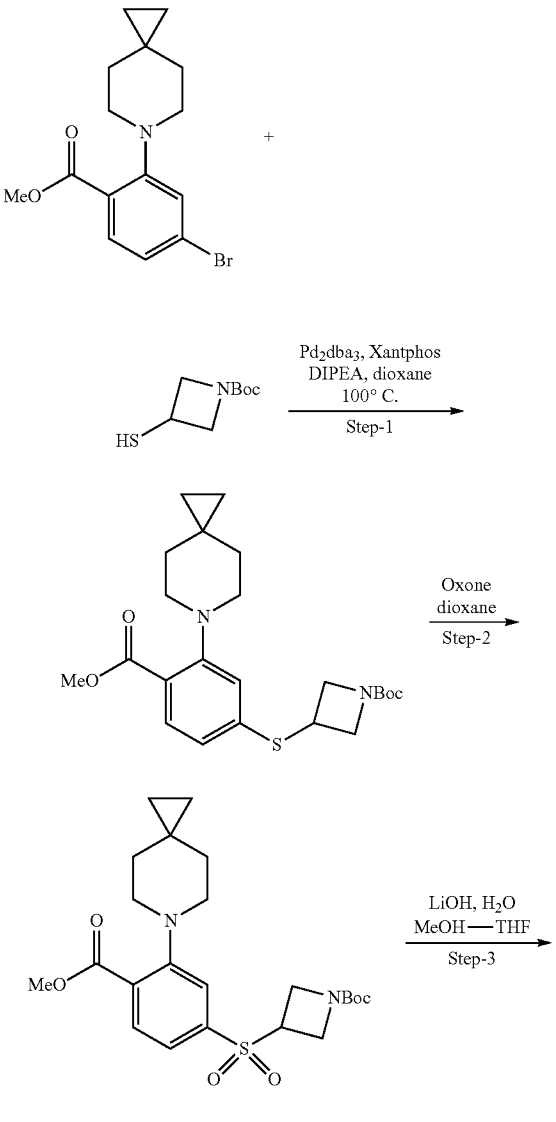

-continued

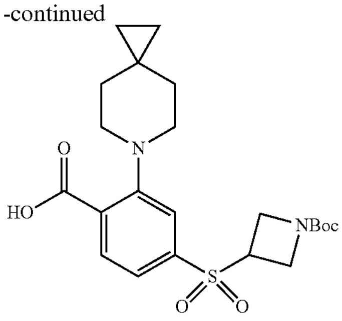

Intermediate 15

Step 1: A mixture of methyl 4-bromo-2-(6-azaspiro[2.5] octan-6-yl)benzoate (10.5 g, 32.4 mmol, Intermediate 9-2), DIPEA (8.37 mL, 64.8 mmol), Xantphos (1.87 g, 3.24 mmol) and $Pd_2(dba)_3$ (2.97 g, 3.24 mmol) in dioxane was bubbled with argon flow, then tert-butyl 3-mercaptoazetidine-1-carboxylate (7.66 mL, 40.5 mmol) was added. The mixture was stirred at 100° C. for 18 h. The mixture was cooled down to room temperature, concentrated and purified through a Biotage SNAP 340 g column eluting with a gradient of 0% to 25% EtOAc-EtOH (3:1) in heptane to provide tert-butyl 3-((4-(methoxycarbonyl)-3-(6-azaspiro [2.5]octan-6-yl)phenyl)thio)azetidine-1-carboxylate (13.8 g, 32.0 mmol, 99% yield) as a light-yellow sticky solid. $^1H$ NMR (500 MHz, DMSO-$d_6$) δ ppm 7.55 (d, J=8.04 Hz, 1H), 6.79 (s, 1H), 6.76 (d, J=8.14 Hz, 1H), 4.34-4.43 (m, 2H), 4.27-4.34 (m, 1H), 3.79 (s, 3H), 3.70 (dd, J=4.67, 8.56 Hz, 2H), 2.97-3.04 (m, 4H), 1.41-1.51 (m, 4H), 1.38 (s, 9H), 0.29-0.37 (m, 1H).

Step 2: To a solution of tert-butyl 3-((4-(methoxycarbonyl)-3-(6-azaspiro[2.5]octan-6-yl)phenyl)thio)azetidine-1-carboxylate (13.85 g, 32.0 mmol) in 1,4-dioxane (300 mL) was added Oxone monopersulfate (39.4 g, 64.0 mmol) in 150 mL water. The reaction mixture was stirred at room temperature for 5 h before adding 150 mL of ethyl acetate and 150 mL of water. This mixture was stirred for 10 min and the organic layer was separated, the aqueous layer was extracted with ethyl acetate. The combined organics were washed with brine, dried, filtered, and concentrated. The crude material was purified through a Biotage SNAP 340 g column eluting with a gradient of 0% to 25% EtOAc-EtOH (3:1) in heptane to give tert-butyl 3-((4-(methoxycarbonyl)-3-(6-azaspiro[2.5]octan-6-yl)phenyl)sulfonyl)azetidine-1-carboxylate (12.8 g, 27.5 mmol, 86% yield) as an off-white solid. $^1H$ NMR (500 MHz, DMSO-$d_6$) δ 7.75 (d, J=8.04 Hz, 1H), 7.44-7.50 (m, 2H), 4.48-4.55 (m, 1H), 4.09 (br. s., 2H), 3.97-4.02 (m, 2H), 3.86 (s, 3H), 3.04-3.17 (m, 4H), 1.42-1.51 (m, 4H), 1.38 (s, 9H), 0.35 (s, 4H).

Step 3: A mixture of tert-butyl 3-((4-(methoxycarbonyl)-3-(6-azaspiro[2.5]octan-6-yl)phenyl)sulfonyl) azetidine-1-carboxylate (12.77 g, 27.5 mmol) and lithium hydroxide monohydrate (11.53 g, 275 mmol) in THF-water-MeOH (1:1:1, 230 mL) was stirred at room temperature for 15 h. The mixture was concentrated under reduced pressure to remove some organic solvent. The solution was acidified with 2N HCl to pH<3. The precipitate was filtered and dried to give 4-((1-(tert-butoxycarbonyl)azetidin-3-yl)sulfonyl)-2-(6-azaspiro[2.5]octan-6-yl)benzoic acid (10.6 g, 23.5 mmol, 86% yield) as an off-white solid. $^1H$ NMR (500 MHz, DMSO-$d_6$) δ ppm 8.03 (d, J=8.30 Hz, 1H), 7.93 (d, J=1.82 Hz, 1H), 7.72 (dd, J=1.69, 8.17 Hz, 1H), 4.48-4.60 (m, 1H), 4.10 (br. s., 2H), 3.99-4.06 (m, 2H), 3.14-3.22 (m, 4H), 1.49-1.59 (m, 4H), 1.38 (s, 9H), 0.41 (s, 4H).

Intermediate 16: 4-(Cyclopropanesulfonimidoyl)-2-(6-azaspiro[2.5]octan-6-yl)benzoic acid

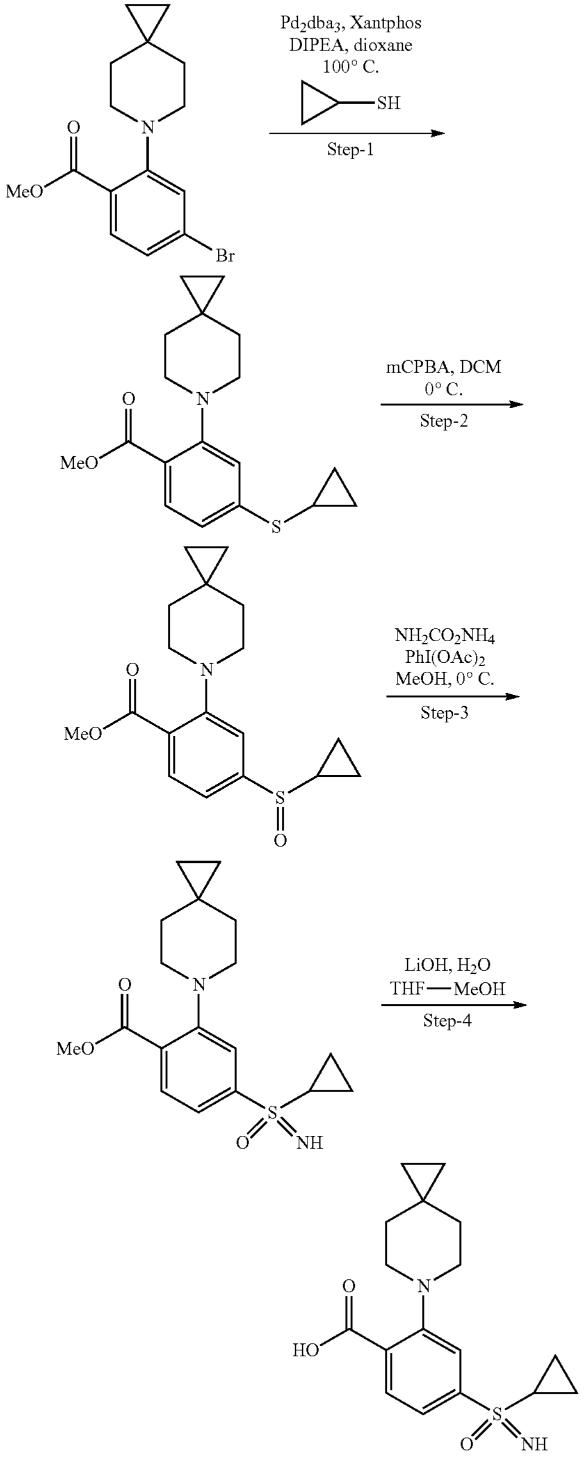

Intermediate 16

Step 1: To a mixture of methyl 4-bromo-2-(6-azaspiro[2.5]octan-6-yl)benzoate (3.69 g, 11.4 mmol, Intermediate 9-2), DIPEA (2.94 mL, 22.8 mmol), Xantphos (0.659 g, 1.14 mmol) and $Pd_2(dba)_3$ (1.04 g, 1.14 mmol) in 1,4-dioxane, was added cyclopropanethiol (0.928 mL, 12.5 mmol). The mixture was stirred at 100° C. for 16 h. The mixture was diluted with water and extracted with ethyl acetate. The organic extracts were washed with brine, dried, and concentrated. The mixture was purified through a Biotage SNAP 100 g column eluting with a gradient of 0% to 20% EtOAc-EtOH (3:1) in heptane to provide methyl 4-(cyclopropylthio)-2-(6-azaspiro[2.5]octan-6-yl)benzoate (3.42 g, 10.8 mmol, 95% yield) as a yellow oil. $^1H$ NMR (500 MHz, DMSO-d6) δ 7.57 (d, J=8.04 Hz, 1H), 7.00 (d, J=1.82 Hz, 1H), 6.93 (d, J=8.21 Hz, 1H), 3.79 (s, 3H), 2.95-3.04 (m, 4H), 2.26-2.36 (m, 1H), 1.43-1.49 (m, 4H), 1.07-1.16 (m, 2H), 0.55-0.66 (m, 2H), 0.33 (s, 4H).

Step 2: To a mixture of methyl 4-(cyclopropylthio)-2-(6-azaspiro[2.5]octan-6-yl)benzoate (3.35 g, 10.6 mmol) in DCM at 0° C., was added 3-chloroperoxybenzoic acid (2.367 g, 13.72 mmol). The mixture was stirred at 0° C. for 30 min. The reaction was quenched with sat. $NaHCO_3$ and extracted with ethyl acetate. The organic extract was washed with brine, dried, and concentrated. The mixture was purified through a Biotage SNAP 100 g column eluting with a gradient of 0% to 40% EtOAc-EtOH (3:1) in heptane to provide methyl 4-(cyclopropylsulfinyl)-2-(6-azaspiro[2.5]octan-6-yl)benzoate (3.34 g, 10.0 mmol, 95% yield) as a yellow oil. $^1H$ NMR (500 MHz, DMSO-d6) δ 7.70 (d, J=8.04 Hz, 1H), 7.30-7.47 (m, 1H), 7.22 (d, J=8.02 Hz, 1H), 3.84 (s, 3H), 3.03-3.11 (m, 4H), 2.52-2.55 (m, 1H), 1.43-1.51 (m, 4H), 0.88-1.01 (m, 3H), 0.77-0.88 (m, 1H), 0.34 (s, 4H).

Step 3: To a solution of methyl 4-(cyclopropylsulfinyl)-2-(6-azaspiro[2.5]octan-6-yl)benzoate (3.33 g, 9.99 mmol) in methanol were added iodobenzene diacetate (6.43 g, 20.0 mmol) and ammonium carbamate (3.12 g, 39.9 mmol) at 0° C. and the mixture was stirred at 0° C. for 1 h. The reaction was quenched with water and extracted with ethyl acetate and DCM. The combined organic extracts were washed with brine, dried, and concentrated. The mixture was purified through a Biotage SNAP 100 g column eluting with a gradient of 0% to 60% EtOAc-EtOH (3:1) in heptane to provide methyl 4-(cyclopropanesulfonimidoyl)-2-(6-azaspiro[2.5]octan-6-yl)benzoate (1.89 g, 5.42 mmol, 54.3% yield) as an off-white solid. $^1H$ NMR (500 MHz, DMSO-d6) δ 7.70 (d, J=8.04 Hz, 1H), 7.53 (d, J=1.56 Hz, 1H), 7.43 (dd, J=1.56, 8.04 Hz, 1H), 4.29 (s, 1H), 3.85 (s, 3H), 3.01-3.13 (m, 4H), 2.67-2.75 (m, 1H), 1.43-1.51 (m, 4H), 1.05-1.14 (m, 1H), 0.87-1.00 (m, 3H), 0.35 (s, 4H).

Step 4: A mixture of methyl 4-(cyclopropanesulfonimidoyl)-2-(6-azaspiro[2.5]octan-6-yl)benzoate (1.89 g, 5.42 mmol) and lithium hydroxide monohydrate (0.683 g, 16.3 mmol) in THF-water-MeOH (2:1:1, 32 mL) was stirred at room temperature for 15 h. The mixture was concentrated under reduced pressure to remove some organic solvent. The solution was acidified with 2N HCl to pH<3 The mixture was extracted with DCM (2×). The combined extracts were washed with brine, dried and concentrated to give 4-(cyclopropanesulfonimidoyl)-2-(6-azaspiro[2.5]octan-6-yl)benzoic acid (1.80 g, 5.38 mmol, 99% yield) as an off-white solid. $^{1}$H NMR (500 MHz, DMSO-d6) δ 8.08 (d, J=8.30 Hz, 1H), 8.01 (d, J=1.56 Hz, 1H), 7.78 (dd, J=1.56, 8.04 Hz, 1H), 4.44 (br. s., 1H), 3.16 (t, J=5.32 Hz, 4H), 2.74-2.81 (m, 1H), 1.58 (t, J=5.19 Hz, 4H), 1.11-1.22 (m, 1H), 0.89-1.04 (m, 3H), 0.43 (s, 4H).

Compounds Containing $Ar^1$ and $Ar^2$

Intermediate 17: N-(6-Fluoropyridin-2-yl)-4-((1-methylcyclopropane)-1-sulfonamido)-2-(6-azaspiro[2.5]octan-6-yl)benzamide

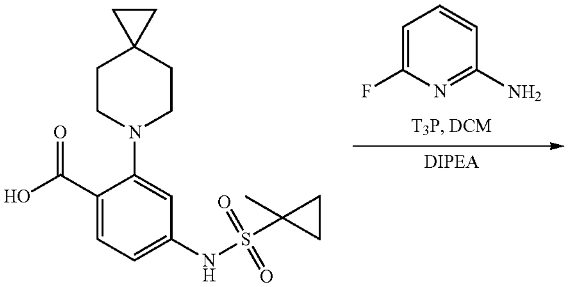

-continued

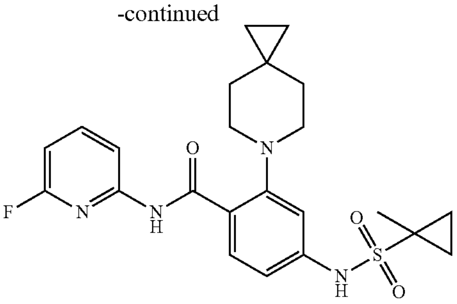

Intermediate 17

To a solution of 4-((1-methylcyclopropane)-1-sulfonamido)-2-(6-azaspiro[2.5]octan-6-yl)benzoic acid (1.0 g, 2.74 mmol, Intermediate 11) in DCM (20 mL) was added 6-fluoropyridin-2-amine (0.308 g, 2.74 mmol, Combi-Blocks), $T_3P$ (50% in ethyl acetate, 1.3 mL, 4.1 mmol) and DIPEA (0.958 mL, 5.49 mmol). The resulting mixture was stirred at room temperature for 16 h. The reaction mixture was quenched with satd. $NaHCO_3$ solution (10 mL) and extracted with DCM (2×25 mL). The combined organic extracts were washed with brine (20 mL), dried over $Na_2SO_4$, filtered, and concentrated under reduced pressure. The crude residue was purified by column chromatography over silica gel using 20% ethyl acetate in hexanes to give the title compound (0.65 g, 52% yield) as an off-white solid. $^{1}$H NMR (400 MHz, DMSO-$d_6$): δ 13.09 (s, 1H), 10.28 (s, 1H), 8.20 (dd, J=8.0, 2.4 Hz, 1H), 8.12-7.92 (m, 2H), 7.36 (d, J=2.2 Hz, 1H), 7.17 (dd, J=8.6, 2.2 Hz, 1H), 6.89 (dd, J=8.0, 2.4 Hz, 1H), 2.97 (t, J=5.4 Hz, 4H), 1.79-1.56 (m, 4H), 1.41 (s, 3H), 1.32-1.14 (m, 2H), 0.90-0.79 (m, 2H), 0.41 (s, 4H). m/z (ESI): 459.1 $(M-H)^{+}$.

TABLE 4

Intermediates 18-36 were prepared following a similar procedure as described for intermediate 17

| Int. # | Chemical Structure | Name | LRMS: (ESI + ve ion) m/z |
|---|---|---|---|
| 18 | 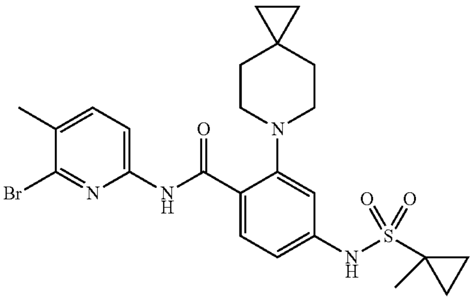 [SMILES: Cc1ccc(NC(=O)c2ccc(NS(=O)(=O)C3(C)CC3)cc2N2CCC3(CC2)CC3)nc1Br] | N-(6-Bromo-5-methylpyridin-2-yl)-4-((1-methylcyclopropane)-1-sulfonamido)-2-(6-azaspiro[2.5]octan-6-yl)benzamide | 533.1/535.1 |
| 19 | 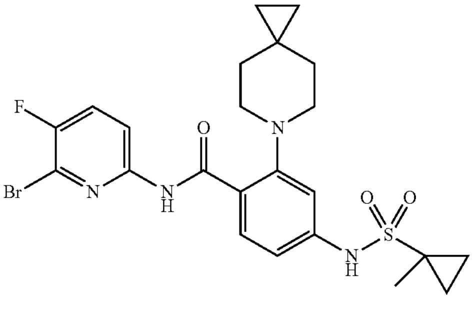 [SMILES: CC1(S(=O)(=O)Nc2ccc(C(=O)Nc3ccc(F)c(Br)n3)c(N3CCC4(CC3)CC4)c2)CC1] | N-(6-Bromo-5-fluoropyridin-2-yl)-4-((1-methylcyclopropane)-1-sulfonamido)-2-(6-azaspiro[2.5]octan-6-yl)benzamide | 537.0/539.0 |

TABLE 4-continued

Intermediates 18-36 were prepared following a similar procedure as described for intermediate 17

| Int. # | Chemical Structure | Name | LRMS: (ESI + ve ion) m/z |
|---|---|---|---|
| 20 | 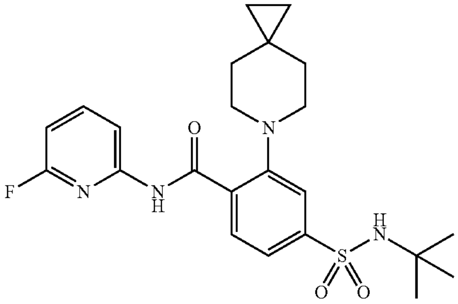 [SMILES: CC(C)(C)NS(=O)(=O)c1ccc(C(=O)Nc2cccc(F)n2)c(N2CCC3(CC2)CC3)c1] | 4-(N-(tert-Butyl)sulfamoyl)-N-(6-fluoropyridin-2-yl)-2-(6-azaspiro[2.5]octan-6-yl)benzamide | 461.2 |
| 21 | 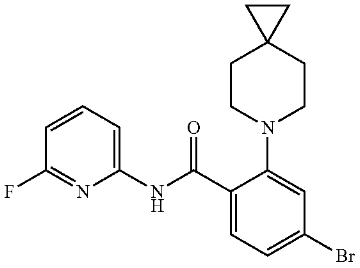 [SMILES: O=C(Nc1cccc(F)n1)c1ccc(Br)cc1N1CCC2(CC1)CC2] | 4-Bromo-N-(6-fluoropyridin-2-yl)-2-(6-azaspiro[2.5]octan-6-yl)benzamide | 406.0/408.0 |
| 22 | 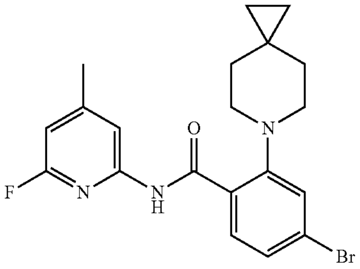 [SMILES: Cc1cc(F)nc(NC(=O)c2ccc(Br)cc2N2CCC3(CC2)CC3)c1] | 4-Bromo-N-(6-fluoro-4-methylpyridin-2-yl)-2-(6-azaspiro[2.5]octan-6-yl)benzamide | 418.1/420.1 |
| 23 | 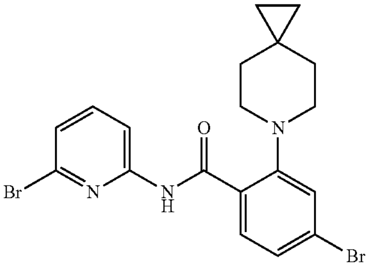 [SMILES: O=C(Nc1cccc(Br)n1)c1ccc(Br)cc1N1CCC2(CC1)CC2] | 4-Bromo-N-(6-bromopyridin-2-yl)-2-(6-azaspiro[2.5]octan-6-yl)benzamide | 466.2/468.2 |
| 24 | 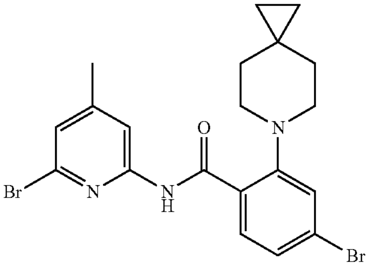 [SMILES: Cc1cc(Br)nc(NC(=O)c2ccc(Br)cc2N2CCC3(CC2)CC3)c1] | 4-Bromo-N-(6-bromo-4-methylpyridin-2-yl)-2-(6-azaspiro[2.5]octan-6-yl)benzamide | 479.9/481.9 |

TABLE 4-continued

Intermediates 18-36 were prepared following a similar procedure as described for intermediate 17

| Int. # | Chemical Structure | Name | LRMS: (ESI + ve ion) m/z |
|---|---|---|---|
| 25 | 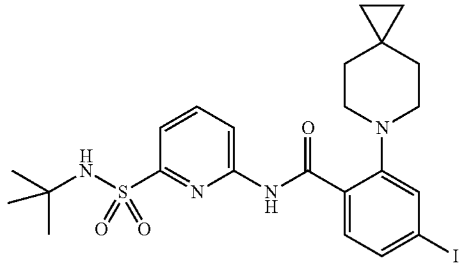 [SMILES: CC(C)(C)NS(=O)(=O)c1cccc(NC(=O)c2ccc(I)cc2N2CCC3(CC2)CC3)n1] | N-(6-(N-(tert-Butyl)sulfamoyl)pyridin-2-yl)-4-iodo-2-(6-azaspiro[2.5]octan-6-yl)benzamide | 569.3 |
| 26 | 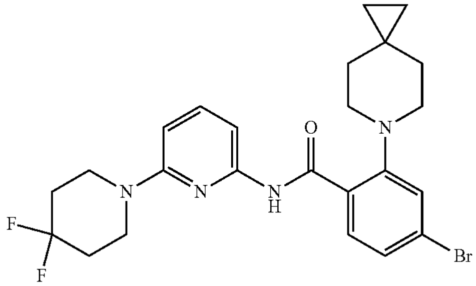 [SMILES: O=C(Nc1cccc(N2CCC(F)(F)CC2)n1)c1ccc(Br)cc1N1CCC2(CC1)CC2] | 4-Bromo-N-(6-(4,4-difluoropiperidin-1-yl)pyridin-2-yl)-2-(6-azaspiro[2.5]octan-6-yl)benzamide | 505.2/507.2 |
| 27 | 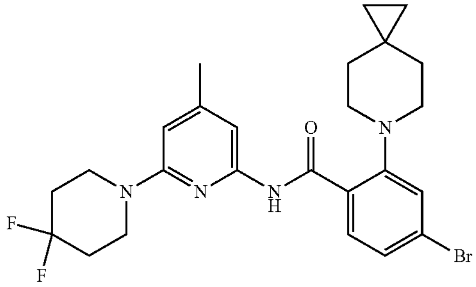 [SMILES: Cc1cc(NC(=O)c2ccc(Br)cc2N2CCC3(CC2)CC3)nc(N2CCC(F)(F)CC2)c1] | 4-Bromo-N-(6-(4,4-difluoropiperidin-1-yl)-4-methylpyridin-2-yl)-2-(6-azaspiro[2.5]octan-6-yl)benzamide | 519.3/521.3 |
| 28 | 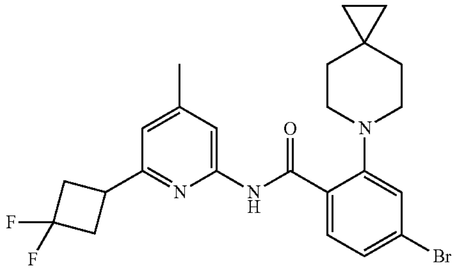 [SMILES: Cc1cc(NC(=O)c2ccc(Br)cc2N2CCC3(CC2)CC3)nc(C2CC(F)(F)C2)c1] | 4-Bromo-N-(6-(3,3-difluorocyclobutyl)-4-methylpyridin-2-yl)-2-(6-azaspiro[2.5]octan-6-yl)benzamide | 490.1/492.1 |
| 29 | 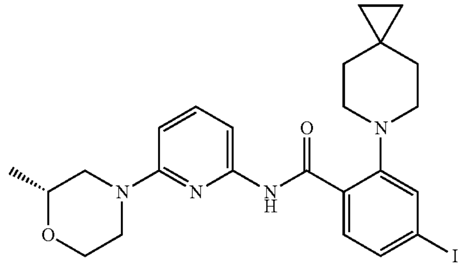 [SMILES: C[C@@H]1CN(c2cccc(NC(=O)c3ccc(I)cc3N3CCC4(CC3)CC4)n2)CCO1] | (R)-4-Iodo-N-(6-(2-methylmorpholino)pyridin-2-yl)-2-(6-azaspiro[2.5]octan-6-yl)benzamide | 491.2/493.2 |

TABLE 4-continued

Intermediates 18-36 were prepared following a similar procedure as described for intermediate 17

| Int. # | Chemical Structure | Name | LRMS: (ESI + ve ion) m/z |
|---|---|---|---|
| 30 | 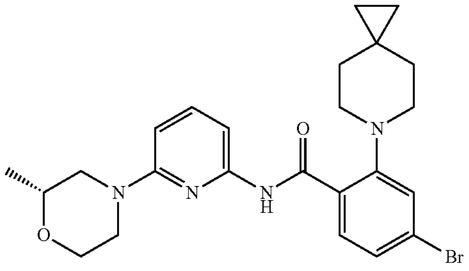 [SMILES: C[C@@H]1CN(c2cccc(NC(=O)c3ccc(Br)cc3N3CCC4(CC3)CC4)n2)CCO1] | (R)-4-Bromo-N-(6-(2-methylmorpholino)pyridin-2-yl)-2-(6-azaspiro[2.5]octan-6-yl)benzamide | 485.2/487.2 |
| 31 | 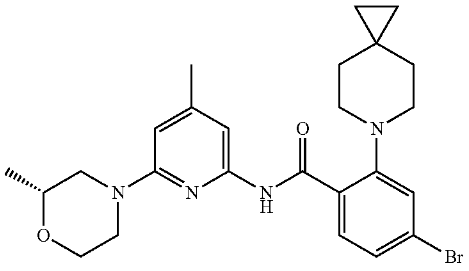 | (R)-4-Bromo-N-(4-methyl-6-(2-methylmorpholino)pyridin-2-yl)-2-(6-azaspiro[2.5]octan-6-yl)benzamide | 499.2/501.2 |
| 32 | 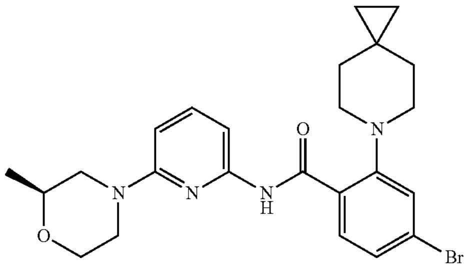 [SMILES: C[C@H]1CN(c2cccc(NC(=O)c3ccc(Br)cc3N3CCC4(CC3)CC4)n2)CCO1] | (S)-4-Bromo-N-(6-(2-methylmorpholino)pyridin-2-yl)-2-(6-azaspiro[2.5]octan-6-yl)benzamide | 485.2/487.2 |
| 33 | 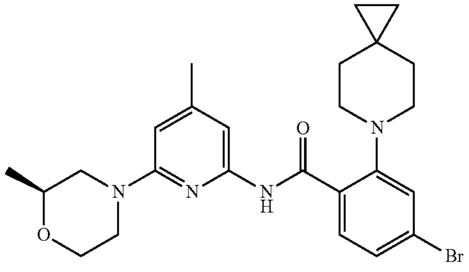 [SMILES: Cc1cc(NC(=O)c2ccc(Br)cc2N2CCC3(CC2)CC3)nc(N2CCO[C@@H](C)C2)c1] | (S)-4-Bromo-N-(4-methyl-6-(2-methylmorpholino)pyridin-2-yl)-2-(6-azaspiro[2.5]octan-6-yl)benzamide | 499.2/501.2 |
| 34 | 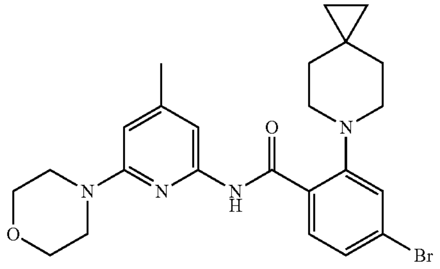 [SMILES: Cc1cc(NC(=O)c2ccc(Br)cc2N2CCC3(CC2)CC3)nc(N2CCOCC2)c1] | 4-Bromo-N-(4-methyl-6-morpholinopyridin-2-yl)-2-(6-azaspiro[2.5]octan-6-yl)benzamide | 485.2/487.2 |

TABLE 4-continued

| Intermediates 18-36 were prepared following a similar procedure as described for intermediate 17 | | | |
|---|---|---|---|
| Int. # | Chemical Structure | Name | LRMS: (ESI + ve ion) m/z |
| 35 | 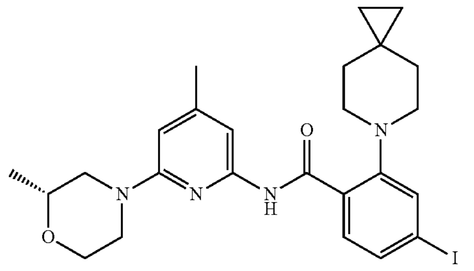 [SMILES: Cc1cc(NC(=O)c2ccc(I)cc2N2CCC3(CC2)CC3)nc(N2CCO[C@H](C)C2)c1] | (R)-4-Iodo-N-(4-methyl-6-(2-methylmorpholino)pyridin-2-yl)-2-(6-azaspiro[2.5]octan-6-yl)benzamide | 547.3 |
| 36 | 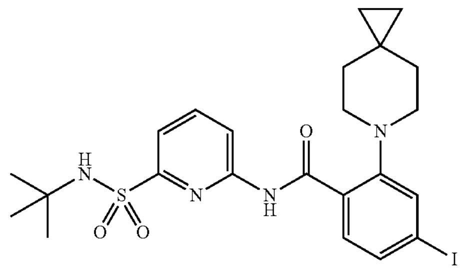 [SMILES: CC(C)(C)NS(=O)(=O)c1cccc(NC(=O)c2ccc(I)cc2N2CCC3(CC2)CC3)n1] | N-(6-(N-(tert-Butyl)sulfamoyl)pyridin-2-yl)-4-iodo-2-(6-azaspiro[2.5]octan-6-yl)benzamide | 569.3 |
| 37 | 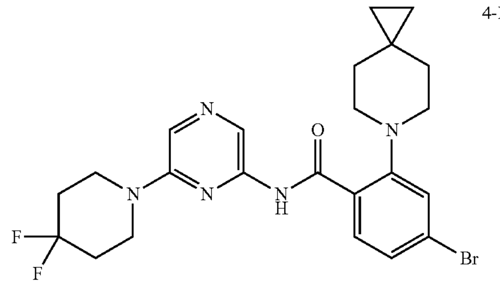 | 4-Bromo-N-(6-(4,4-difluoropiperidin-1-yl)pyrazin-2-yl)-2-(6-azaspiro[2.5]octan-6-yl)benzamide | 506.1/508.1 |

Intermediate 38: 4-Iodo-2-(6-azaspiro[2.5]octan-6-yl)-N-(6-(3,3,3-trifluoropropoxy)pyridin-2-yl)benzamide

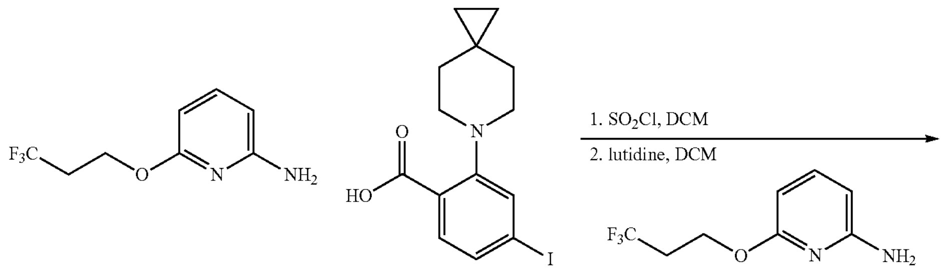

-continued

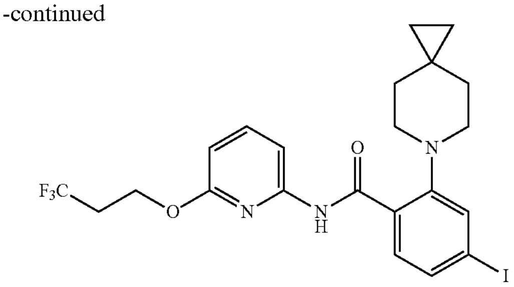

Intermediate 38

4-Iodo-2-(6-azaspiro[2.5]octan-6-yl)benzoic acid (3.0 g, 8.4 mmol, Intermediate 9) was suspended in DCM (10 mL) under argon. Thionyl chloride (1.463 g, 12.29 mmol, Sigma-Aldrich Corporation) was added and the mixture stirred at rt for 15 min. The mixture was evaporated to dryness under reduced pressure. The crude residue was azeotroped with toluene (2×100 mL) and suspended in dichloromethane (50 mL) under argon. A solution of 6-(3,3,3-trifluoropropoxy)pyridin-2-amine (2.0 g, 9.7 mmol, Intermediate 6) and 2,6-lutidine (3.68 g, 34.3 mmol, Sigma-Aldrich Corporation) in dichloromethane (10 mL) was added in one portion. The yellow mixture was stirred at rt for 20 min then evaporated to dryness under reduced pressure. The crude solids were triturated in methanol (30 mL) for 20 min then filtered through a sintered glass frit. The solids were dried under a stream of nitrogen to give 4-iodo-2-(6-azaspiro[2.5]octan-6-yl)-N-(6-(3,3,3-trifluoropropoxy)pyridin-2-yl)benzamide (3.8 g, 7.0 mmol, 83% yield). $^{1}H$ NMR (400 MHz, DMSO-$d_6$) δ ppm 0.36 (s, 4H) 1.58-180 (m, 4H) 2.83 (dt, J=10.94, 5.42 Hz, 2H) 2.91-3.13 (m, 4H) 4.49 (t, J=5.29 Hz, 2H) 6.58 (d, J=7.88 Hz, 1H) 7.60-8.00 (m, 5H) 13.20 (br s, 1H)

TABLE 5

Intermediates 38-1 to 38-3 were prepared following a similar procedure as described for intermediate 38

| Int. # | Chemical Structure | Name | LRMS: (ESI + ve ion) m/z |
|---|---|---|---|
| 38-1 | 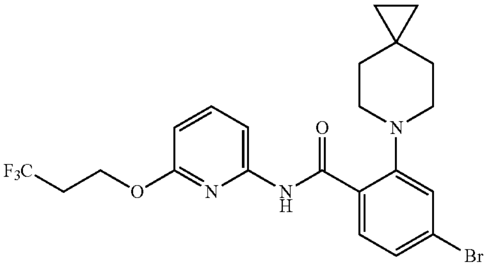 [SMILES: O=C(Nc1cccc(OCCC(F)(F)F)n1)c1ccc(Br)cc1N1CCC2(CC1)CC2] | 4-Bromo-2-(6-azaspiro[2.5]octan-6-yl)-N-(6-(3,3,3-trifluoropropoxy)pyridin-2-yl)benzamide | 498.1/500.1 |
| 38-2 | 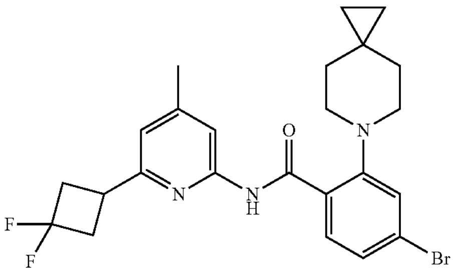 [SMILES: Cc1cc(NC(=O)c2ccc(Br)cc2N2CCC3(CC2)CC3)nc(C2CC(F)(F)C2)c1] | 4-Bromo-N-(6-(3,3-difluorocyclobutyl)-4-methylpyridin-2-yl)-2-(6-azaspiro[2.5]octan-6-yl)benzamide | 490.1/492.1 |
| 38-3 | 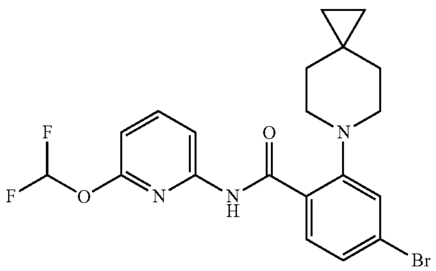 [SMILES: O=C(Nc1cccc(OC(F)F)n1)c1ccc(Br)cc1N1CCC2(CC1)CC2] | 4-Bromo-N-(6-(difluoromethoxy)pyridin-2-yl)-2-(6-azaspiro[2.5]octan-6-yl)benzamide | 452.1/454.1 |

Intermediate 39: 4-Bromo-N-(6-(3,3-difluoroazetidin-1-yl)-4-methylpyridin-2-yl)-2-(6-azaspiro[2.5]octan-6-yl)benzamide

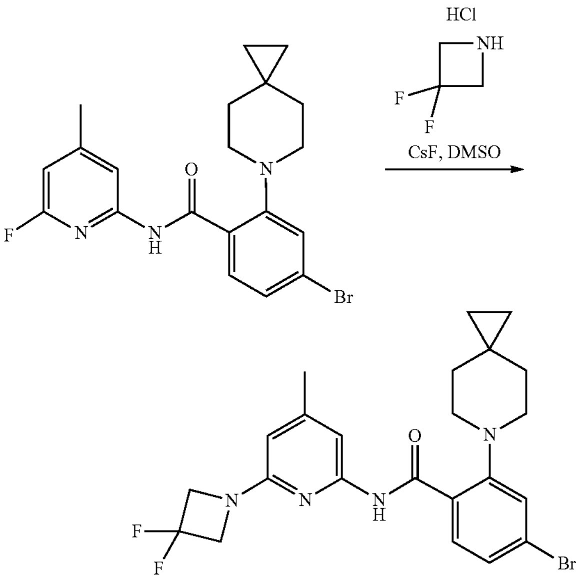

Intermediate 39

A mixture of 4-bromo-N-(6-bromo-4-methylpyridin-2-yl)-2-(6-azaspiro[2.5]octan-6-yl)benzamide (5.0 g, 10 mmol, Int. 22), 3,3-difluoroazetidine hydrochloride (2.027 g, 15.65 mmol, Combi-Blocks) and CsF (9.51 g, 62.6 mmol) in DMSO (50 mL) was stirred at 145° C. for 60 h. The reaction mixture was diluted with ice-water (200 mL) and was stirred for 30 min. The precipitate was filtered and was purified by flash column chromatography using a gradient of 0% to 5% EtOAc in petroleum ether to provide 4-bromo-N-(6-(3,3-difluoroazetidin-1-yl)-4-methylpyridin-2-yl)-2-(6-azaspiro[2.5]octan-6-yl)benzamide (2.4 g, 4.8 mmol, 46% yield) as a white solid. $^1$H NMR (300 MHz, DMSO-$d_6$): δ ppm 13.05 (s, 1H), 8.03 (d, J=8.7 Hz, 1H), 7.67 (s, 1H), 7.53-7.56 (m, 2H), 6.21 (s, 1H), 4.32-4.41 (m, 4H), 3.33 (t, J=5.1 Hz, 4H), 2.28 (s, 3H), 1.72 (br s, 4H), 0.37 (s, 4H). m/z (ESI): 491.1 $(M+H)^+$.

Intermediate 40: Ethyl 2-sulfamoylpropanoate

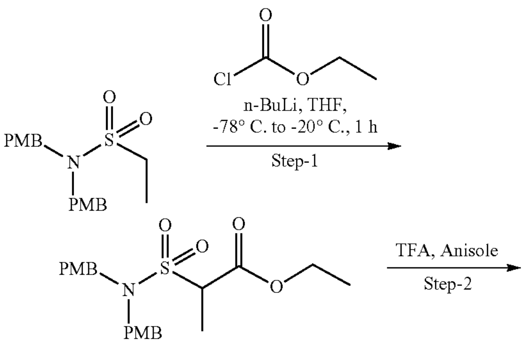

-continued

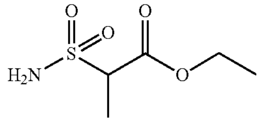

Intermediate 40

Step 1: To a solution of N,N-bis(4-methoxybenzyl)ethanesulfonamide (200.0 g, 572.0 mmol) in tetrahydrofuran (4000 mL) was added nBuLi (1.6 M in hexane, 608.0 mL, 973.0 mmol) at −78° C. slowly and stirred for 30 min. Ethyl carbonochloridate (92.0 mL, 973.0 mmol) in THF (50 mL) was added to the reaction mixture and stirred at −78° C. for 1 h. The reaction mixture was quenched with HCl (1.5 N, 3000 mL) and extracted with EtOAc (2×3000 mL). The organic extract was dried over sodium sulphate, filtered and concentrated in reduced pressure to give the crude material of ethyl 2-(N,N-bis(4-methoxybenzyl)sulfamoyl)propanoate (250.0 g, 60% pure) as yellow oil. The $^1$H-NMR showed desired peaks and proceeded to next step without any purification.

Step 2: To solution of ethyl 2-(N,N-bis(4-methoxybenzyl)sulfamoyl)propanoate (600.0 g, 1.4 mol) in trifluoroacetic acid (2.50 L, 32.45 mol) was added anisole (500.0 mL, 4.57 mol) and stirred at room temperature for 3 h. The reaction mixture was concentrated under reduced pressure, quenched with 10% cold aqueous $NaHCO_3$ solution (3 L) and extracted with EtOAc (2×3 L). The organic layer was dried over sodium sulfate, filtered and concentrated under reduced pressure. The crude residue was purified by column chromatography over silica gel using 25% ethyl acetate in hexanes to give a pale yellow solid (168 g) which was dissolved in DCM (1 L) and precipitated by the addition of hexanes (3000 mL). The solid was filtered, dried under vacuum to give the title compound (109.0 g, 42% yield) as a white solid. $^1$H NMR (400 MHz, DMSO-$d_6$) δ ppm 7.14 (s, 2H), 4.15 (q, J=7.1 Hz, 2H), 3.98 (q, J=7.0 Hz, 1H), 1.45 (d, J=7.0 Hz, 3H), 1.21 (t, J=7.1 Hz, 3H). m/z (ESI): 180.1 $(M-H)^+$.

EXAMPLES

General Methods and Representatives Examples

Method A (Pd-catalyzed Br—S Coupling)

Example 1: 4-(N-(2-Hydroxyethyl)sulfamoyl)-2-(6-azaspiro[2.5]octan-6-yl)-N-(6-(3,3,3-trifluoropropoxy)pyridin-2-yl)benzamide

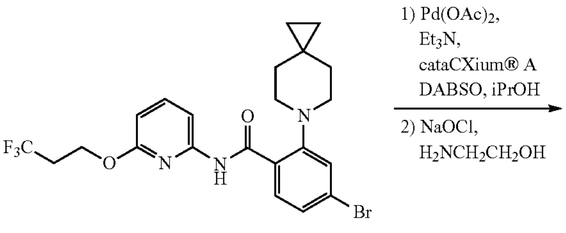

-continued

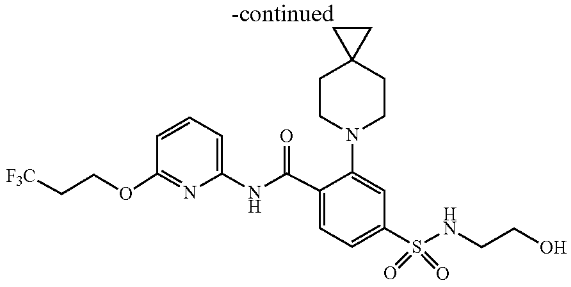

A glass vial was charged with 4-bromo-2-(6-azaspiro[2.5]octan-6-yl)-N-(6-(3,3,3-trifluoropropoxy)pyridin-2-yl)benzamide (348 mg, 0.70 mmol Intermediate 38-1), 1,4-diazabicyclo[2.2.2]octane bis(sulfur dioxide) adduct (DABSO) (101 mg, 0.42 mmol, Sigma-Aldrich), diacetoxypalladium (16 mg, 0.07 mmol, Strem), rac-((3R,5R,7R)-adamantan-1-yl)((3S,5S,7S)-adamantan-1-yl)(butyl)phosphane (cataCXium® A) (38 mg, 0.11 mmol, Strem), triethylamine (194 uL, 1.40 mmol), and iPrOH (3 mL). The tube was degassed for 3 min, sealed, and heated at 80° C. in an oil bath for 3 h. The heterogeneous mixture was cooled to RT and treated with 2-aminoethan-1-ol (85 mg, 1.4 mmol, Sigma-Aldrich) followed by sodium hypochlorite solution (10% wt., 1040 mg, 1.40 mmol, Sigma-Aldrich) and stirred at RT for 18 h. EtOAc (20 mL) and water (5 mL) were added to the heterogeneous mixture. The insoluble solid was filtered off. The filter cake was washed with 2×2 mL of water followed by 2×4 mL of EtOAc. The combined organic extracts were separated and concentrated. The residue was purified by silica gel chromatography (20% to 80% EtOAc in heptane) to give 4-(N-(2-hydroxyethyl)sulfamoyl)-2-(6-azaspiro[2.5]octan-6-yl)-N-(6-(3,3,3-trifluoropropoxy)pyridin-2-yl)benzamide (106 mg, 0.19 mmol, 28% yield) as a light yellow solid. $^1$H NMR (400 MHz, DMSO-$d_6$) δ 13.04 (s, 1H), 8.26 (d, J=8.09 Hz, 1H), 7.91 (d, J=7.67 Hz, 1H), 7.77-7.87 (m, 3H), 7.72 (d, J=7.26 Hz, 1H), 6.62 (d, J=8.09 Hz, 1H), 4.71 (t, J=5.08 Hz, 1H), 4.53 (t, J=6.01 Hz, 2H), 3.33-3.44 (m, 2H), 3.09 (m, 4H), 2.77-2.93 (m, 4H), 1.73 (s, 4H), 0.39 (s, 4H). m/z (ESI): $(M+H)^+$ 543.2.

TABLE 6

Examples 1-1 to 1-13 were prepared following a similar procedure as described for Example 1

| Ex. # | Chemical Structure | Name | LRMS: (ESI + ve ion) m/z |
|---|---|---|---|
| 1-1 | 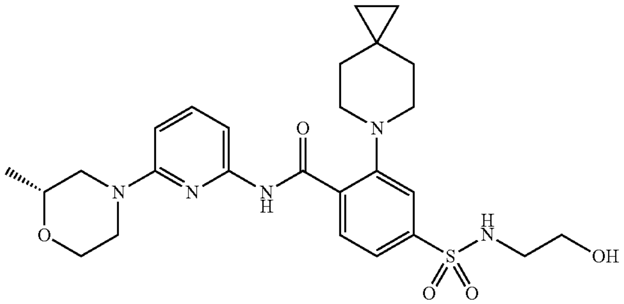 [SMILES: C[C@@H]1CN(c2cccc(NC(=O)c3ccc(S(=O)(=O)NCCO)cc3N3CCC4(CC3)CC4)n2)CCO1] | (R)-4-(N-(2-Hydroxyethyl)sulfamoyl)-N-(6-(2-methylmorpholino)pyridin-2-yl)-2-(6-azaspiro[2.5]octan-6-yl)benzamide | 530.0 |
| 1-2 | 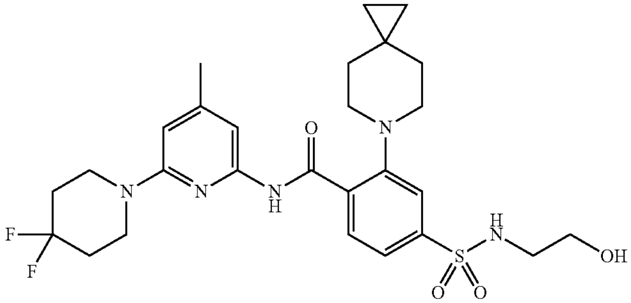 [SMILES: Cc1cc(NC(=O)c2ccc(S(=O)(=O)NCCO)cc2N2CCC3(CC2)CC3)nc(N2CCC(F)(F)CC2)c1] | N-(6-(4,4-Difluoropiperidin-1-yl)-4-methylpyridin-2-yl)-4-(N-(2-hydroxyethyl)sulfamoyl)-2-(6-azaspiro[2.5]octan-6-yl)benzamide | 564.2 |
| 1-3 | 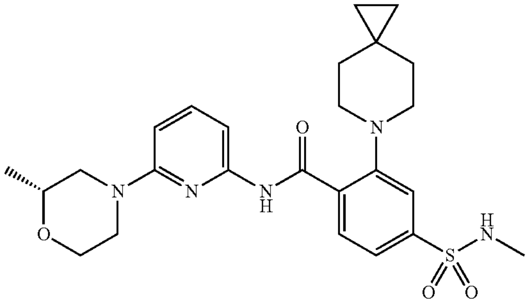 | (R)-N-(6-(2-Methylmorpholino)pyridin-2-yl)-4-(N-methylsulfamoyl)-2-(6-azaspiro[2.5]octan-6-yl)benzamide | 500.1 |

TABLE 6-continued

Examples 1-1 to 1-13 were prepared following a similar procedure as described for Example 1

| Ex. # | Chemical Structure | Name | LRMS: (ESI + ve ion) m/z |
|---|---|---|---|
| 1-4 | 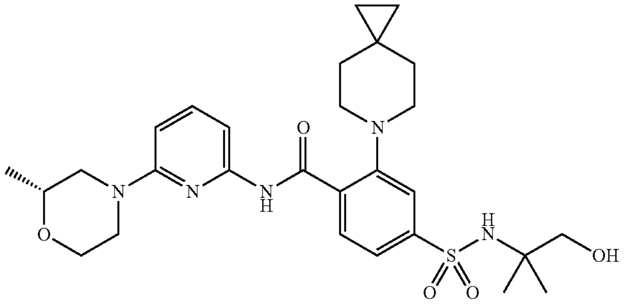 [SMILES: C[C@@H]1CN(c2cccc(NC(=O)c3ccc(S(=O)(=O)NC(C)(C)CO)cc3N3CCC4(CC3)CC4)n2)CCO1] | (R)-4-(N-(1-Hydroxy-2-methylpropan-2-yl)sulfamoyl)-N-(6-(2-methylmorpholino)pyridin-2-yl)-2-(6-azaspiro[2.5]octan-6-yl)benzamide | 558.2 |
| 1-5 | 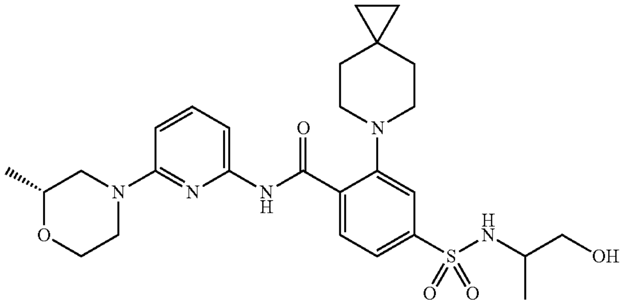 [SMILES: CC(CO)NS(=O)(=O)c1ccc(C(=O)Nc2cccc(N3CCO[C@H](C)C3)n2)c(N2CCC3(CC2)CC3)c1] | 4-(N-(1-Hydroxypropan-2-yl)sulfamoyl)-N-(6-((R)-2-methylmorpholino)pyridin-2-yl)-2-(6-azaspiro[2.5]octan-6-yl)benzamide | 544.1 |
| 1-6 | 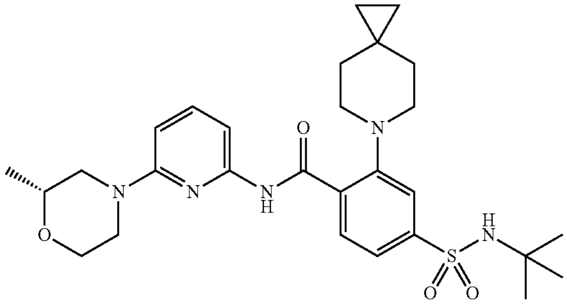 [SMILES: C[C@@H]1CN(c2cccc(NC(=O)c3ccc(S(=O)(=O)NC(C)(C)C)cc3N3CCC4(CC3)CC4)n2)CCO1] | (R)-4-(N-(tert-Butyl)sulfamoyl)-N-(6-(2-methylmorpholino)pyridin-2-yl)-2-(6-azaspiro[2.5]octan-6-yl)benzamide | 542.3 |
| 1-7 | 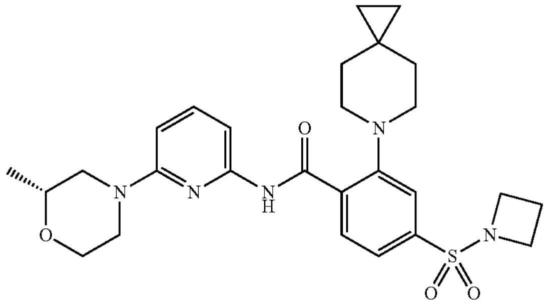 [SMILES: C[C@@H]1CN(c2cccc(NC(=O)c3ccc(S(=O)(=O)N4CCC4)cc3N3CCC4(CC3)CC4)n2)CCO1] | (R)-4-(Azetidin-1-ylsulfonyl)-N-(6-(2-methylmorpholino)pyridin-2-yl)-2-(6-azaspiro[2.5]octan-6-yl)benzamide | 526.1 |
| 1-8 | 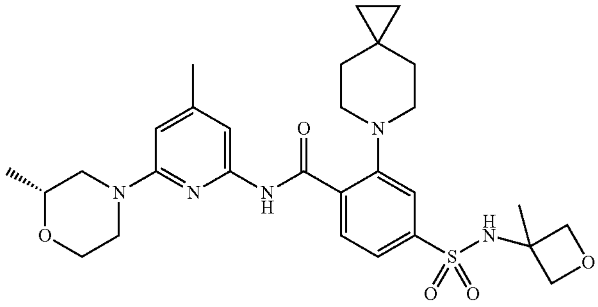 [SMILES: Cc1cc(NC(=O)c2ccc(S(=O)(=O)NC3(C)COC3)cc2N2CCC3(CC2)CC3)nc(N2CCO[C@H](C)C2)c1] | (R)-N-(4-Methyl-6-(2-methylmorpholino)pyridin-2-yl)-4-(N-(3-methyloxetan-3-yl)sulfamoyl)-2-(6-azaspiro[2.5]octan-6-yl)benzamide | 570.4 |

TABLE 6-continued

| Examples 1-1 to 1-13 were prepared following a similar procedure as described for Example 1 | | | |
|---|---|---|---|
| Ex. # | Chemical Structure | Name | LRMS: (ESI + ve ion) m/z |
| 1-9 | 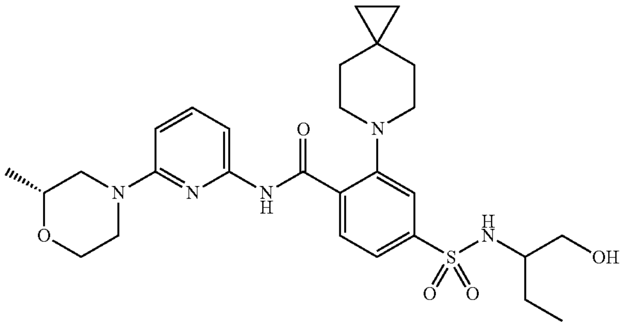 [SMILES: CCC(CO)NS(=O)(=O)c1ccc(C(=O)Nc2cccc(N3CCO[C@H](C)C3)n2)c(N2CCC3(CC2)CC3)c1] | 4-(N-(1-Hydroxybutan-2-yl)sulfamoyl)-N-(6-((R)-2-methylmorpholino)pyridin-2-yl)-2-(6-azaspiro[2.5]octan-6-yl)benzamide | 558.2 |
| 1-10 | 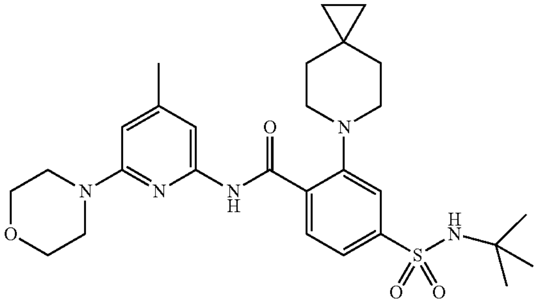 [SMILES: Cc1cc(NC(=O)c2ccc(S(=O)(=O)NC(C)(C)C)cc2N2CCC3(CC2)CC3)nc(N2CCOCC2)c1] | 4-(N-(tert-Butyl)sulfamoyl)-N-(4-methyl-6-morpholinopyridin-2-yl)-2-(6-azaspiro[2.5]octan-6-yl)benzamide | 542.0 |
| 1-11 | 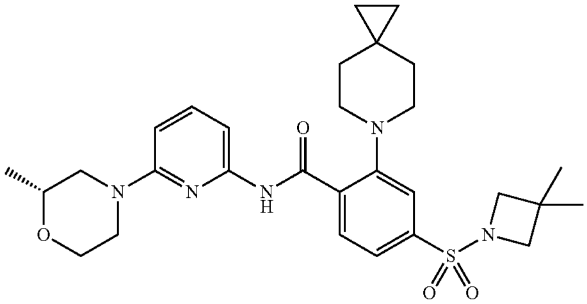 | (R)-4-((3,3-Dimethylazetidin-1-yl)sulfonyl)-N-(6-(2-methylmorpholino)pyridin-2-yl)-2-(6-azaspiro[2.5]octan-6-yl)benzamide | 554.2 |
| 1-12 | 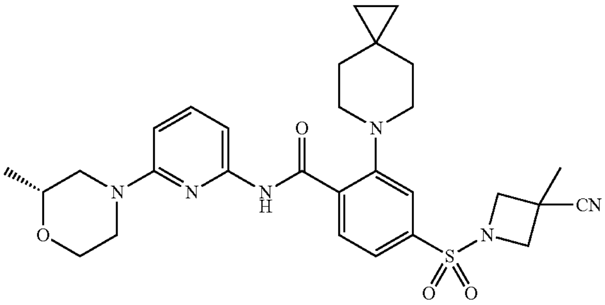 [SMILES: C[C@@H]1CN(c2cccc(NC(=O)c3ccc(S(=O)(=O)N4CC(C)(C#N)C4)cc3N3CCC4(CC3)CC4)n2)CCO1] | (R)-4-((3-Cyano-3-methylazetidin-1-yl)sulfonyl)-N-(6-(2-methylmorpholino)pyridin-2-yl)-2-(6-azaspiro[2.5]octan-6-yl)benzamide | 565.3 |

TABLE 6-continued

Examples 1-1 to 1-13 were prepared following a similar procedure as described for Example 1

| Ex. # | Chemical Structure | Name | LRMS: (ESI + ve ion) m/z |
|---|---|---|---|
| 1-13 | 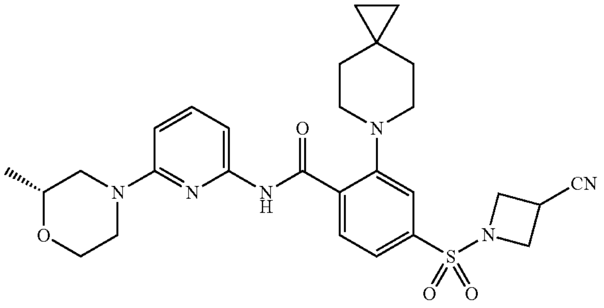 [SMILES: C[C@@H]1CN(c2cccc(NC(=O)c3ccc(S(=O)(=O)N4CC(C#N)C4)cc3N3CCC4(CC3)CC4)n2)CCO1] | (R)-4-((3-Cyanoazetidin-1-yl)sulfonyl)-N-(6-(2-methylmorpholino)pyridin-2-yl)-2-(6-azaspiro[2.5]octan-6-yl)benzamide | 551.2 |

Method B (Sulfone formation)

Example 2: (R)-4-(Isopropylsulfonyl)-N-(6-(2-methylmorpholino)pyridin-2-yl)-2-(6-azaspiro[2.5]octan-6-yl)benzamide

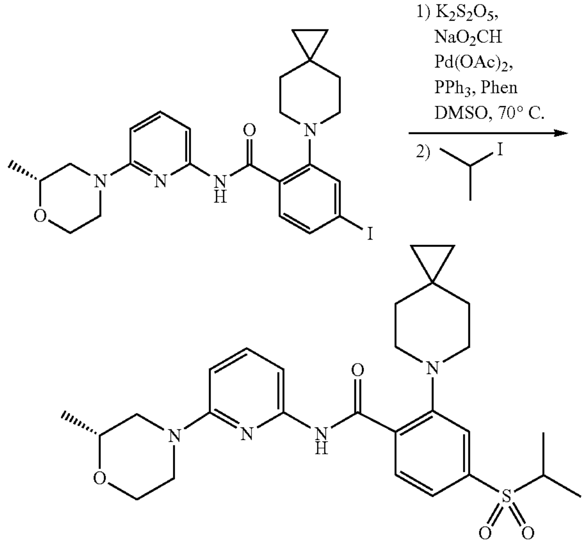

A mixture of (R)-4-iodo-N-(6-(2-methylmorpholino)pyridin-2-yl)-2-(6-azaspiro[2.5]octan-6-yl)benzamide (89 mg, 0.17 mmol, Intermediate 29), triphenylphosphine (6 mg, 0.025 mmol, Aldrich St. Louis, MO USA), 1,10-phenanthroline (24 mg, 0.132 mmol, Aldrich St. Louis, USA), palladium(ii) acetate (5 mg, 0.025 mmol, Strem Chemicals, Inc. Newburyport, MA USA), sodium formate (25 mg, 0.37 mmol, Thermo Fisher Scientific, Grand Island, NY USA), and tetrabutylammonium bromide (59 mg, 0.18 mmol, Aldrich St. Louis, MO USA) in DMSO (2 mL) under $N_2$ was stirred at 70° C. for 3 h. Then, the mixture was cooled to room temperature and isopropyl iodide (0.025 mL, 0.25 mmol, Aldrich St. Louis, MO USA) was added. The mixture was then stirred at room temperature for 18 h. Then, the mixture was diluted with water (20 mL) and was then extracted with EtOAc (2×40 mL). The combined organic extracts were then dried over $Na_2SO_4$ and concentrated. Chromatographic purification of the residue (silica gel, 0%-30% EtOAc/heptane) provided (R)-4-(isopropylsulfonyl)-N-(6-(2-methylmorpholino)pyridin-2-yl)-2-(6-azaspiro[2.5]octan-6-yl)benzamide (46 mg, 0.09 mmol, 36% yield) as a light yellow solid. $^1$H NMR (400 MHz, DMSO-$d_6$) δ 12.63 (s, 1H), 8.31 (d, J=8.22 Hz, 1H), 7.82 (d, J=1.37 Hz, 1H), 7.77 (dd, J=1.56, 8.22 Hz, 1H), 7.57-7.66 (m, 2H), 6.64 (d, J=7.83 Hz, 1H), 4.17 (br d, J=11.93 Hz, 1H), 4.08 (br d, J=12.52 Hz, 1H), 3.93 (dd, J=3.33, 11.35 Hz, 1H), 3.49-3.67 (m, 3H), 3.37 (quin, J=6.65 Hz, 1H), 3.10 (br t, J=5.18 Hz, 4H), 2.85 (dt, J=3.52, 12.32 Hz, 1H), 1.72 (br s, 4H), 1.13-1.28 (m, 9H), 0.39 (s, 4H). m/z (ESI): 513.2 $(M+H)^+$.

TABLE 7

Examples 2-1 to 2-7 were prepared following a similar procedure as described for Example 2

| Ex. # | Chemical Structure | Name | LRMS: (ESI + ve ion) m/z |
|---|---|---|---|
| 2-1 | 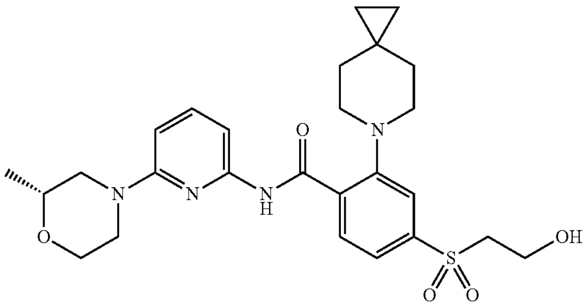 [SMILES: C[C@@H]1CN(c2cccc(NC(=O)c3ccc(S(=O)(=O)CCO)cc3N3CCC4(CC3)CC4)n2)CCO1] | (R)-4-((2-Hydroxyethyl)sulfonyl)-N-(6-(2-methylmorpholino)pyridin-2-yl)-2-(6-azaspiro[2.5]octan-6-yl)benzamide | 515.2 |

TABLE 7-continued

| Examples 2-1 to 2-7 were prepared following a similar procedure as described for Example 2 | | | |
|---|---|---|---|
| Ex. # | Chemical Structure | Name | LRMS: (ESI + ve ion) m/z |
| 2-2 | 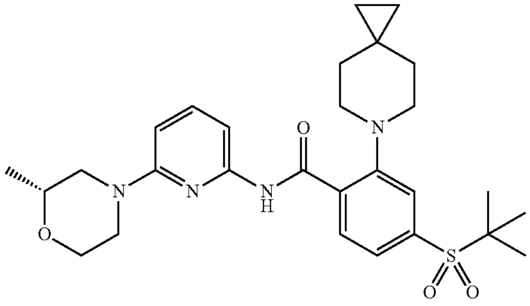 [SMILES: C[C@@H]1CN(c2cccc(NC(=O)c3ccc(S(=O)(=O)C(C)(C)C)cc3N3CCC4(CC3)CC4)n2)CCO1] | (R)-4-(tert-Butylsulfonyl)-N-(6-(2-methylmorpholino)pyridin-2-yl)-2-(6-azaspiro[2.5]octan-6-yl)benzamide | 527.0 |
| 2-3 | 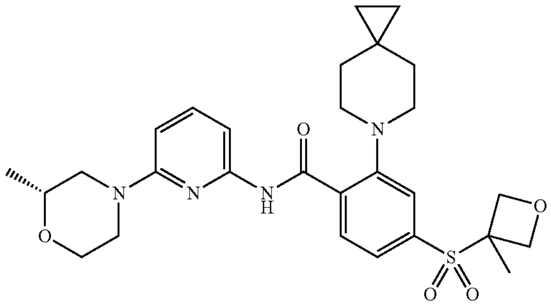 [SMILES: C[C@@H]1CN(c2cccc(NC(=O)c3ccc(S(=O)(=O)C4(C)COC4)cc3N3CCC4(CC3)CC4)n2)CCO1] | (R)-N-(6-(2-Methylmorpholino)pyridin-2-yl)-4-((3-methyloxetan-3-yl)sulfonyl)-2-(6-azaspiro[2.5]octan-6-yl)benzamide | 541.3 |
| 2-4 | 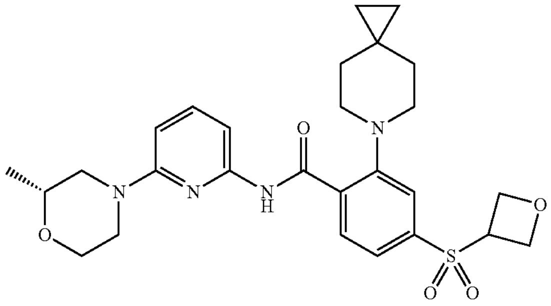 [SMILES: C[C@@H]1CN(c2cccc(NC(=O)c3ccc(S(=O)(=O)C4COC4)cc3N3CCC4(CC3)CC4)n2)CCO1] | (R)-N-(6-(2-Methylmorpholino)pyridin-2-yl)-4-(oxetan-3-ylsulfonyl)-2-(6-azaspiro[2.5]octan-6-yl)benzamide | 527.2 |
| 2-5 | 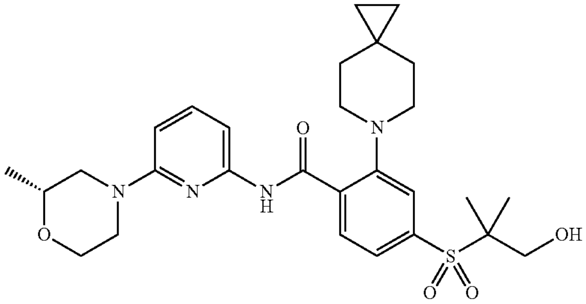 [SMILES: C[C@@H]1CN(c2cccc(NC(=O)c3ccc(S(=O)(=O)C(C)(C)CO)cc3N3CCC4(CC3)CC4)n2)CCO1] | (R)-4-((1-Hydroxy-2-methylpropan-2-yl)sulfonyl)-N-(6-(2-methylmorpholino)pyridin-2-yl)-2-(6-azaspiro[2.5]octan-6-yl)benzamide | 543.2 |

TABLE 7-continued

Examples 2-1 to 2-7 were prepared following a similar procedure as described for Example 2

| Ex. # | Chemical Structure | Name | LRMS: (ESI + ve ion) m/z |
|---|---|---|---|
| 2-6 | 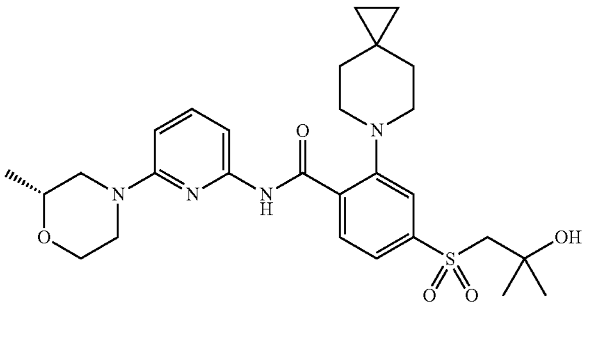 [SMILES: C[C@@H]1CN(c2cccc(NC(=O)c3ccc(S(=O)(=O)CC(C)(C)O)cc3N3CCC4(CC3)CC4)n2)CCO1] | (R)-4-((2-Hydroxy-2-methylpropyl)sulfonyl)-N-(6-(2-methylmorpholino)pyridin-2-yl)-2-(6-azaspiro[2.5]octan-6-yl)benzamide | 543.2 |
| 2-7 | 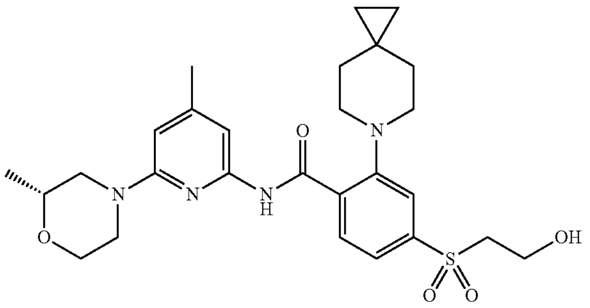 [SMILES: Cc1cc(NC(=O)c2ccc(S(=O)(=O)CCO)cc2N2CCC3(CC2)CC3)nc(N2CCO[C@H](C)C2)c1] | (R)-4-((2-Hydroxyethyl)sulfonyl)-N-(4-methyl-6-(2-methylmorpholino)pyridin-2-yl)-2-(6-azaspiro[2.5]octan-6-yl)benzamide | 529.2 |

Method C (SNAr)

Example 3: (R)—N-(6-(3-Hydroxypiperidin-1-yl)pyridin-2-yl)-4-((1-methylcyclopropane)-1-sulfonamido)-2-(6-azaspiro[2.5]octan-6-yl)benzamide

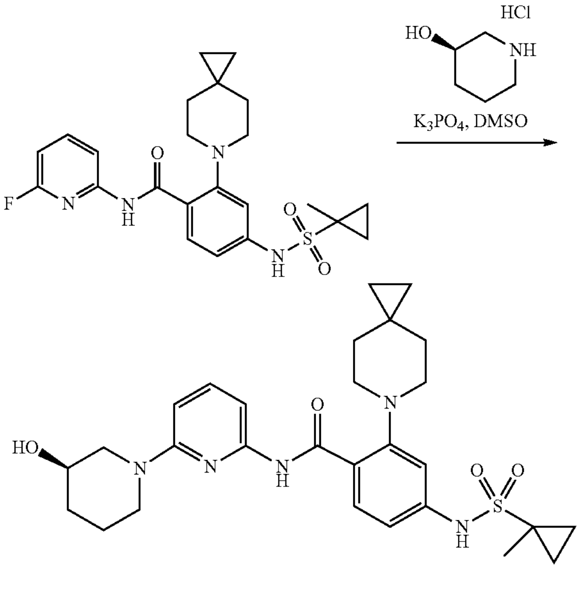

To a solution of N-(6-fluoropyridin-2-yl)-4-((1-methylcyclopropane)-1-sulfonamido)-2-(6-azaspiro[2.5]octan-6-yl)benzamide (0.20 g, 0.44 mmol, Intermediate 17) in DMSO (2 mL) was added (R)-piperidin-3-ol hydrochloride (0.060 g, 0.44 mmol, Essen Scientific) and potassium phosphate tribasic (0.278 g, 1.31 mmol). The reaction mixture was stirred at 130° C. for 16 h, before cooled, quenched with water (5 mL), and extracted with ethyl acetate (2×10 mL). The combined organic extracts were washed with brine solution (10 mL), dried over $Na_2SO_4$, filtered, and concentrated under reduced pressure. The crude residue was purified by column chromatography over silica gel using 30-50% ethyl acetate in hexanes to give the title compound (0.1 g, 43% yield) as an off-white solid. $^1H$ NMR (400 MHz, DMSO-$d_6$) δ 12.85 (s, 1H), 10.23 (s, 1H), 8.06 (d, J=8.6 Hz, 1H), 7.52 (d, J=6.1 Hz, 2H), 7.34 (s, 1H), 7.14 (d, J=8.6 Hz, 1H), 6.65-6.34 (m, 1H), 4.78 (d, J=4.6 Hz, 1H), 4.13 (d, J=11.7 Hz, 1H), 4.05-3.85 (m, 1H), 3.63-3.46 (m, 1H), 3.10-2.74 (m, 6H), 1.99-1.58 (m, 5H), 1.42 (d, J=13.8 Hz, 5H), 1.20 (s, 3H), 0.84 (d, J=5.6 Hz, 2H), 0.38 (s, 4H). m/z (ESI): 540.2 $(M+H)^+$.

TABLE 8

| Ex. # | Chemical Structure | Name | LRMS: (ESI + ve ion) m/z |
|---|---|---|---|
| Examples 3-1 to 3-23 were prepared following a similar procedure as described for Example 3 | | | |
| 3-1 | 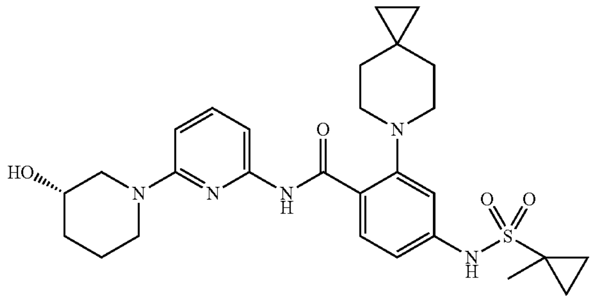 | (S)-N-(6-(3-Hydroxypiperidin-1-yl)pyridin-2-yl)-4-((1-methylcyclopropane)-1-sulfonamido)-2-(6-azaspiro[2.5]octan-6-yl)benzamide | 540.2 |
| 3-2 | 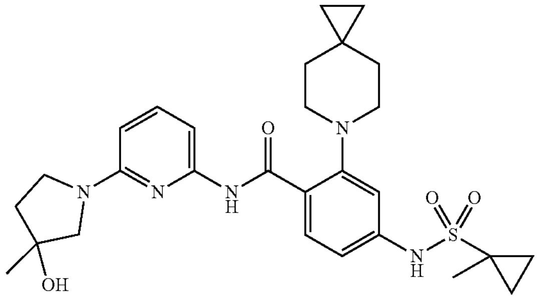 [SMILES: CC1(O)CCN(c2cccc(NC(=O)c3ccc(NS(=O)(=O)C4(C)CC4)cc3N3CCC4(CC3)CC4)n2)C1] | N-(6-(3-Hydroxy-3-methylpyrrolidin-1-yl)pyridin-2-yl)-4-((1-methylcyclopropane)-1-sulfonamido)-2-(6-azaspiro[2.5]octan-6-yl)benzamide | 540.2 |
| 3-3 | 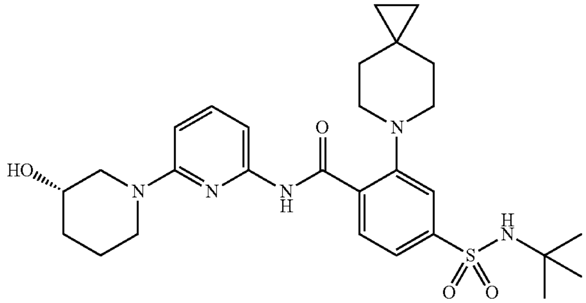 [SMILES: CC(C)(C)NS(=O)(=O)c1ccc(C(=O)Nc2cccc(N3CCC[C@H](O)C3)n2)c(N2CCC3(CC2)CC3)c1] | (S)-4-(N-(tert-Butyl)sulfamoyl)-N-(6-(3-hydroxypiperidin-1-yl)pyridin-2-yl)-2-(6-azaspiro[2.5]octan-6-yl)benzamide | 542.3 |
| 3-4 | 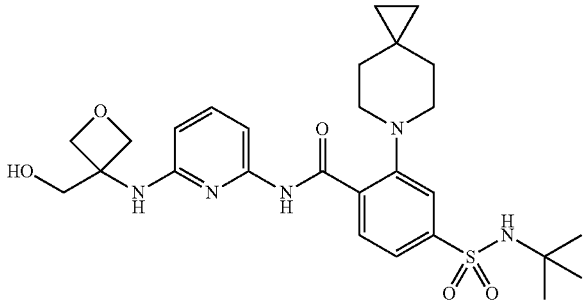 [SMILES: CC(C)(C)NS(=O)(=O)c1ccc(C(=O)Nc2cccc(NC3(CO)COC3)n2)c(N2CCC3(CC2)CC3)c1] | 4-(N-(tert-Butyl)sulfamoyl)-N-(6-((3-(hydroxymethyl)oxetan-3-yl)amino)pyridin-2-yl)-2-(6-azaspiro[2.5]octan-6-yl)benzamide | 544.3 |
| 3-5 | 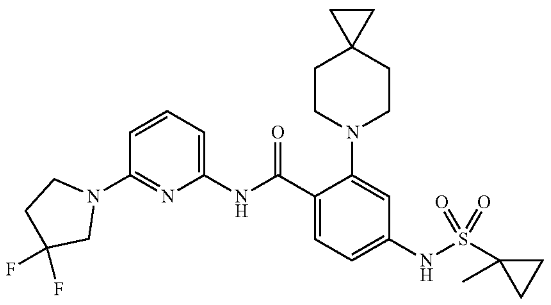 [SMILES: CC1(S(=O)(=O)Nc2ccc(C(=O)Nc3cccc(N4CCC(F)(F)C4)n3)c(N3CCC4(CC3)CC4)c2)CC1] | N-(6-(3,3-Difluoropyrrolidin-1-yl)pyridin-2-yl)-4-((1-methylcyclopropane)-1-sulfonamido)-2-(6-azaspiro[2.5]octan-6-yl)benzamide | 546.2 |

TABLE 8-continued

| Examples 3-1 to 3-23 were prepared following a similar procedure as described for Example 3 | | | |
|---|---|---|---|
| Ex. # | Chemical Structure | Name | LRMS: (ESI + ve ion) m/z |
| 3-6 | 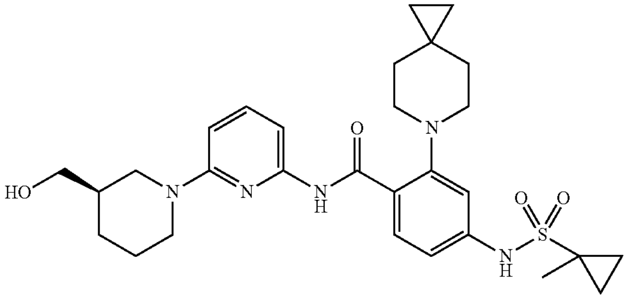 [SMILES: CC1(S(=O)(=O)Nc2ccc(C(=O)Nc3cccc(N4CCC[C@@H](CO)C4)n3)c(N3CCC4(CC3)CC4)c2)CC1] | (R)-N-(6-(3-(Hydroxymethyl)piperidin-1-yl)pyridin-2-yl)-4-((1-methylcyclopropane)-1-sulfonamido)-2-(6-azaspiro[2.5]octan-6-yl)benzamide | 554.2 |
| 3-7 | 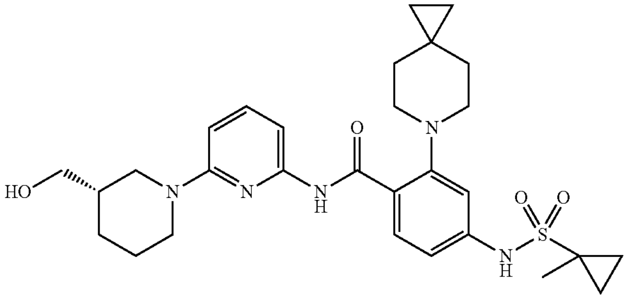 | (S)-N-(6-(3-(Hydroxymethyl)piperidin-1-yl)pyridin-2-yl)-4-((1-methylcyclopropane)-1-sulfonamido)-2-(6-azaspiro[2.5]octan-6-yl)benzamide | 554.2 |
| 3-8 | 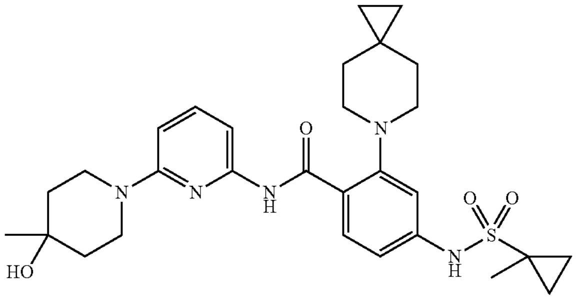 | N-(6-(4-Hydroxy-4-methylpiperidin-1-yl)pyridin-2-yl)-4-((1-methylcyclopropane)-1-sulfonamido)-2-(6-azaspiro[2.5]octan-6-yl)benzamide | 554.2 |
| 3-9 | 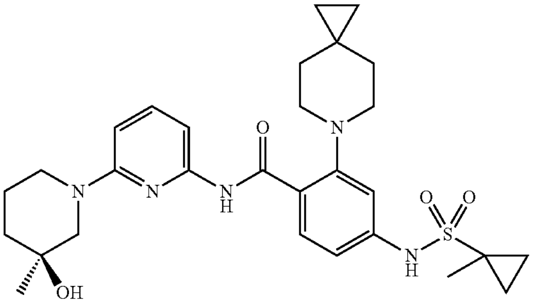 [SMILES: CC1(S(=O)(=O)Nc2ccc(C(=O)Nc3cccc(N4CCC[C@](C)(O)C4)n3)c(N3CCC4(CC3)CC4)c2)CC1] | (S)-N-(6-(3-Hydroxy-3-methylpiperidin-1-yl)pyridin-2-yl)-4-((1-methylcyclopropane)-1-sulfonamido)-2-(6-azaspiro[2.5]octan-6-yl)benzamide | 554.2 |

TABLE 8-continued

| Ex. # | Chemical Structure | Name | LRMS: (ESI + ve ion) m/z |
|---|---|---|---|
| | Examples 3-1 to 3-23 were prepared following a similar procedure as described for Example 3 | | |
| 3-10 | 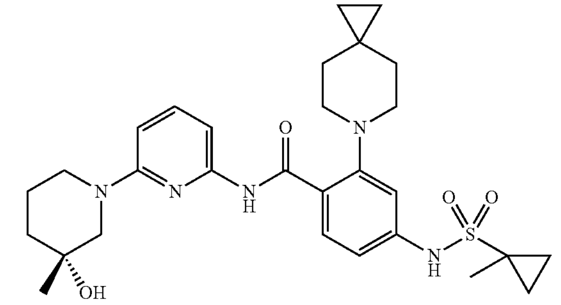 [SMILES: CC1(S(=O)(=O)Nc2ccc(C(=O)Nc3cccc(N4CCC[C@@](C)(O)C4)n3)c(N3CCC4(CC3)CC4)c2)CC1] | (R)-N-(6-(3-Hydroxy-3-methylpiperidin-1-yl)pyridin-2-yl)-4-((1-methylcyclopropane)-1-sulfonamido)-2-(6-azaspiro[2.5]octan-6-yl)benzamide | 554.2 |
| 3-11 | 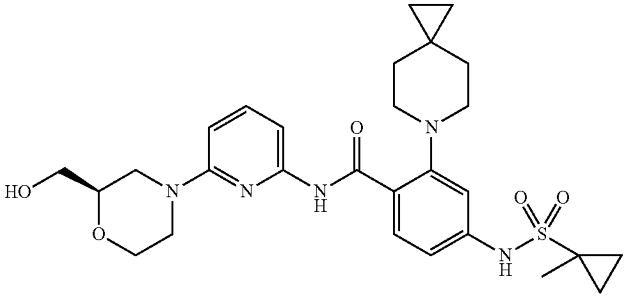 [SMILES: CC1(S(=O)(=O)Nc2ccc(C(=O)Nc3cccc(N4CCO[C@@H](CO)C4)n3)c(N3CCC4(CC3)CC4)c2)CC1] | (R)-N-(6-(2-(Hydroxymethyl)morpholino)pyridin-2-yl)-4-((1-methylcyclopropane)-1-sulfonamido)-2-(6-azaspiro[2.5]octan-6-yl)benzamide | 556.2 |
| 3-12 | 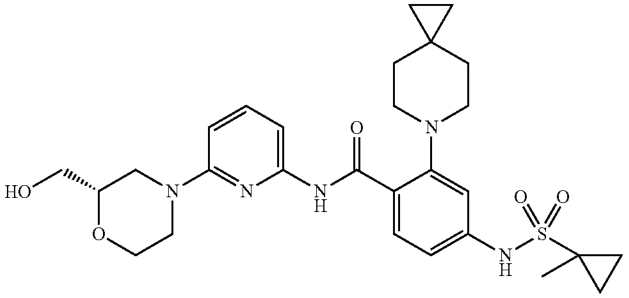 [SMILES: CC1(S(=O)(=O)Nc2ccc(C(=O)Nc3cccc(N4CCO[C@H](CO)C4)n3)c(N3CCC4(CC3)CC4)c2)CC1] | (S)-N-(6-(2-(Hydroxymethyl)morpholino)pyridin-2-yl)-4-((1-methylcyclopropane)-1-sulfonamido)-2-(6-azaspiro[2.5]octan-6-yl)benzamide | 556.2 |
| 3-13 | 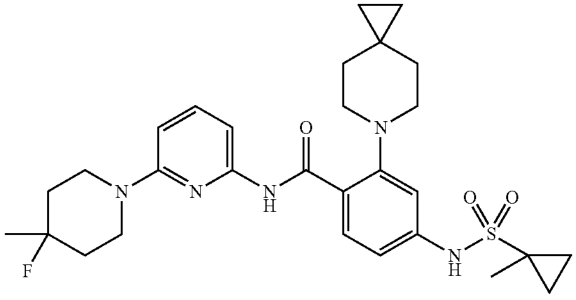 [SMILES: CC1(F)CCN(c2cccc(NC(=O)c3ccc(NS(=O)(=O)C4(C)CC4)cc3N3CCC4(CC3)CC4)n2)CC1] | N-(6-(4-Fluoro-4-methylpiperidin-1-yl)pyridin-2-yl)-4-((1-methylcyclopropane)-1-sulfonamido)-2-(6-azaspiro[2.5]octan-6-yl)benzamide | 556.3 |
| 3-14 | 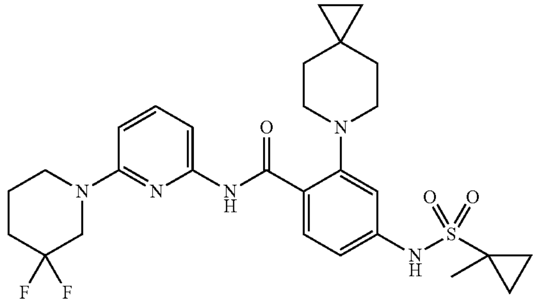 [SMILES: CC1(S(=O)(=O)Nc2ccc(C(=O)Nc3cccc(N4CCCC(F)(F)C4)n3)c(N3CCC4(CC3)CC4)c2)CC1] | N-(6-(3,3-Difluoropiperidin-1-yl)pyridin-2-yl)-4-((1-methylcyclopropane)-1-sulfonamido)-2-(6-azaspiro[2.5]octan-6-yl)benzamide | 560.2 |

TABLE 8-continued

Examples 3-1 to 3-23 were prepared following a similar procedure as described for Example 3

| Ex. # | Chemical Structure | Name | LRMS: (ESI + ve ion) m/z |
|---|---|---|---|
| 3-15 | 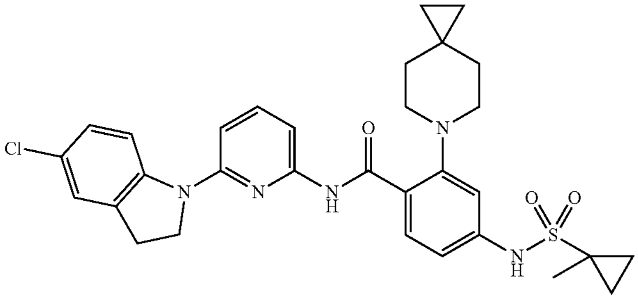 [SMILES: CC1(S(=O)(=O)Nc2ccc(C(=O)Nc3cccc(N4CCc5cc(Cl)ccc54)n3)c(N3CCC4(CC3)CC4)c2)CC1] | N-(6-(5-Chloroindolin-1-yl)pyridin-2-yl)-4-((1-methylcyclopropane)-1-sulfonamido)-2-(6-azaspiro[2.5]octan-6-yl)benzamide | 592.2 |
| 3-16 | 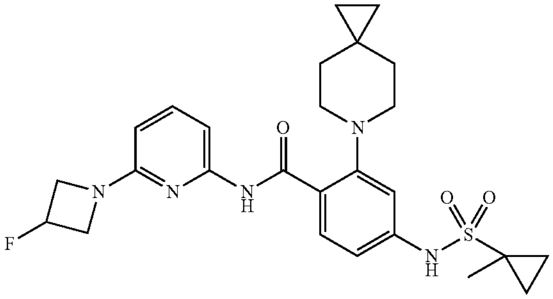 [SMILES: CC1(S(=O)(=O)Nc2ccc(C(=O)Nc3cccc(N4CC(F)C4)n3)c(N3CCC4(CC3)CC4)c2)CC1] | N-(6-(3-Fluoroazetidin-1-yl)pyridin-2-yl)-4-((1-methylcyclopropane)-1-sulfonamido)-2-(6-azaspiro[2.5]octan-6-yl)benzamide | 514.2 |
| 3-17 | 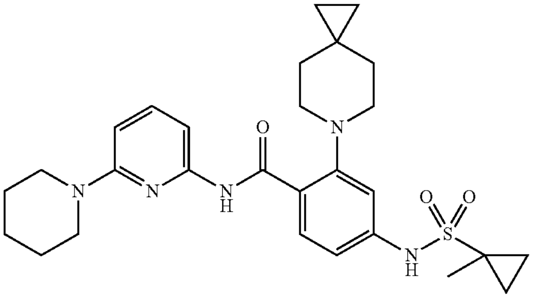 [SMILES: CC1(S(=O)(=O)Nc2ccc(C(=O)Nc3cccc(N4CCCCC4)n3)c(N3CCC4(CC3)CC4)c2)CC1] | 4-((1-Methylcyclopropane)-1-sulfonamido)-N-(6-(piperidin-1-yl)pyridin-2-yl)-2-(6-azaspiro[2.5]octan-6-yl)benzamide | 524.2 |
| 3-18 | 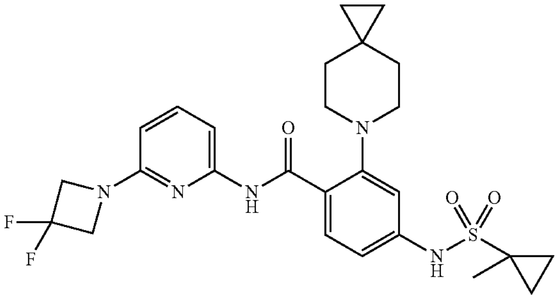 [SMILES: CC1(S(=O)(=O)Nc2ccc(C(=O)Nc3cccc(N4CC(F)(F)C4)n3)c(N3CCC4(CC3)CC4)c2)CC1] | N-(6-(3,3-Difluoroazetidin-1-yl)pyridin-2-yl)-4-((1-methylcyclopropane)-1-sulfonamido)-2-(6-azaspiro[2.5]octan-6-yl)benzamide | 532.2 |
| 3-19 | 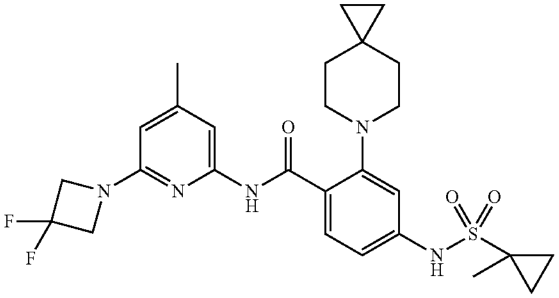 [SMILES: Cc1cc(NC(=O)c2ccc(NS(=O)(=O)C3(C)CC3)cc2N2CCC3(CC2)CC3)nc(N2CC(F)(F)C2)c1] | N-(6-(3,3-Difluoroazetidin-1-yl)-4-methylpyridin-2-yl)-4-((1-methylcyclopropane)-1-sulfonamido)-2-(6-azaspiro[2.5]octan-6-yl)benzamide | 546.2 |

TABLE 8-continued

| Examples 3-1 to 3-23 were prepared following a similar procedure as described for Example 3 | | | |
|---|---|---|---|
| Ex. # | Chemical Structure | Name | LRMS: (ESI + ve ion) m/z |
| 3-20 | 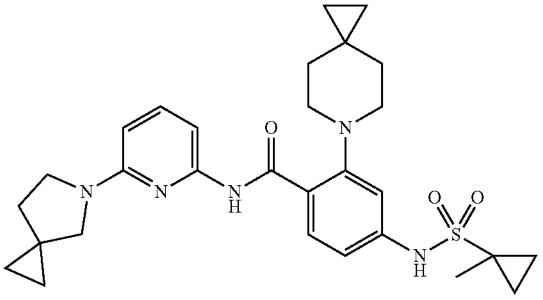 [SMILES: CC1(S(=O)(=O)Nc2ccc(C(=O)Nc3cccc(N4CCC5(CC5)C4)n3)c(N3CCC4(CC3)CC4)c2)CC1] | N-(6-(5-Azaspiro[2.4]heptan-5-yl)pyridin-2-yl)-4-((1-methylcyclopropane)-1-sulfonamido)-2-(6-azaspiro[2.5]octan-6-yl)benzamide | 536.2 |
| 3-21 | 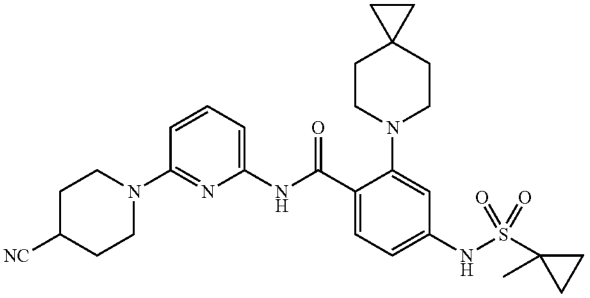 [SMILES: CC1(S(=O)(=O)Nc2ccc(C(=O)Nc3cccc(N4CCC(C#N)CC4)n3)c(N3CCC4(CC3)CC4)c2)CC1] | N-(6-(4-Cyanopiperidin-1-yl)pyridin-2-yl)-4-((1-methylcyclopropane)-1-sulfonamido)-2-(6-azaspiro[2.5]octan-6-yl)benzamide | 549.2 |
| 3-22 | 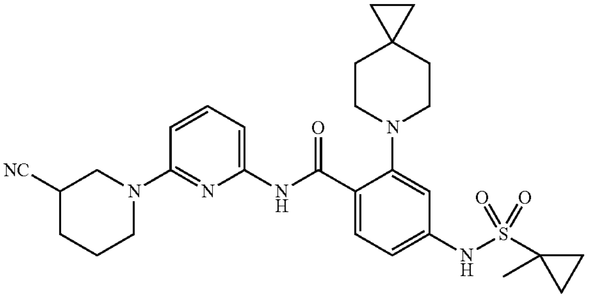 [SMILES: CC1(S(=O)(=O)Nc2ccc(C(=O)Nc3cccc(N4CCCC(C#N)C4)n3)c(N3CCC4(CC3)CC4)c2)CC1] | N-(6-(3-Cyanopiperidin-1-yl)pyridin-2-yl)-4-((1-methylcyclopropane)-1-sulfonamido)-2-(6-azaspiro[2.5]octan-6-yl)benzamide | 549.2 |
| 3-23 | 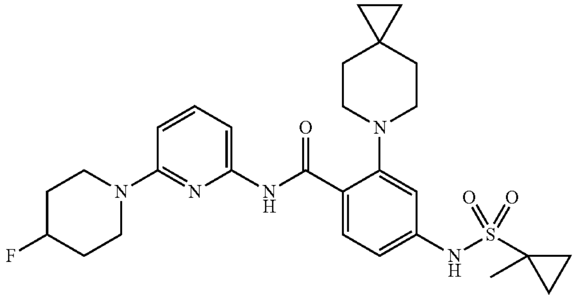 [SMILES: CC1(S(=O)(=O)Nc2ccc(C(=O)Nc3cccc(N4CCC(F)CC4)n3)c(N3CCC4(CC3)CC4)c2)CC1] | N-(6-(4-Fluoropiperidin-1-yl)pyridin-2-yl)-4-((1-methylcyclopropane)-1-sulfonamido)-2-(6-azaspiro[2.5]octan-6-yl)benzamide | 542.2 |

Method D (Amide Coupling)

Example 4: (R)—N-(6-(3-Hydroxypiperidin-1-yl)pyridin-2-yl)-4-((methylsulfonyl)methyl)-2-(6-azaspiro[2.5]octan-6-yl)benzamide

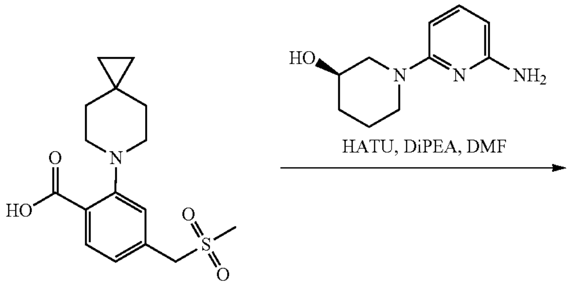

-continued

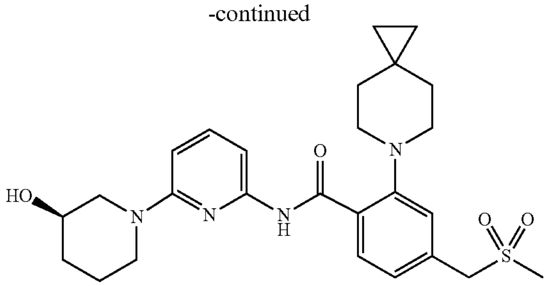

To a solution of 4-((methylsulfonyl)methyl)-2-(6-azaspiro[2.5]octan-6-yl)benzoic acid (200 mg, 0.618 mmol, Intermediate 14) in DMF (3 mL) were added (R)-1-(6-aminopyridin-2-yl)piperidin-3-ol (0.143 g, 0.742 mmol, Intermediate 4-5), HATU (353 mg, 0.928 mmol) and DIPEA (216 μL, 1.24 mmol) and stirred at room temperature for 12 h. The reaction mixture was quenched with water (20 mL) and extracted with ethyl acetate (3×20 mL). The combined organic extracts were washed with brine (20 mL), dried over $Na_2SO_4$, filtered, and concentrated under reduced pressure. The crude residue was purified by column chromatography over silica gel using 50% ethyl acetate in hexanes to give the title compound (0.20 g, 65% yield) as a yellow solid. $^1H$ NMR (400 MHz, DMSO-$d_6$): δ 13.06 (s, 1H), 8.15-8.13 (m, 1H), 7.58-7.50 (m, 3H), 7.37 (d, J=7.8 Hz, 1H), 6.55 (d, J=8.2 Hz, 1H), 4.80 (dd, J=7.0, 3.6 Hz, 1H), 4.59 (s, 2H), 4.13 (d, J=12.4 Hz, 1H), 3.94 (d, J=12.4 Hz, 1H), 3.60-2.80 (m, 7H), 1.73 (b s, 4H), 1.42 (b s, 4H), 1.42 (q, J=6.4 Hz, 3H), 0.39 (s, 4H). m/z (ESI): 499.1 $(M+H)^+$.

TABLE 9

Examples 4-1 to 4-19 were prepared following a similar procedure as described for Example 4

| Ex. # | Chemical Structure | Name | LRMS: (ESI + ve ion) m/z |
|---|---|---|---|
| 4-1 | 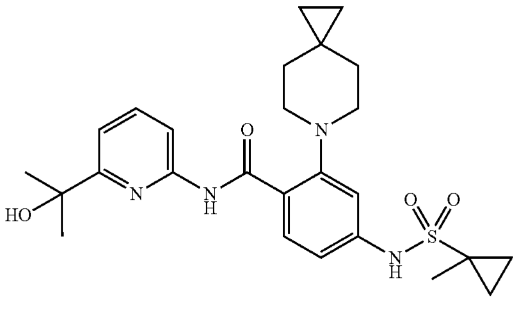 [SMILES: CC(C)(O)c1cccc(NC(=O)c2ccc(NS(=O)(=O)C3(C)CC3)cc2N2CCC3(CC2)CC3)n1] | N-(6-(2-Hydroxypropan-2-yl)pyridin-2-yl)-4-((1-methylcyclopropane)-1-sulfonamido)-2-(6-azaspiro[2.5]octan-6-yl)benzamide | 499.3 |
| 4-2 | 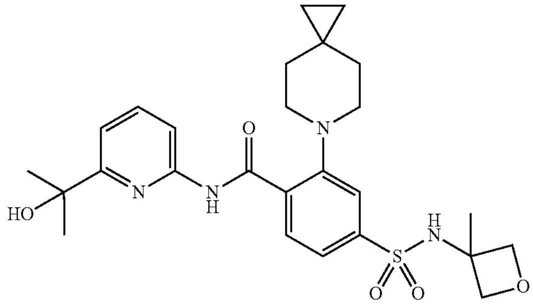 [SMILES: CC1(NS(=O)(=O)c2ccc(C(=O)Nc3cccc(C(C)(C)O)n3)c(N3CCC4(CC3)CC4)c2)COC1] | N-(6-(2-Hydroxypropan-2-yl)pyridin-2-yl)-4-(N-(3-methyloxetan-3-yl)sulfamoyl)-2-(6-azaspiro[2.5]octan-6-yl)benzamide | 515.2 |

TABLE 9-continued

| Examples 4-1 to 4-19 were prepared following a similar procedure as described for Example 4 | | | |
|---|---|---|---|
| Ex. # | Chemical Structure | Name | LRMS: (ESI + ve ion) m/z |
| 4-3 | 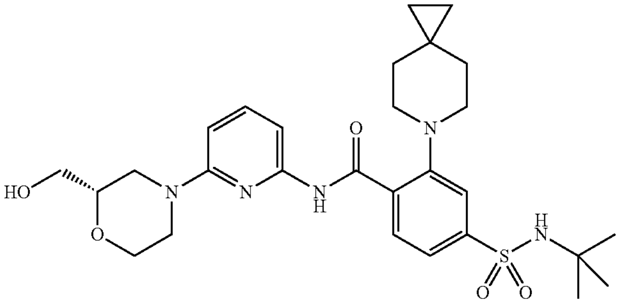 [SMILES: CC(C)(C)NS(=O)(=O)c1ccc(C(=O)Nc2cccc(N3CCO[C@H](CO)C3)n2)c(N2CCC3(CC2)CC3)c1] | (S)-4-(N-(tert-Butyl)sulfamoyl)-N-(6-(2-(hydroxymethyl)morpholino)pyridin-2-yl)-2-(6-azaspiro[2.5]octan-6-yl)benzamide | 558.0 |
| 4-4 | 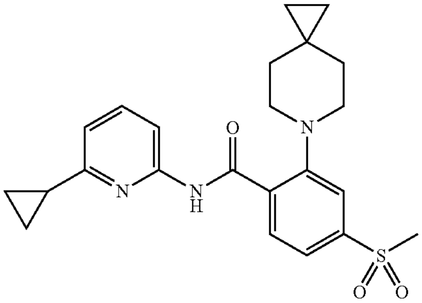 [SMILES: CS(=O)(=O)c1ccc(C(=O)Nc2cccc(C3CC3)n2)c(N2CCC3(CC2)CC3)c1] | N-(6-Cyclopropylpyridin-2-yl)-4-(methylsulfonyl)-2-(6-azaspiro[2.5]octan-6-yl)benzamide | 426.2 |
| 4-5 | 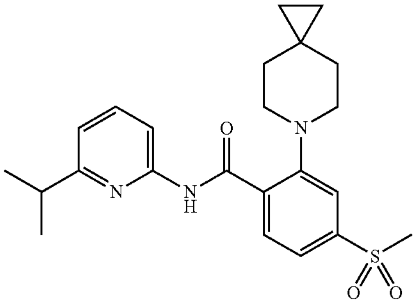 [SMILES: CC(C)c1cccc(NC(=O)c2ccc(S(C)(=O)=O)cc2N2CCC3(CC2)CC3)n1] | N-(6-Isopropylpyridin-2-yl)-4-(methylsulfonyl)-2-(6-azaspiro[2.5]octan-6-yl)benzamide | 428.2 |
| 4-6 | 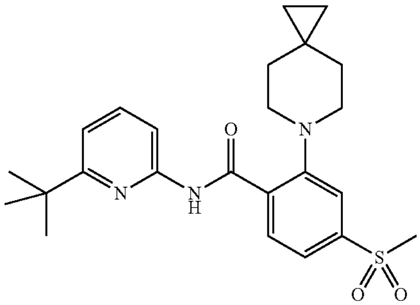 [SMILES: CC(C)(C)c1cccc(NC(=O)c2ccc(S(C)(=O)=O)cc2N2CCC3(CC2)CC3)n1] | N-(6-(tert-Butyl)pyridin-2-yl)-4-(methylsulfonyl)-2-(6-azaspiro[2.5]octan-6-yl)benzamide | 442.2 |
| 4-7 | 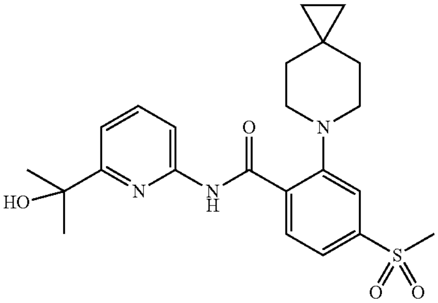 [SMILES: CC(C)(O)c1cccc(NC(=O)c2ccc(S(C)(=O)=O)cc2N2CCC3(CC2)CC3)n1] | N-(6-(2-Hydroxypropan-2-yl)pyridin-2-yl)-4-(methylsulfonyl)-2-(6-azaspiro[2.5]octan-6-yl)benzamide | 444.2 |

TABLE 9-continued

| Examples 4-1 to 4-19 were prepared following a similar procedure as described for Example 4 | | | |
|---|---|---|---|
| Ex. # | Chemical Structure | Name | LRMS: (ESI + ve ion) m/z |
| 4-8 | 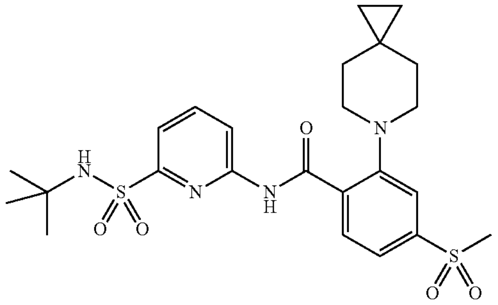 [SMILES: CC(C)(C)NS(=O)(=O)c1cccc(NC(=O)c2ccc(S(C)(=O)=O)cc2N2CCC3(CC2)CC3)n1] | N-(6-(N-(tert-Butyl)sulfamoyl)pyridin-2-yl)-4-(methylsulfonyl)-2-(6-azaspiro[2.5]octan-6-yl)benzamide | 521.2 |
| 4-9 | 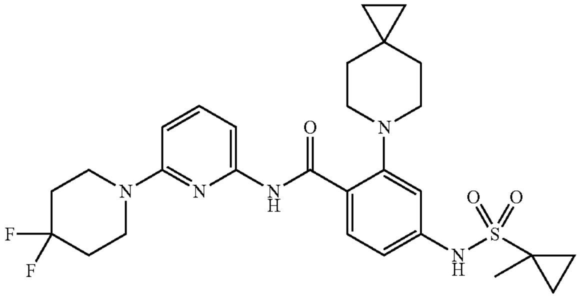 [SMILES: CC1(S(=O)(=O)Nc2ccc(C(=O)Nc3cccc(N4CCC(F)(F)CC4)n3)c(N3CCC4(CC3)CC4)c2)CC1] | N-(6-(4,4-Difluoropiperidin-1-yl)pyridin-2-yl)-4-((1-methylcyclopropane)-1-sulfonamido)-2-(6-azaspiro[2.5]octan-6-yl)benzamide | 560.2 |
| 4-10 | 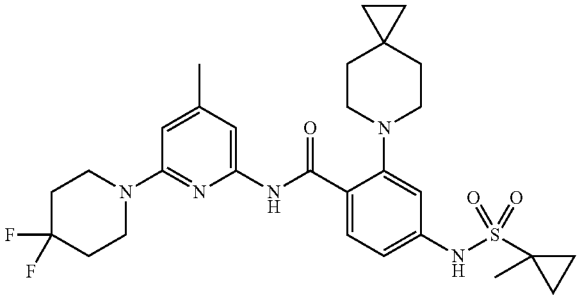 | N-(6-(4,4-Difluoropiperidin-1-yl)-4-methylpyridin-2-yl)-4-((1-methylcyclopropane)-1-sulfonamido)-2-(6-azaspiro[2.5]octan-6-yl)benzamide | 574.2 |
| 4-11 | 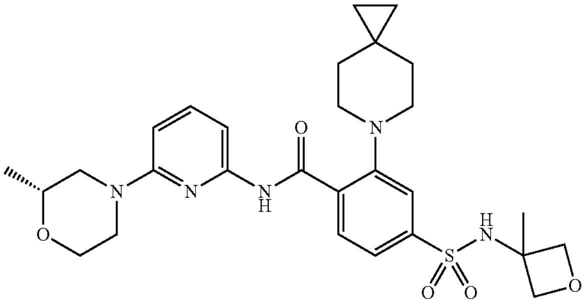 [SMILES: C[C@@H]1CN(c2cccc(NC(=O)c3ccc(S(=O)(=O)NC4(C)COC4)cc3N3CCC4(CC3)CC4)n2)CCO1] | (R)-N-(6-(2-Methylmorpholino)pyridin-2-yl)-4-(N-(3-methyloxetan-3-yl)sulfamoyl)-2-(6-azaspiro[2.5]octan-6-yl)benzamide | 556.2 |

TABLE 9-continued

| Ex. # | Chemical Structure | Name | LRMS: (ESI + ve ion) m/z |
|---|---|---|---|
| | Examples 4-1 to 4-19 were prepared following a similar procedure as described for Example 4 | | |
| 4-12 | 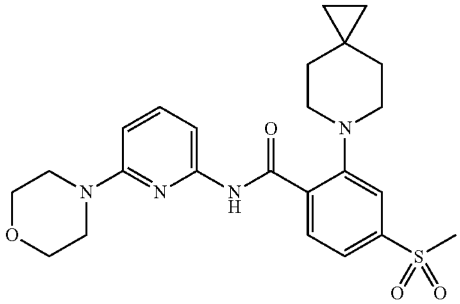 [SMILES: CS(=O)(=O)c1ccc(C(=O)Nc2cccc(N3CCOCC3)n2)c(N2CCC3(CC2)CC3)c1] | 4-(Methylsulfonyl)-N-(6-morpholinopyridin-2-yl)-2-(6-azaspiro[2.5]octan-6-yl)benzamide | 471.2 |
| 4-13 | 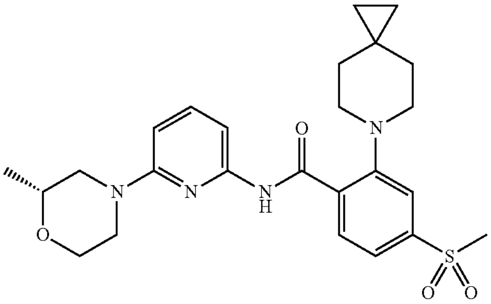 | (R)-N-(6-(2-Methylmorpholino)pyridin-2-yl)-4-(methylsulfonyl)-2-(6-azaspiro[2.5]octan-6-yl)benzamide | 485.1 |
| 4-14 | 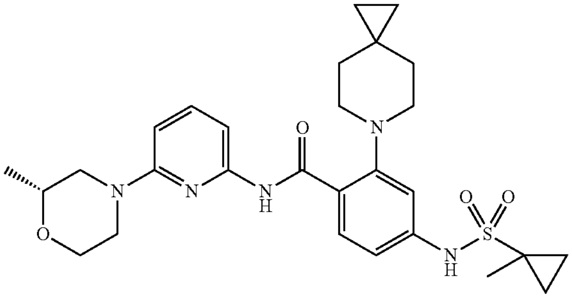 [SMILES: C[C@@H]1CN(c2cccc(NC(=O)c3ccc(NS(=O)(=O)C4(C)CC4)cc3N3CCC4(CC3)CC4)n2)CCO1] | (R)-4-((1-Methylcyclopropane)-1-sulfonamido)-N-(6-(2-methylmorpholino)pyridin-2-yl)-2-(6-azaspiro[2.5]octan-6-yl)benzamide | 540.2 |
| 4-15 | 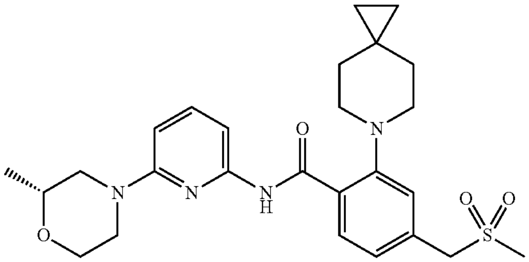 | (R)-N-(6-(2-Methylmorpholino)pyridin-2-yl)-4-((methylsulfonyl)methyl)-2-(6-azaspiro[2.5]octan-6-yl)benzamide | 499.2 |
| 4-16 | 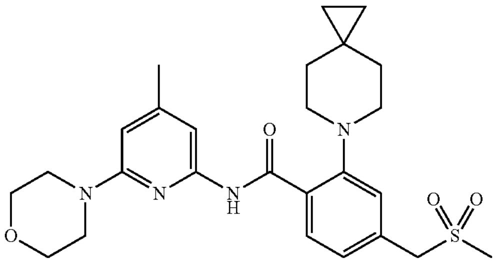 [SMILES: Cc1cc(NC(=O)c2ccc(CS(C)(=O)=O)cc2N2CCC3(CC2)CC3)nc(N2CCOCC2)c1] | N-(4-Methyl-6-morpholinopyridin-2-yl)-4-((methylsulfonyl)methyl)-2-(6-azaspiro[2.5]octan-6-yl)benzamide | 499.2 |

TABLE 9-continued

Examples 4-1 to 4-19 were prepared following a similar procedure as described for Example 4

| Ex. # | Chemical Structure | Name | LRMS: (ESI + ve ion) m/z |
|---|---|---|---|
| 4-17 | 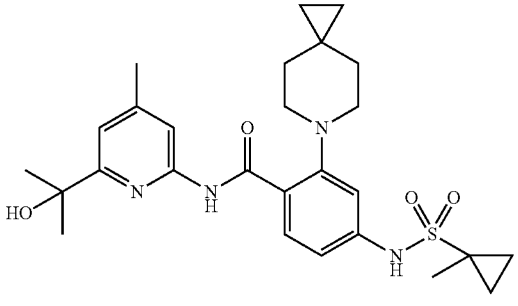 [SMILES: Cc1cc(NC(=O)c2ccc(NS(=O)(=O)C3(C)CC3)cc2N2CCC3(CC2)CC3)nc(C(C)(C)O)c1] | N-(6-(2-Hydroxypropan-2-yl)-4-methylpyridin-2-yl)-4-((1-methylcyclopropane)-1-sulfonamido)-2-(6-azaspiro[2.5]octan-6-yl)benzamide | 513.2 |
| 4-18 | 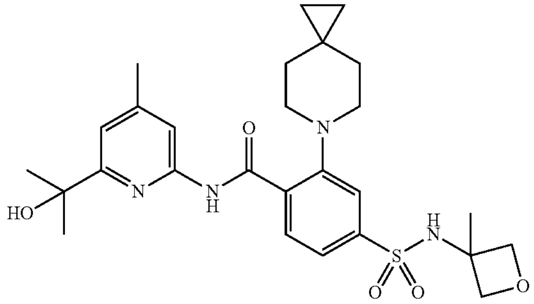 [SMILES: Cc1cc(NC(=O)c2ccc(S(=O)(=O)NC3(C)COC3)cc2N2CCC3(CC2)CC3)nc(C(C)(C)O)c1] | N-(6-(2-Hydroxypropan-2-yl)-4-methylpyridin-2-yl)-4-(N-(3-methyloxetan-3-yl)sulfamoyl)-2-(6-azaspiro[2.5]octan-6-yl)benzamide | 529.3 |
| 4-19 | 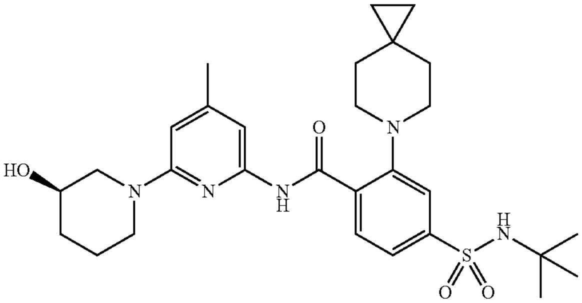 [SMILES: Cc1cc(NC(=O)c2ccc(S(=O)(=O)NC(C)(C)C)cc2N2CCC3(CC2)CC3)nc(N2CCC[C@@H](O)C2)c1] | (R)-4-(N-(tert-Butyl)sulfamoyl)-N-(6-(3-hydroxypiperidin-1-yl)-4-methylpyridin-2-yl)-2-(6-azaspiro[2.5]octan-6-yl)benzamide | 556.1 |

Method E (Cu-catalyzed Sulfonamide Formation)

Example 5: 4-((2-Hydroxyethyl)sulfonamido)-2-(6-azaspiro[2.5]octan-6-yl)-N-(6-(3,3,3-trifluoropropoxy)pyridin-2-yl)benzamide

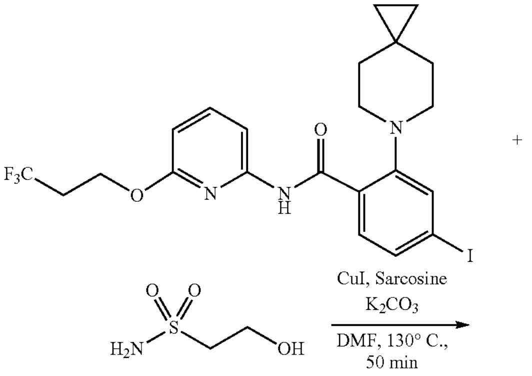

-continued

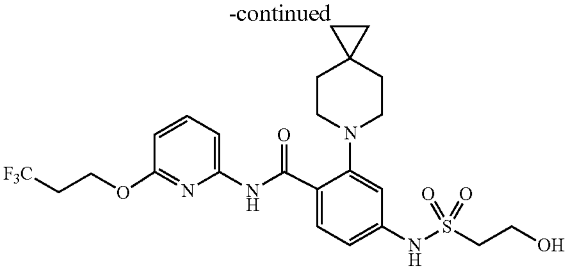

2-Hydroxyethane-1-sulfonamide (0.741 g, 5.92 mmol, Wuxi AppTec), sarcosine (0.172 g, 1.93 mmol, Ark Pharm, Inc.), copper(I) iodide (0.241 g, 1.26 mmol, Sigma-Aldrich Corporation), potassium carbonate (2.78 g, 20.1 mmol, Thermo Fisher Scientific) and 4-iodo-2-(6-azaspiro[2.5]octan-6-yl)-N-(6-(3,3,3-trifluoropropoxy)pyridin-2-yl)benzamide (2.74 g, 5.02 mmol, Intermediate 38) were combined in degassed dry N,N-dimethylformamide (5 mL) under argon and heated to 130° C. for 50 min. The reaction was cooled to ambient temperature, water (100 mL) and ethyl acetate (150 mL) were added and the phases mixed and separated. The organic layer was washed with satd $NH_4Cl$:$NH_4OH$:$H_2O$ (1:1:8, 2×75 mL) and evaporated to dryness under reduced pressure. The crude product was suspended in toluene (30 mL) and heated to 90° C. for 15 min. The mixture was cooled to ambient temperature and the solids were filtered off and dried under a stream of nitrogen. The white solids were suspended in water (100 mL) and heated to 90° C. for 20 minutes. The mixture was cooled to ambient temperature and the solids dried under a stream of nitrogen to give 4-((2-hydroxyethyl)sulfonamido)-2-(6-azaspiro[2.5]octan-6-yl)-N-(6-(3,3,3-trifluoropropoxy)pyridin-2-yl)benzamide (2.41 g, 4.44 mmol, 88% yield). $^1H$ NMR (500 MHz, DMSO-$d_6$) δ 13.18 (s, 1H), 10.19 (br s, 1H), 8.08 (d, J=8.72 Hz, 1H), 7.91 (d, J=7.80 Hz, 1H), 7.76 (t, J=7.96 Hz, 1H), 7.29 (d, J=1.99 Hz, 1H), 7.14 (dd, J=2.07, 8.64 Hz, 1H), 6.57 (d, J=7.96 Hz, 1H), 4.93 (br s, 1H), 4.52 (t, J=6.12 Hz, 2H), 3.77 (t, J=6.43 Hz, 2H), 3.37 (t, J=6.43 Hz, 2H), 3.00 (br t, J=4.74 Hz, 4H), 2.80-2.87 (m, 2H), 1.74 (br s, 4H), 0.39 (s, 4H). m/z (ESI): 543.2.2 $(M+H)^+$.

Example 6: N-(6-(4,4-Difluoropiperidin-1-yl)-4-methylpyridin-2-yl)-4-((2-hydroxyethyl)sulfonamido)-2-(6-azaspiro[2.5]octan-6-yl)benzamide

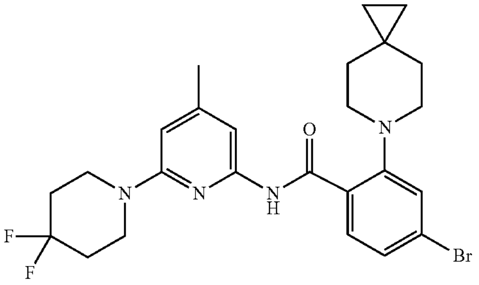

+

-continued

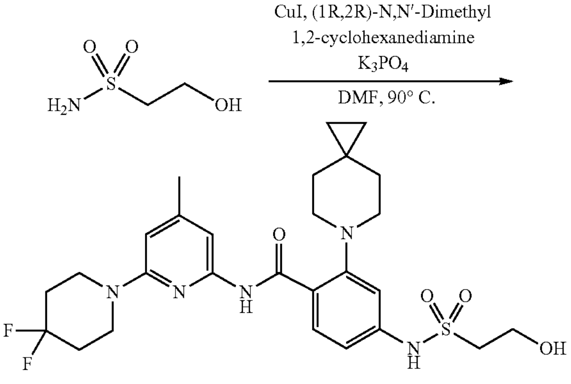

A mixture of 4-bromo-N-(6-(4,4-difluoropiperidin-1-yl)-4-methylpyridin-2-yl)-2-(6-azaspiro[2.5]octan-6-yl)benzamide (1.0 g, 1.9 mmol, Intermediate 27), methyl 2-sulfamoylacetate (0.361 g, 2.89 mmol, Wuxi AppTec), potassium phosphate (1.23 g, 5.78 mmol), (1R,2R)—N1,N2-dimethylcyclohexane-1,2-diamine (0.137 g, 0.963 mmol) and copper(I) iodide (0.183 g, 0.963 mmol) in DMF (20 mL) was heated at 90° C. for 16 h. Then the reaction mixture was filtered through a plug of celite. The filtrate was diluted with EtOAc, washed with water, brine, dried over $Na_2SO_4$, filtered, and concentrated. The residue was purified by flash column chromatography eluting with a gradient of 0% to 40% EtOAc in petroleum ether to provide N-(6-(4,4-difluoropiperidin-1-yl)-4-methylpyridin-2-yl)-4-((2-hydroxyethyl)sulfonamido)-2-(6-azaspiro[2.5]octan-6-yl)benzamide (0.580 g, 1.02 mmol, 53% yield) as off-white solid. $^1H$ NMR (400 MHz, DMSO-$d_6$) δ ppm 12.85 (s, 1H), 8.04 (d, J=8.6 Hz, 1H), 7.51 (s, 1 H), 7.23 (d, J=2.2 Hz, 1H), 7.09 (dd, J=8.7, 2.1 Hz, 1H), 6.56 (s, 1H), 3.74 (dt, J=12.5, 6.2 Hz, 6H), 2.97 (t, J=5.2 Hz, 4H), 2.26 (s, 3H), 1.99 (tt, J=13.6, 5.4 Hz, 3H), 1.79 (s, 4H), 1.60 (br s, 4H), 0.38 (s, 4H). m/z (ESI): 564.2 $(M+H)^+$.

TABLE 10

Examples 7-1 to 7-44 were prepared following similar procedures as described for Examples 5 to 6

| Ex. # | Chemical Structure | Name | LRMS: (ESI + ve ion) m/z |
|---|---|---|---|
| 7-1 | 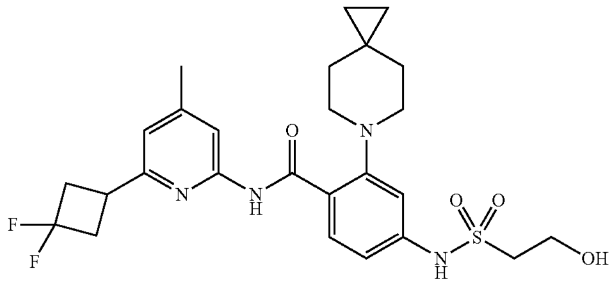 [SMILES: Cc1cc(NC(=O)c2ccc(NS(=O)(=O)CCO)cc2N2CCC3(CC2)CC3)nc(C2CC(F)(F)C2)c1] | N-(6-(3,3-Difluorocyclobutyl)-4-methylpyridin-2-yl)-4-((2-hydroxyethyl)sulfonamido)-2-(6-azaspiro[2.5]octan-6-yl)benzamide | 535.2 |

TABLE 10-continued

| Ex. # | Chemical Structure | Name | LRMS: (ESI + ve ion) m/z |
|---|---|---|---|
| | Examples 7-1 to 7-44 were prepared following similar procedures as described for Examples 5 to 6 | | |
| 7-2 | 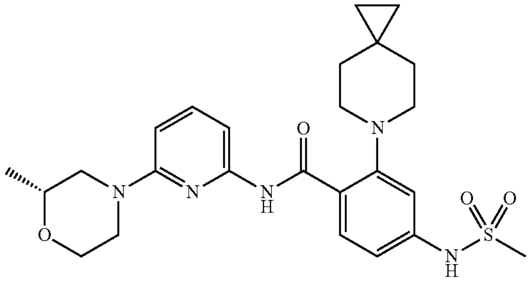 | (R)-N-(6-(2-Methylmorpholino)pyridin-2-yl)-4-(methylsulfonamido)-2-(6-azaspiro[2.5]octan-6-yl)benzamide | 500.2 |
| 7-3 | 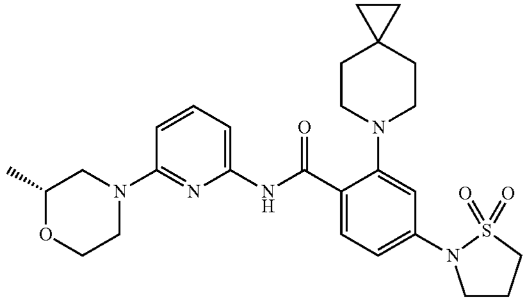 [SMILES: C[C@@H]1CN(c2cccc(NC(=O)c3ccc(N4CCCS4(=O)=O)cc3N3CCC4(CC3)CC4)n2)CCO1] | (R)-4-(1,1-Dioxidoisothiazolidin-2-yl)-N-(6-(2-methylmorpholino)pyridin-2-yl)-2-(6-azaspiro[2.5]octan-6-yl)benzamide | 526.1 |
| 7-4 | 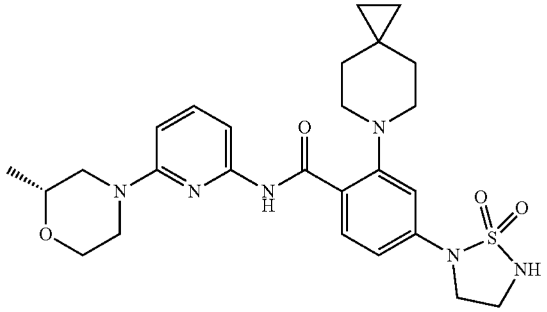 [SMILES: C[C@@H]1CN(c2cccc(NC(=O)c3ccc(N4CCNS4(=O)=O)cc3N3CCC4(CC3)CC4)n2)CCO1] | (R)-4-(1,1-Dioxido-1,2,5-thiadiazolidin-2-yl)-N-(6-(2-methylmorpholino)pyridin-2-yl)-2-(6-azaspiro[2.5]octan-6-yl)benzamide | 527.2 |
| 7-5 | 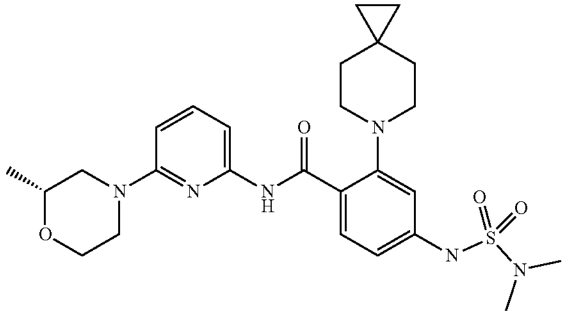 | (R)-4-((N,N-Dimethylsulfamoyl)amino)-N-(6-(2-methylmorpholino)pyridin-2-yl)-2-(6-azaspiro[2.5]octan-6-yl)benzamide | 529.0 |

TABLE 10-continued

| Examples 7-1 to 7-44 were prepared following similar procedures as described for Examples 5 to 6 | | | |
|---|---|---|---|
| Ex. # | Chemical Structure | Name | LRMS: (ESI + ve ion) m/z |
| 7-6 | 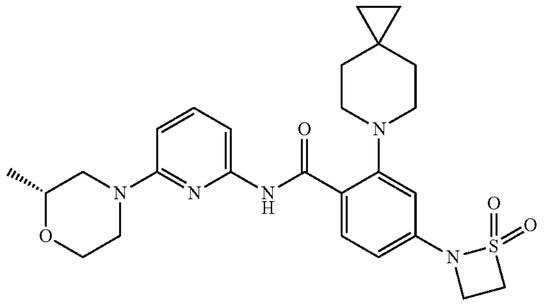 [SMILES: C[C@@H]1CN(c2cccc(NC(=O)c3ccc(N4CCS4(=O)=O)cc3N3CCC4(CC3)CC4)n2)CCO1] | (R)-4-(1,1-Dioxido-1,2-thiazetidin-2-yl)-N-(6-(2-methylmorpholino)pyridin-2-yl)-2-(6-azaspiro[2.5]octan-6-yl)benzamide | 512.3 |
| 7-7 | 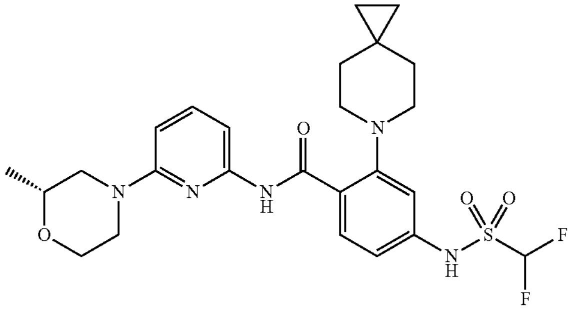 [SMILES: C[C@@H]1CN(c2cccc(NC(=O)c3ccc(NS(=O)(=O)C(F)F)cc3N3CCC4(CC3)CC4)n2)CCO1] | (R)-4-((Difluoromethyl)sulfonamido)-N-(6-(2-methylmorpholino)pyridin-2-yl)-2-(6-azaspiro[2.5]octan-6-yl)benzamide | 536.2 |
| 7-8 | 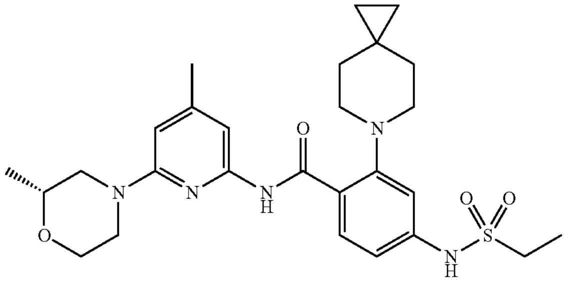 [SMILES: CCS(=O)(=O)Nc1ccc(C(=O)Nc2cc(C)cc(N3CCO[C@H](C)C3)n2)c(N2CCC3(CC2)CC3)c1] | (R)-4-(Ethylsulfonamido)-N-(4-methyl-6-(2-methylmorpholino)pyridin-2-yl)-2-(6-azaspiro[2.5]octan-6-yl)benzamide | 528.2 |
| 7-9 | 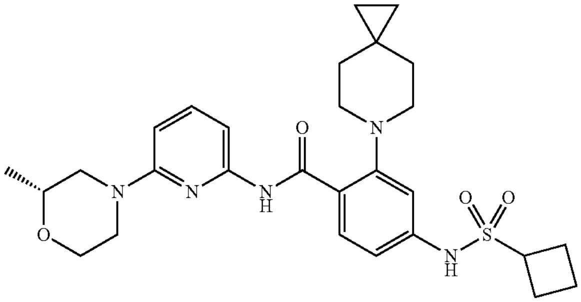 [SMILES: C[C@@H]1CN(c2cccc(NC(=O)c3ccc(NS(=O)(=O)C4CCC4)cc3N3CCC4(CC3)CC4)n2)CCO1] | (R)-4-(Cyclobutanesulfonamido)-N-(6-(2-methylmorpholino)pyridin-2-yl)-2-(6-azaspiro[2.5]octan-6-yl)benzamide | 540.2 |
| 7-10 | 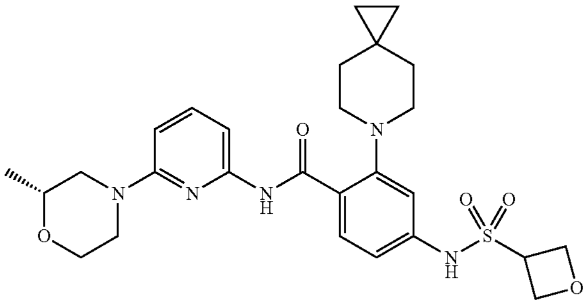 [SMILES: C[C@@H]1CN(c2cccc(NC(=O)c3ccc(NS(=O)(=O)C4COC4)cc3N3CCC4(CC3)CC4)n2)CCO1] | (R)-N-(6-(2-Methylmorpholino)pyridin-2-yl)-4-(oxetane-3-sulfonamido)-2-(6-azaspiro[2.5]octan-6-yl)benzamide | 542.2 |

TABLE 10-continued

| Examples 7-1 to 7-44 were prepared following similar procedures as described for Examples 5 to 6 | | | |
|---|---|---|---|
| Ex. # | Chemical Structure | Name | LRMS: (ESI + ve ion) m/z |
| 7-11 | 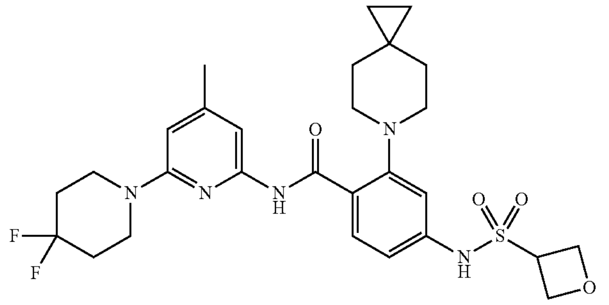 [SMILES: Cc1cc(NC(=O)c2ccc(NS(=O)(=O)C3COC3)cc2N2CCC3(CC2)CC3)nc(N2CCC(F)(F)CC2)c1] | N-(6-(4,4-Difluoropiperidin-1-yl)-4-methylpyridin-2-yl)-4-(oxetane-3-sulfonamido)-2-(6-azaspiro[2.5]octan-6-yl)benzamide | 576.2 |
| 7-12 | 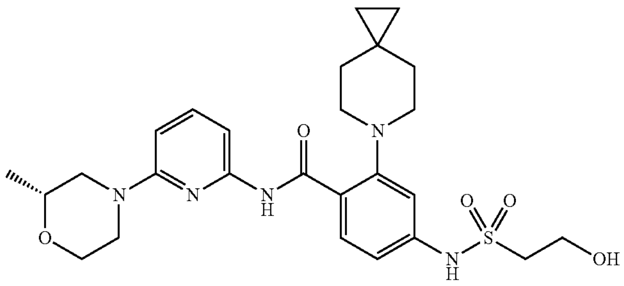 [SMILES: C[C@@H]1CN(c2cccc(NC(=O)c3ccc(NS(=O)(=O)CCO)cc3N3CCC4(CC3)CC4)n2)CCO1] | (R)-4-((2-Hydroxyethyl)sulfonamido)-N-(6-(2-methylmorpholino)pyridin-2-yl)-2-(6-azaspiro[2.5]octan-6-yl)benzamide | 530.2 |
| 7-13 | 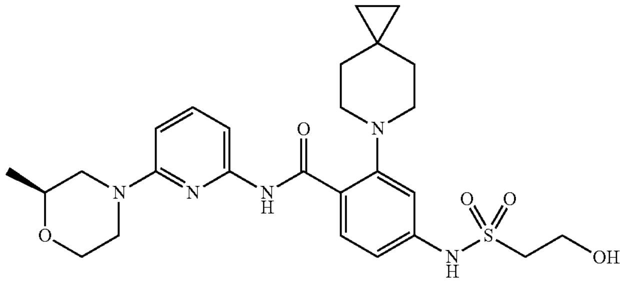 [SMILES: C[C@H]1CN(c2cccc(NC(=O)c3ccc(NS(=O)(=O)CCO)cc3N3CCC4(CC3)CC4)n2)CCO1] | (S)-4-((2-Hydroxyethyl)sulfonamido)-N-(6-(2-methylmorpholino)pyridin-2-yl)-2-(6-azaspiro[2.5]octan-6-yl)benzamide | 530.2 |
| 7-14 | 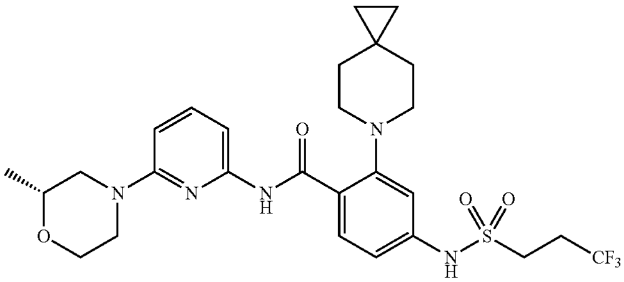 [SMILES: C[C@@H]1CN(c2cccc(NC(=O)c3ccc(NS(=O)(=O)CCC(F)(F)F)cc3N3CCC4(CC3)CC4)n2)CCO1] | (R)-N-(6-(2-Methylmorpholino)pyridin-2-yl)-2-(6-azaspiro[2.5]octan-6-yl)-4-((3,3,3-trifluoropropyl)sulfonamido)benzamide | 582.2 |
| 7-15 | 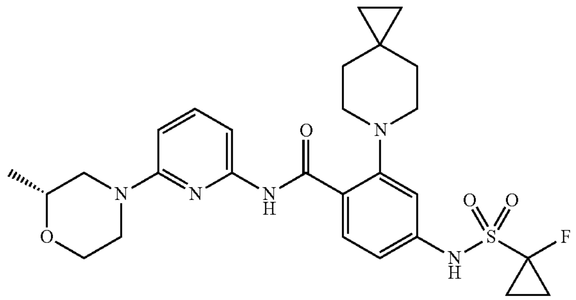 [SMILES: C[C@@H]1CN(c2cccc(NC(=O)c3ccc(NS(=O)(=O)C4(F)CC4)cc3N3CCC4(CC3)CC4)n2)CCO1] | (R)-4-((1-Fluorocyclopropane)-1-sulfonamido)-N-(6-(2-methylmorpholino)pyridin-2-yl)-2-(6-azaspiro[2.5]octan-6-yl)benzamide | 544.2 |

TABLE 10-continued

Examples 7-1 to 7-44 were prepared following similar procedures as described for Examples 5 to 6

| Ex. # | Chemical Structure | Name | LRMS: (ESI + ve ion) m/z |
|---|---|---|---|
| 7-16 | 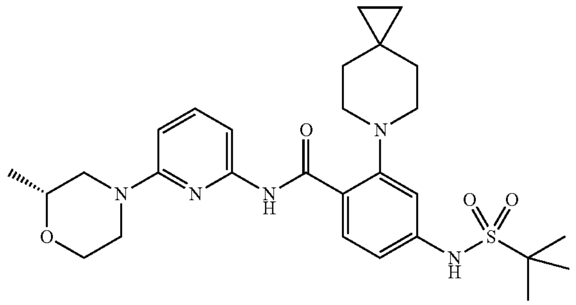 [SMILES: C[C@@H]1CN(c2cccc(NC(=O)c3ccc(NS(=O)(=O)C(C)(C)C)cc3N3CCC4(CC3)CC4)n2)CCO1] | (R)-4-((1,1-Dimethylethyl)sulfonamido)-N-(6-(2-methylmorpholino)pyridin-2-yl)-2-(6-azaspiro[2.5]octan-6-yl)benzamide | 542.2 |
| 7-17 | 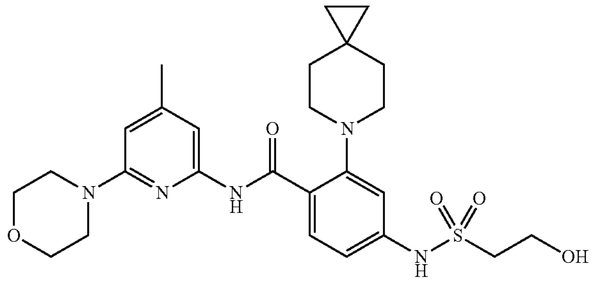 [SMILES: Cc1cc(NC(=O)c2ccc(NS(=O)(=O)CCO)cc2N2CCC3(CC2)CC3)nc(N2CCOCC2)c1] | 4-((2-Hydroxyethyl)sulfonamido)-N-(4-methyl-6-morpholinopyridin-2-yl)-2-(6-azaspiro[2.5]octan-6-yl)benzamide | 530.2 |
| 7-18 | 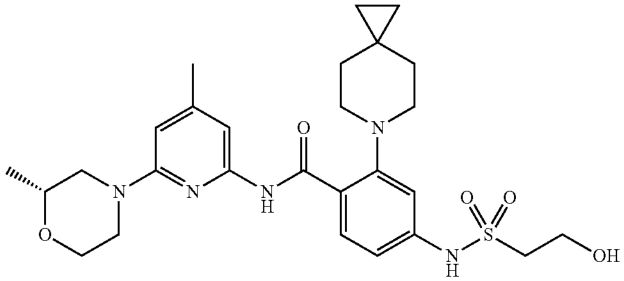 [SMILES: Cc1cc(NC(=O)c2ccc(NS(=O)(=O)CCO)cc2N2CCC3(CC2)CC3)nc(N2CCO[C@H](C)C2)c1] | (R)-4-((2-Hydroxyethyl)sulfonamido)-N-(4-methyl-6-(2-methylmorpholino)pyridin-2-yl)-2-(6-azaspiro[2.5]octan-6-yl)benzamide | 544.2 |
| 7-19 | 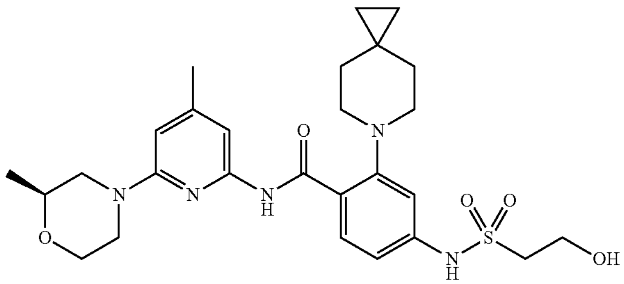 [SMILES: Cc1cc(NC(=O)c2ccc(NS(=O)(=O)CCO)cc2N2CCC3(CC2)CC3)nc(N2CCO[C@@H](C)C2)c1] | (S)-4-((2-Hydroxyethyl)sulfonamido)-N-(4-methyl-6-(2-methylmorpholino)pyridin-2-yl)-2-(6-azaspiro[2.5]octan-6-yl)benzamide | 544.2 |
| 7-20 | 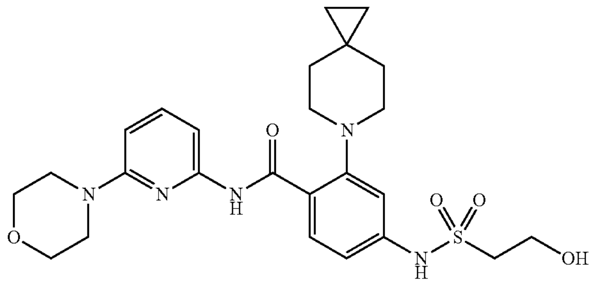 [SMILES: O=C(Nc1cccc(N2CCOCC2)n1)c1ccc(NS(=O)(=O)CCO)cc1N1CCC2(CC1)CC2] | 4-((2-Hydroxyethyl)sulfonamido)-N-(6-morpholinopyridin-2-yl)-2-(6-azaspiro[2.5]octan-6-yl)benzamide | 516.2 |

TABLE 10-continued

| Examples 7-1 to 7-44 were prepared following similar procedures as described for Examples 5 to 6 | | | |
|---|---|---|---|
| Ex. # | Chemical Structure | Name | LRMS: (ESI + ve ion) m/z |
| 7-21 | 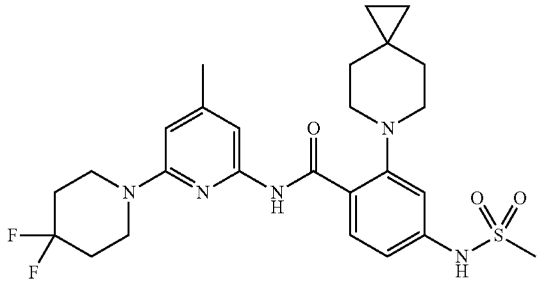 [SMILES: Cc1cc(NC(=O)c2ccc(NS(C)(=O)=O)cc2N2CCC3(CC2)CC3)nc(N2CCC(F)(F)CC2)c1] | N-(6-(4,4-Difluoropiperidin-1-yl)-4-methylpyridin-2-yl)-4-(methylsulfonamido)-2-(6-azaspiro[2.5]octan-6-yl)benzamide | 534.2 |
| 7-22 | 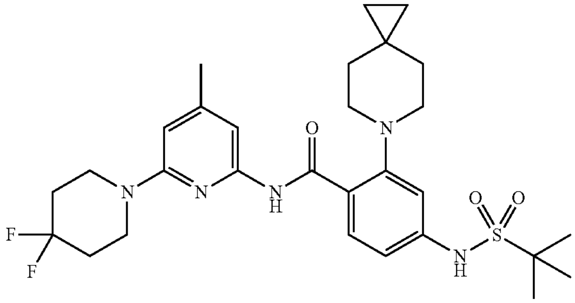 [SMILES: Cc1cc(NC(=O)c2ccc(NS(=O)(=O)C(C)(C)C)cc2N2CCC3(CC2)CC3)nc(N2CCC(F)(F)CC2)c1] | N-(6-(4,4-Difluoropiperidin-1-yl)-4-methylpyridin-2-yl)-4-((1,1-dimethylethyl)sulfonamido)-2-(6-azaspiro[2.5]octan-6-yl)benzamide | 576.3 |
| 7-23 | 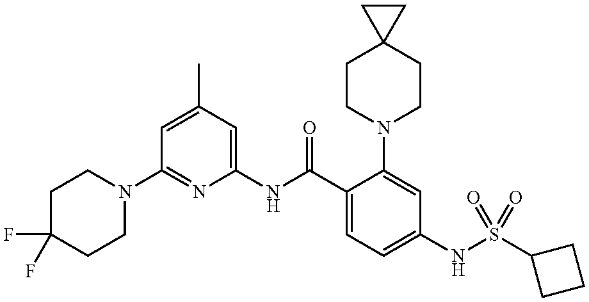 [SMILES: Cc1cc(NC(=O)c2ccc(NS(=O)(=O)C3CCC3)cc2N2CCC3(CC2)CC3)nc(N2CCC(F)(F)CC2)c1] | 4-(Cyclobutanesulfonamido)-N-(6-(4,4-difluoropiperidin-1-yl)-4-methylpyridin-2-yl)-2-(6-azaspiro[2.5]octan-6-yl)benzamide | 574.2 |
| 7-24 | 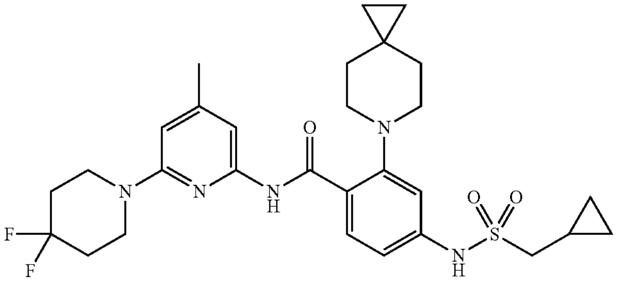 [SMILES: Cc1cc(NC(=O)c2ccc(NS(=O)(=O)CC3CC3)cc2N2CCC3(CC2)CC3)nc(N2CCC(F)(F)CC2)c1] | 4-((Cyclopropylmethyl)sulfonamido)-N-(6-(4,4-difluoropiperidin-1-yl)-4-methylpyridin-2-yl)-2-(6-azaspiro[2.5]octan-6-yl)benzamide | 574.2 |
| 7-25 | 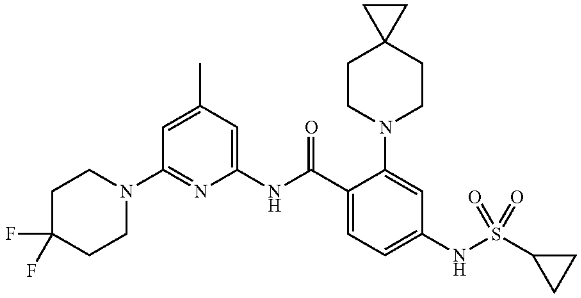 [SMILES: Cc1cc(NC(=O)c2ccc(NS(=O)(=O)C3CC3)cc2N2CCC3(CC2)CC3)nc(N2CCC(F)(F)CC2)c1] | 4-(Cyclopropanesulfonamido)-N-(6-(4,4-difluoropiperidin-1-yl)-4-methylpyridin-2-yl)-2-(6-azaspiro[2.5]octan-6-yl)benzamide | 560.2 |

TABLE 10-continued

Examples 7-1 to 7-44 were prepared following similar procedures as described for Examples 5 to 6

| Ex. # | Chemical Structure | Name | LRMS: (ESI + ve ion) m/z |
| --- | --- | --- | --- |
| 7-26 | 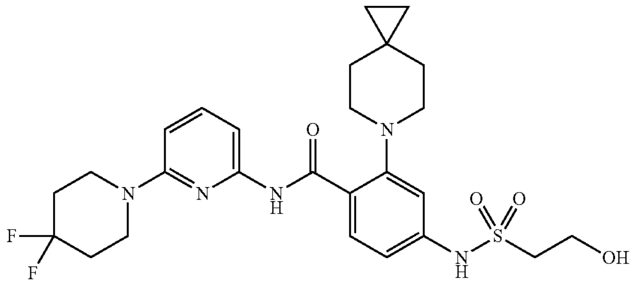 | N-(6-(4,4-Difluoropiperidin-1-yl)pyridin-2-yl)-4-((2-hydroxyethyl)sulfonamido)-2-(6-azaspiro[2.5]octan-6-yl)benzamide | 550.2 |
| 7-27 | 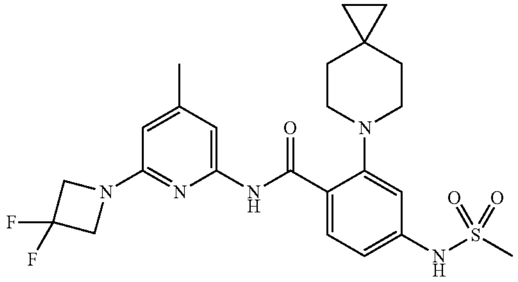 [SMILES: Cc1cc(NC(=O)c2ccc(NS(C)(=O)=O)cc2N2CCC3(CC2)CC3)nc(N2CC(F)(F)C2)c1] | N-(6-(3,3-Difluoroazetidin-1-yl)-4-methylpyridin-2-yl)-4-(methylsulfonamido)-2-(6-azaspiro[2.5]octan-6-yl)benzamide | 506.2 |
| 7-28 | 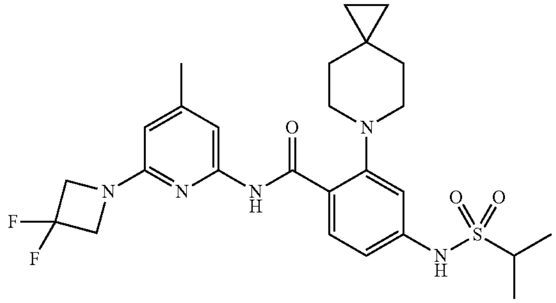 [SMILES: Cc1cc(NC(=O)c2ccc(NS(=O)(=O)C(C)C)cc2N2CCC3(CC2)CC3)nc(N2CC(F)(F)C2)c1] | N-(6-(3,3-Difluoroazetidin-1-yl)-4-methylpyridin-2-yl)-4-((1-methylethyl)sulfonamido)-2-(6-azaspiro[2.5]octan-6-yl)benzamide | 534.2 |
| 7-29 | 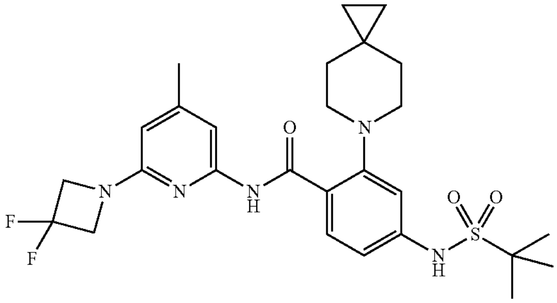 [SMILES: Cc1cc(NC(=O)c2ccc(NS(=O)(=O)C(C)(C)C)cc2N2CCC3(CC2)CC3)nc(N2CC(F)(F)C2)c1] | N-(6-(3,3-Difluoroazetidin-1-yl)-4-methylpyridin-2-yl)-4-((1,1-dimethylethyl)sulfonamido)-2-(6-azaspiro[2.5]octan-6-yl)benzamide | 548.2 |
| 7-30 | 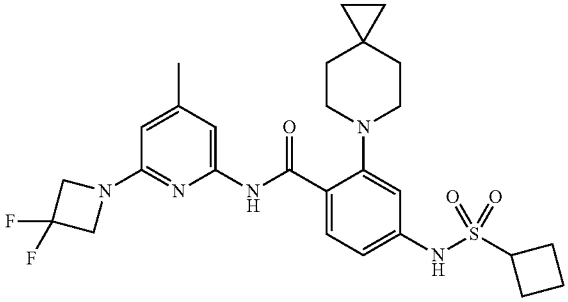 [SMILES: Cc1cc(NC(=O)c2ccc(NS(=O)(=O)C3CCC3)cc2N2CCC3(CC2)CC3)nc(N2CC(F)(F)C2)c1] | 4-(Cyclobutanesulfonamido)-N-(6-(3,3-difluoroazetidin-1-yl)-4-methylpyridin-2-yl)-2-(6-azaspiro[2.5]octan-6-yl)benzamide | 546.2 |

TABLE 10-continued

Examples 7-1 to 7-44 were prepared following similar procedures as described for Examples 5 to 6

| Ex. # | Chemical Structure | Name | LRMS: (ESI + ve ion) m/z |
|---|---|---|---|
| 7-31 | 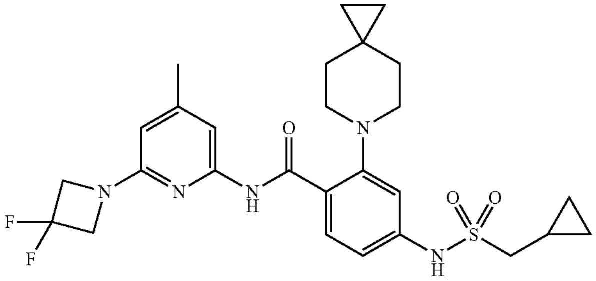 [SMILES: Cc1cc(NC(=O)c2ccc(NS(=O)(=O)CC3CC3)cc2N2CCC3(CC2)CC3)nc(N2CC(F)(F)C2)c1] | 4-((Cyclopropylmethyl)sulfonamido)-N-(6-(3,3-difluoroazetidin-1-yl)-4-methylpyridin-2-yl)-2-(6-azaspiro[2.5]octan-6-yl)benzamide | 546.2 |
| 7-32 | 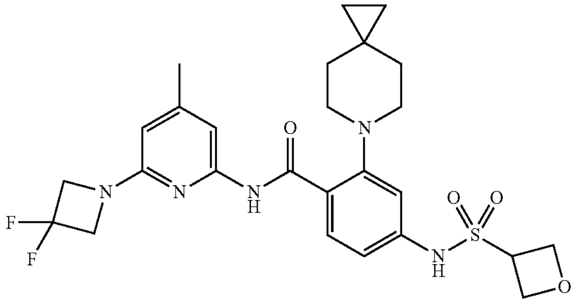 [SMILES: Cc1cc(NC(=O)c2ccc(NS(=O)(=O)C3COC3)cc2N2CCC3(CC2)CC3)nc(N2CC(F)(F)C2)c1] | N-(6-(3,3-Difluoroazetidin-1-yl)-4-methylpyridin-2-yl)-4-(oxetane-3-sulfonamido)-2-(6-azaspiro[2.5]octan-6-yl)benzamide | 548.2 |
| 7-33 | 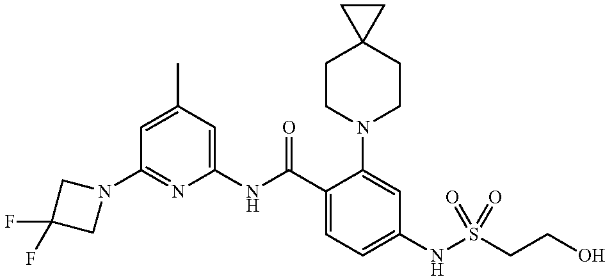 [SMILES: Cc1cc(NC(=O)c2ccc(NS(=O)(=O)CCO)cc2N2CCC3(CC2)CC3)nc(N2CC(F)(F)C2)c1] | N-(6-(3,3-Difluoroazetidin-1-yl)-4-methylpyridin-2-yl)-4-((2-hydroxyethyl)sulfonamido)-2-(6-azaspiro[2.5]octan-6-yl)benzamide | 522.1 |
| 7-34 | 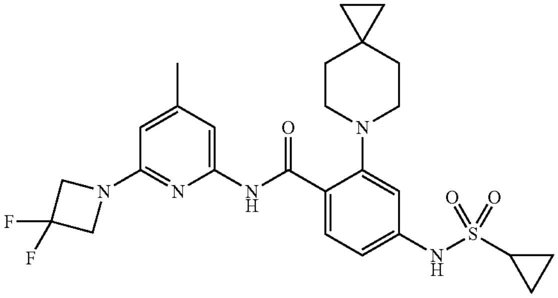 [SMILES: Cc1cc(NC(=O)c2ccc(NS(=O)(=O)C3CC3)cc2N2CCC3(CC2)CC3)nc(N2CC(F)(F)C2)c1] | 4-(Cyclopropanesulfonamido)-N-(6-(3,3-difluoroazetidin-1-yl)-4-methylpyridin-2-yl)-2-(6-azaspiro[2.5]octan-6-yl)benzamide | 532.2 |
| 7-35 | 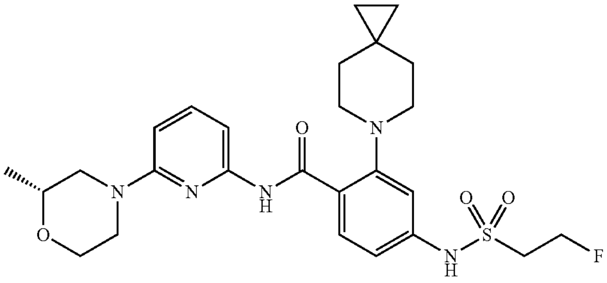 [SMILES: C[C@@H]1CN(c2cccc(NC(=O)c3ccc(NS(=O)(=O)CCF)cc3N3CCC4(CC3)CC4)n2)CCO1] | (R)-4-((2-Fluoroethyl)sulfonamido)-N-(6-(2-methylmorpholino)pyridin-2-yl)-2-(6-azaspiro[2.5]octan-6-yl)benzamide | 532.3 |

TABLE 10-continued

Examples 7-1 to 7-44 were prepared following similar procedures as described for Examples 5 to 6

| Ex. # | Chemical Structure | Name | LRMS: (ESI + ve ion) m/z |
|---|---|---|---|
| 7-36 | 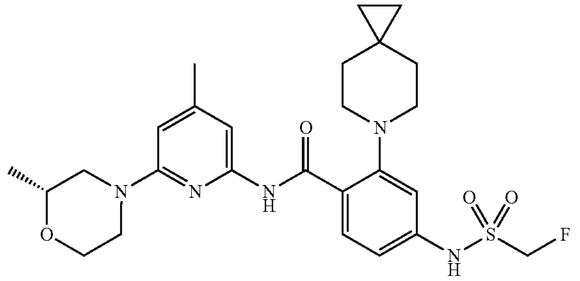 [SMILES: Cc1cc(NC(=O)c2ccc(NS(=O)(=O)CF)cc2N2CCC3(CC2)CC3)nc(N2CCO[C@H](C)C2)c1] | (R)-4-((Fluoromethyl)sulfonamido)-N-(4-methyl-6-(2-methylmorpholino)pyridin-2-yl)-2-(6-azaspiro[2.5]octan-6-yl)benzamide | 532.3 |
| 7-37 | 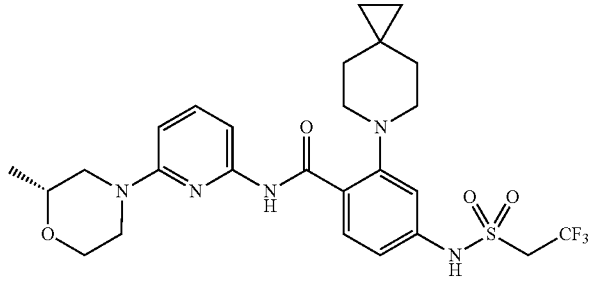 [SMILES: C[C@@H]1CN(c2cccc(NC(=O)c3ccc(NS(=O)(=O)CC(F)(F)F)cc3N3CCC4(CC3)CC4)n2)CCO1] | (R)-4-(Ethylsulfonamido)-N-(6-(2-methylmorpholino)pyridin-2-yl)-2-(6-azaspiro[2.5]octan-6-yl)benzamide | 514.3 |
| 7-38 | 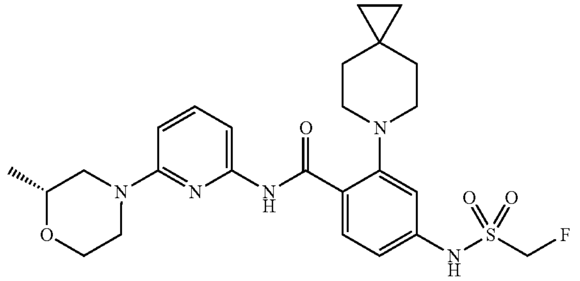 [SMILES: C[C@@H]1CN(c2cccc(NC(=O)c3ccc(NS(=O)(=O)CF)cc3N3CCC4(CC3)CC4)n2)CCO1] | (R)-4-((Fluoromethyl)sulfonamido)-N-(6-(2-methylmorpholino)pyridin-2-yl)-2-(6-azaspiro[2.5]octan-6-yl)benzamide | 518.2 |
| 7-39 | 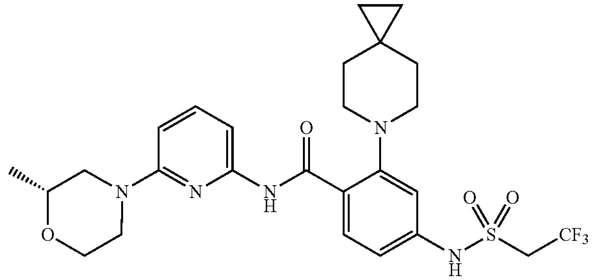 [SMILES: C[C@@H]1CN(c2cccc(NC(=O)c3ccc(NS(=O)(=O)CC(F)(F)F)cc3N3CCC4(CC3)CC4)n2)CCO1] | (R)-N-(6-(2-methylmorpholino)pyridin-2-yl)-2-(6-azaspiro[2.5]octan-6-yl)-4-((2,2,2-trifluoroethyl)sulfonamido)benzamide | 568.3 |
| 7-40 | 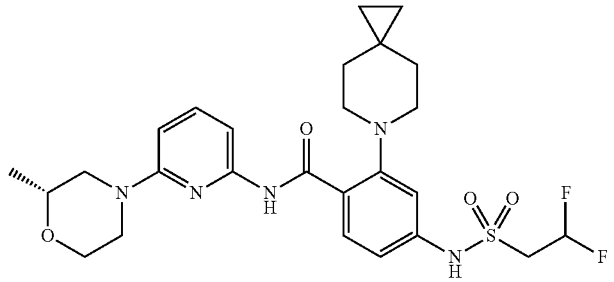 [SMILES: C[C@@H]1CN(c2cccc(NC(=O)c3ccc(NS(=O)(=O)CC(F)F)cc3N3CCC4(CC3)CC4)n2)CCO1] | (R)-4-((2,2-Difluoroethyl)sulfonamido)-N-(6-(2-methylmorpholino)pyridin-2-yl)-2-(6-azaspiro[2.5]octan-6-yl)benzamide | 551.2 |

TABLE 10-continued

| Examples 7-1 to 7-44 were prepared following similar procedures as described for Examples 5 to 6 | | | |
|---|---|---|---|
| Ex. # | Chemical Structure | Name | LRMS: (ESI + ve ion) m/z |
| 7-41 | 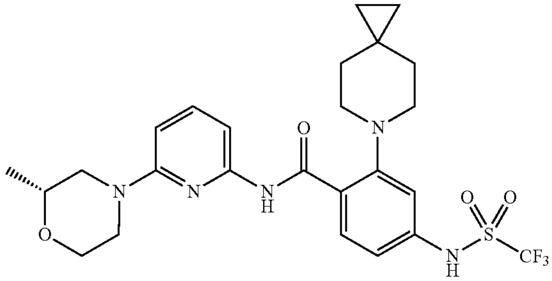 [SMILES: C[C@@H]1CN(c2cccc(NC(=O)c3ccc(NS(=O)(=O)C(F)(F)F)cc3N3CCC4(CC3)CC4)n2)CCO1] | (R)-N-(6-(2-Methylmorpholino)pyridin-2-yl)-2-(6-azaspiro[2.5]octan-6-yl)-4-((trifluoromethyl)sulfonamido)benzamide | 554.2 |
| 7-42 | 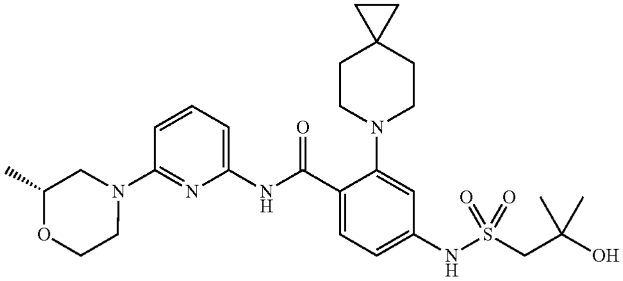 [SMILES: C[C@@H]1CN(c2cccc(NC(=O)c3ccc(NS(=O)(=O)CC(C)(C)O)cc3N3CCC4(CC3)CC4)n2)CCO1] | (R)-4-((2-Hydroxy-2-methylpropyl)sulfonamido)-N-(6-(2-methylmorpholino)pyridin-2-yl)-2-(6-azaspiro[2.5]octan-6-yl)benzamide | 558.3 |
| 7-43 | 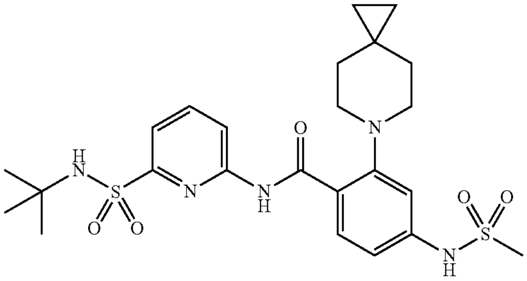 [SMILES: CC(C)(C)NS(=O)(=O)c1cccc(NC(=O)c2ccc(NS(C)(=O)=O)cc2N2CCC3(CC2)CC3)n1] | N-(6-(N-(tert-Butyl)sulfamoyl)pyridin-2-yl)-4-(methylsulfonamido)-2-(6-azaspiro[2.5]octan-6-yl)benzamide | 536.2 |
| 7-44 | 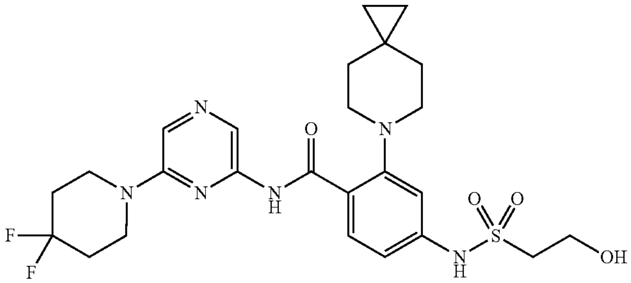 [SMILES: O=C(Nc1cncc(N2CCC(F)(F)CC2)n1)c1ccc(NS(=O)(=O)CCO)cc1N1CCC2(CC1)CC2] | N-(6-(4,4-Difluoropiperidin-1-yl)pyrazin-2-yl)-4-((2-hydroxyethyl)sulfonamido)-2-(6-azaspiro[2.5]octan-6-yl)benzamide | 551.2 |

Example 8-1: (R)-4-((2-Hydroxy-1-methylethyl) sulfonamido)-2-(6-azaspiro[2.5]octan-6-yl)-N-(6-(3, 3,3-trifluoropropoxy)pyridin-2-yl)benzamide and Example 8-2: (S) 4-((2-hydroxy-1-methylethyl) sulfonamido)-2-(6-azaspiro[2.5]octan-6-yl)-N-(6-(3, 3,3-trifluoropropoxy)pyridin-2-yl)benzamide
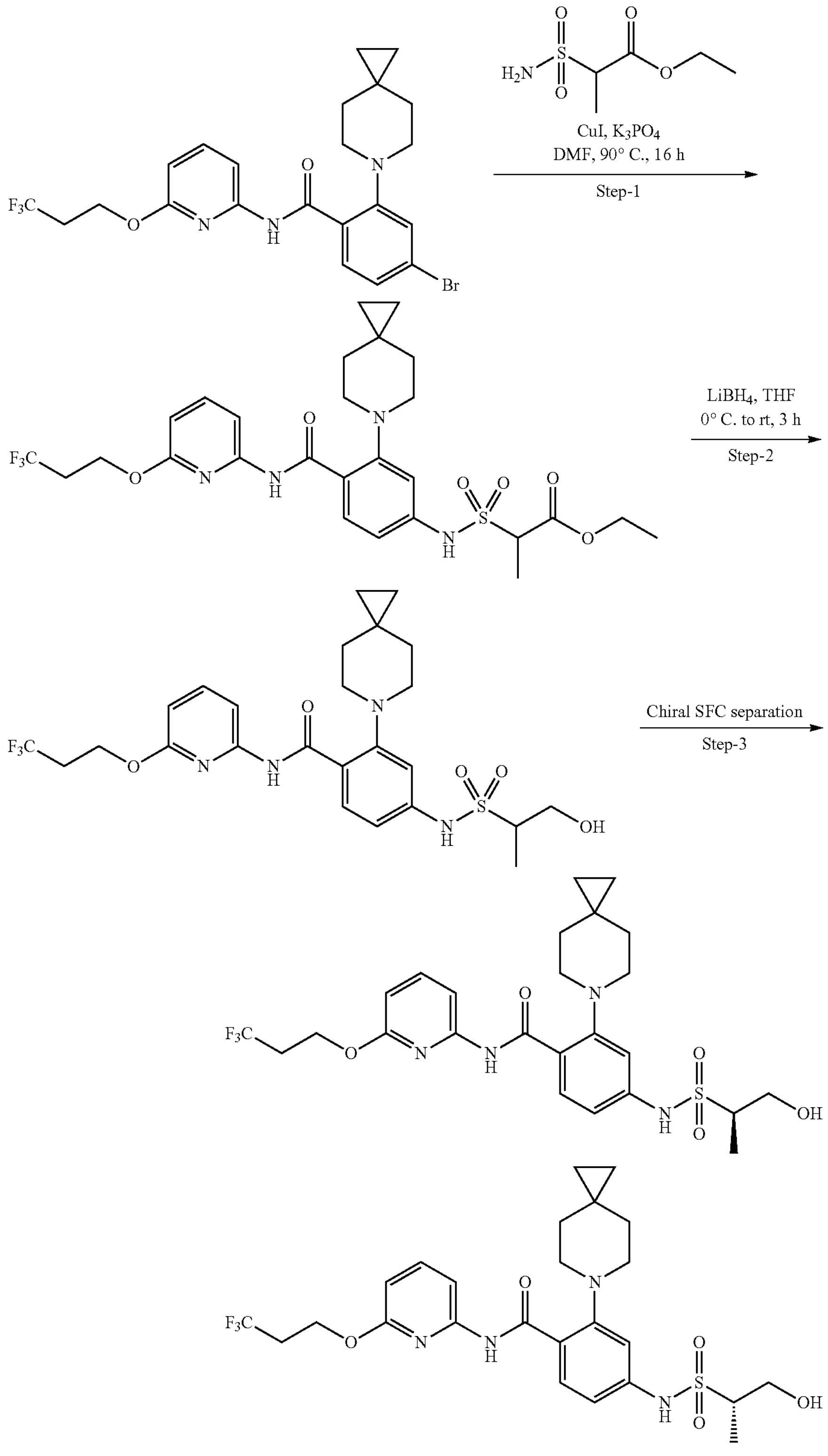

Step 1: A mixture of 4-bromo-2-(6-azaspiro[2.5]octan-6-yl)-N-(6-(3,3,3-trifluoropropoxy)pyridin-2-yl)benzamide (0.63 g, 1.3 mmol, Intermediate 38-1), ethyl 2-sulfamoylpropanoate (0.275 g, 1.52 mmol, Intermediate 40), potassium phosphate tribasic (0.537 g, 2.53 mmol), (1R,2R)—N1,N2-dimethylcyclohexane-1,2-diamine (0.090 g, 0.63 mmol) and copper iodide (0.241 g, 1.26 mmol) in DMF (10 mL) was heated at 90° C. for 16 h. Then the reaction mixture was filtered, diluted with EtOAc, and washed with water, brine, dried over $Na_2SO_4$, filtered, and concentrated. The concentrate was purified by flash column chromatography eluting with a gradient of 0% to 50% EtOAc in petroleum ether to provide ethyl 2-(N-(3-(6-azaspiro[2.5]octan-6-yl)-4-((6-(3,3,3-trifluoropropoxy)pyridin-2-yl)carbamoyl)phenyl)sulfamoyl)propanoate (0.56 g, 0.94 mmol, 74% yield) as white solid. $^1$H NMR (400 MHz, DMSO-$d_6$) δ 13.19 (s, 1H), 10.68 (s, 1H), 8.09 (d, J=8.7 Hz, 1H), 7.91 (d, J=7.9 Hz, 1H), 7.77 (t, J=7.9 Hz, 1H), 7.32 (d, J=2.2 Hz, 1H), 7.16 (dd, J=8.6, 2.2 Hz, 1H), 6.58 (d, J=8.0 Hz, 1H), 4.51 (t, J=6.1 Hz, 2H), 4.32 (q, J=6.9 Hz, 1H), 4.07 (qd, J=7.1, 5.2 Hz, 2H), 3.00 (d, J=5.0 Hz, 4H), 2.84 (qt, J=11.5, 6.0 Hz, 2H), 1.74 (s, 4H), 1.49 (d, J=6.9 Hz, 3H), 1.14 (t, J=7.1 Hz, 3H), 0.39 (s, 4H). m/z (ESI): 598.8 $(M+H)^+$.

Step-2: To a solution of ethyl 2-(N-(3-(6-azaspiro[2.5]octan-6-yl)-4-((6-(3,3,3-trifluoropropoxy)pyridin-2-yl)carbamoyl)phenyl)sulfamoyl)propanoate (0.56 g, 0.94 mmol) in THF (12 mL) was added $LiBH_4$ (1.871 mL, 3.74 mmol) at −78° C. Then the reaction mixture was slowly warmed up to room temperature over 2 h before it was quenched with a saturated solution of $NH_4Cl$ (20 mL) and was extracted with EtOAc (2×25 mL). The combined organic extracts were washed with brine, dried over $Na_2SO_4$, filtered, and concentrated. The concentrate was purified by flash column chromatography eluting with a gradient of 0% to 50% EtOAc in petroleum ether to provide 4-((2-hydroxy-1-methylethyl)sulfonamido)-2-(6-azaspiro[2.5]octan-6-yl)-N-(6-(3,3,3-trifluoropropoxy)pyridin-2-yl)benzamide (0.45 g, 0.81 mmol, 86% yield) as white solid. m/z (ESI): 557.2 $(M+H)^+$. The racemic mixture was subject to chiral separation by SFC, using a column-Lux A1 (250×21.2 mm, 5 μm), mobile phase: 80:20 (A: B), A=liquid $CO_2$, B=Methanol, flow rate: 80 mL/min to yield.

Example 8-1: (R)-4-((2-Hydroxy-1-methylethyl)sulfonamido)-2-(6-azaspiro[2.5]octan-6-yl)-N-(6-(3,3,3-trifluoropropoxy)pyridin-2-yl)benzamide. First eluting peak. $^1$H NMR (400 MHz, DMSO-$d_6$) δ ppm 13.18 (s, 1H), 10.22 (s, 1H), 8.07 (d, J=8.6 Hz, 1H), 7.90 (d, J=7.8 Hz, 1H), 7.76 (t, J=8.0 Hz, 1H), 7.31 (d, J=2.2 Hz, 1H), 7.16 (dd, J=8.6, 2.1 Hz, 1H), 6.57 (dd, J=8.1, 0.8 Hz, 1H), 5.03 (s, 1H), 4.51 (t, J=6.1 Hz, 2H), 3.85 (dd, J=11.1, 4.4 Hz, 1H), 3.49 (dd, J=11.1, 7.6 Hz, 1H), 3.30 (m, 1H), 2.87-3.24 (m, 4H), 2.83 (tt, J=11.5, 6.0 Hz, 2H), 1.74 (br s, 4H), 1.30 (d, J=6.9 Hz, 3H), 0.39 (s, 4H). m/z (ESI): 557.1 $(M+H)^+$.

Example 8-2: (S)-4-((2-Hydroxy-1-methylethyl)sulfonamido)-2-(6-azaspiro[2.5]octan-6-yl)-N-(6-(3,3,3-trifluoropropoxy)pyridin-2-yl)benzamide. Second eluting peak $^1$H NMR (400 MHz, DMSO-$d_6$) δ ppm 13.18 (s, 1H), 10.22 (s, 1H), 8.07 (d, J=8.6 Hz, 1H), 7.78-8.03 (m, 1H), 7.75 (d, J=7.9 Hz, 1H), 7.31 (d, J=2.2 Hz, 1H), 7.16 (dd, J=8.7, 2.2 Hz, 1H), 6.57 (d, J=8.0 Hz, 1H), 5.03 (s, 1H), 4.51 (t, J=6.0 Hz, 2H), 3.85 (dd, J=11.1, 4.4 Hz, 1H), 3.48-3.57 (m, 2H), 3.30 (td, J=6.9, 4.3 Hz, 1H), 2.99 (t, J=5.3 Hz, 4H), 2.82 (tt, J=11.4, 5.9 Hz, 2H), 1.74 (br s, 4H), 1.29 (d, J=6.9 Hz, 3H), 0.39 (s, 4H). m/z (ESI): 557.1 $(M+H)^+$.

The stereochemistry was arbitrary assigned.

TABLE 11

Examples 9-1 to 9-18 were prepared following a similar procedure as described for Examples 8-1 and 8-2

| Ex. # | Chemical Structure | Name | LRMS: (ESI + ve ion) m/z |
|---|---|---|---|
| 9-1 | 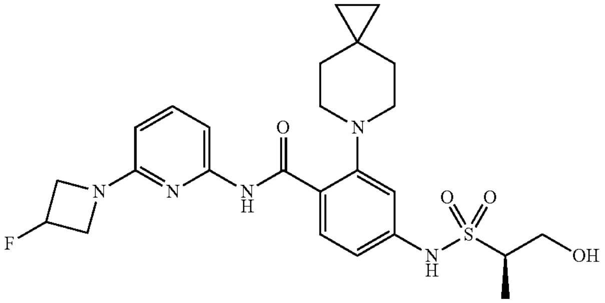 [SMILES: C[C@H](CO)S(=O)(=O)Nc1ccc(C(=O)Nc2cccc(N3CC(F)C3)n2)c(N2CCC3(CC2)CC3)c1] | (R)-N-(6-(3-Fluoroazetidin-1-yl)pyridin-2-yl)-4-((2-hydroxy-1-methylethyl)sulfonamido)-2-(6-azaspiro[2.5]octan-6-yl)benzamide | 518.2 |
| 9-2 | 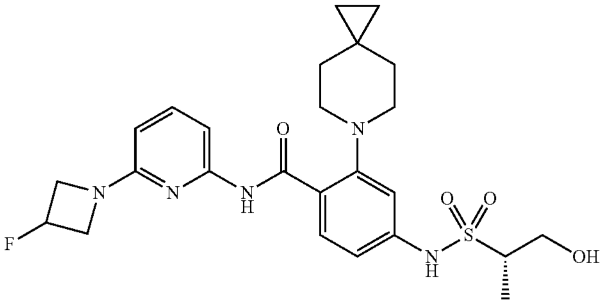 [SMILES: C[C@@H](CO)S(=O)(=O)Nc1ccc(C(=O)Nc2cccc(N3CC(F)C3)n2)c(N2CCC3(CC2)CC3)c1] | (S)-N-(6-(3-Fluoroazetidin-1-yl)pyridin-2-yl)-4-((2-hydroxy-1-methylethyl)sulfonamido)-2-(6-azaspiro[2.5]octan-6-yl)benzamide | 518.2 |

TABLE 11-continued

| Ex. # | Chemical Structure | Name | LRMS: (ESI + ve ion) m/z |
|---|---|---|---|
| Examples 9-1 to 9-18 were prepared following a similar procedure as described for Examples 8-1 and 8-2 | | | |
| 9-3 | 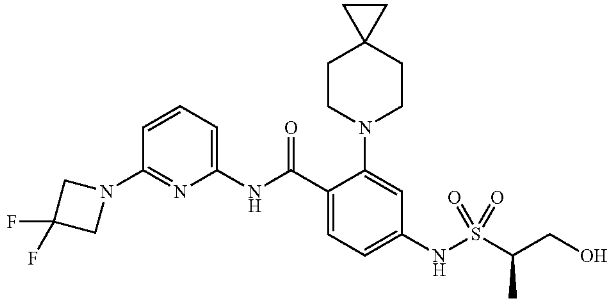 [SMILES: C[C@H](CO)S(=O)(=O)Nc1ccc(C(=O)Nc2cccc(N3CC(F)(F)C3)n2)c(N2CCC3(CC2)CC3)c1] | (R)-N-(6-(3,3-Difluoroazetidin-1-yl) pyridin-2-yl)-4-((2-hydroxy-1-methylethyl)sulfonamido)-2-(6-azaspiro[2.5]octan-6-yl)benzamide | 536.2 |
| 9-4 | 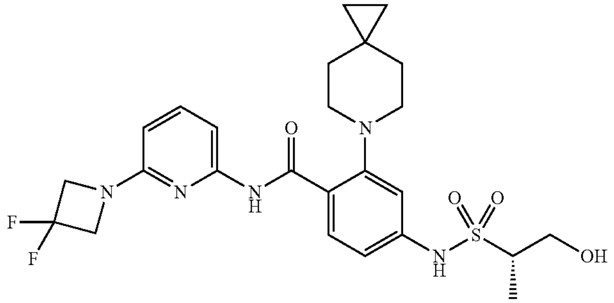 [SMILES: C[C@@H](CO)S(=O)(=O)Nc1ccc(C(=O)Nc2cccc(N3CC(F)(F)C3)n2)c(N2CCC3(CC2)CC3)c1] | (S)-N-(6-(3,3-Difluoroazetidin-1-yl) pyridin-2-yl)-4-((2-hydroxy-1-methylethyl)sulfonamido)-2-(6-azaspiro[2.5]octan-6-yl)benzamide | 536.2 |
| 9-5 | 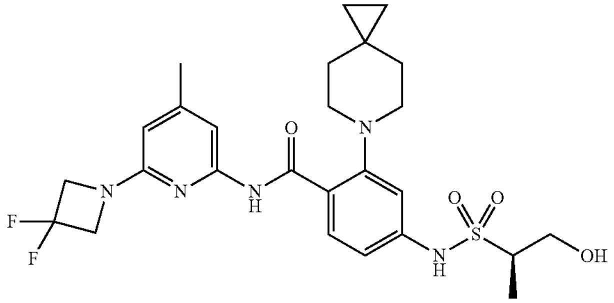 [SMILES: Cc1cc(NC(=O)c2ccc(NS(=O)(=O)[C@H](C)CO)cc2N2CCC3(CC2)CC3)nc(N2CC(F)(F)C2)c1] | (R)-N-(6-(3,3-Difluoroazetidin-1-yl)-4-methylpyridin-2-yl)-4-((2-hydroxy-1-methylethyl)sulfonamido)-2-(6-azaspiro[2.5]octan-6-yl)benzamide | 550.2 |
| 9-6 | 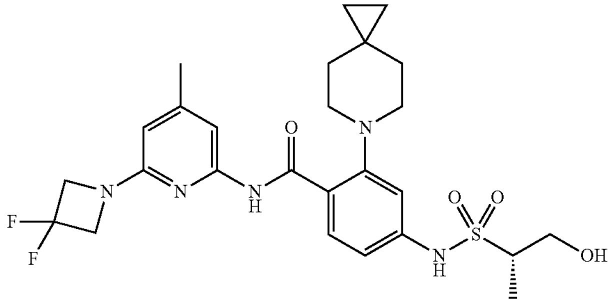 | (S)-N-(6-(3,3-Difluoroazetidin-1-yl)-4-methylpyridin-2-yl)-4-((2-hydroxy-1-methylethyl)sulfonamido)-2-(6-azaspiro[2.5]octan-6-yl)benzamide | 550.2 |

TABLE 11-continued

| Examples 9-1 to 9-18 were prepared following a similar procedure as described for Examples 8-1 and 8-2 | | | |
|---|---|---|---|
| Ex. # | Chemical Structure | Name | LRMS: (ESI + ve ion) m/z |
| 9-7 | 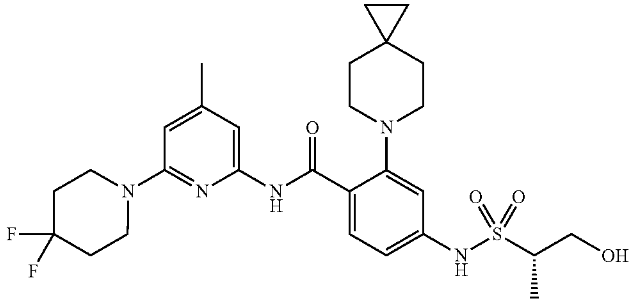 | (S)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide | 578.2 |
| 9-8 | 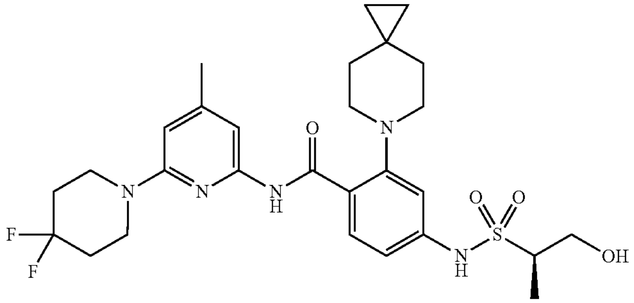 [SMILES: Cc1cc(NC(=O)c2ccc(NS(=O)(=O)[C@H](C)CO)cc2N2CCC3(CC2)CC3)nc(N2CCC(F)(F)CC2)c1] | (R)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide | 578.2 |
| 9-9 | 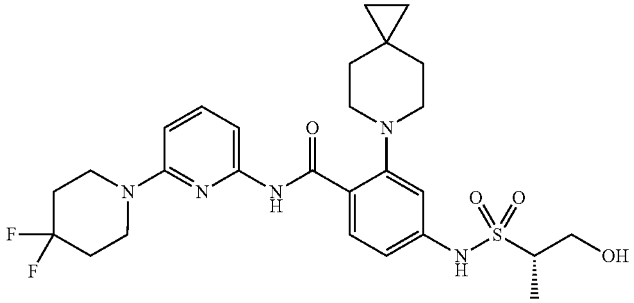 [SMILES: C[C@@H](CO)S(=O)(=O)Nc1ccc(C(=O)Nc2cccc(N3CCC(F)(F)CC3)n2)c(N2CCC3(CC2)CC3)c1] | (S)-N-(6-(4,4-Difluoropiperidin-1-yl) pyridin-2-yl)-4-((2-hydroxy-1-methylethyl)sulfonamido)-2-(6-azaspiro[2.5]octan-6-yl)benzamide | 564.2 |
| 9-10 | 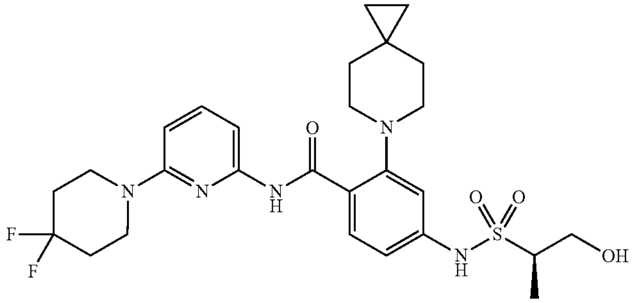 [SMILES: C[C@H](CO)S(=O)(=O)Nc1ccc(C(=O)Nc2cccc(N3CCC(F)(F)CC3)n2)c(N2CCC3(CC2)CC3)c1] | (R)-N-(6-(4,4-Difluoropiperidin-1-yl)pyridin-2-yl)-4-((2-hydroxy-1-methylethyl)sulfonamido)-2-(6-azaspiro[2.5]octan-6-yl)benzamide | 564.2 |

TABLE 11-continued

| Examples 9-1 to 9-18 were prepared following a similar procedure as described for Examples 8-1 and 8-2 | | | |
|---|---|---|---|
| Ex. # | Chemical Structure | Name | LRMS: (ESI + ve ion) m/z |
| 9-11 | 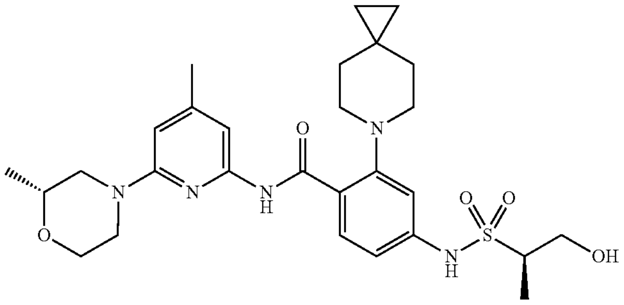 [SMILES: Cc1cc(NC(=O)c2ccc(NS(=O)(=O)[C@H](C)CO)cc2N2CCC3(CC2)CC3)nc(N2CCO[C@H](C)C2)c1] | 4-(((R)-2-Hydroxy-1-methylethyl) sulfonamido)-N-(4-methyl-6-((R)-2-methylmorpholino)pyridin-2-yl)-2-(6-azaspiro[2.5]octan-6-yl)benzamide | 558.2 |
| 9-12 | 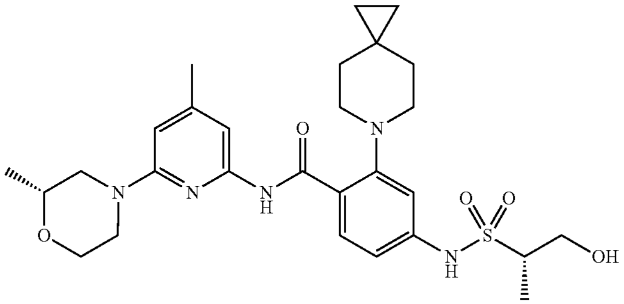 [SMILES: Cc1cc(NC(=O)c2ccc(NS(=O)(=O)[C@@H](C)CO)cc2N2CCC3(CC2)CC3)nc(N2CCO[C@H](C)C2)c1] | 4-(((S)-2-Hydroxy-1-methylethyl) sulfonamido)-N-(4-methyl-6-((R)-2-methylmorpholino)pyridin-2-yl)-2-(6-azaspiro[2.5]octan-6-yl)benzamide | 558.2 |
| 9-13 | 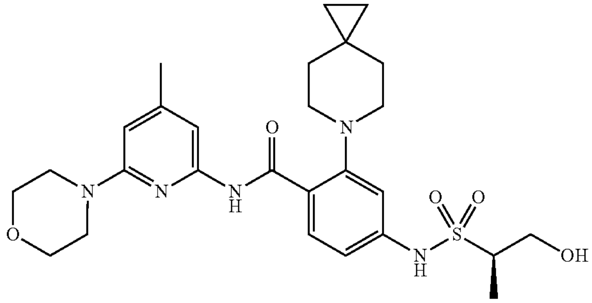 [SMILES: Cc1cc(NC(=O)c2ccc(NS(=O)(=O)[C@H](C)CO)cc2N2CCC3(CC2)CC3)nc(N2CCOCC2)c1] | (R)-4-((2-Hydroxy-1-methylethyl) sulfonamido)-N-(4-methyl-6-morpholinopyridin-2-yl)-2-(6-azaspiro[2.5]octan-6-yl)benzamide | 544.2 |
| 9-14 | 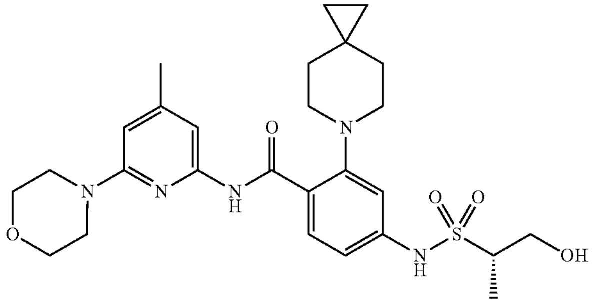 [SMILES: Cc1cc(NC(=O)c2ccc(NS(=O)(=O)[C@@H](C)CO)cc2N2CCC3(CC2)CC3)nc(N2CCOCC2)c1] | (S)-4-((2-Hydroxy-1-methylethyl) sulfonamido)-N-(4-methyl-6-morpholinopyridin-2-yl)-2-(6-azaspiro[2.5]octan-6-yl)benzamide | 544.2 |

TABLE 11-continued

Examples 9-1 to 9-18 were prepared following a similar procedure as described for Examples 8-1 and 8-2

| Ex. # | Chemical Structure | Name | LRMS: (ESI + ve ion) m/z |
|---|---|---|---|
| 9-15 | 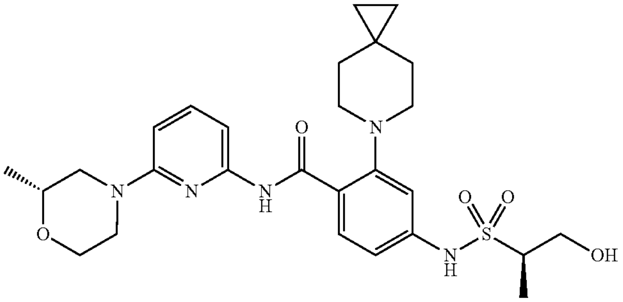 [SMILES: C[C@@H]1CN(c2cccc(NC(=O)c3ccc(NS(=O)(=O)[C@H](C)CO)cc3N3CCC4(CC3)CC4)n2)CCO1] | 4-(((R)-2-Hydroxy-1-methylethyl) sulfonamido)-N-(6-((R)-2-methylmorpholino)pyridin-2-yl)-2-(6-azaspiro[2.5]octan-6-yl)benzamide | 544.2 |
| 9-16 | 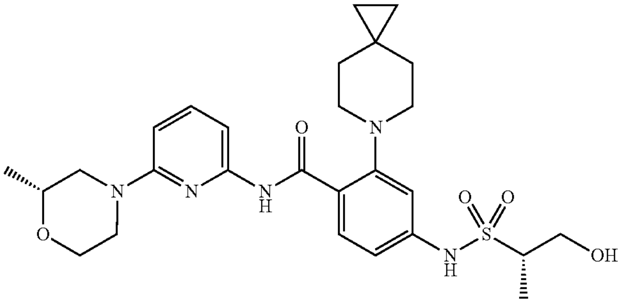 [SMILES: C[C@@H]1CN(c2cccc(NC(=O)c3ccc(NS(=O)(=O)[C@@H](C)CO)cc3N3CCC4(CC3)CC4)n2)CCO1] | 4-(((S)-2-Hydroxy-1-methylethyl) sulfonamido)-N-(6-((R)-2-methylmorpholino)pyridin-2-yl)-2-(6-azaspiro[2.5]octan-6-yl)benzamide | 544.2 |
| 9-17 | 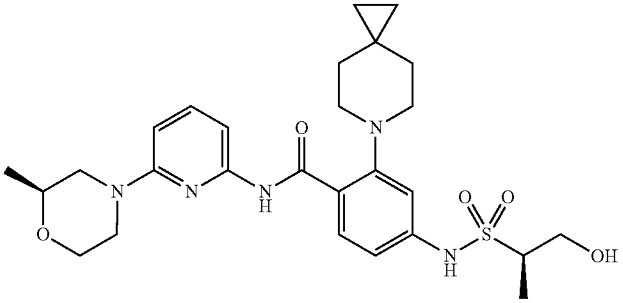 [SMILES: C[C@H](CO)S(=O)(=O)Nc1ccc(C(=O)Nc2cccc(N3CCO[C@@H](C)C3)n2)c(N2CCC3(CC2)CC3)c1] | 4-(((R)-2-Hydroxy-1-methylethyl) sulfonamido)-N-(6-((S)-2-methylmorpholino)pyridin-2-yl)-2-(6-azaspiro[2.5]octan-6-yl)benzamide | 544.2 |
| 9-18 | 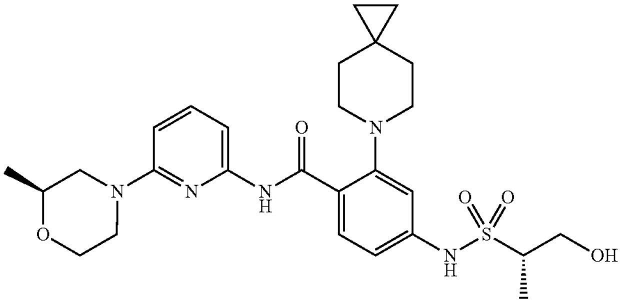 [SMILES: C[C@H]1CN(c2cccc(NC(=O)c3ccc(NS(=O)(=O)[C@@H](C)CO)cc3N3CCC4(CC3)CC4)n2)CCO1] | 4-(((S)-2-Hydroxy-1-methylethyl) sulfonamido)-N-(6-((S)-2-methylmorpholino)pyridin-2-yl)-2-(6-azaspiro[2.5]octan-6-yl)benzamide | 544.2 |

Example 10: N-(6-(4,4-Difluoropiperidin-1-yl)-4-methylpyridin-2-yl)-4-((1-(hydroxymethyl)cyclopropane)-1-sulfonamido)-2-(6-azaspiro[2.5]octan-6-yl) benzamide

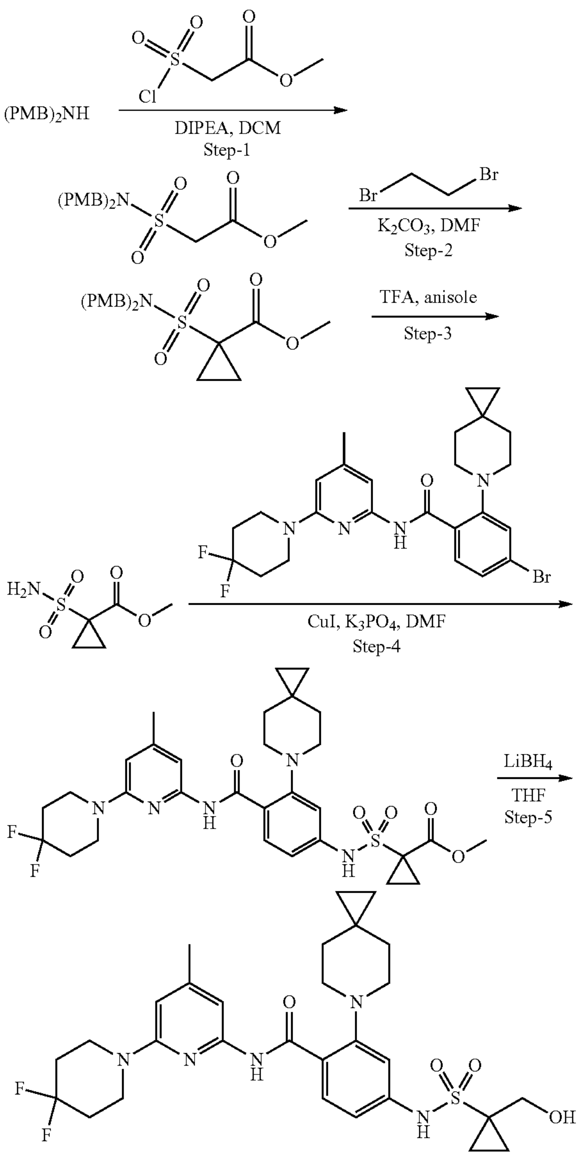

Step 1: To a solution of bis(4-methoxybenzyl)amine (8.95 g, 34.8 mmol) in DCM (50 mL) were added DIPEA (6.06 mL, 43.5 mmol) and methyl 2-(chlorosulfonyl)acetate (5.0 g, 29 mmol) at 0° C. The reaction mixture was stirred at room temperature for 16 h before it was quenched with ice water and extracted with DCM. The organic layer was washed with a saturated aqueous solution of sodium bicarbonate, water, and brine. The organic extract was dried over $Na_2SO_4$, filtered, and concentrated. The concentrate was purified by flash column chromatography using a gradient of 15% ethyl acetate in petroleum ether to provide methyl 2-(NN-bis(4-methoxybenzyl)sulfamoyl)acetate (5.5 g, 14 mmol, 48% yield) as pale yellow gum. $^1H$ NMR (400 MHz, DMSO-$d_6$): δ ppm 7.14 (d, J=8.4 Hz, 4H), 6.86 (d, J=8.4 Hz, 4H), 4.31 (s, 2H), 4.25 (s, 4H), 3.73 (s, 6H), 3.70 (s, 3H). m/z (ESI): 392.1 $(M-H)^-$.

Step 2: A mixture of methyl 2-(NN-bis(4-methoxybenzyl) sulfamoyl)acetate (1.0 g, 2.5 mmol), $K_2CO_3$ (1.054 g, 7.62 mmol) and 1,2-dibromoethane (0.716 g, 3.81 mmol) in DMF (5 mL) was stirred at 65° C. for 16 h. The reaction mixture was quenched with ice water and was extracted with EtOAc. The organic extract was washed with water and brine, dried over $Na_2SO_4$, filtered, and concentrated. The concentrate was purified by flash column chromatography using a gradient of 5% ethyl acetate in petroleum ether to provide methyl 1-(N,N-bis(4-methoxybenzyl)sulfamoyl)cyclopropane-1-carboxylate (750 mg, 1.79 mmol, 70% yield) as pale yellow gum. $^1H$ NMR (300 MHz, DMSO-d6): δ ppm 7.04-7.21 (m, 4H), 6.83-6.94 (m, 4H), 4.32 (s, 4H), 3.72 (s, 6H), 3.69 (s, 3H), 1.67 (q, J=4.8, 3.6 Hz, 2H), 1.56 (q, J=5.7, 4.8 Hz, 2H).

Step 3: A mixture of methyl 1-(NN-bis(4-methoxybenzyl) sulfamoyl)cyclopropane-1-carboxylate (2.33 g, 5.55 mmol), TFA (23 mL) and anisole (3.03 mL, 27.8 mmol) was stirred at room temperature for 16 h. The reaction mixture was concentrated, and the concentrate was treated with an aqueous saturated solution of sodium bicarbonate solution and was extracted with dichloromethane. The organic extract was washed with water and brine, dried over $Na_2SO_4$, filtered, and concentrated. The concentrate was purified by flash column chromatography using a gradient of 50% ethyl acetate in petroleum ether to provide methyl 1-sulfamoylcyclopropane-1-carboxylate (0.59 g, 3.3 mmol, 59% yield) as white solid. $^1H$ NMR (400 MHz, DMSO-$d_6$) δ ppm 7.08 (br s, 2H), 3.70 (s, 3H), 1.48-1.52 (m, 4H). m/z (ESI): 180.0 $(M+H)^+$.

Step 4: A mixture of 4-bromo-N-(2-(4,4-difluoropiperidin-1-yl)-6-methylpyridin-4-yl)-2-(6-azaspiro[2.5]octan-6-yl)benzamide (0.20 g, 0.38 mmol, Intermediate 27), methyl 1-sulfamoylcyclopropane-1-carboxylate (0.103 g, 0.578 mmol), copper (I) iodide (0.073 g, 0.38 mmol), potassium phosphate tribasic (0.163 g, 0.770 mmol), (1R,2R)—N1, N2-dimethylcyclohexane-1,2-diamine (0.027 g, 0.19 mmol) in DMF (3 mL) was heated at 90° C. for 16 h. Then the reaction was filtered through a plug of celite and the filtrate was diluted with EtOAc and was washed with water and brine, dried over $Na_2SO_4$, filtered, and concentrated. The concentrate was purified by flash column chromatography using a gradient of 28% to 35% EtOAc in petroleum ether to provide methyl 1-(N-(4-((6-(4,4-difluoropiperidin-1-yl)-4-methylpyridin-2-yl)carbamoyl)-3-(6-azaspiro[2.5]octan-6-yl)phenyl)sulfamoyl)cyclopropane-1-carboxylate (0.15 g, 0.24 mmol, 63.1% yield) as white solid. m/z (ESI): 618.2 $(M+H)^+$.

Step 5: To a solution of methyl 1-(N-(4-((6-(4,4-difluoropiperidin-1-yl)-4-methylpyridin-2-yl)carbamoyl)-3-(6-azaspiro[2.5]octan-6-yl)phenyl)sulfamoyl)cyclopropane-1-carboxylate (0.150 g, 0.243 mmol) in THF (8 mL) was added lithium borohydride (0.486 mL, 0.971 mmol) at −78° C. The reaction mixture was slowly warmed up to room temperature over 2 h before it was quenched with an aqueous saturated solution of ammonium chloride and was extracted with ethyl acetate. The organic layer washed with water and brine, dried over $Na_2SO_4$, filtered, and concentrated. The concentrate was purified by flash column chromatography using a gradient of 40% to 45% EtOAc in petroleum ether to afford N-(6-(4,4-difluoropiperidin-1-yl)-4-methylpyridin-2-yl)-4-((1-(hydroxymethyl)cyclopropane)-1-sulfonamido)-2-(6-azaspiro[2.5]octan-6-yl)benzamide (0.090 g, 0.15 mmol, 63% yield) as white solid. $^1H$ NMR (400 MHz, DMSO-$d_6$): δ ppm 12.89 (s, 1H), 10.13 (s, 1H), 8.04 (d, J=8.6 Hz, 1H), 7.51 (s, 1H), 7.32 (d, J=2.2 Hz, 1H), 7.13 (dd, J=8.6, 2.1 Hz, 1H), 6.57 (s, 1H), 4.98 (t, J=6.2 Hz, 1H), 3.55-3.86 (m, 6H), 2.96 (s, 4H), 2.26 (s, 3H), 1.98 (q, J=8.7, 7.5 Hz, 4H), 1.65-1.75 (m, 4H), 1.06-1.19 (m, 2H), 0.93-1.06 (m, 2H), 0.39 (s, 4H). m/z (ESI): 590.2 $(M+H)^+$.

TABLE 12

Examples 10-1 to 10-2 were prepared following a similar procedure as described for Example 10

| Ex. # | Chemical Structure | Name | LRMS: (ESI + ve ion) m/z |
|---|---|---|---|
| 10-1 | 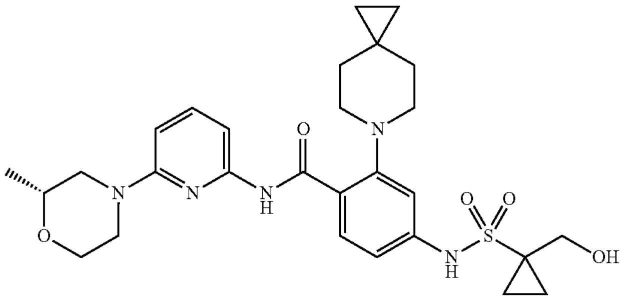 [SMILES: C[C@@H]1CN(c2cccc(NC(=O)c3ccc(NS(=O)(=O)C4(CO)CC4)cc3N3CCC4(CC3)CC4)n2)CCO1] | (R)-4-((1-(Hydroxymethyl)cyclopropane)-1-sulfonamido)-N-(6-(2-methylmorpholino) pyridin-2-yl)-2-(6-azaspiro[2.5]octan-6-yl) benzamide | 556.2 |
| 10-2 | 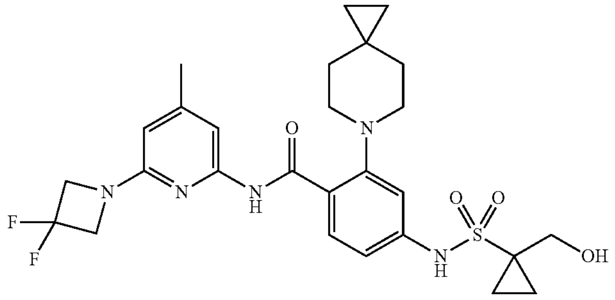 [SMILES: Cc1cc(NC(=O)c2ccc(NS(=O)(=O)C3(CO)CC3)cc2N2CCC3(CC2)CC3)nc(N2CC(F)(F)C2)c1] | N-(6-(3,3-Difluoroazetidin-1-yl)-4-methylpyridin-2-yl)-4-((1-(hydroxymethyl)cyclopropane)-1-sulfonamido)-2-(6-azaspiro[2.5]octan-6-yl)benzamide | 562.2 |

Method E (Cu-Catalyzed Sulfonamide Formation Followed by Reduction)

Example 11: N-(6-(3,3-difluoroazetidin-1-yl)-4-methylpyridin-2-yl)-4-((2-hydroxyethyl)sulfonamido)-2-(6-azaspiro[2.5]octan-6-yl)benzamide

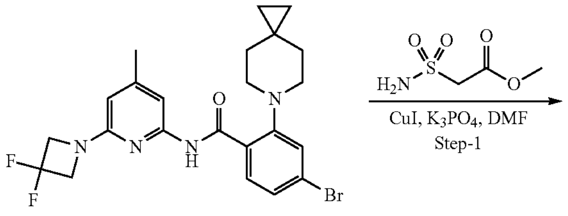

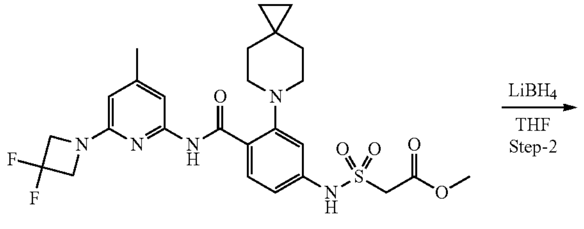

-continued

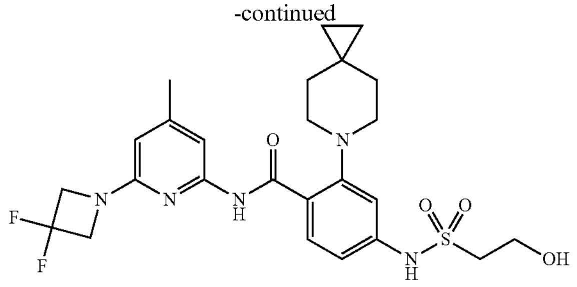

Step 1: A mixture of 4-bromo-N-(6-(3,3-difluoroazetidin-1-yl)-4-methylpyridin-2-yl)-2-(6-azaspiro[2.5]octan-6-yl) benzamide (0.17 g, 0.35 mmol, Intermediate 39), methyl 2-sulfamoylacetate (0.079 g, 0.52 mmol), copper (I) iodide (0.066 g, 0.35 mmol), potassium phosphate tribasic (0.147 g, 0.692 mmol), (1R,2R)—N1,N2-dimethylcyclohexane-1,2-diamine (0.025 g, 0.17 mmol) in DMF (4 mL) was heated at 90° C. for 16 h. Then the reaction mixture was filtered through a plug of celite. The filtrate was diluted with EtOAc and washed with water and brine, dried over $Na_2SO_4$, filtered, and concentrated. The concentrate was purified by flash column chromatography using a gradient of 0%-30% EtOAc in petroleum ether to provide methyl 2-(N-(4-((6-(3,3-difluoroazetidin-1-yl)-4-methylpyridin-2-yl)carbamoyl)-3-(6-azaspiro[2.5]octan-6-yl)phenyl)sulfamoyl)acetate (0.16 g, 0.28 mmol, 82% yield) as semi solid. $^1H$ NMR (400 MHz, DMSO-d6): δ ppm 13.12 (br s, 1H), 10.65 (s, 1H), 8.07 (dd, J=8.6, 1.8 Hz, 1H), 7.57 (s, 1H), 7.28 (t, J=2.0 Hz, 1H), 7.15 (dt, J=8.6, 2.0 Hz, 1H), 6.19 (s, 1H), 4.32-4.46 (m, 6H), 3.64 (s, 3H), 2.98 (t, J=5.0 Hz, 4H), 2.28 (s, 3H), 1.76 (br s, 4H), 0.39 (s, 4H). m/z (ESI): 564.2 $(M+H)^+$.

Step 2: To a solution of methyl 2-(N-(4-((6-(3,3-difluoroazetidin-1-yl)-4-methylpyridin-2-yl)carbamoyl)-3-(6-azaspiro[2.5]octan-6-yl)phenyl)sulfamoyl)acetate (0.16 g, 0.28 mmol) in THF (3.2 mL) was added a 2M solution of lithium borohydride in THF (0.284 mL, 0.568 mmol) dropwise at 0° C. The reaction mixture was slowly warmed to room temperature over 1 h before it was quenched with an aqueous saturated solution of ammonium chloride and was extracted with ethyl acetate. The organic layer washed with water and brine, dried over $Na_2SO_4$, filtered, and concentrated. The concentrate was purified by reverse phase column chromatography using a gradient of 0-60% acetonitrile in water to afford N-(6-(3,3-difluoroazetidin-1-yl)-4-methylpyridin-2-yl)-4-((2-hydroxyethyl)sulfonamido)-2-(6-azaspiro[2.5]octan-6-yl)benzamide (0.095 g, 0.18 mmol, 62% yield) as white solid. $^1$H NMR (400 MHz, DMSO-$d_6$): δ ppm 13.08 (s, 1H), 10.20 (s, 1H), 8.05 (d, J=8.6 Hz, 1H), 7.56 (s, 1H), 7.26 (d, J=2.2 Hz, 1H), 7.12 (dd, J=8.6, 2.2 Hz, 1H), 6.18 (s, 1H), 4.93 (br s, 1H), 4.36 (t, J=12.4 Hz, 4H), 3.75 (q, J=6.0 Hz, 2H), 3.35 (t, J=6.5 Hz, 2H), 2.96 (t, J=5.3 Hz, 4H), 2.27 (s, 3H), 1.74 (br s, 4H), 0.38 (s, 4H). m/z (ESI): 564.2 $(M+H)^+$.

Examples 12-1 and 12-2: 2-(6-Azaspiro[2.5]octan-6-yl)-4-(S-cyclopropylsulfonimidoyl)-N-(6-((2R)-2-methyl-4-morpholinyl)-2-pyridinyl)benzamide and 2-(6-azaspiro[2.5]octan-6-yl)-4-(R-cyclopropylsulfonimidoyl)-N-(6-((2R)-2-methyl-4-morpholinyl)-2-pyridinyl)benzamide

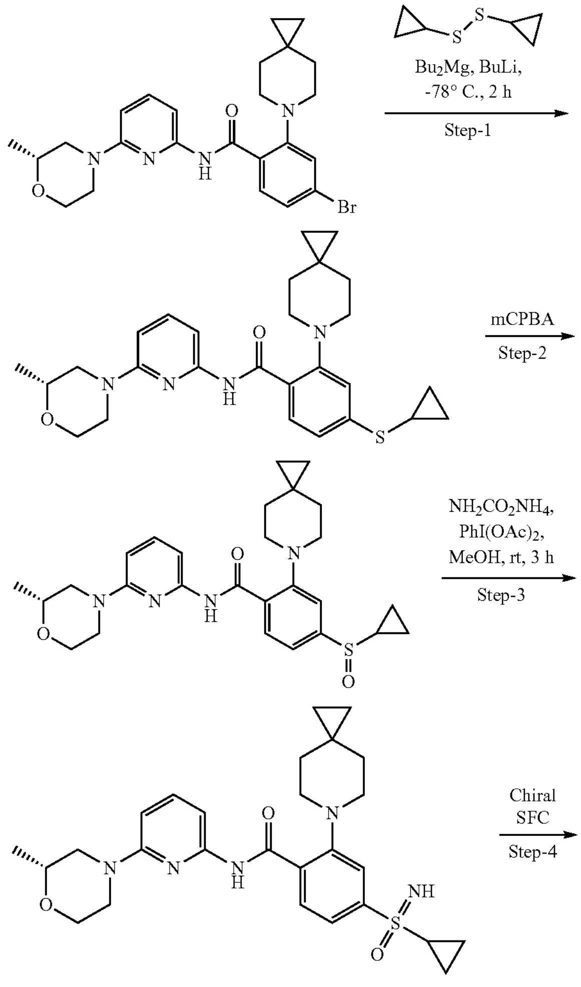

-continued

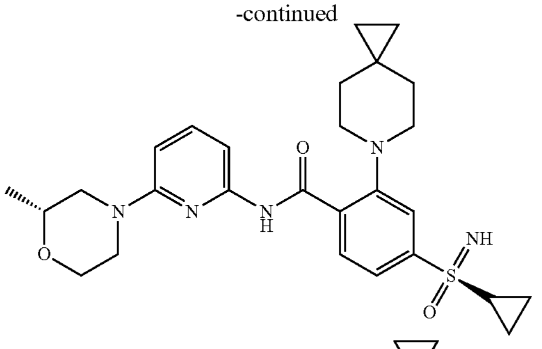

+

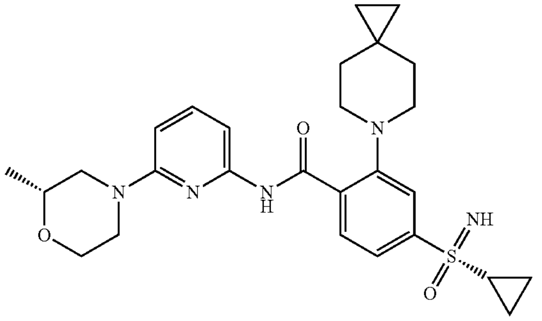

Step 1: To a solution of (R)-4-bromo-N-(6-(2-methylmorpholino)pyridin-2-yl)-2-(6-azaspiro[2.5]octan-6-yl)benzamide (1.0 g, 2.1 mmol, Intermediate 30) in THF (20 mL) was added dibutyl magnesium (1.0 M solution in THF, 1.24 mL, 1.24 mmol) dropwise at 0° C. and stirred for 10 min. The reaction mixture was cooled to −78° C. and was added n-butyl lithium (2.5 M in solution in hexanes, 0.989 mL, 2.47 mmol) and stirred for 10 min. 1,2-dicyclopropyldisulfane (0.301 g, 2.06 mmol, Wuxi AppTec) was added dropwise and stirred at room temperature for 2 h. The reaction mixture was quenched with 2N HCl (20 mL) and extracted with ethyl acetate (2×20 mL). The combined organic extracts were washed with brine (20 mL), dried over sodium sulfate, filtered, and concentrated under reduced pressure. The crude residue was purified by flash chromatography through a Redi-Sep pre-packed silica gel column (40 g), eluting with a gradient of 30% ethyl acetate in hexanes to give (R)-4-(cyclopropylthio)-N-(6-(2-methylmorpholino)pyridin-2-yl)-2-(6-azaspiro[2.5]octan-6-yl)benzamide (0.90 g, 91% yield) as a pale yellow solid. $^1$H NMR (400 MHz, DMSO-$d_6$): δ 12.91 (s, 1H), 8.06 (d, J=8.4 Hz, 1H), 7.70-7.59 (m, 2H), 7.40-7.26 (m, 2H), 6.61-6.58 (m, 1H), 4.11 (dd, J=25.9, 12.9 Hz, 2H), 3.93 (dd, J=11.5, 3.2 Hz, 1H), 3.62-3.55 (m, 2H), 3.03 (t, J=5.5 Hz, 4H), 2.83 (td, J=12.2, 3.4 Hz, 1H), 2.38 (dq, J=7.3, 3.8, 3.2 Hz, 1H), 1.72 (s, 4H), 1.20-1.16 (m, 6H), 0.66-0.62 (m, 2H), 0.38 (d, J=1.6 Hz, 4H). m/z (ESI): 479.2 $(M+H)^+$.

Step 2: To a solution of (R)-4-(cyclopropylthio)-N-(6-(2-methylmorpholino)pyridin-2-yl)-2-(6-azaspiro[2.5]octan-6-yl)benzamide (0.90 g, 1.9 mmol) in dichloromethane (10 mL) was added m-CPBA (43.3 mg, 0.188 mmol) at 0° C. and stirred at same temperature for 3 h. The reaction mixture was quenched with 10% aqueous sodium bicarbonate solution (15 mL) and extracted with DCM (2×20 mL). The combined organic extracts were washed with brine solution (20 mL), dried over sodium sulphate, filtered, and concentrated under reduced pressure. The crude residue was purified by flash chromatography through a Redi-Sep pre-packed silica gel column (40 g), eluting with a gradient of 1% to 50% ethyl acetate in hexanes to give 4-(cyclopropylsulfinyl)-N-(6-((R)-2-methylmorpholino)pyridin-2-yl)-2-(6-azaspiro[2.5]octan-6-yl)benzamide (650 mg, 70% yield) as a pale yellow solid. $^1$H NMR (400 MHz, Chloroform-d): δ 12.89 (s, 1H), 8.23 (d, J=8.3 Hz, 1H), 7.81 (dd, J=7.9, 4.6

Hz, 1H), 7.57 (td, J=8.0, 3.3 Hz, 1H), 7.30 (dd, J=8.3, 1.8 Hz, 1H), 7.25 (d, J=1.8 Hz, 1H), 6.42 (dd, J=8.2, 3.7 Hz, 1H), 4.18-3.95 (m, 3H), 3.81-3.65 (m, 2H), 3.09 (q, J=6.3, 5.6 Hz, 4H), 2.97 (tt, J=12.8, 11.7, 2.7 Hz, 1H), 2.63 (ddd, J=12.7, 10.4, 1.9 Hz, 1H), 2.23 (tt, J=7.3, 4.4 Hz, 1H), 1.31-1.27 (m, 4H), 1.19-1.15 (m, 5H), 0.77-0.73 (m, 2H), 0.40 (d, J=1.7 Hz, 4H). m/z (ESI): 495.2 $(M+H)^+$.

Step 3: To a solution of 4-(cyclopropylsulfinyl)-N-(6-((R)-2-methylmorpholino)pyridin-2-yl)-2-(6-azaspiro[2.5]octan-6-yl)benzamide (0.65 g, 1.30 mmol) in MeOH (20 mL) were added iodobenzene diacetate (1.27 g, 3.94 mmol) and ammonium carbamate (410 mg, 5.26 mmol) at 0° C. and for 10 min and warmed to room temperature and stirred for 12 h. The reaction mixture was quenched with water (10 mL) and extracted with ethyl acetate (2×10 mL). The combined organic extracts were washed with brine solution (10 mL), dried over sodium sulfate, filtered, and concentrated under reduced pressure. The crude residue was purified by flash chromatography through a Redi-Sep pre-packed silica gel column (40 g), eluting with a gradient of 40% ethyl acetate in hexanes to give 4-(cyclopropanesulfonimidoyl)-N-(6-((R)-2-methylmorpholino)pyridin-2-yl)-2-(6-azaspiro[2.5]octan-6-yl)benzamide (150 mg, racemic) as a pale yellow solid. $^1$H NMR (400 MHz, Chloroform-d): δ 12.67 (s, 1H), 8.45 (dd, J=8.3, 1.2 Hz, 1H), 7.93 (t, J=1.5 Hz, 1H), 7.84 (dt, J=8.3, 1.5 Hz, 1H), 7.82-7.72 (m, 1H), 7.66-7.56 (m, 1H), 6.46 (d, J=8.2 Hz, 1H), 4.22-3.92 (m, 3H), 3.92-3.62 (m, 2H), 3.33-3.11 (m, 4H), 2.99 (td, J=12.2, 3.5 Hz, 1H), 2.77-2.55 (m, 2H), 2.01-1.69 (m, 4H), 1.47 (ddt, J=9.9, 7.0, 5.0 Hz, 1H), 1.30 (dd, J=6.2, 1.0 Hz, 3H), 1.28-1.20 (m, 2H), 1.18-1.08 (m, 1H), 1.00 (qd, J=8.0, 6.0 Hz, 1H), 0.43 (d, J=1.1 Hz, 4H). m z (ESI): 510.2 $(M+H)^+$. The racemic mixture was separated by chiral separation by SFC using a (S,S)Whelk-01 (250×30 mm, 5 μm) column, mobile phase: 70:30 (A: B), A=liquid $CO_2$, B=Methanol, flow rate: 70 mL/min to give:

Example 12-1: 2-(6-Azaspiro[2.5]octan-6-yl)-4-(S-cyclopropylsulfonimidoyl)-N-(6-((2R)-2-methyl-4-morpholinyl)-2-pyridinyl)benzamide. $^1$H NMR (400 MHz, Chloroform-d) δ 12.64 (s, 1H), 8.44 (d, J=8.1 Hz, 1H), 7.93 (d, J=1.7 Hz, 1H), 7.83 (dd, J=8.3, 1.8 Hz, 1H), 7.77 (d, J=7.8 Hz, 1H), 7.60 (t, J=8.0 Hz, 1H), 6.46 (d, J=8.1 Hz, 1H), 4.13-4.01 (m, 3H), 3.80-3.64 (m, 2H), 3.19-3.13 (m, 4H), 2.98 (td, J=12.2, 3.6 Hz, 1H), 2.67-2.60 (m, 2H), 2.01-1.50 (m, 3H), 1.47 (ddt, J=9.7, 6.8, 4.8 Hz, 1H), 1.32-1.26 (m, 6H), 1.15 (qd, J=7.9, 4.9 Hz, 1H), 1.05-0.95 (m, 1H), 0.42 (s, 4H). m/z (ESI): 510.2 $(M+H)^+$.

Example 12-2: 2-(6-Azaspiro[2.5]octan-6-yl)-4-(R-cyclopropylsulfonimidoyl)-N-(6-((2R)-2-methyl-4-morpholinyl)-2-pyridinyl)benzamide. $^1$H NMR (400 MHz, Chloroform-d): δ 12.65 (s, 1H), 8.44 (d, J=8.2 Hz, 1H), 7.93 (d, J=1.7 Hz, 1H), 7.83 (dd, J=8.2, 1.8 Hz, 1H), 7.77 (d, J=7.8 Hz, 1H), 7.59 (t, J=8.1 Hz, 1H), 6.45 (d, J=8.3 Hz, 1H), 4.13-3.95 (m, 3H), 3.73 (dddd, J=17.1, 9.9, 8.1, 5.2 Hz, 2H), 3.19-3.13 (m, 4H), 2.98 (td, J=12.3, 3.6 Hz, 1H), 2.63 (dq, J=10.8, 3.9 Hz, 2H), 2.01-1.50 (m, 3H), 1.47 (dtd, J=10.2, 4.8, 2.4 Hz, 1H), 1.32-1.29 (m, 2H), 1.29 (d, J=6.2 Hz, 4H), 1.14 (ddd, J=10.1, 7.9, 3.8 Hz, 1H), 0.99 (dtd, J=9.0, 7.4, 4.9 Hz, 1H), 0.42 (s, 4H). m/z (ESI): 510.2 $(M+H)^+$. The stereochemistry was arbitrary assigned.

TABLE 13

Examples 13-1 to 13-4 were prepared following a similar procedure for examples 12-1 and 12-2

| Ex. # | Chemical Structure | Name | LRMS: (ESI + ve ion) m/z |
|---|---|---|---|
| 13-1 | 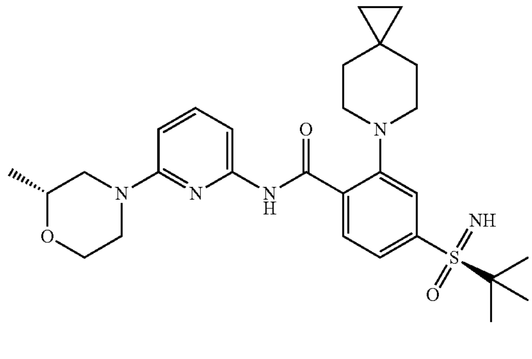 [SMILES: C[C@@H]1CN(c2cccc(NC(=O)c3ccc([S@](=N)(=O)C(C)(C)C)cc3N3CCC4(CC3)CC4)n2)CCO1] | N-(6-((R)-2-Methylmorpholino)pyridin-2-yl)-4-((R)-2-methylpropan-2-ylsulfonimidoyl)-2-(6-azaspiro[2.5]octan-6-yl)benzamide | 526.2 |
| 13-2 | 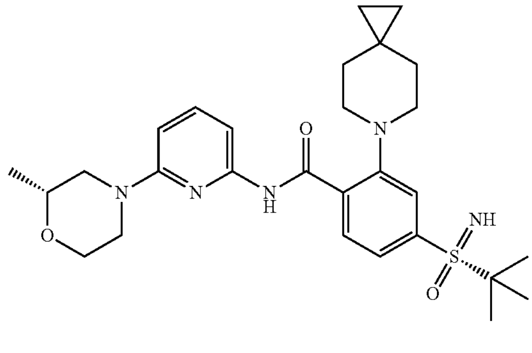 [SMILES: C[C@@H]1CN(c2cccc(NC(=O)c3ccc([S@@](=N)(=O)C(C)(C)C)cc3N3CCC4(CC3)CC4)n2)CCO1] | N-(6-((R)-2-Methylmorpholino)pyridin-2-yl)-4-((S)-2-methylpropan-2-ylsulfonimidoyl)-2-(6-azaspiro[2.5]octan-6-yl)benzamide | 526.2 |

TABLE 13-continued

| Ex. # | Chemical Structure | Name | LRMS: (ESI + ve ion) m/z |
|---|---|---|---|
| Examples 13-1 to 13-4 were prepared following a similar procedure for examples 12-1 and 12-2 | | | |
| 13-3 | 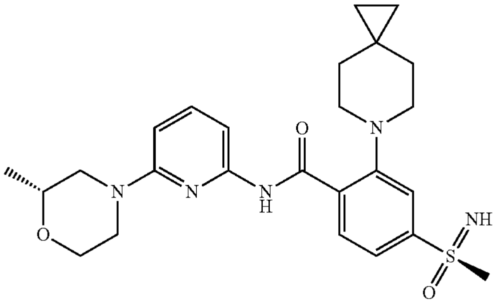 | 2-(6-Azaspiro[2.5]octan-6-yl)-N-(6-((2R)-2-methyl-4-morpholinyl)-2-pyridinyl)-4-(S-methylsulfonimidoyl)benzamide | 484.5 |
| 13-4 | 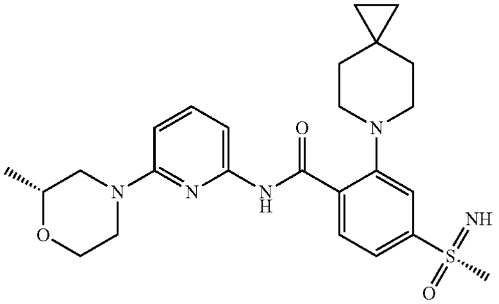 | 2-(6-Azaspiro[2.5]octan-6-yl)-N-(6-((2R)-2-methyl-4-morpholinyl)-2-pyridinyl)-4-(R-methylsulfonimidoyl)benzamide | 484.5 |

Example 14: N-(6-(cyclopropylmethoxy)pyridin-2-yl)-4-((1-methylcyclopropane)-1-sulfonamido)-2-(6-azaspiro[2.5]octan-6-yl)benzamide

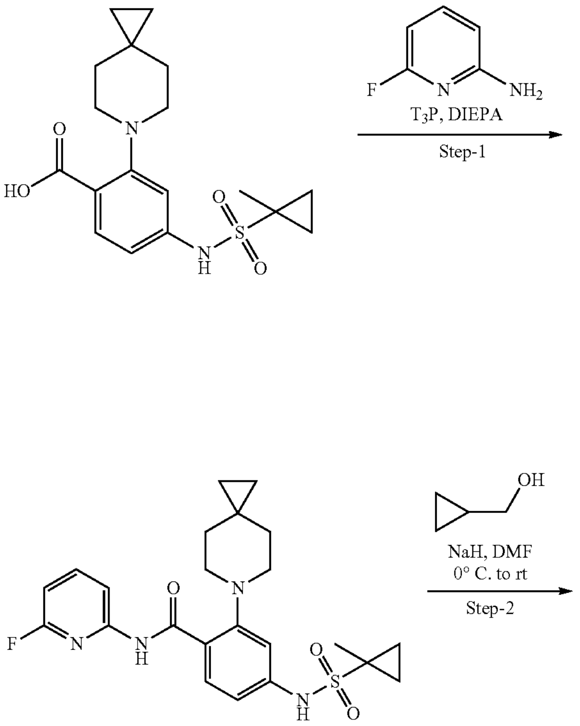

-continued

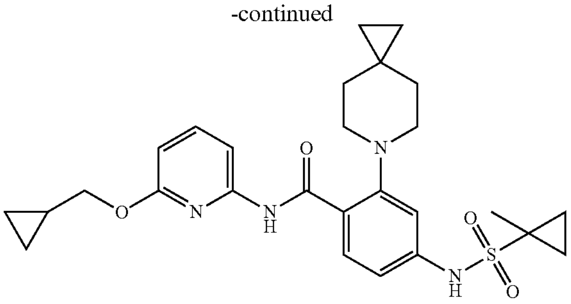

Step 1: A solution of 4-((1-methylcyclopropane)-1-sulfonamido)-2-(6-azaspiro[2.5]octan-6-yl)benzoic acid (5.0 g, 14 mmol, Intermediate 11) in DCM (50 mL) were treated with DIPEA (7.19 mL, 41.2 mmol), 6-fluoropyridin-2-amine (1.84 g, 16.5 mmol) followed by $T_3P$ (17.46 g, 27.4 mmol, 50% in EtOAc, Spectrochem) at rt. Then the reaction mixture was stirred for 16 h before it was quenched with water and was extracted with DCM. The organic extract was washed with brine, dried over $Na_2SO_4$, filtered, and concentrated. The concentrate was purified by flash column chromatography by eluting with a gradient of 15% to 20% EtOAc in petroleum ether to provide N-(6-fluoropyridin-2-yl)-4-((1-methylcyclopropane)-1-sulfonamido)-2-(6-azaspiro[2.5]octan-6-yl)benzamide (3.0 g, 6.5 mmol, 48% yield) as off-white solid. $^1$H NMR (400 MHz, DMSO-$d_6$): δ ppm 13.09 (s, 1H), 10.28 (s, 1H), 8.20 (d, J=7.7 Hz, 1H), 8.03 (t, J=9.0 Hz, 2H), 7.36 (s, 1H), 7.17 (d, J=8.5 Hz, 1H), 6.89 (d, J=8.0 Hz, 1H), 2.97 (t, J=5.3 Hz, 4H), 1.67 (s, 4H), 1.41 (s, 3H), 1.21 (s, 2H), 0.81-0.89 (m, 2H), 0.41 (s, 4H). m z (ESI): 459.1 $(M+H)^+$.

Step 2: A solution of cyclopropylmethanol (23.59 mg, 0.327 mmol) in DMF (1.5 mL) was treated with sodium hydride (13.08 mg, 0.327 mmol, 60% in mineral oil) at 0° C. under $N_2$ atmosphere and was stirred for 10 min. Then a solution of N-(6-fluoropyridin-2-yl)-4-((1-methylcyclopropane)-1-sulfonamido)-2-(6-azaspiro[2.5]octan-6-yl)benzamide (100 mg, 0.218 mmol) in DMF (0.5 mL) was added to the reaction mixture. The resulting solution was stirred at rt for 2 h before it was quenched with an aqueous saturated solution of $NH_4Cl$ and extracted with EtOAc. The organic extract was washed with brine, dried over $Na_2SO_4$, filtered, and concentrated. The concentrate was purified by reverse phase HPLC to provide N-(6-(cyclopropylmethoxy)pyridin-2-yl)-4-((1-methylcyclopropane)-1-sulfonamido)-2-(6-azaspiro[2.5]octan-6-yl)benzamide as white solid. $^1H$ NMR (400 MHz, DMSO-$d_6$): δ ppm 13.20 (s, 1H), 10.22 (br s, 1H), 8.08 (d, J=8.6 Hz, 1H), 7.85 (d, J=7.8 Hz, 1H), 7.72 (t, J=7.9 Hz, 1H), 7.36 (d, J=2.2 Hz, 1H), 7.17 (dd, J=8.7, 2.2 Hz, 1H), 6.56 (d, J=8.0 Hz, 1H), 4.12 (d, J=7.2 Hz, 2H), 2.98 (d, J=5.3 Hz, 4H), 1.71 (br s, 4H), 1.41 (s, 3H), 1.24-1.35 (m, 1H), 1.17-1.27 (m, 2H), 0.80-0.88 (m, 2H), 0.55-0.64 (m, 2H), 0.39 (s, 4H), 0.28-0.36 (m, 2H). m/z (ESI): 511.2 $(M+H)^+$.

Example 15: N-(6-(cyclopropylmethoxy)pyridin-2-yl)-4-((1-methylcyclopropane)-1-sulfonamido)-2-(6-azaspiro[2.5]octan-6-yl)benzamide

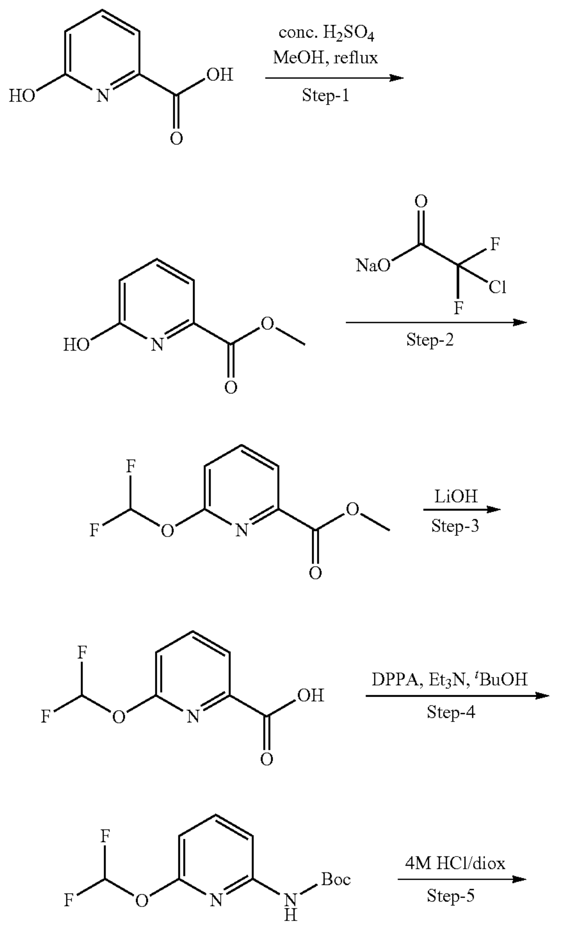

-continued

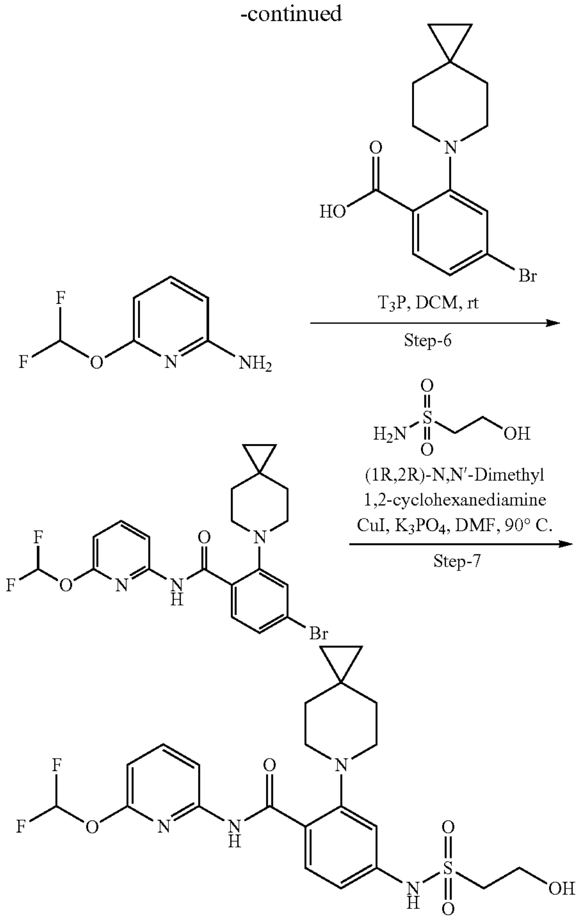

Step 1: To a solution of 6-hydroxypicolinic acid (5.0 g, 36 mmol) in MeOH (83 mL) was dropwise added $H_2SO_4$ (4.79 mL, 90 mmol) at rt. The reaction mixture was then heated at reflux for 18 h before volatiles were evaporated and the concentrate was neutralized with $NaHCO_3$ (100 mL) solution slowly to maintain pH of 7-8. Then the reaction mixture was extracted with $CH_2Cl_2$. The organic layer was washed with water and brine, dried over $Na_2SO_4$, filtered, and concentrated. The concentrate was triturated with petroleum ether to provide methyl 6-hydroxypicolinate (4.2 g, 27 mmol, 76% yield) as white solid. $^1H$ NMR (400 MHz, DMSO-$d_6$) δ ppm 11.54 (s, 1H), 7.64 (dd, J=8.9, 7.0 Hz, 1H), 7.16 (dd, J=7.0, 1.0 Hz, 1H), 6.73 (dd, J=8.9, 1.0 Hz, 1H), 3.84 (s, 3H). m/z (ESI): 154.1 $(M+H)^+$.

Step 2: A solution of methyl 6-hydroxypicolinate (1.0 g, 6.4 mmol) and sodium 2-chloro-2,2-difluoroacetate (1.971 g, 12.93 mmol, TCI India) in acetonitrile (25 mL) was heated at 85° C. for 72 h. Then the reaction mixture was cooled to rt and was evaporated to dryness to afford methyl 6-(difluoromethoxy)picolinate (2.1 g, 6.3 mmol, 98% yield) as yellow oil which was used in next step without further purification. $^1H$ NMR (400 MHz, DMSO-$d_6$) δ ppm 8.12 (ddd, J=11.3, 6.7, 2.7 Hz, 1H), 7.92-7.97 (m, 1H), 7.50-7.91 (m, 1H), 7.34-7.42 (m, 1H), 3.89 (s, 3H). m/z (ESI): 204.1 $(M+H)^+$.

Step 3: To a solution of methyl 6-(difluoromethoxy) picolinate (2.0 g, 5.9 mmol) in THF (90 mL) was added LiOH (11.81 mL, 23.63 mmol, 2 M solution in $H_2O$). The reaction mixture was stirred at rt for 16 h before it was quenched with 1N HCl (pH=2-3) and was extracted with $CH_2Cl_2$. The organic layer was washed with brine, dried over $Na_2SO_4$, filtered, and concentrated to provide 6-(difluoromethoxy)picolinic acid as a light-yellow solid which was used in next step without purification. $^1$H NMR (300 MHz, DMSO-$d_6$) δ ppm 13.34 (s, 1H), 8.02-8.19 (m, 1H), 7.91 (d, J=7.4 Hz, 1H), 7.79 (t, J=72.6 Hz, 1H), 7.34 (d, J=8.2 Hz, 1H). m/z (ESI): 190.0 $(M+H)^+$.

Step 4: To a solution of 6-(difluoromethoxy)picolinic acid (0.80 g, 4.1 mmol) in a mixture of tert-butanol (2.5 mL) and toluene (28 mL) were added $Et_3N$ (2.30 mL, 16.51 mmol) followed by diphenyl phosphorazidate (1.31 mL, 6.19 mmol) at rt under $N_2$ atmosphere. The reaction mixture was heated at 100° C. for 16 h before it was neutralized aqueous $NaHCO_3$ solution (100 mL) and was extracted with EtOAc (2×50 mL). The combined organic layers were dried over $Na_2SO_4$, filtered, and concentrated. The concentrate was purified by flash column chromatography using a gradient of 2% to 5% EtOAc in petroleum ether to provide tert-butyl (6-(difluoromethoxy)pyridin-2-yl)carbamate (0.51 g, 1.9 mmol, 47% yield) as light-yellow oil. $^1$H NMR (400 MHz, DMSO-$d_6$) δ ppm 9.85 (s, 1H), 7.83 (t, J=8 Hz, 1H), 7.73-7.36 (m, 2H), 6.66 (d, J=12 Hz, 1H), 1.47 (s, 9H). m/z (ESI): 204.1 $(M-{}^iBu)^+$, 161.1 $(M-Boc)^+$.

Step 5: To a solution of tert-butyl (6-(difluoromethoxy)pyridin-2-yl)carbamate (0.50 g, 1.9 mmol) in 1,4-dioxane (3.0 mL) was added 4.0 M HCl in Dioxane (9.98 mL, 39.9 mmol) at rt over 5 min. The reaction mixture was stirred for 6 h before it was quenched with a saturated aqueous solution of $NaHCO_3$ solution (100 mL) and was extracted with $CH_2Cl_2$. The organic extracts were washed with brine, dried over $Na_2SO_4$, filtered, and concentrated to provide 6-(difluoromethoxy)pyridin-2-amine (0.31 g, 1.8 mmol, 95% yield) as orange oil which was used in next step without purification. $^1$H NMR (300 MHz, DMSO-$d_6$) δ ppm 7.21-7.79 (m, 2H), 6.23 (d, J=7.7 Hz, 3H), 6.05 (d, J=7.7 Hz, 1H). m/z (ESI): 161.1 $(M+H)^+$.

Step 6: To a solution of 4-bromo-2-(6-azaspiro[2.5]octan-6-yl)benzoic acid (0.40 g, 1.3 mmol, Intermediate 9-1) in DCM (5.0 mL) were added DIPEA (0.676 mL, 3.87 mmol) followed by $T_3P$ (2.28 mL, 3.87 mmol, 50% in Ethyl acetate) at rt and stirred for 15 min. Then a solution of 6-(difluoromethoxy)pyridin-2-amine (0.327 g, 1.93 mmol) in dichloromethane (2.0 mL) was added to the reaction mixture. The resulting mixture was stirred at it for 16 h before it was quenched with water (50 mL) and was extracted with $CH_2Cl_2$. The combined organic layers were washed with brine, dried over $Na_2SO_4$, filtered, and concentrated. The concentrate was purified by flash column chromatography using a gradient of 0% to 17% EtOAc in petroleum ether to provide 4-bromo-N-(6-(difluoromethoxy)pyridin-2-yl)-2-(6-azaspiro[2.5]octan-6-yl)benzamide (0.30 g, 0.62 mmol, 48% yield) as light-yellow gummy liquid. H NMR (300 MHz, DMSO-$d_6$) δ ppm 13.45 (s, 1H), 7.92-8.17 (m, 3H), 7.70-7.80 (m, 1H), 7.57 (d, J=6.7 Hz, 2H), 6.84 (d, J=7.9 Hz, 1H), 3.05 (t, J=5.3 Hz, 4H), 1.69 (s, 4H), 0.38 (s, 4H). m/z (ESI): 452.0, 454.0 $(M+H)^+$.

Step 7: A mixture of 4-bromo-N-(6-(difluoromethoxy)pyridin-2-yl)-2-(6-azaspiro[2.5]octan-6-yl)benzamide (0.30 g, 0.66 mmol), 2-hydroxyethane-1-sulfonamide (0.125 g, 0.995 mmol), potassium phosphate (0.422 g, 1.99 mmol), (1R,2R)—N1,N2-dimethylcyclohexane-1,2-diamine (0.094 g, 0.66 mmol) and copper(I) iodide (0.126 g, 0.663 mmol) in DMF (3.0 mL) was heated at 90° C. for 16 h. The reaction mixture was filtered through a plug of celite and the filtrate was diluted with EtOAc. The organic layer was washed with water, brine, dried over $Na_2SO_4$, filtered, and concentrated. The concentrate was purified by flash column chromatography eluting with 5% to 44% EtOAc in petroleum ether to provide N-(6-(difluoromethoxy)pyridin-2-yl)-4-((2-hydroxyethyl)sulfonamido)-2-(6-azaspiro[2.5]octan-6-yl)benzamide (0.18 g, 0.36 mmol, 54% yield) as white solid. $^1$H NMR (400 MHz, DMSO-$d_6$) δ ppm 13.50 (s, 1H), 10.26 (s, 1H), 8.11 (t, J=8.0 Hz, 2H), 7.96 (t, J=8.0 Hz, 1H), 7.30 (d, J=2.2 Hz, 1H), 7.16 (dd, J=8.7, 2.2 Hz, 1H), 6.81 (d, J=8.0 Hz, 1H), 4.96 (t, J=5.6 Hz, 1H), 3.77 (q, J=6.0 Hz, 2H), 3.38 (d, J=6.4 Hz, 2H), 2.99 (t, J=5.5 Hz, 4H), 1.72 (br s, 4H), 0.40 (s, 4H). m/z (ESI): 497.1 $(M+H)^+$.

Example 16: N-(6-(2-hydroxy-2-methylpropoxy)pyridin-2-yl)-4-((2-hydroxyethyl)sulfonamido)-2-(6-azaspiro[2.5]octan-6-yl)benzamide

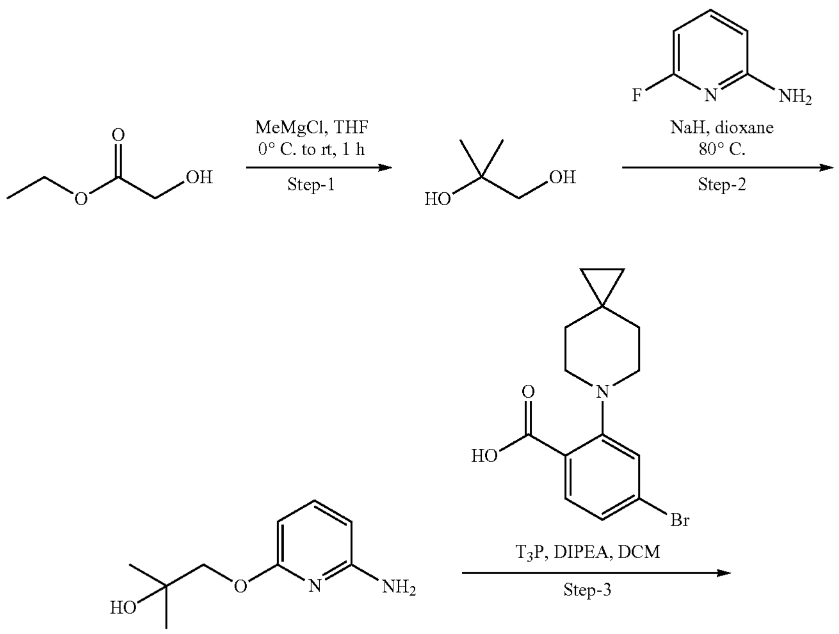

-continued

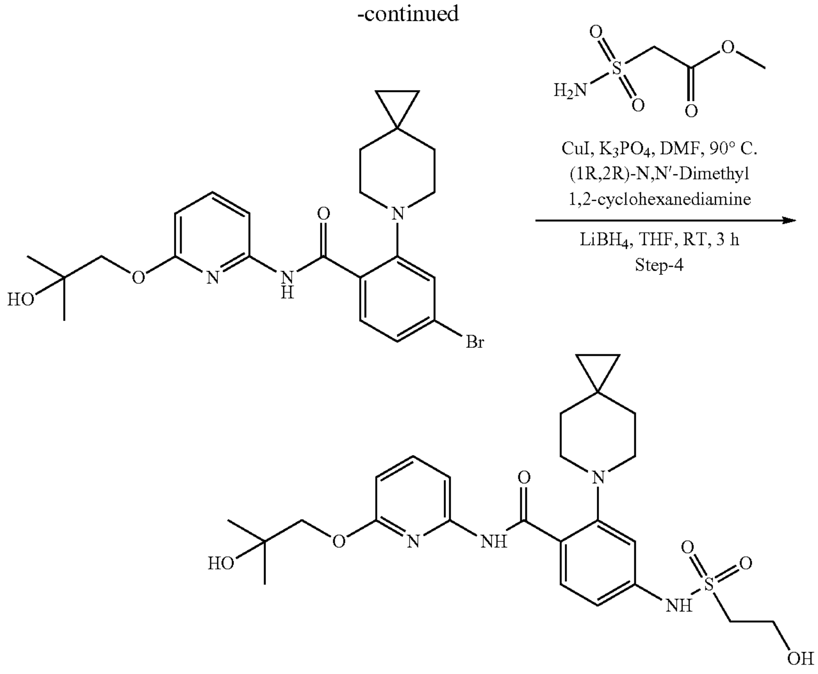

Step 1: To a solution of ethyl 2-hydroxyacetate (5.0 g, 48 mmol, Combi-Blocks) in THF (100 mL) was added methyl magnesium chloride (48.0 mL, 3.0 M in THF, 144 mmol) and the reaction mixture was stirred at 0° C. for 30 min. The reaction mixture was quenched with a saturated aqueous $NH_4Cl$ solution and extracted with EtOAc. The organic extract was washed with brine, dried over $Na_2SO_4$, filtered, and concentrated to provide 2-methylpropane-1,2-diol (2.3 g, 26 mmol 53% yield) as light-yellow oil. $^1H$ NMR (300 MHz, DMSO-$d_6$) δ ppm 4.49 (t, J=5.8 Hz, 1H), 4.10 (br s, 1H), 3.12-3.16 (m, 2H), 1.03 (s, 6H).

Step 2: To a solution of 6-fluoropyridin-2-amine (0.700 g, 6.24 mmol) and 2-methylpropane-1,2-diol (0.844 g, 9.37 mmol) in dioxane (7 mL) at rt was added and NaH (60% in mineral oil, 0.749 g, 18.7 mmol). The reaction mixture was stirred at 80° C. for 4 h, cooled to rt, quenched with saturated aqueous $NH_4Cl$ solution, and was extracted with EtOAc. The organic extract was washed with brine, dried over $Na_2SO_4$, filtered, concentrated and purified by flash column chromatography, eluting with a gradient of 10% to 80% ethyl acetate in petroleum ether to provide 1-((6-aminopyridin-2-yl)oxy)-2-methylpropan-2-ol (0.60 g, 3.3 mmol, 53% yield) as orange oil. $^1H$ NMR (400 MHz, DMSO-$d_6$) δ ppm 7.25-7.29 (m, 1H), 5.97 (d, J=7.8 Hz, 1H), 5.87 (d, J=7.8 Hz, 1H), 5.82 (s, 2H), 4.56 (s, 1H), 3.88 (s, 2H), 1.15 (s, 6H). m/z (ESI): 183.2 $(M+H)^+$.

Step 3: A mixture of 4-bromo-2-(6-azaspiro[2.5]octan-6-yl)benzoic acid (0.30 g, 0.97 mmol, Intermediate 9-1), DIPEA (0.203 mL, 1.16 mmol), $T_3P$ (50% in ethyl acetate, 0.691 mL, 1.16 mmol) and 1-((6-aminopyridin-2-yl)oxy)-2-methylpropan-2-ol (0.211 g, 1.16 mmol) in DCM (3 mL) was stirred at room temperature for 4 h. The reaction mixture was diluted with water and was extracted with ethyl acetate. The organic extract was washed with brine, dried over $Na_2SO_4$, filtered, concentrated and purified by flash column chromatography, eluting with a gradient of 5% to 30% ethyl acetate in petroleum ether to provide 4-bromo-N-(6-(2-hydroxy-2-methylpropoxy)pyridin-2-yl)-2-(6-azaspiro[2.5]octan-6-yl)benzamide (0.20 g, 0.42 mmol, 44% yield) as off white solid. $^1H$ NMR (400 MHz, DMSO-$d_6$) δ ppm 13.08 (s, 1H), 8.05 (d, J=8.4 Hz, 1H), 7.85 (d, J=7.8 Hz, 1H), 7.69-7.76 (m, 2H), 7.55-7.59 (m, 1H), 6.59 (d, J=8.0 Hz, 1H), 4.60 (s, 1H), 4.06 (s, 2H), 3.06 (t, J=5.3 Hz, 4H), 1.73 (br s, 4H), 1.22 (s, 6H), 0.39 (s, 4H). m/z (ESI): 476.1 $(M+H)^+$.

Step 4: A mixture of 4-bromo-N-(6-(2-hydroxy-2-methylpropoxy)pyridin-2-yl)-2-(6-azaspiro[2.5]octan-6-yl)benzamide (0.27 g, 0.57 mmol), methyl 2-sulfamoylacetate (0.131 g, 0.854 mmol), potassium phosphate (0.302 g, 1.42 mmol), (1R,2R)—N1,N2-dimethylcyclohexane-1,2-diamine (0.040 g, 0.28 mmol) and copper(I) iodide (0.108 g, 0.569 mmol) in DMF (4 mL) was stirred at 90° C. for 16 h. The reaction mixture was diluted with water and extracted with ethyl acetate. The organic extract was washed with brine, dried over $Na_2SO_4$, filtered, concentrated and purified by flash column chromatography, eluting with a gradient of 10% to 80% ethyl acetate in petroleum ether to provide methyl 2-(N-(4-((6-(2-hydroxy-2-methylpropoxy)pyridin-2-yl)carbamoyl)-3-(6-azaspiro[2.5]octan-6-yl)phenyl)sulfamoyl)acetate (0.25 g, 0.46 mmol, 80% yield) as light yellow oil. m/z (ESI): 547.2 $(M+H)^+$.

To a solution of methyl 2-(N-(4-((6-(2-hydroxy-2-methylpropoxy)pyridin-2-yl)carbamoyl)-3-(6-azaspiro[2.5]octan-6-yl)phenyl)sulfamoyl)acetate (0.24 g, 0.44 mmol) in THF (3.75 mL) was added $LiBH_4$ (0.439 mL, 0.878 mmol) at −30° C. and the resulting mixture was stirred at room temperature for 2 h. The reaction mixture was quenched with a saturated aqueous $NH_4Cl$ solution and was extracted with EtOAc. The organic extract was washed with brine, dried over $Na_2SO_4$, filtered, concentrated, and purified by flash column chromatography, eluting with a gradient of 30% to 90% ethyl acetate in petroleum ether to provide N-(6-(2-hydroxy-2-methylpropoxy)pyridin-2-yl)-4-((2-hydroxyethyl)sulfonamido)-2-(6-azaspiro[2.5]octan-6-yl)benzamide (0.091 g, 0.18 mmol, 40% yield) as off white solid. $^1H$ NMR (400 MH-z, DMSO-$d_6$): δ ppm 13.10 (br s, 1H), 8.07 (d, J=8.7 Hz, 1H), 7.84 (d, J=7.6 Hz, 1H), 7.72 (t, J=7.9 Hz, 1H), 7.28 (d, J=2.2 Hz, 1H), 7.12 (dd, J=8.6, 2.1 Hz, 1H), 6.55 (d, J=8.0 Hz, 1H), 4.58 (s, 1H), 4.05 (s, 2H), 3.76 (t, J=6.5 Hz, 2H), 3.35 (t, J=6.5 Hz, 2H), 2.99 (t, J=5.2 Hz, 4H), 1.75 (br s, 4H), 1.21 (s, 6H), 0.39 (s, 4H). m/z (ESI): 519.2 $(M+H)^+$.

TABLE 14

Examples 16-1 to 16-9 were prepared following a similar procedure for Example 16

| Ex. # | Chemical Structure | Name | LRMS: (ESI + ve ion) m/z |
|---|---|---|---|
| 16-1 | 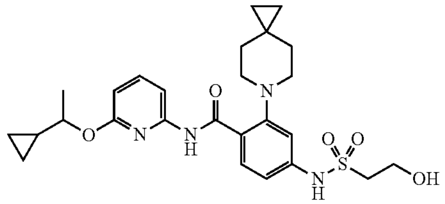 [SMILES: CC(Oc1cccc(NC(=O)c2ccc(NS(=O)(=O)CCO)cc2N2CCC3(CC2)CC3)n1)C1CC1] | N-(6-(1-Cyclopropylethoxy)pyridin-2-yl)-4-((2-hydroxyethyl)sulfonamido)-2-(6-azaspiro[2.5]octan-6-yl)benzamide | 515.2 |
| 16-2 | 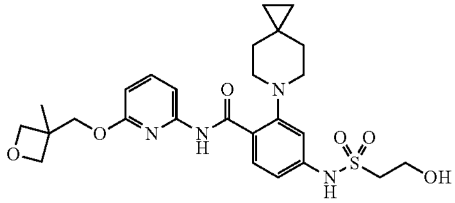 [SMILES: CC1(COc2cccc(NC(=O)c3ccc(NS(=O)(=O)CCO)cc3N3CCC4(CC3)CC4)n2)COC1] | 4-((2-Hydroxyethyl)sulfonamido)-N-(6-((3-methyloxetan-3-yl)methoxy)pyridin-2-yl)-2-(6-azaspiro[2.5]octan-6-yl)benzamide | 531.2 |
| 16-3 | 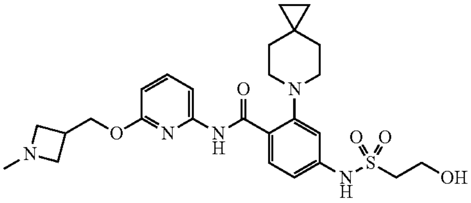 [SMILES: CN1CC(COc2cccc(NC(=O)c3ccc(NS(=O)(=O)CCO)cc3N3CCC4(CC3)CC4)n2)C1] | 4-((2-Hydroxyethyl)sulfonamido)-N-(6-((1-methylazetidin-3-yl)methoxy)pyridin-2-yl)-2-(6-azaspiro[2.5]octan-6-yl)benzamide | 530.2 |
| 16-4 | 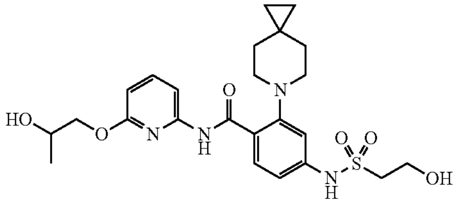 [SMILES: CC(O)COc1cccc(NC(=O)c2ccc(NS(=O)(=O)CCO)cc2N2CCC3(CC2)CC3)n1] | 4-((2-Hydroxyethyl)sulfonamido)-N-(6-(2-hydroxypropoxy)pyridin-2-yl)-2-(6-azaspiro[2.5]octan-6-yl)benzamide | 505.2 |
| 16-5 | 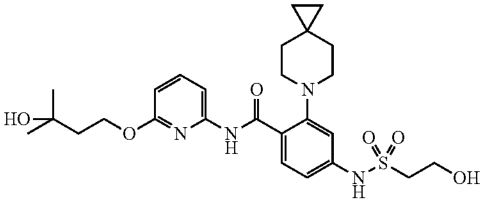 [SMILES: CC(C)(O)CCOc1cccc(NC(=O)c2ccc(NS(=O)(=O)CCO)cc2N2CCC3(CC2)CC3)n1] | N-(6-(3-Hydroxy-3-methylbutoxy)pyridin-2-yl)-4-((2-hydroxyethyl)sulfonamido)-2-(6-azaspiro[2.5]octan-6-yl)benzamide | 533.2 |
| 16-6 | 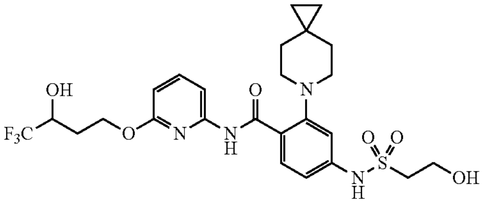 [SMILES: O=C(Nc1cccc(OCCC(O)C(F)(F)F)n1)c1ccc(NS(=O)(=O)CCO)cc1N1CCC2(CC1)CC2] | 4-((2-Hydroxyethyl)sulfonamido)-2-(6-azaspiro[2.5]octan-6-yl)-N-(6-(4,4,4-trifluoro-3-hydroxybutoxy)pyridin-2-yl)benzamide | 573.2 |
| 16-7 | 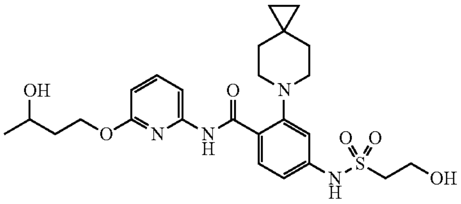 [SMILES: CC(O)CCOc1cccc(NC(=O)c2ccc(NS(=O)(=O)CCO)cc2N2CCC3(CC2)CC3)n1] | N-(6-(3-Hydroxybutoxy)pyridin-2-yl)-4-((2-hydroxyethyl)sulfonamido)-2-(6-azaspiro[2.5]octan-6-yl)benzamide | 519.2 |

TABLE 14-continued

| Ex. # | Chemical Structure | Name | LRMS: (ESI + ve ion) m/z |
|---|---|---|---|
| Examples 16-1 to 16-9 were prepared following a similar procedure for Example 16 | | | |
| 16-8 | 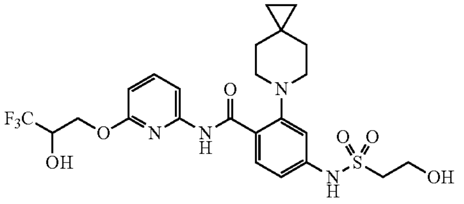 [SMILES: O=C(Nc1cccc(OCC(O)C(F)(F)F)n1)c1ccc(NS(=O)(=O)CCO)cc1N1CCC2(CC1)CC2] | 4-((2-Hydroxyethyl)sulfonamido)-2-(6-azaspiro[2.5]octan-6-yl)-N-(6-(3,3,3-trifluoro-2-hydroxypropoxy)pyridin-2-yl)benzamide | 559.2 |
| 16-9 | 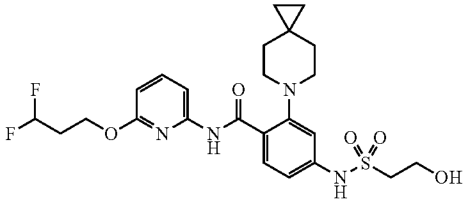 [SMILES: O=C(Nc1cccc(OCCC(F)F)n1)c1ccc(NS(=O)(=O)CCO)cc1N1CCC2(CC1)CC2] | N-(6-(3,3-Difluoropropoxy)pyridin-2-yl)-4-((2-hydroxyethyl)sulfonamido)-2-(6-azaspiro[2.5]octan-6-yl)benzamide | 525.2 |

Example 17: 4-((2-Hydroxyethyl)sulfonamido)-N-(4-methyl-6-(3,3,3-trifluoropropoxy)pyridin-2-yl)-2-(6-azaspiro[2.5]octan-6-yl)benzamide

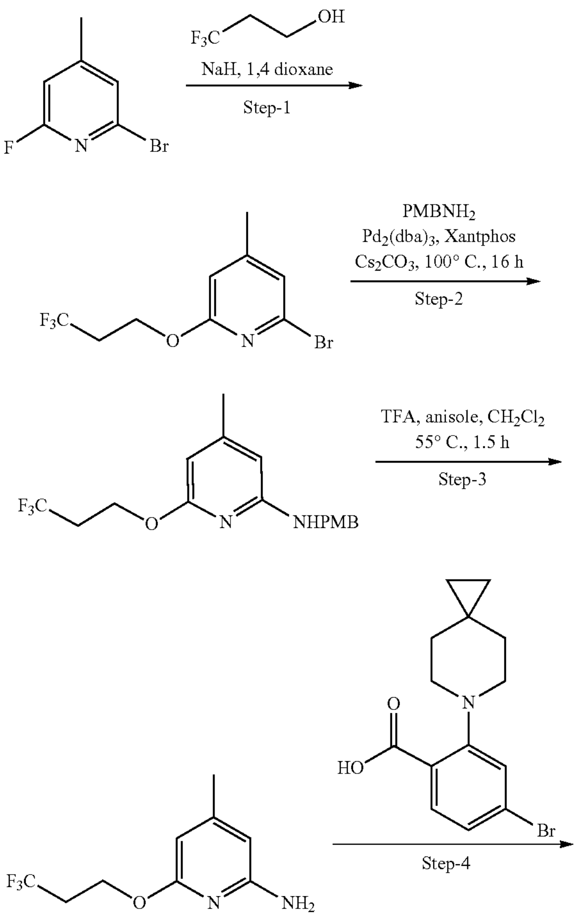

-continued

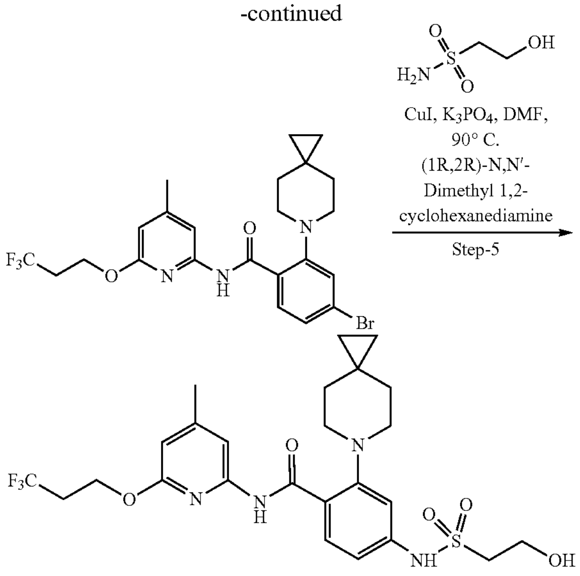

Step 1: To a solution of 3,3,3-trifluoropropan-1-ol (0.550 g, 4.83 mmol) in 1,4-dioxane (10 mL) was added sodium hydride (0.386 g, 9.64 mmol, 60% in oil) at 10° C. and stirred for 30 min at room temperature. A solution of 2-bromo-6-fluoro-4-methylpyridine (0.61 g, 3.2 mmol, Combi-Blocks) in dioxane (4 mL) was added to the reaction mixture. The resulting solution was stirred at room temperature for 2 h before it was quenched with ice cold water and was extracted with ethyl acetate. The organic extract was washed with brine, dried over $Na_2SO_4$, filtered, concentrated and purified by flash column chromatography, eluting with a gradient of 0% to 4% ethyl acetate in petroleum ether to provide 2-bromo-4-methyl-6-(3,3,3-trifluoropropoxy)pyridine (0.76 g, 85% yield) as clear oil. $^1H$ NMR (400 MHz, Chloroform-d): 6 ppm 6.96 (s, 1H), 6.53 (s, 1H), 4.51-4.56 (m, 2H), 2.56-2.66 (m, 2H), 2.29 (s, 3H). m/z (ESI): 284.0 $(M+H)^+$.

Step 2: A mixture of 2-bromo-4-methyl-6-(3,3,3-trifluoropropoxy)pyridine (0.71 g, 2.5 mmol), (4-methoxyphenyl)

methanamine (0.514 g, 3.75 mmol), cesium carbonate (2.443 g, 7.50 mmol), xantphos (0.289 g, 0.500 mmol) and $Pd_2(dba)_3$ (0.023 g, 0.025 mmol) in 1,4-dioxane (14 mL) was stirred at 100° C. for 16 h. The reaction mixture was filtered through a celite bed and the filtrate was washed with water, brine, dried over $Na_2SO_4$ and concentrated. The concentrate was purified by flash column chromatography using 6% ethyl acetate in petroleum ether to afford N-(4-methoxybenzyl)-4-methyl-6-(3,3,3-trifluoropropoxy)pyridin-2-amine (0.65 g, 1.91 mmol, 76% yield) as yellow solid. $^1H$ NMR (300 MHz, DMSO-$d_6$): δ ppm 7.23 (d, J=8.7 Hz, 2H), 6.94 (t, J=5.9 Hz, 1H), 6.82-6.90 (m, 2H), 5.89 (s, 1H), 5.71 (s, 1H), 4.33 (t, J=6.1 Hz, 4H), 3.71 (s, 3H), 2.56-2.66 (m, 2H), 2.07 (s, 3H). m/z (ESI): 341.1 $(M+H)^+$.

Step 3: A solution of N-(4-methoxybenzyl)-4-methyl-6-(3,3,3-trifluoropropoxy)pyridin-2-amine (0.30 g, 0.88 mmol), anisole (0.193 mL, 1.76 mmol), TFA (1.5 mL, 19 mmol) in dichloromethane (3 mL) was stirred at 55° C. for 1.5 h. Then the reaction mixture was concentrated, and the residue was dissolved in water and basified to pH ~8 with 10% sodium bicarbonate and was extracted with ethyl acetate. The organic extract was washed with brine, dried over $Na_2SO_4$, filtered, concentrated and purified by flash column chromatography, eluting with a gradient of 10% to 20% ethyl acetate in petroleum ether to provide 4-methyl-6-(3,3,3-trifluoropropoxy)pyridin-2-amine (0.16 g, 0.73 mmol, 82% yield) as a yellow oil. $^1H$ NMR (300 MHz, DMSO-$d_6$): δ ppm 5.88 (s, 1H), 5.74 (s, 1H), 4.30 (t, J=6.1 Hz, 2H), 2.60-2.68 (m, 2H), 2.05 (s, 3H). m/z (ESI): 221.1 $(M+H)^+$.

Step 4: A mixture of 4-methyl-6-(3,3,3-trifluoropropoxy)pyridin-2-amine (0.16 g, 0.73 mmol), 4-bromo-2-(6-azaspiro[2.5]octan-6-yl)benzoic acid (0.270 g, 0.872 mmol, Intermediate 9-1), $Et_3N$ (0.304 mL, 2.18 mmol) and $T_3P$ (50% solution in ethyl acetate, 1.386 g, 2.180 mmol) in 1,2-dimethoxyethane (4 mL) was heated at 80° C. for 16 h. The reaction mixture was quenched with ice cold water and was extracted with ethyl acetate. The organic extract was washed with brine, dried over $Na_2SO_4$, filtered, concentrated and purified by flash column chromatography, eluting with a gradient of 0% to 8% ethyl acetate in petroleum ether to provide 4-bromo-N-(4-methyl-6-(3,3,3-trifluoropropoxy)pyridin-2-yl)-2-(6-azaspiro[2.5]octan-6-yl)benzamide (0.20 g, 0.39 mmol, 54% yield) as white solid. $^1H$ NMR (300 MHz, DMSO-$d_6$): δ ppm 13.04 (s, 1H), 8.02 (d, J=8.5 Hz, 1H), 7.77 (s, 1H), 7.68 (d, J=2.0 Hz, 1H), 7.56 (dd, J=8.4, 1.9 Hz, 1H), 6.45 (s, 1H), 4.49 (t, J=6.1 Hz, 2H), 3.05 (t, J=5.3 Hz, 4H), 2.82 (dt, J=11.5, 5.8 Hz, 2H), 2.31 (s, 3H), 1.66-1.78 (m, 4H), 0.37 (s, 4H). m/z (ESI): 512.1 $(M+H)^+$.

Step 5: A mixture of 4-bromo-N-(4-methyl-6-(3,3,3-trifluoropropoxy)pyridin-2-yl)-2-(6-azaspiro[2.5]octan-6-yl) benzamide (0.20 g, 0.39 mmol), 2-hydroxyethane-1-sulfonamide (0.073 g, 0.59 mmol), potassium phosphate tribasic (0.166 g, 0.781 mmol), copper(I) iodide (0.074 g, 0.39 mmol) and (1R,2R)—N,N-dimethyl-1,2-cyclohexanediamine (0.028 g, 0.20 mmol) in DMF (3 mL) was stirred at 95° C. for 16 h. The reaction mixture was quenched with ice cold water and was extracted with ethyl acetate. The organic extract was washed with brine, dried over $Na_2SO_4$, filtered, concentrated and purified by reverse phase column chromatography using a gradient of 65% acetonitrile in water to provide 4-((2-hydroxyethyl)sulfonamido)-N-(4-methyl-6-(3,3,3-trifluoropropoxy)pyridin-2-yl)-2-(6-azaspiro[2.5]octan-6-yl)benzamide (0.166 g, 0.298 mmol, 76% yield) as a white solid. $^1H$ NMR (400 MHz, DMSO-$d_6$): δ ppm 13.09 (s, 1H), 10.21 (br s, 1H), 8.06 (d, J=8.6 Hz, 1H), 7.78 (s, 1H), 7.27 (d, J=2.1 Hz, 1H), 7.13 (dd, J=8.6, 2.1 Hz, 1H), 6.42 (s, 1H), 4.96 (br s, 1H), 4.49 (t, J=6.1 Hz, 2H), 3.76 (t, J=6.4 Hz, 2H), 3.38-3.40 (m, 2H), 2.96-3.20 (m, 4H), 2.76-2.88 (m, 2H), 2.31 (s, 3H), 1.60-1.80 (m, 4H), 0.38 (s, 4H). m/z (ESI): 557.2 $(M+H)^+$.

TABLE 15

Examples 17-1 to 17-3 were prepared following a similar procedure as described for example 17

| Ex. # | Chemical Structure | Name | LRMS: (ESI + ve ion) m/z |
|---|---|---|---|
| 17-1 | 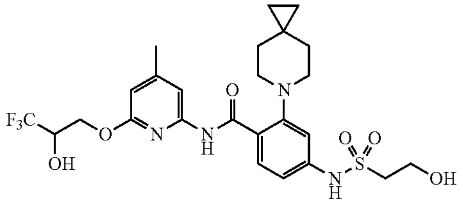 [SMILES: Cc1cc(NC(=O)c2ccc(NS(=O)(=O)CCO)cc2N2CCC3(CC2)CC3)nc(OCC(O)C(F)(F)F)c1] | 4-((2-Hydroxyethyl)sulfonamido)-N-(4-methyl-6-(3,3,3-trifluoro-2-hydroxypropoxy)pyridin-2-yl)-2-(6-azaspiro[2.5]octan-6-yl)benzamide | 573.2 |
| 17-2 | 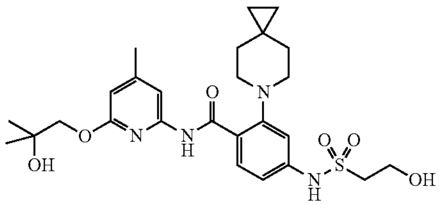 [SMILES: Cc1cc(NC(=O)c2ccc(NS(=O)(=O)CCO)cc2N2CCC3(CC2)CC3)nc(OCC(C)(C)O)c1] | N-(6-(2-Hydroxy-2-methylpropoxy)-4-methylpyridin-2-yl)-4-((2-hydroxyethyl)sulfonamido)-2-(6-azaspiro[2.5]octan-6-yl)benzamide | 533.2 |

TABLE 15-continued

| Ex. # | Chemical Structure | Name | LRMS: (ESI + ve ion) m/z |
|---|---|---|---|
| Examples 17-1 to 17-3 were prepared following a similar procedure as described for example 17 | | | |
| 17-3 | 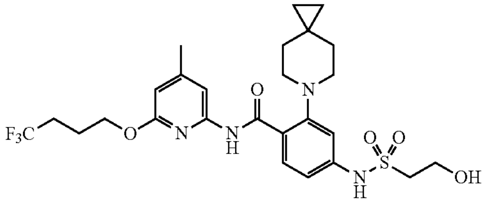 [SMILES: Cc1cc(NC(=O)c2ccc(NS(=O)(=O)CCO)cc2N2CCC3(CC2)CC3)nc(OCCCC(F)(F)F)c1] | 4-((2-Hydroxyethyl)sulfonamido)-N-(4-methyl-6-(4,4,4-trifluorobutoxy)pyridin-2-yl)-2-(6-azaspiro[2.5]octan-6-yl)benzamide | 571.2 |

Example 18: 4-((2-Hydroxyethyl)sulfonamido)-N-(5-methyl-6-morpholinopyridin-2-yl)-2-(6-azaspiro[2.5]octan-6-yl)benzamide

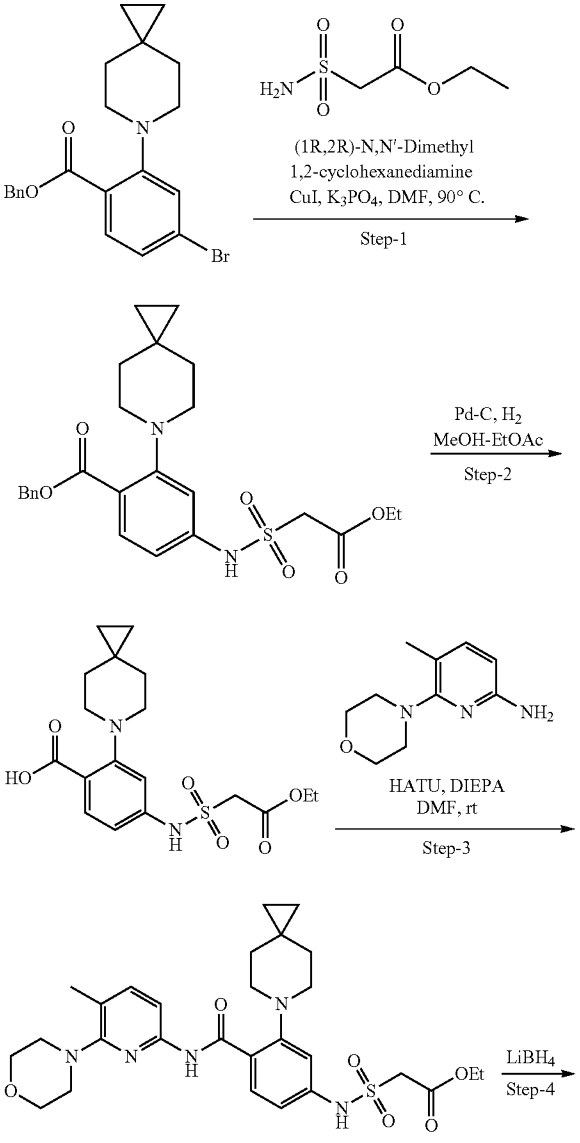

-continued

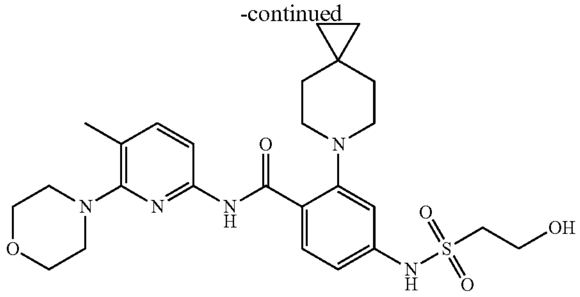

Step 1: A mixture of benzyl 4-bromo-2-(6-azaspiro[2.5]octan-6-yl)benzoate (1.0 g, 2.5 mmol, Intermediate 9-4), ethyl 2-sulfamoylacetate (0.626 g, 3.75 mmol), potassium phosphate (1.06 g, 5.00 mmol), copper(I) iodide (0.476 g, 2.50 mmol). (1R,2R)—N1,N2-dimethylcyclohexane-1,2-diamine (0.178 g, 1.25 mmol) in DMF (15 mL) was heated at 90° C. for 16 h. Then the reaction mixture was filtered through a plug of celite and the filtrate was diluted with EtOAc, washed with water, brine, dried over $Na_2SO_4$, filtered, and concentrated. The concentrate was purified by flash column chromatography eluting with a gradient of 0% to 25% EtOAc in petroleum ether to provide benzyl 4-((2-ethoxy-2-oxoethyl)sulfonamido)-2-(6-azaspiro[2.5]octan-6-yl)benzoate (0.75 g, 1.5 mmol, 53% yield) as orange oil. $^1H$ NMR (400 MHz, DMSO-$d_6$): δ ppm 10.45 (s, 1H), 7.64 (d, J=8.5 Hz, 1H), 7.29-7.48 (m, 5H), 6.93 (d, J=2.1 Hz, 1H), 6.79 (dd, J=8.5, 2.0 Hz, 1H), 5.28 (s, 2H), 4.31 (s, 2H), 4.05 (dq, J=19.5, 7.1 Hz, 2H), 2.94 (t, J=5.3 Hz, 4H), 1.37 (t, J=5.3 Hz, 4H), 1.16 (dt, J=11.2, 7.1 Hz, 3H), 0.28 (s, 4H). m/z (ESI): 487.2 $(M+H)^+$.

Step 2: To a solution of benzyl 4-((2-ethoxy-2-oxoethyl)sulfonamido)-2-(6-azaspiro[2.5]octan-6-yl)benzoate (0.55 g, 1.1 mmol) in ethyl acetate (3 mL) and methanol (6 mL) was added palladium on carbon (10%, 0.28 g, 0.26 mmol) and stirring was continued under hydrogen atmosphere (1 atm) for 2 h. Then the reaction mixture was filtered through celite bed, washed with methanol (150 mL). The filtrate was concentrate and triturated with $Et_2O$ to provide 4-((2-ethoxy-2-oxoethyl)sulfonamido)-2-(6-azaspiro[2.5]octan-6-yl)benzoic acid (0.55 g, 1.4 mmol, 90% yield) as off white solid. $^1H$ NMR (400 MHz, DMSO-$d_6$): δ ppm 10.69 (s, 1H), 7.93 (d, J=8.6 Hz, 1H), 7.31 (d, J=2.1 Hz, 1H), 7.12 (dd, J=8.7, 2.1 Hz, 1H), 4.31 (s, 2H), 4.07 (q, J=7.1 Hz, 2H), 3.00 (t, J=5.4 Hz, 4H), 1.57 (s, 4H), 1.14 (t, J=7.1 Hz, 3H), 0.42 (s, 4H). m/z (ESI): 397.1 $(M+H)^+$.

Step 3: To a solution of 5-methyl-6-morpholinopyridin-2-amine (45.0 mg, 0.232 mmol, Intermediate 8) in DMF (3 mL) were added 4-((2-ethoxy-2-oxoethyl)sulfonamido)-2-

(6-azaspiro[2.5]octan-6-yl)benzoic acid (92 mg, 0.23 mmol), DIPEA (48.8 μL, 0.279 mmol) and HATU (106 mg, 0.279 mmol) at room temperature. Then the reaction mixture was stirred for 12 h before it was quenched with water and was extracted with EtOAc. The organic layer was washed with brine, dried over $Na_2SO_4$, filtered, and concentrated. The concentrate was purified by flash column chromatography eluting with 15% ethyl acetate in petroleum ether to provide ethyl 2-(N-(4-((5-methyl-6-morpholinopyridin-2-yl)carbamoyl)-3-(6-azaspiro[2.5]octan-6-yl)phenyl)sulfamoyl)acetate (50 mg, 0.087 mmol, 38% yield) as pale yellow solid. m/z (ESI): 572.2 $(M+H)^+$.

Step 4: To a solution of ethyl 2-(N-(4-((5-methyl-6-morpholinopyridin-2-yl)carbamoyl)-3-(6-azaspiro[2.5]octan-6-yl)phenyl)sulfamoyl)acetate (50 mg, 0.087 mmol) in THF (10 mL) was added lithium borohydride (65.6 μL, 0.131 mmol, 2M in THF) at 0° C. Then the reaction mixture was stirred at rt for 3 h before it was quenched with an aqueous saturated solution of ammonium chloride and was extracted with EtOAc. The combined organic layers were washed with brine, dried over $Na_2SO_4$, filtered, and concentrated. The concentrate was purified by flash column chromatography eluting with 30% ethyl acetate in petroleum ether to provide 4-((2-hydroxyethyl)sulfonamido)-N-(5-methyl-6-morpholinopyridin-2-yl)-2-(6-azaspiro[2.5]octan-6-yl)benzamide (30 mg, 0.057 mmol, 64.8% yield) as white solid. $^1H$ NMR (400 MHz, DMSO-$d_6$): δ ppm 13.10 (d, J=5.4 Hz, 1H), 10.21 (s, 1H), 8.08 (dd, J=9.6, 3.7 Hz, 1H), 7.83 (t, J=6.8 Hz, 1H), 7.55 (dd, J=9.2, 4.2 Hz, 1H), 7.26 (d, J=5.4 Hz, 1H), 7.13 (dd, J=8.7, 2.3 Hz, 1H), 4.95 (s, 1H), 3.75 (m, 6H), 3.11 (q, J=4.4 Hz, 4H), 2.97 (d, J=6.6 Hz, 4H), 2.69 (d, J=2.9 Hz, 2H), 2.22 (s, 3H), 1.77 (br s, 4H), 0.38 (d, J=5.7 Hz, 4H). m/z (ESI): 530.2 $(M+H)^+$.

Example 19: (R)—N-(4-cyclopropyl-6-(2-methylmorpholino)pyridin-2-yl)-4-((2-hydroxyethyl)sulfonamido)-2-(6-azaspiro[2.5]octan-6-yl)benzamide

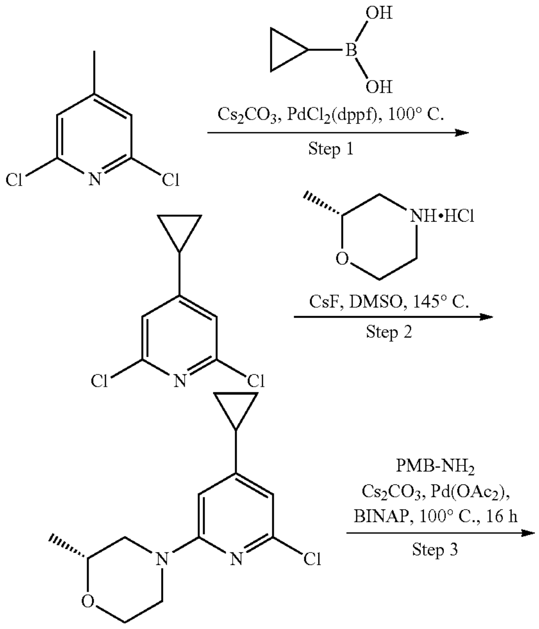

-continued

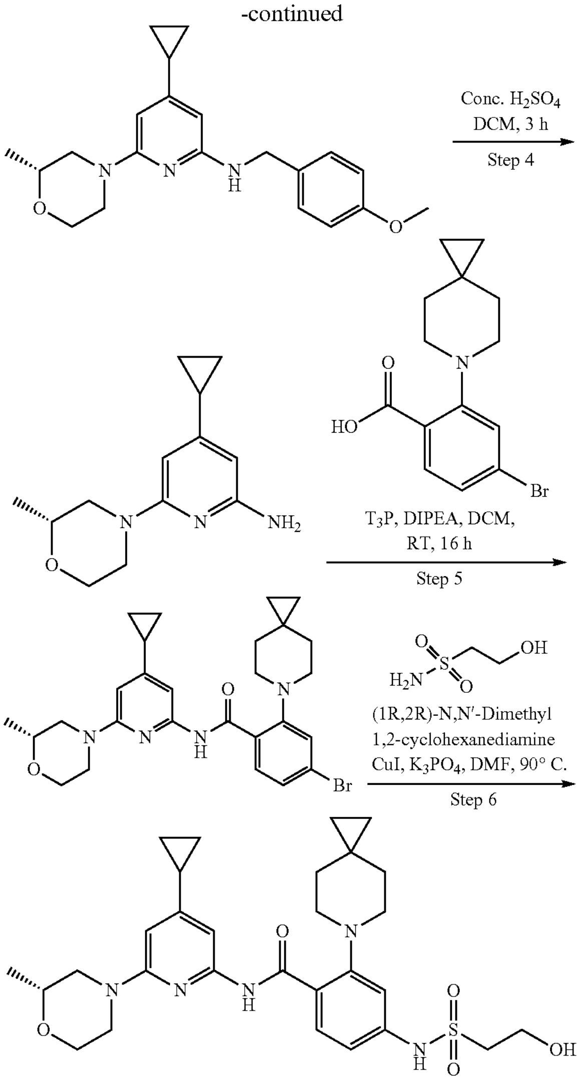

Step 1: A mixture of 2,6-dichloro-4-iodopyridine (1.8 g, 6.6 mmol, Combi-Blocks), cyclopropylboronic acid (0.565 g, 6.57 mmol, Combi-Blocks), potassium carbonate (0.908 g, 6.57 mmol) and Xphos-Pd-G3 (0.278 g, 0.329 mmol, Strem chemicals) in 1,4-dioxane (10 mL) was stirred at 100° C. for 3 h. The reaction mixture was filtered through a celite bed. The filtrate was concentrated and the residue was triturated with diethyl ether to get 2,6-dichloro-4-cyclopropylpyridine (0.95 g, 5.0 mmol, 77% yield) as brown semi solid.

Step 2: A mixture of 2,6-dichloro-4-cyclopropylpyridine (0.90 g, 4.8 mmol) and (R)-2-methylmorpholine hydrochloride (0.988 g, 7.18 mmol, Suzhou chemicals) and CsF (2.91 g, 19.1 mmol) in DMSO (9 mL) was stirred at 145° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 5% to 50% ethyl acetate in petroleum ether to provide (R)-4-(6-chloro-4-cyclopropylpyridin-2-yl)-2-methylmorpholine (1.1 g, 4.4 mmol, 91% yield) as orange oil. $^1H$ NMR (300 MHz, DMSO-$d_6$): δ ppm 6.50 (s, 1H), 6.39 (s, 1H), 3.84-4.11 (m, 4H), 3.50 (dt, J=11.7, 2.6 Hz, 2H), 2.78 (td, J=12.3, 3.5 Hz, 1H), 1.87 (td, J=8.5, 4.3 Hz, 1H), 1.15 (d, J=6.2 Hz, 3H), 0.98 (dt, J=8.4, 3.3 Hz, 2H), 0.78-0.85 (m, 2H). m/z (ESI): 253.1 $(M+H)^+$.

Step 3: A mixture of (R)-4-(6-chloro-4-cyclopropylpyridin-2-yl)-2-methylmorpholine (1.0 g, 4.0 mmol), (4-methoxyphenyl)methanamine (0.775 mL, 5.93 mmol), $Cs_2CO_3$ (2.58 g, 7.91 mmol), BINAP (0.246 g, 0.396 mmol) and palladium (II) acetate (0.089 g, 0.40 mmol) in dioxane (15 mL) was stirred at 100° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 5% to 40% ethyl acetate in petroleum ether to provide (R)-4-cyclopropyl-N-(4-methoxybenzyl)-6-(2-methylmorpholino)pyridin-2-amine (1.2 g, 3.4 mmol, 86% yield) as orange oil. $^1H$ NMR (300 MHz, DMSO-$d_6$): δ ppm 7.15-7.28 (m, 2H), 6.74-6.92 (m, 2H), 6.48 (t, J=6.0 Hz, 1H), 5.61 (s, 1H), 5.54 (s, 1H), 4.29 (d, J=6.0 Hz, 2H), 3.79-4.06 (m, 4H), 3.71 (s, 3H), 3.40-3.52 (m, 2H), 2.26-2.36 (m, 1H), 1.63 (td, J=8.0, 4.0 Hz, 1H), 1.11 (d, J=6.2 Hz, 3H), 0.80-0.89 (m, 2H), 0.58-0.66 (m, 2H). m/z (ESI): 354.2 $(M+H)^+$.

Step 4: A mixture of (R)-4-cyclopropyl-N-(4-methoxybenzyl)-6-(2-methylmorpholino)pyridin-2-amine (1.0 g, 2.8 mmol) and $H_2SO_4$ (1.51 mL, 28.3 mmol) in dichloromethane (20 mL) was stirred at room temperature for 2 h. The reaction mixture was basified with 1 N NaOH (pH=9) and was extracted with EtOAc. The organic extract was washed with brine, dried over $Na_2SO_4$, filtered, concentrated to provide (R)-4-cyclopropyl-6-(2-methylmorpholino)pyridin-2-amine as brown sticky liquid. $^1H$ NMR (400 MHz, DMSO-$d_6$): δ ppm 5.64-5.78 (m, 1H), 5.52 (d, J=2.4 Hz, 1H), 5.39 (br s, 2H), 4.00 (d, J=12.6 Hz, 1H), 3.81-3.94 (m, 2H), 3.46-3.52 (m, 2H), 2.62 (td, J=12.3, 3.3 Hz, 1H), 2.29 (td, J=12.7, 2.2 Hz, 1H), 1.61-1.69 (m, 1H), 1.13 (d, J=6.2 Hz, 3H), 0.84-0.88 (m, 2H), 0.62-0.66 (m, 2H). m/z (ESI): 234.2 $(M+H)^+$.

Step 5: A mixture of 4-bromo-2-(6-azaspiro[2.5]octan-6-yl)benzoic acid (0.50 g, 1.6 mmol, Intermediate 9-1) and DIPEA (0.845 mL, 4.84 mmol), 2,4,6-tripropyl-1,3,5,2,4,6-trioxatriphosphinane 2,4,6-trioxide (50% in ethyl acetate, 1.452 mL, 4.84 mmol) and (R)-4-cyclopropyl-6-(2-methylmorpholino)pyridin-2-amine (0.40 g, 1.7 mmol) in dichloromethane (15 mL) was stirred at room temperature for 16 h. The reaction mixture was diluted with water and was extracted with ethyl acetate. The organic extract was washed with brine, dried over $Na_2SO_4$, filtered, concentrated and purified by flash column chromatography, eluting with a gradient of 10% to 80% ethyl acetate in petroleum ether to provide (R)-4-bromo-N-(4-cyclopropyl-6-(2-methylmorpholino)pyridin-2-yl)-2-(6-azaspiro[2.5]octan-6-yl)benzamide (0.50 g, 0.94 mmol, 58% yield) as white sticky solid. $^1H$ NMR (400 MHz, DMSO-$d_6$): δ ppm 12.67 (s, 1H), 8.00 (d, J=8.5 Hz, 1H), 7.63 (s, 1H), 7.53 (d, J=8.5 Hz, 1H), 7.34 (s, 1H), 6.35 (s, 1H), 4.01-4.18 (m, 3H), 3.90 (dd, J=11.1, 3.1 Hz, 1H), 3.51-3.63 (m, 2H), 3.01 (t, J=5.5 Hz, 4H), 2.78 (td, J=12.3, 3.5 Hz, 1H), 1.87 (td, J=8.5, 4.3 Hz, 1H), 1.69 (br s, 4H), 1.16 (d, J=6.3 Hz, 3H), 0.98-1.04 (m, 2H), 0.72-0.80 (m, 2H), 0.35 (s, 4H). m/z (ESI): 525.1 $(M+H)^+$.

Step 6: A mixture of (R)-4-bromo-N-(4-cyclopropyl-6-(2-methylmorpholino)pyridin-2-yl)-2-(6-azaspiro[2.5]octan-6-yl)benzamide (0.30 g, 0.57 mmol), 2-hydroxyethane-1-sulfonamide (0.107 g, 0.856 mmol), tripotassium phosphate (0.303 g, 1.43 mmol), (1R,2R)—N1,N2-dimethylcyclohexane-1,2-diamine (0.041 g, 0.28 mmol) and copper(I) iodide (0.109 g, 0.571 mmol) in N, N-dimethylformamide (9 mL) was stirred at 90° C. for 16 h. The reaction mixture was quenched with water and was extracted with ethyl acetate. The organic extract was washed with brine, dried over $Na_2SO_4$, filtered, concentrated, and purified by flash column chromatography, eluting with a gradient of 20% to 80% ethyl acetate in petroleum ether to provide (R)—N-(4-cyclopropyl-6-(2-methylmorpholino)pyridin-2-yl)-4-((2-hydroxyethyl)sulfonamido)-2-(6-azaspiro[2.5]octan-6-yl) benzamide (0.155 g, 0.272 mmol, 48% yield) as white solid. $^1H$ NMR (400 MHz, DMSO-$d_6$): δ ppm 12.73 (s, 1H), 8.04 (dd, J=8.7, 2.9 Hz, 1H), 7.37 (d, J=2.8 Hz, 1H), 7.23 (t, J=2.6 Hz, 1H), 7.10 (dt, J=8.7, 2.6 Hz, 1H), 6.34 (d, J=2.7 Hz, 1H), 4.14 (d, J=12.9 Hz, 1H), 4.10 (d, J=12.9 Hz, 1H), 3.91 (d, J=11.3 Hz, 1H), 3.76 (t, J=6.5 Hz, 2H), 3.53-3.61 (m, 2H), 3.01 (t, J=5.5 Hz, 4H), 2.79 (td, J=9.2, 4.6 Hz, 1H), 2.42-2.48 (m, 2H), 1.82-1.92 (m, 2H), 1.68 (br s, 4H), 1.18 (d, J=6.2 Hz, 3H), 1.00 (d, J=8.2 Hz, 2H), 0.77 (d, J=5.2 Hz, 2H), 0.37 (s, 4H). m/z (ESI): 570.2 $(M+H)^+$.

Example 20: (R)-4-((2-Hydroxyethyl)sulfonamido)-N-(6-(2-methylmorpholino)-4-(trifluoromethyl)pyridin-2-yl)-2-(6-azaspiro[2.5]octan-6-yl)benzamide

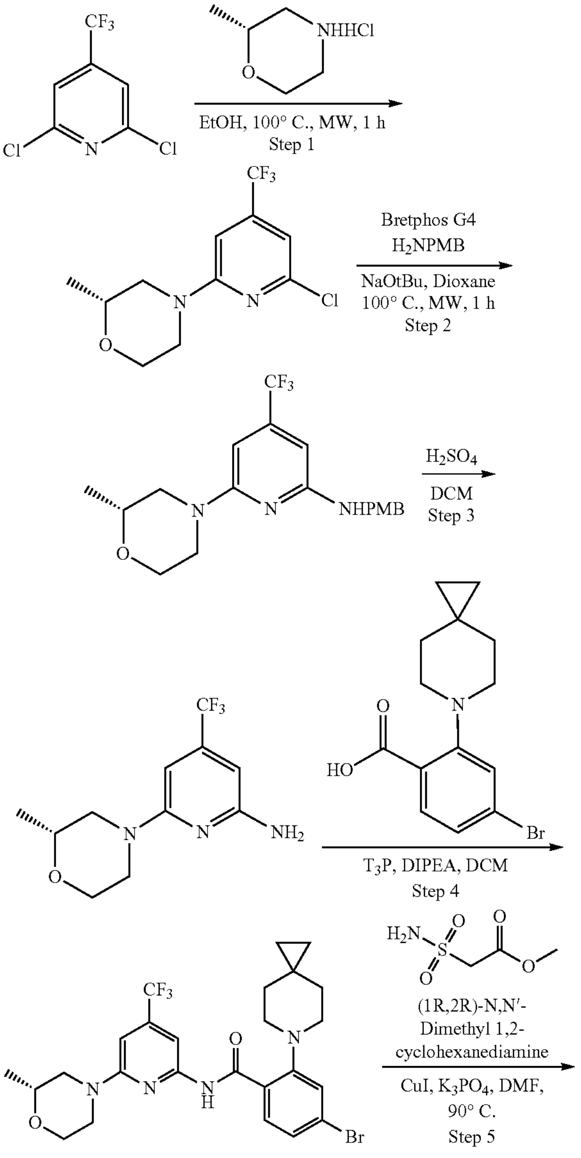

-continued

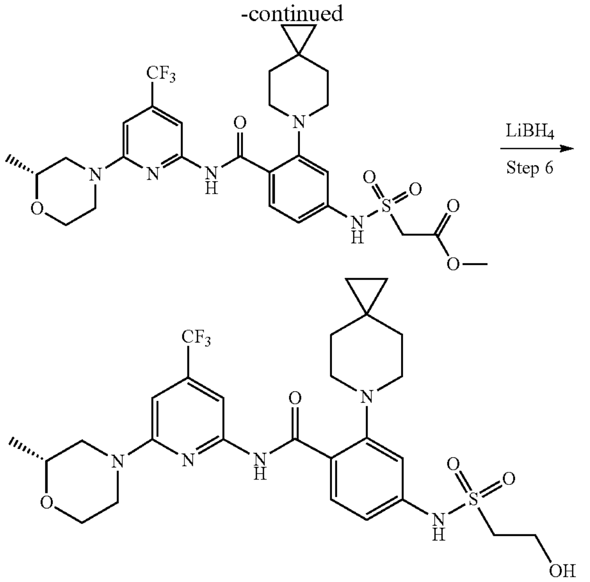

Step 1: A mixture of 2,6-dichloro-4-(trifluoromethyl)pyridine (6.0 g, 28 mmol, Combi-Blocks), (R)-2-methylmorpholine hydrochloride (4.59 g, 33.3 mmol), DIPEA (9.70 mL, 55.6 mmol) in ethanol (30 mL) was heated at 100° C. in a microwave for 1 h. The reaction mixture was concentrated and purified by flash column chromatography eluting with a gradient of 0% to 20% ethyl acetate in petroleum ether to provide (R)-4-(6-chloro-4-(trifluoromethyl)pyridin-2-yl)-2-methylmorpholine (6.0 g, 21 mmol, 77% yield) as off white solid. $^1$H NMR (400 MHz, DMSO-$d_6$): δ ppm 7.11 (s, 1H), 6.97 (s, 1H), 4.02-4.25 (m, 2H), 3.76-3.97 (m, 1H), 3.39-3.63 (m, 2H), 2.92 (td, J=3.5, 12.5 Hz, 1H), 2.60 (dd, J=10.4, 13.0 Hz, 1H), 1.15 (d, J=6.2 Hz, 3H). m/z (ESI): 281.1 $(M+H)^+$.

Step 2: A mixture of (R)-4-(6-chloro-4-(trifluoromethyl)pyridin-2-yl)-2-methylmorpholine (2.0 g, 7.1 mmol), (4-methoxyphenyl)methanamine (1.173 g, 8.55 mmol) and DIPEA (2.489 mL, 14.25 mmol) in NMP (10 mL) was stirred at 180° C. in a microwave for 1 h. The reaction mixture was diluted with water and extracted with ethyl acetate. The organic extract was washed with brine, dried over $Na_2SO_4$, filtered, concentrated and purified by flash column chromatography, eluting with a gradient of 0% to 25% ethyl acetate in petroleum ether to provide (R)—N-(4-methoxybenzyl)-6-(2-methylmorpholino)-4-(trifluoromethyl)pyridin-2-amine (1.5 g, 2.8 mmol, 39% yield) as colorless oil. $^1$H NMR (400 MHz, DMSO-$d_6$): δ ppm 7.25 (dd, J=4.7, 7.1 Hz, 2H), 6.76-6.98 (m, 2H), 6.05 (d, J=6.4 Hz, 2H), 4.37 (d, J=5.8 Hz, 2H), 3.89-4.15 (m, 2H), 3.75-3.95 (m, 1H), 3.73 (s, 3H), 3.38-3.60 (m, 2H), 2.63-2.89 (m, 1H), 2.41 (dd, J=10.3, 12.7 Hz, 1H), 1.22 (d, J=6.2 Hz 3H). m/z (ESI): 382.1 $(M+H)^+$.

Step 3: A mixture of (R)—N-(4-methoxybenzyl)-6-(2-methylmorpholino)-4-(trifluoromethyl)pyridin-2-amine (1.5 g, 3.9 mmol) and $H_2SO_4$ (2.096 mL, 39.3 mmol) in dichloromethane (50 mL) was stirred at room temperature for 5 h. The reaction mixture was concentrated, and the residue was dissolved in ice cold water, basified with 10% NaOH (pH 10) and extracted with EtOAc. The organic extract was washed with brine, dried over $Na_2SO_4$, filtered, concentrated, and purified by reverse phase column chromatography, eluting with a gradient of 0% to 80% acetonitrile in water to provide (R)-6-(2-methylmorpholino)-4-(trifluoromethyl)pyridin-2-amine (0.30 g, 1.1 mmol, 29% yield) as light yellow solid. $^1$H NMR (400 MHz, DMSO-$d_6$): δ ppm 6.13 (br s, 2H), 6.08 (s, 1H), 5.98 (d, J=1.1 Hz, 1H), 4.05-4.16 (m, 1H), 3.94-4.05 (m, 1H), 3.87 (ddd, J=1.4, 3.6, 11.5 Hz, 1H), 3.41-3.59 (m, 2H), 2.74 (ddd, J=3.5, 11.8, 12.8 Hz, 1H), 2.42 (dd, J=10.4, 12.8 Hz, 1H), 1.13 (d, J=6.2 Hz, 3H). m/z (ESI): 262.1 $(M+H)^+$.

Step 4: A mixture of 4-bromo-2-(6-azaspiro[2.5]octan-6-yl)benzoic acid (0.20 g, 0.64 mmol, Intermediate 9-1), (R)-6-(2-methylmorpholino)-4-(trifluoromethyl)pyridin-2-amine (0.253 g, 0.967 mmol), DIPEA (0.338 mL, 1.93 mmol) and $T_3P$ (50% in EtOAc, 1.231 g, 1.934 mmol) in dichloromethane (5 mL) was stirred at room temperature for 16 h. The reaction mixture was diluted with water and was extracted with ethyl acetate. The organic extract was washed with brine, dried over $Na_2SO_4$, filtered, concentrated and purified by flash column chromatography eluting with a gradient of 0% to 30% ethyl acetate in petroleum ether to provide (R)-4-bromo-N-(6-(2-methylmorpholino)-4-(trifluoromethyl)pyridin-2-yl)-2-(6-azaspiro[2.5]octan-6-yl)benzamide (0.30 g, 0.54 mmol, 84% yield) as white solid. $^1$H NMR (400 MHz, DMSO-$d_6$): δ ppm 13.20 (s, 1H), 8.04 (d, J=8.4 Hz, 1H), 7.82 (s, 1H), 7.71 (d, J=2.0 Hz, 1H), 7.57 (dd, J=1.9, 8.5 Hz, 1H), 6.92 (s, 1H), 4.24 (dd, J=12.9, 21.6 Hz, 2H), 3.94 (d, J=11.4 Hz, 1H), 3.33-3.72 (m, 2H), 3.06 (s, 4H), 2.52 (m, 1H), 2.93 (t, J=11.6 Hz, 1H), 1.70 (s, 4H), 1.38 (d, J=5.1 Hz, 3H), 0.38 (s, 4H). m/z (ESI): 553.1, 555.1 $(M+H)^+$.

Step 5: A mixture of (R)-4-bromo-N-(6-(2-methylmorpholino)-4-(trifluoromethyl)pyridin-2-yl)-2-(6-azaspiro[2.5]octan-6-yl)benzamide (0.30 g, 0.54 mmol), methyl 2-sulfamoylacetate (0.125 g, 0.813 mmol), potassium phosphate (0.230 g, 1.08 mmol), (1R,2R)—N1,N2-dimethylcyclohexane-1,2-diamine (0.039 g, 0.27 mmol) and copper(I) iodide (0.103 g, 0.542 mmol) in N, N-dimethylformamide (5 mL) was stirred at 90° C. for 16 h. The reaction mixture was diluted with water and was extracted with ethyl acetate. The organic extract was washed with brine, dried over $Na_2SO_4$, filtered, concentrated and purified by flash column chromatography eluting with a gradient of 0% to 40% ethyl acetate in petroleum ether to provide methyl (R)-2-(N-(4-((6-(2-methylmorpholino)-4-(trifluoromethyl)pyridin-2-yl)carbamoyl)-3-(6-azaspiro[2.5]octan-6-yl)phenyl)sulfamoyl)acetate (0.25 g, 0.40 mmol, 74% yield) as off white solid. $^1$H NMR (400 MHz, DMSO-$d_6$): δ ppm 13.21 (s, 1H), 10.69 (s, 1H), 8.04 (d, J=8.6 Hz, 1H), 7.77 (s, 1H), 7.25 (d, J=2.2 Hz, 1H), 7.12 (dd, J=2.1, 8.7 Hz, 1H), 6.82 (s, 1H), 4.45 (s, 2H), 4.02-4.27 (m, 2H), 3.90 (dd, J=3.4, 11.5 Hz, 1H), 3.51-3.65 (m, 4H), 2.91-3.02 (m, 4H), 2.55-2.64 (m, 1H), 1.96 (s, 2H), 1.66 (s, 4H), 1.15 (dd, J=4.3, 6.7 Hz, 3H), 0.34 (s, 4H). m/z (ESI): 626.1 $(M+H)^+$.

Step 6: To a solution of methyl (R)-2-(N-(4-((6-(2-methylmorpholino)-4-(trifluoromethyl)pyridin-2-yl)carbamoyl)-3-(6-azaspiro[2.5]octan-6-yl)phenyl)sulfamoyl)acetate (0.25 g, 0.40 mmol) in THF (5 mL) was added $LiBH_4$ (2.0M in THF, 0.599 mL, 1.20 mmol) at −78° C. and stirred at room temperature for 1 h. The reaction mixture was quenched with a saturated aqueous solution of $NH_4Cl$ and was extracted with EtOAc. The organic extract was washed with brine, dried over $Na_2SO_4$, filtered, concentrated and purified by reverse phase column chromatography, eluting with a gradient of 0% to 60% acetonitrile and water to provide (R)-4-((2-hydroxyethyl)sulfonamido)-N-(6-(2-methylmorpholino)-4-(trifluoromethyl)pyridin-2-yl)-2-(6-azaspiro[2.5]octan-6-yl)benzamide (0.10 g, 0.17 mmol, 42% yield) as white solid. $^1$H NMR (400 MHz, DMSO-$d_6$): δ ppm 13.22 (s, 1H), 10.23 (s, 1H), 8.07 (d, J=8.6 Hz, 1H), 7.83 (s, 1H), 7.27 (d, J=2.2 Hz, 1H), 7.13 (dd, J=2.1, 8.7 Hz, 1H), 6.88 (s, 1H), 4.94 (s, 1H), 4.14-4.34 (m, 2H), 3.93 (d, J=10.7 Hz, 1H), 3.76 (t, J=6.5 Hz, 2H), 3.57 (t, J=11.4 Hz, 2H), 3.36 (t, J=6.4 Hz, 2H), 2.86-3.06 (m, 5H), 2.60 (m, 1H), 1.71 (s, 4H), 1.18 (d, J=6.2 Hz, 3H), 0.38 (s, 4H). m/z (ESI): 598.2 $(M+H)^+$.

Example 21: N-(5-Cyano-6-(4,4-difluoropiperidin-1-yl)pyridin-2-yl)-4-((2-hydroxyethyl)sulfonamido)-2-(6-azaspiro[2.5]octan-6-yl)benzamide

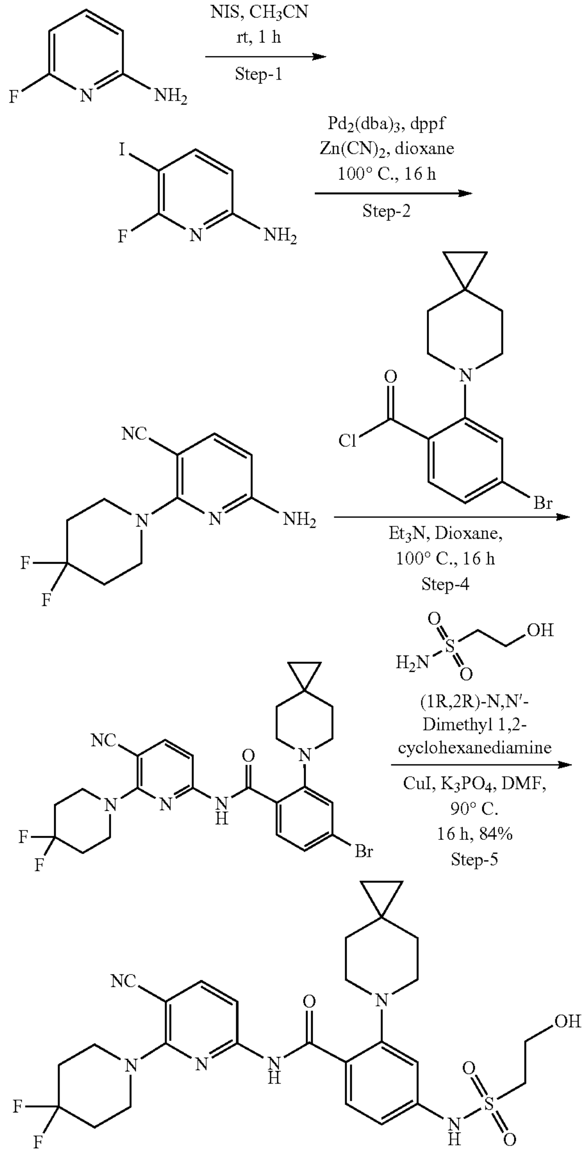

Step 1: A mixture of 6-fluoropyridin-2-amine (5.0 g, 45 mmol, Combi-Blocks) and N-iodosuccinimide (10.5 g, 46.8 mmol) in acetonitrile (50 mL) was stirred at 10° C. for 30 min and then at room temperature for 1 h. The reaction mixture was concentrated, and the residue was diluted with water. The precipitated solid was filtered and purified by flash column chromatography eluting with 0% to 30% EtOAc in petroleum ether to provide 6-fluoro-5-iodopyridin-2-amine (8.9 g, 37 mmol, 84% yield) as brown solid. $^1H$ NMR (300 MHz, DMSO-$d_6$): δ ppm 7.74 (t, J=8.8 Hz, 1H), 6.53 (s, 2H), 6.19 (dd, J=8.3, 2.3 Hz, 1H). m/z (ESI): 238.9 $(M+H)^+$.

Step 2: A mixture of 6-fluoro-5-iodopyridin-2-amine (1.0 g, 4.2 mmol), $Zn(CN)_2$ (0.296 g, 2.52 mmol), $Pd_2(dba)_3$ (0.192 g, 0.210 mmol) and dppf (0.233 g, 0.420 mmol) in dioxane (9 mL) and water (1 mL) was stirred at 100° C. for 16 h. The reaction mixture was filtered through a celite bed and the filtrate was washed with water, brine, dried over anhydrous $Na_2SO_4$, filtered, and concentrated. The concentrate was purified by flash column chromatography using 0% to 50% ethyl acetate in petroleum ether to provide 6-amino-2-fluoronicotinonitrile (0.51 g, 3.7 mmol, 89% yield) as brown solid. $^1H$ NMR (300 MHz, DMSO-$d_6$): δ ppm 7.81 (t, J=9.1 Hz, 1H), 7.64 (s, 1H), 7.51 (s, 2H). m/z (ESI): 138.1 $(M+H)^+$.

Step 3: A mixture of 6-amino-2-fluoronicotinonitrile (0.50 g, 3.6 mmol), 4,4-difluoropiperidine hydrochloride (1.322 g, 8.39 mmol) and DIPEA (5.10 mL, 29.2 mmol) in DMSO (5 mL) was stirred at 145° C. for 16 h. The reaction mixture was concentrated and purified by flash column chromatography, eluting with 15% to 25% EtOAc in petroleum ether to provide 6-amino-2-(4,4-difluoropiperidin-1-yl)nicotinonitrile (0.60 g, 2.5 mmol, 69.1% yield) as yellow solid. $^1H$ NMR (400 MHz, DMSO-$d_6$): δ ppm 7.52 (d, J=8.4 Hz, 1H), 6.82 (s, 2H), 5.99 (d, J=8.5 Hz, 1H), 3.60-3.68 (m, 4H), 2.00-2.10 (m, 4H). m/z (ESI): 239.1 $(M+H)^+$.

Step 4: A mixture of 4-bromo-2-(6-azaspiro[2.5]octan-6-yl)benzoic acid (0.3 g, 0.967 mmol, Intermediate 9-1), oxalyl chloride (0.127 mL, 1.451 mmol) and DMF (a drop) in dichloromethane (5 mL) was stirred at 0° C. for 2 h. The reaction mixture was concentrated, and the residue was dissolved in dioxane (10 mL). A solution of 6-amino-2-(4,4-difluoropiperidin-1-yl)nicotinonitrile (0.230 g, 0.967 mmol) and triethylamine (0.404 mL, 2.90 mmol) in 1,4-dioxane (3 mL) was added to the above solution and the resulting mixture was stirred at 100° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 5% to 15% ethyl acetate in petroleum ether to provide 4-bromo-N-(5-cyano-6-(4,4-difluoropiperidin-1-yl)pyridin-2-yl)-2-(6-azaspiro[2.5]octan-6-yl)benzamide (0.19 g, 0.36 mmol, 37% yield) as off white solid. $^1H$ NMR (400 MHz, DMSO-$d_6$): δ ppm 13.40 (s, 1H), 8.14 (d, J=8.4 Hz, 1H), 8.03 (d, J=8.5 Hz, 1H), 7.84 (d, J=8.5 Hz, 1H), 7.73 (d, J=2.0 Hz, 1H), 7.58 (dd, J=8.5, 1.9 Hz, 1H), 3.76-3.83 (m, 4H), 3.06 (t, J=5.3 Hz, 4H), 2.08-2.20 (m, 4H), 1.68 (br s, 4H), 0.39 (s, 4H). m/z (ESI): 532.1 $(M+H)^+$.

Step 5: A mixture of 4-bromo-N-(5-cyano-6-(4,4-difluoropiperidin-1-yl)pyridin-2-yl)-2-(6-azaspiro[2.5]octan-6-yl) benzamide (0.19 g, 0.36 mmol), 2-hydroxyethane-1-sulfonamide (0.067 g, 0.54 mmol), potassium phosphate tribasic (0.152 g, 0.716 mmol), (1R,2R)—N1,N2-dimethylcyclohexane-1,2-diamine (0.025 g, 0.18 mmol) and copper(I) iodide (0.068 g, 0.36 mmol) in N, N-dimethylformamide (3 mL) was stirred at 90° C. for 16 h. The reaction mixture was diluted with water and was extracted with ethyl acetate. The organic extract was washed with brine, dried over $Na_2SO_4$, filtered, concentrated, and purified by preparative HPLC using 0.1% TFA in acetonitrile and water to provide N-(5-cyano-6-(4,4-difluoropiperidin-1-yl)pyridin-2-yl)-4-((2-hydroxyethyl)sulfonamido)-2-(6-azaspiro[2.5]octan-6-yl)benzamide 2,2,2-trifluoroacetate (0.040 g, 0.058 mmol, 16% yield) as white solid. $^1H$ NMR (400 MHz, DMSO-$d_6$): δ ppm 13.45 (s, 1H), 10.28 (s, 1H), 8.09 (dd, J=12.7, 8.5 Hz, 2H), 7.84 (d, J=8.4 Hz, 1H), 7.28 (d, J=2.2 Hz, 1H), 7.14 (dd, J=8.7, 2.1 Hz, 1H), 4.95 (br s, 1H), 3.72-3.82 (m, 6H), 3.37 (t, J=6.4 Hz, 2H), 2.92-3.00 (m, 4H), 2.08-2.18 (m, 4H), 1.70 (br s, 4H), 0.39 (s, 4H). m/z (ESI): 575.2 $(M+H)^+$.

Example 22: N-(6-(4,4-Difluoropiperidin-1-yl)-5-methylpyridin-2-yl)-4-((2-hydroxyethyl)sulfonamido)-2-(6-azaspiro[2.5]octan-6-yl)benzamide

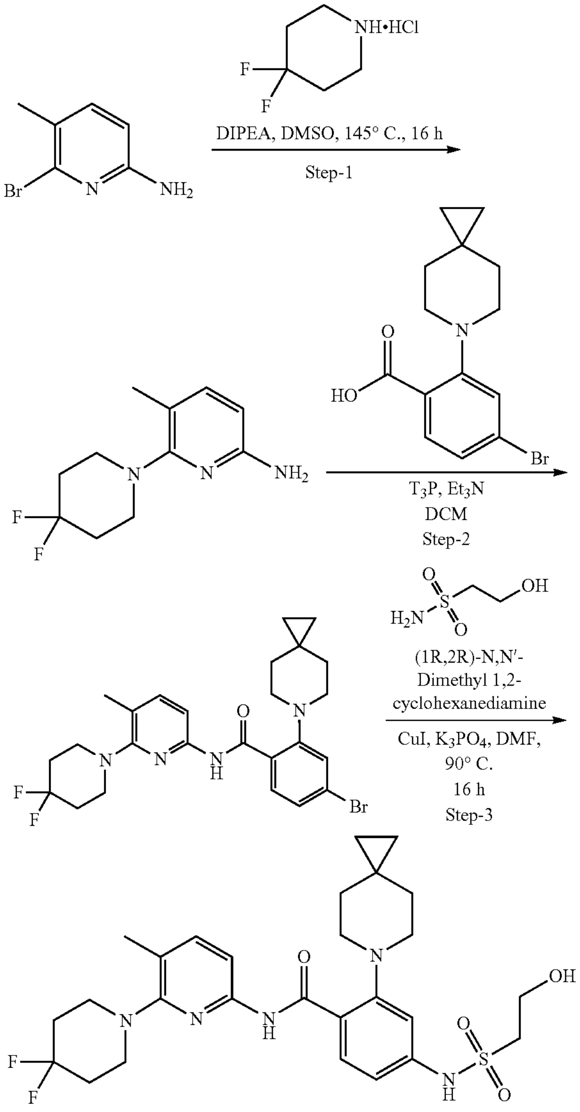

Step 1: A mixture of 6-bromo-5-methylpyridin-2-amine (650 mg, 3.48 mmol, Sibian chemicals), 4,4-difluoropiperidine hydrochloride (1643 mg, 10.43 mmol, Combi-Blocks) and DIPEA (3035 μL, 17.38 mmol) in NMP (6.5 mL) was heated at 180° C. for 8 h. The reaction mixture was diluted with water and was extracted with ethyl acetate. The organic extract was washed with brine, dried over $Na_2SO_4$, filtered, concentrated and purified by flash column chromatography, eluting with a gradient of 0% to 30% ethyl acetate in petroleum ether to provide 6-(4,4-difluoropiperidin-1-yl)-5-methylpyridin-2-amine (350 mg, 1.54 mmol, 44.3% yield) as pale yellow gum. $^1H$ NMR (300 MHz, DMSO-$d_6$): δ ppm 7.12 (dd, J=7.9, 2.3 Hz, 1H), 6.05 (dd, J=8.0, 2.2 Hz, 1H), 5.47 (s, 2H), 3.08 (q, J=3.9, 2.5 Hz, 4H), 1.26-2.48 (m, 7H). m/z (ESI): 228.1 $(M+H)^+$.

Step 2: A mixture of 4-bromo-2-(6-azaspiro[2.5]octan-6-yl)benzoic acid (573 mg, 1.85 mmol, Intermediate 9-1), triethylamine (644 μL, 4.62 mmol), $T_3P$ (50% in ethyl acetate, 1.47 g, 2.31 mmol) and 6-(4,4-difluoropiperidin-1-yl)-5-methylpyridin-2-amine (350 mg, 1.54 mmol) in DCM (5 mL) was stirred at room temperature for 16 h. The reaction mixture was diluted with water and was extracted with ethyl acetate. The organic extract was washed with brine, dried over $Na_2SO_4$, filtered, concentrated and purified by flash column chromatography, eluting with a gradient of 0% to 15% ethyl acetate in petroleum ether to provide 4-bromo-N-(6-(4,4-difluoropiperidin-1-yl)-5-methylpyridin-2-yl)-2-(6-azaspiro[2.5]octan-6-yl)benzamide (500 mg, 0.96 mmol, 62.5% yield) as pale yellow solid.

$^1H$ NMR (400 MHz, DMSO-$d_6$): δ ppm 13.01 (s, 1H), 8.04 (d, J=8.6 Hz, 1H), 7.85 (d, J=8.0 Hz, 1H), 7.67 (d, J=2.0 Hz, 1H), 7.15-7.66 (m, 2H), 3.09-3.32 (m, 4H), 3.04 (t, J=5.3 Hz, 4H), 2.24 (s, 3H), 1.91-2.23 (m, 4H), 1.21-1.99 (m, 4H), 0.38 (s, 4H). m/z (ESI): 519.1 $(M+H)^+$.

Step 3: A mixture of 4-bromo-N-(6-(4,4-difluoropiperidin-1-yl)-5-methylpyridin-2-yl)-2-(6-azaspiro[2.5]octan-6-yl)benzamide (200 mg, 0.385 mmol), 2-hydroxyethane-1-sulfonamide (72.3 mg, 0.578 mmol), potassium phosphate tribasic (163 mg, 0.770 mmol), (1R,2R)—N,N-dimethyl-1,2-cyclohexanediamine (27.4 mg, 0.193 mmol) and copper(I) iodide (73.3 mg, 0.385 mmol) in N,N-dimethylformamide (2 mL) was stirred at 100° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 0% to 30% ethyl acetate in petroleum ether to provide N-(6-(4,4-difluoropiperidin-1-yl)-5-methylpyridin-2-yl)-4-((2-hydroxyethyl)sulfonamido)-2-(6-azaspiro[2.5]octan-6-yl)benzamide (100 mg, 0.177 mmol, 46.1% yield) as off white solid. $^1H$ NMR (400 MHz, DMSO-$d_6$): δ ppm 13.03 (s, 1H), 10.21 (br s, 1H), 8.07 (d, J=8.6 Hz, 1H), 7.86 (d, J=8.0 Hz, 1H), 7.57 (d, J=8.1 Hz, 1H), 7.26 (d, J=2.2 Hz, 1H), 7.12 (dd, J=8.7, 2.1 Hz, 1H), 4.95 (br s, 1H), 3.74-4.80 (m, 2H), 3.36-3.40 (m, 2H), 3.20-3.28 (m, 4H), 2.92-3.02 (m, 4H), 2.24 (s, 3H), 2.09-2.16 (m, 4H), 1.70-1.90 (m, 4H), 0.38 (s, 4H). m/z (ESI): 564.2 $(M+H)^+$.

Example 23: N-(6-(4,4-difluorocyclohexyl)-4-methylpyridin-2-yl)-4-((2-hydroxyethyl)sulfonamido)-2-(6-azaspiro[2.5]octan-6-yl)benzamide

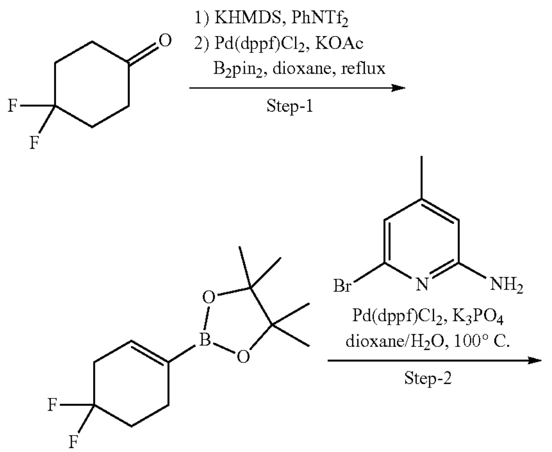

-continued

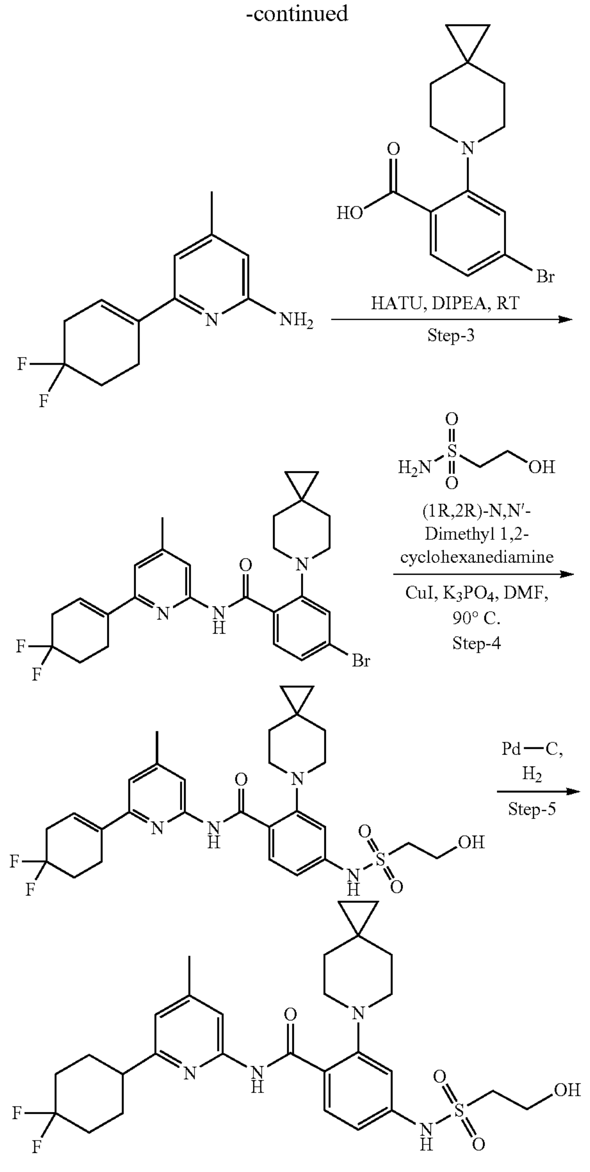

Step 1: To a solution of 4,4-difluorocyclohexan-1-one (1.0 g, 7.5 mmol, Combi-Blocks) in THF (10 mL) was added LiHMDS (1.0 M in THF, 8.95 mL, 8.95 mmol) at −78° C. The reaction mixture was stirred for 1 h before 1,1,1-trifluoro-N-phenyl-N-((trifluoromethyl)sulfonyl)methane-sulfonamide (2.93 g, 8.20 mmol) was added at −78° C. and the resulting solution was slowly warmed to room temperature and stirred for 16 h. The reaction mixture was quenched with water and extracted with ethyl acetate. The organic extract was washed with brine, dried over $Na_2SO_4$, filtered, and concentrated. To a solution of the residue in 1,4-dioxane (20 mL) were added potassium acetate (1.46 g, 14.91 mmol), bispinacolato diboron (2.272 g, 8.95 mmol) and $PdCl_2$(dppf) (0.546 g, 0.746 mmol). The reaction mixture was stirred at 100° C. for 16 h before it was diluted with water and was extracted with ethyl acetate. The organic extract was washed with brine, dried over $Na_2SO_4$, filtered, concentrated and purified by flash column chromatography, eluting with a gradient of 10% to 20% ethyl acetate in petroleum ether to provide 2-(4,4-difluorocyclohex-1-en-1-yl)-4,4,5,5-tetramethyl-1,3,2-dioxaborolane (900 mg, 3.69 mmol, 49.5% yield) as yellow oil. $^1$H NMR (400 MHz, Chloroform-d): 6 ppm 6.41 (t, J=3.7 Hz, 1H), 2.53-2.68 (m, 2H), 2.43 (t, J=6.7 Hz, 2H), 1.91-2.06 (m, 2H), 1.29 (s, 12H).

Step 2: A mixture of 6-bromo-4-methylpyridin-2-amine (800 mg, 4.28 mmol), 2-(4,4-difluorocyclohex-1-en-1-yl)-4,4,5,5-tetramethyl-1,3,2-dioxaborolane (1.148 g, 4.70 mmol), potassium phosphate tribasic (1907 mg, 8.98 mmol) and $PdCl_2$(dppf)-$CH_2Cl_2$ adduct (349 mg, 0.428 mmol) in 1,4-dioxane (9 mL) and water (3 mL) was stirred at 100° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 20% to 30% ethyl acetate in petroleum ether to provide 6-(4,4-difluorocyclohex-1-en-1-yl)-4-methylpyridin-2-amine (800 mg, 3.57 mmol, 83% yield) as brown gummy solid. $^1$H NMR (400 MHz, DMSO-$d_6$): δ ppm 6.49 (d, J=2.4 Hz, 1H), 6.41 (dt, J=5.0, 3.0 Hz, 1H), 6.18 (s, 1H), 5.73 (s, 2H), 2.59-2.77 (m, 4H), 2.12 (s, 3H), 2.0-2.10 (m, 2H). m/z (ESI): 225.1 $(M+H)^+$.

Step 3: A mixture of 4-bromo-2-(6-azaspiro[2.5]octan-6-yl)benzoic acid (200 mg, 0.645 mmol, Intermediate 9-1), DIPEA (338 μL, 1.93 mmol), HATU (368 mg, 0.967 mmol) and 6-(4,4-difluorocyclohex-1-en-1-yl)-4-methylpyridin-2-amine (217 mg, 0.967 mmol) in DMF (5 mL) was stirred at 100° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 10% to 20% ethyl acetate in petroleum ether to provide 4-bromo-N-(6-(4,4-difluorocyclohex-1-en-1-yl)-4-methylpyridin-2-yl)-2-(6-azaspiro[2.5]octan-6-yl)benzamide (150 mg, 0.290 mmol, 45.0% yield) as grey solid. $^1$H NMR (300 MHz, Chloroform-d): 6 ppm 13.21 (s, 1H), 8.09-8.26 (m, 2H), 7.37-7.55 (m, 2H), 7.04 (t, J=1.0 Hz, 1H), 6.52-6.60 (m, 1H), 3.10 (t, J=5.4 Hz, 4H), 2.74-2.90 (Wm, 4H), 2.40 (s, 3H), 2.14-2.28 (m, 2H), 1.70-1.90 (m, 4H), 0.43 (s, 4H). m/z (ESI): 516.1 $(M+H)^+$.

Step 4: A mixture of 4-bromo-N-(6-(4,4-difluorocyclohex-1-en-1-yl)-4-methylpyridin-2-yl)-2-(6-azaspiro[2.5]octan-6-yl)benzamide (150 mg, 0.290 mmol), 2-hydroxyethane-1-sulfonamide (54 mg, 0.436 mmol), potassium phosphate tribasic (154 mg, 0.726 mmol), (1R,2R)—N1, N2-dimethylcyclohexane-1,2-diamine (21 mg, 0.145 mmol) and copper(I) iodide (55.3 mg, 0.290 mmol) in DMF (5 mL) was stirred at 100° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 30% to 40% ethyl acetate in petroleum ether to provide N-(6-(4,4-difluorocyclohex-1-en-1-yl)-4-methylpyridin-2-yl)-4-((2-hydroxyethyl)sulfonamido)-2-(6-azaspiro[2.5]octan-6-yl)benzamide (150 mg, 0.268 mmol, 92% yield) as yellow oil. $^1$H NMR (400 MHz, DMSO-$d_6$): δ ppm 13.35 (s, 1H), 8.02-8.12 (m, 2H), 7.96 (s, 1H), 7.27 (s, 1H), 7.22 (s, 1H), 7.13 (d, J=8.9 Hz, 1H), 6.63 (m, 1H), 3.76 (d, J=6.6 Hz, 2H), 2.99 (s, 2H), 2.90 (s, 4H), 2.81 (s, 1H), 2.74 (s, 1H), 2.47 (d, J=2.4 Hz, 2H), 2.37 (s, 2H), 2.19 (s, 3H), 1.70-1.90 (m, 4H), 0.40 (s, 4H). m/z (ESI): 561.2 $(M+H)^+$.

Step 5: A mixture of N-(6-(4,4-difluorocyclohex-1-en-1-yl)-4-methylpyridin-2-yl)-4-((2-hydroxyethyl)sulfonamido)-2-(6-azaspiro[2.5]octan-6-yl)benzamide (100 mg, 0.178 mmol) and 10% Pd/C (50 mg, 0.047 mmol) in ethanol (5 mL) was stirred at room temperature under hydrogen atmosphere (14 psi) for 6 h. The reaction mixture was filtered through a celite bed. The filtrate was concentrated and the residue was triturated with diethyl ether and hexanes to provide N-(6-(4,4-difluorocyclohexyl)-4-methylpyridin-2-yl)-4-((2-hydroxyethyl)sulfonamido)-2-(6-azaspiro[2.5]octan-6-yl)benzamide (10.6 mg, 0.019 mmol, 1011% yield) as off white solid. $^1$H NMR (400 MHz, DMSO-$d_6$): δ ppm 13.28 (s, 1H), 7.98 (t, J=6.0 Hz, 2H), 7.15 (d, J=2.2 Hz, 1H), 6.98-7.05 (m, 1H), 6.86 (s, 1H), 3.73 (t, J=6.6 Hz, 2H), 3.24 (t, J=6.6 Hz, 2H), 2.95 (d, J=5.5 Hz, 4H), 2.72-2.80 (m, 1H), 2.31 (s, 3H), 1.90-2.12 (m, 8H), 1.70-1.84 (m, 4H), 0.36 (s, 4H). m/z (ESI): 563.2 $(M+H)^+$.

Example 24: (R)—N-(5-fluoro-6-(2-methylmorpholino)pyridin-2-yl)-4-((2-hydroxyethyl)sulfonamido)-2-(6-azaspiro[2.5]octan-6-yl)benzamide

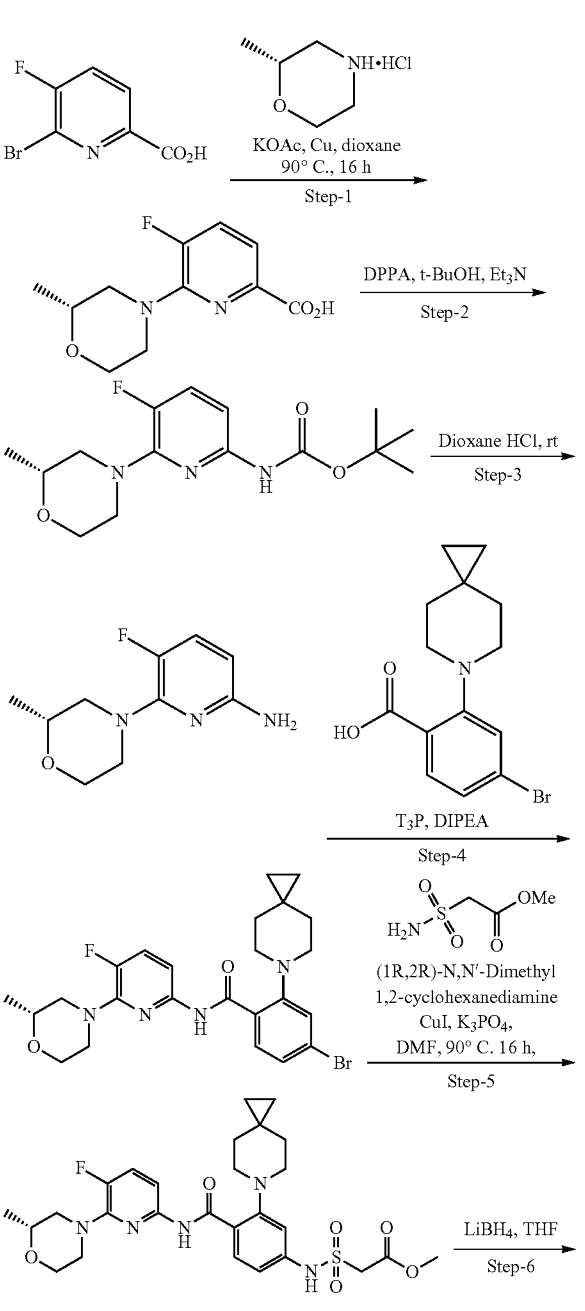

-continued

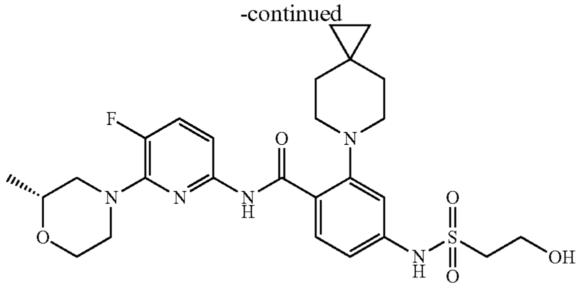

Step 1: A mixture of 6-bromo-5-fluoropicolinic acid (3.0 g, 14 mmol, Combi-Blocks), (R)-2-methylmorpholine hydrochloride (2.25 g, 16.36 mmol, Combi-Blocks), potassium acetate (2.94 g, 30.0 mmol) and copper powder (0.867 g, 13.6 mmol) in 1,4-dioxane (15 mL) was stirred at 90° C. for 16 h. The reaction mixture was filtered through a celite bed, diluted with water and was extracted with ethyl acetate. The organic extract was washed with brine, dried over $Na_2SO_4$, filtered, concentrated and purified by flash column chromatography, eluting with a gradient of 40% to 75% ethyl acetate in petroleum ether to provide (R)-5-fluoro-6-(2-methylmorpholino)picolinic acid (1.3 g, 5.4 mmol, 40% yield) as light yellow solid. $^1$H NMR (400 MHz, DMSO-$d_6$) δ ppm 12.91 (b s, 1H), 7.65 (dd, J=13.1, 8.1 Hz, 1H), 7.54 (dd, J=8.0, 3.0 Hz, 1H), 3.94 (t, J=2.2 Hz, 1H), 3.80-3.92 (m, 2H), 3.64 (tdd, J=11.9, 5.7, 2.6 Hz, 2H), 2.96 (ddd, J=12.9, 11.7, 3.4 Hz, 1H), 2.65 (dd, J=12.8, 10.2 Hz, 1H), 1.15 (d, J=6.2 Hz, 3H). m/z (ESI): 241.1 $(M+H)^+$.

Step 2: A mixture of (R)-5-fluoro-6-(2-methylmorpholino)picolinic acid (1.3 g, 5.4 mmol), triethylamine (1.095 g, 10.82 mmol) and diphenyl phosphorazidate (1.787 g, 6.49 mmol) in tert-butanol (13 mL) was stirred at 90° C. for 16 h. The reaction mixture was concentrated and purified by flash column chromatography, eluting with a gradient of 0% to 30% ethyl acetate in petroleum ether to provide tert-butyl (R)-(5-fluoro-6-(2-methylmorpholino)pyridin-2-yl)carbamate (1.2 g, 3.8 mmol, 71% yield) as pale yellow solid. $^1$H NMR (300 MHz, DMSO-$d_6$) δ ppm 9.91 (s, 1H), 7.40-7.58 (m, 1H), 7.20 (d, J=19.6 Hz, 1H), 3.82-3.94 (m, 1H), 3.67-3.80 (m, 2H), 3.58-3.69 (m, 2H), 2.83-3.09 (m, 1H), 2.63 (dt, J=12.2, 9.5 Hz, 1H), 1.20 (d, J=18.9 Hz, 9H), 1.12 (d, J=6.2 Hz, 3H). m/z (ESI): 312.1 $(M+H)^+$.

Step 3: To a solution of tert-butyl (R)-(5-fluoro-6-(2-methylmorpholino)pyridin-2-yl)carbamate (1.2 g, 3.8 mmol) in dichloromethane (12 mL) was added hydrochloric acid in 1,4-dioxane (10 mL, 20 mmol) at 0° C. and stirred at room temperature for 4 h. The reaction mixture was concentrated, and the residue was diluted with ice water (50 mL), basified (pH 9) with an aqueous 10% sodium bicarbonate solution, and extracted with ethyl acetate. The organic extract was washed with brine, dried over $Na_2SO_4$, filtered, concentrated, and purified by flash column chromatography, eluting with a gradient of 40% to 60% ethyl acetate in petroleum ether to provide (R)-5-fluoro-6-(2-methylmorpholino)pyridin-2-amine (0.63 g, 3.0 mmol, 77% yield) as brown solid. $^1$H NMR (400 MHz, DMSO-$d_6$) δ ppm 7.28-7.43 (m, 1H), 7.18 (t, J=7.7 Hz, 1H), 6.07 (dd, J=8.5, 2.1 Hz, 2H), 3.85 (dd, J=11.5, 3.1 Hz, 1H), 3.60-3.83 (m, 2H), 3.58 (dd, J=11.7, 2.7 Hz, 2H), 2.92 (td, J=12.2, 3.3 Hz, 1H), 2.61 (dd, J=12.7, 10.2 Hz, 1H), 1.11 (d, J=6.1 Hz, 3H). m/z (ESI): 212.1 $(M+H)^+$.

Step 4: To a solution of 4-bromo-2-(6-azaspiro[2.5]octan-6-yl)benzoic acid (1.057 g, 3.41 mmol, Intermediate 9-1) in $CH_2Cl_2$(10 mL) were added DIPEA (1.101 g, 8.52 mmol), $T_3P$ (2.71 g, 4.26 mmol, 50% in EtOAc) and (R)-5-fluoro-6-(2-methylmorpholino)pyridin-2-amine (0.60 g, 2.8 mmol) at room temperature and stirred for 16 h. The reaction mixture was diluted with water and was extracted with $CH_2Cl_2$. The organic extract was washed with brine, dried over $Na_2SO_4$, filtered, and concentrated. The concentrate was purified by flash column chromatography using a gradient of 60% to 80% ethyl acetate in petroleum ether to afford (R)-4-bromo-N-(5-fluoro-6-(2-methylmorpholino)pyridin-2-yl)-2-(6-azaspiro[2.5]octan-6-yl)benzamide (0.38 g, 0.76 mmol, 27% yield) as a pale brown solid. $^1$H NMR (400 MHz, DMSO-$d_6$) δ ppm 13.01 (s, 1H), 8.04 (d, J=8.4 Hz, 1H), 7.75 (dd, J=8.5, 2.5 Hz, 1H), 7.69 (d, J=1.9 Hz, 1H), 7.44-7.66 (m, 2H), 3.89 (d, J=13.1 Hz, 1H), 3.83 (d, J=11.7 Hz, 2H), 3.67 (t, J=10.9 Hz, 2H), 3.05 (d, J=6.1 Hz, 4H), 2.95 (t, J=10.8 Hz, 1H), 2.60-2.68 (m, 1H), 1.70 (s, 4H), 1.16 (d, J=6.2 Hz, 3H), 0.39 (s, 4H). m/z (ESI): 504.1 $(M+H)^+$.

Step 5: A mixture of (R)-4-bromo-N-(5-fluoro-6-(2-methylmorpholino)pyridin-2-yl)-2-(6-azaspiro[2.5]octan-6-yl)benzamide (380 mg, 0.755 mmol), methyl 2-sulfamoylacetate (139 mg, 0.906 mmol), potassium phosphate (320 mg, 1.51 mmol), (1R,2R)—N1,N2-dimethylcyclohexane-1,2-diamine (129 mg, 0.906 mmol) and copper(I) iodide (28.8 mg, 0.151 mmol) in N, N-dimethylformamide (3.8 mL) was stirred at 90° C. for 6 h. The reaction mixture was filtered through a celite bed, diluted with water and was extracted with ethyl acetate. The organic extract was washed with brine, dried over $Na_2SO_4$, filtered, concentrated and purified by flash column chromatography, eluting with a gradient of 40% to 70% ethyl acetate in petroleum ether to provide methyl (R)-2-(N-(4-((5-fluoro-6-(2-methylmorpholino)pyridin-2-yl)carbamoyl)-3-(6-azaspiro[2.5]octan-6-yl)phenyl)sulfamoyl)acetate (200 mg, 0.347 mmol, 46.0% yield) pale yellow gummy liquid. $^1$H NMR (400 MHz, DMSO-$d_6$) δ ppm 13.03 (d, J=4.4 Hz, 1H), 10.66 (s, 1H), 8.09 (d, J=8.6 Hz, 1H), 7.71-7.95 (m, 1H), 7.58 (dd, J=12.8, 8.6 Hz, 1H), 7.28 (dd, J=11.2, 2.2 Hz, 1H), 7.14 (ddd, J=7.3, 5.5, 1.9 Hz, 1H), 4.41 (s, 1H), 4.03 (q, J=7.1 Hz, 2H), 3.80-3.97 (m, 3H), 3.65-3.67 (m, 2H), 3.60 (s, 3H), 2.93-2.99 (m, 3H), 1.99 (s, 2H), 1.73 (s, 4H), 1.16 (d, J=5.8 Hz, 3H), 0.40 (s, 4H). m/z (ESI): 576.2 $(M+H)^+$.

Step 6: To a solution of methyl (R)-2-(N-(4-((5-fluoro-6-(2-methylmorpholino)pyridin-2-yl)carbamoyl)-3-(6-azaspiro[2.5]octan-6-yl)phenyl)sulfamoyl)acetate (200 mg, 0.347 mmol) in THF (4 mL) was added lithium borohydride (2.0 M in THF, 0.521 mL, 1.04 mmol) at 0° C. and stirred at room temperature for 2 h. The reaction mixture was diluted with ice cold water and was extracted with ethyl acetate. The organic extract was washed with brine, dried over $Na_2SO_4$, filtered, concentrated and purified by flash column chromatography, eluting with a gradient of 40% to 80% ethyl acetate in petroleum ether to provide (R)—N-(5-fluoro-6-(2-methylmorpholino)pyridin-2-yl)-4-((2-hydroxyethyl)sulfonamido)-2-(6-azaspiro[2.5]octan-6-yl)benzamide (70 mg, 0.13 mmol, 37% yield) as off white solid. $^1$H NMR (400 MHz, DMSO-$d_6$) δ ppm 12.76-13.48 (m, 1H), 10.22 (s, 1H), 7.88-8.42 (m, 1H), 7.76 (dt, J=9.3, 4.6 Hz, 1H), 7.57 (ddt, J=12.9, 9.1, 3.9 Hz, 1H), 7.27 (d, J=6.1 Hz, 1H), 7.13 (q, J=7.8, 5.2 Hz, 1H), 4.95 (s, 1H), 3.91 (s, 1H), 3.79-3.81 (m, 4H), 3.68 (s, 4H), 2.91-2.97 (m, 5H), 2.64 (d, J=9.0 Hz, 1H), 1.86 (br s, 4H), 0.95-1.31 (m, 3H), 0.38 (br s, 4H). m/z (ESI): 548.2 $(M+H)^+$.

Example 25: (R)—N-(4-Cyano-6-(2-methylmorpholino)pyridin-2-yl)-4-((2-hydroxyethyl)sulfonamido)-2-(6-azaspiro[2.5]octan-6-yl)benzamide

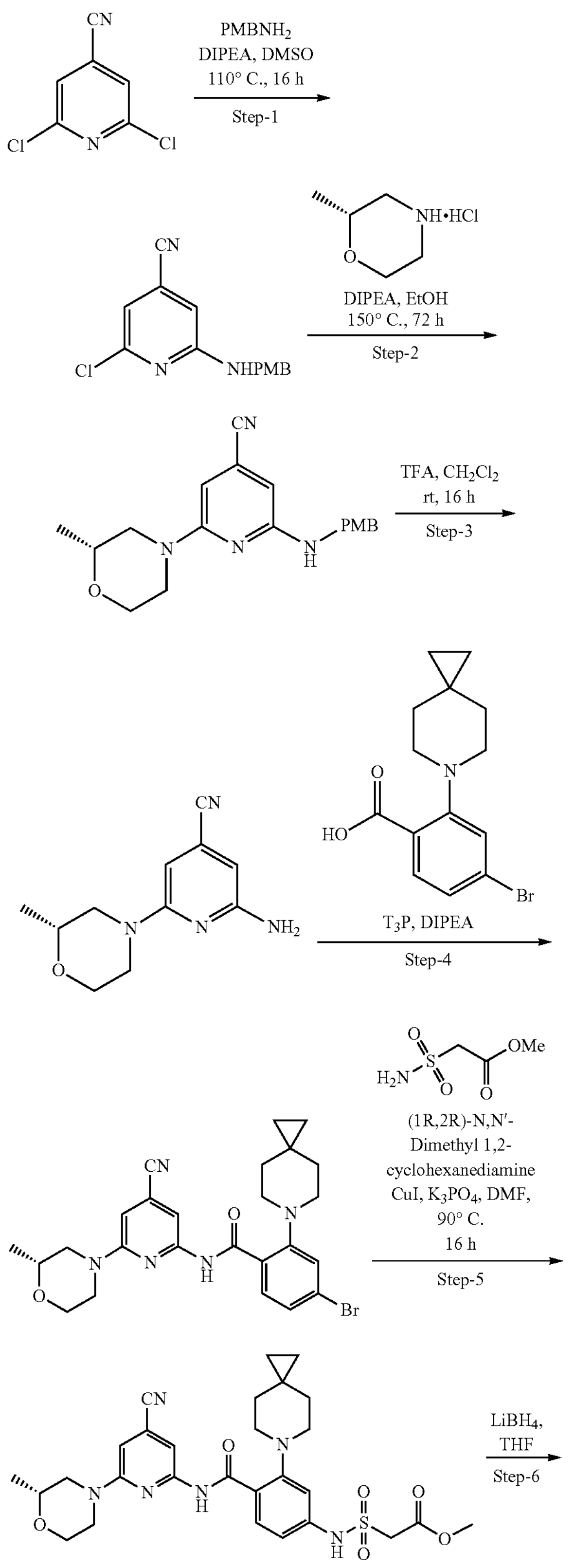

-continued

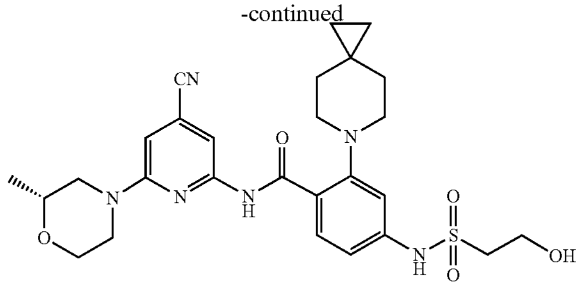

Step 1: A mixture of 2,6-dichloroisonicotinonitrile (3.0 g, 17 mmol, Combi-Blocks), (4-methoxyphenyl)methanamine (2.379 g, 17.34 mmol) and DIPEA (3.03 mL, 17.34 mmol) in dimethyl sulfoxide (30 mL) was stirred at 110° C. for 16 h. The reaction mixture was diluted with water and was extracted with ethyl acetate. The organic extract was washed with brine, dried over $Na_2SO_4$, filtered, concentrated and purified by flash column chromatography, eluting with a gradient of 0% to 20% ethyl acetate in petroleum ether to provide 2-chloro-6-((4-methoxybenzyl)amino)isonicotinonitrile (3.8 g, 14 mmol, 80% yield) as yellow solid. $^1$H NMR (400 MHz, DMSO-$d_6$): δ ppm 7.96-8.02 (m, 1H), 7.22-7.30 (m, 2H), 6.94, (s, 1H), 6.86-6.92 (m, 2H), 6.84 (s, 1H), 4.36 (d, J=5.8 Hz, 2H), 3.72 (s, 3H). m/z (ESI): 274.1 $(M+H)^+$.

Step 2: A mixture of 2-chloro-6-((4-methoxybenzyl) amino) isonicotinonitrile (1.85 g, 6.76 mmol), (R)-2-methylmorpholine hydrochloride (2.139 g, 15.55 mmol, Combi-Blocks) and DIPEA (9.44 mL, 54.1 mmol) in ethanol (20 mL) was stirred at 150° C. for 76 h. The reaction mixture was concentrated and was purified by flash column chromatography, eluting with a gradient of 0% to 10% ethyl acetate in petroleum ether to provide (R)-2-((4-methoxybenzyl)amino)-6-(2-methylmorpholino)isonicotinonitrile (0.59 g, 1.7 mmol, 26% yield) as yellow oil. $^1$H NMR (400 MHz, DMSO-$d_6$): δ ppm 7.28 (br s, 1H), 7.22-7.24 (m, 2H), 6.83-6.91 (m, 2H), 6.21 (s, 1H), 6.06 (s, 1H), 4.35 (d, J=5.9 Hz, 2H), 3.97-4.10 (m, 2H), 3.80-3.88 (m, 1H), 3.72 (s, 3H), 3.39-3.52 (m, 2H), 2.75 (td, J=12.3, 3.5 Hz, 1H), 2.42 (dd, J=12.8, 10.4 Hz, 1H), 1.12 (d, J=6.2 Hz, 3H). m/z (ESI): 339.2 $(M+H)^+$.

Step 3: A mixture of (R)-2-((4-methoxybenzyl)amino)-6-(2-methylmorpholino)isonicotinonitrile (0.59 g, 1.7 mmol) and TFA (2.821 mL, 36.61 mmol) in dichloromethane (6 mL) was stirred at room temperature for 16 h. The reaction mixture was concentrated and was neutralized (pH 7) with 10% $NaHCO_3$ solution and was extracted with dichloromethane. The organic extract was washed with brine, dried over $Na_2SO_4$, filtered, concentrated and purified by flash column chromatography, eluting with a gradient of 0% to 20% ethyl acetate in petroleum ether to provide (R)-2-amino-6-(2-methylmorpholino)isonicotinonitrile (0.325 g, 1.49 mmol, 85% yield) as white solid. $^1$H NMR (300 MHz, DMSO-$d_6$): δ ppm 6.23 (s, 1H), 6.15 (s, 2H), 5.97 (s, 1H), 4.07 (dt, J=12.7, 2.1 Hz, 1H), 3.92-4.02 (m, 2H), 3.38-3.53 (m, 2H), 2.72 (td, J=12.2, 3.6 Hz, 1H), 2.34-2.42 (m, 1H), 1.10 (d, J=6.2 Hz, 3H). m/z (ESI): 219.1 $(M+H)^+$.

Step 4: A mixture of 4-bromo-2-(6-azaspiro[2.5]octan-6-yl)benzoic acid (0.25 g, 0.81 mmol, Intermediate 9-1), DIPEA (0.422 mL, 2.42 mmol), $T_3P$ (50% in ethyl acetate, 1.539 g, 2.418 mmol) and (R)-2-amino-6-(2-methylmorpholino)isonicotinonitrile (0.211 g, 0.967 mmol) in dichloromethane (4 mL) was stirred at room temperature for 18 h. The reaction mixture was diluted with water and was extracted with dichloromethane. The organic extract was washed with brine, dried over $Na_2SO_4$, filtered, concentrated and purified by flash column chromatography, eluting with a gradient of 0% to 20% ethyl acetate in petroleum ether to provide (R)-4-bromo-N-(4-cyano-6-(2-methylmorpholino) pyridin-2-yl)-2-(6-azaspiro[2.5]octan-6-yl)benzamide (0.263 g, 0.515 mmol, 63.9% yield) as white solid. $^1$H NMR (400 MHz, DMSO-$d_6$): δ ppm 13.21 (s, 1H), 8.00-8.10 (m, 1H), 7.76 (s, 1H), 7.71 (d, J=1.9 Hz, 1H), 7.57 (dd, J=8.5, 1.9 Hz, 1H), 7.13 (s, 1H), 4.23 (d, J=12.8 Hz, 1H), 4.17 (d, J=12.9 Hz, 1H), 3.93 (d, J=9.9 Hz, 1H), 3.50-3.61 (m, 2H), 3.0-3.08 (m, 4H), 2.89-2.99 (m, 1H), 2.58-2.64 (m, 1H), 1.68 (br s, 4H), 1.17 (d, J=6.2 Hz, 3H), 0.37 (s, 4H). m/z (ESI): 512.2 $(M+H)^+$.

Step 5: A mixture of (R)-4-bromo-N-(4-cyano-6-(2-methylmorpholino)pyridin-2-yl)-2-(6-azaspiro[2.5]octan-6-yl) benzamide (260 mg, 0.509 mmol), methyl 2-sulfamoylacetate (156 mg, 1.02 mmol), potassium phosphate tribasic (216 mg, 1.02 mmol), copper(I) iodide (194 mg, 1.02 mmol) and (1R,2R)—N,N'-dimethyl-1,2-cyclohexanediamine (72.4 mg, 0.509 mmol) in DMF (2 mL) was stirred at 90° C. for 16 h. The reaction mixture was filtered through a celite pad. The filtrate was washed with water (15 mL), brine (15 mL), dried over sodium sulfate, filtered, and concentrated. The concentrate was purified by flash column chromatography using a gradient of 40% EtOAc in petroleum ether to afford methyl (R)-2-(N-(4-((4-cyano-6-(2-methylmorpholino)pyridin-2-yl)carbamoyl)-3-(6-azaspiro[2.5]octan-6-yl)phenyl)sulfamoyl)acetate (250 mg, 0.429 mmol, 84% yield) as pale yellow gum. m/z (ESI): 583.2 $(M+H)^+$.

Step 6: To a solution of methyl (R)-2-(N-(4-((4-cyano-6-(2-methylmorpholino)pyridin-2-yl)carbamoyl)-3-(6-azaspiro[2.5]octan-6-yl)phenyl)sulfamoyl)acetate (250 mg, 0.429 mmol) in THF (2 mL) was added $LiBH_4$ (2.0 M in THF, 429 μl, 0.858 mmol) at −30° C. The mixture as then stirred at 0° C. for 30 min. The reaction mixture was quenched with a saturated aqueous solution of $NH_4Cl$ and was extracted with EtOAc. The organic extract was washed with brine, dried over $Na_2SO_4$, filtered, concentrated and purified by flash column chromatography, eluting with a gradient of 20% to 50% ethyl acetate in petroleum ether to provide (R)—N-(4-cyano-6-(2-methylmorpholino)pyridin-2-yl)-4-((2-hydroxyethyl)sulfonamido)-2-(6-azaspiro[2.5] octan-6-yl)benzamide (120 mg, 0.216 mmol, 50.4% yield) as white solid. $^1$H NMR (400 MHz, DMSO-d6): δ ppm 13.25 (s, 1H), 10.23 (br s, 1H), 8.07 (dd, J=8.7, 2.9 Hz, 1H), 7.78 (d, J=2.8 Hz, 1H), 7.28 (d, J=3.1 Hz, 1H), 7.07-7.17 (m, 2H), 4.96 (br s, 1H), 4.13-4.26 (m, 2H), 3.93 (d, J=11.4 Hz, 1H), 3.76 (td, J=6.6, 2.5 Hz, 2H), 3.57 (d, J=11.7 Hz, 2H), 3.37 (dd, J=6.7, 2.7 Hz, 2H), 2.88-3.02 (m, 5H), 2.54-2.62 (m, 1H), 1.71 (br s, 4H), 1.17 (d, J=6.3 Hz, 3H), 0.39 (s, 4H). m/z (ESI): 555.2 $(M+H)^+$.

Example 26: 4-((2-Hydroxyethyl)sulfonamido)-N-(6-(2-methylpropan-2-ylsulfonimidoyl)pyridin-2-yl)-2-(6-azaspiro[2.5]octan-6-yl)benzamide

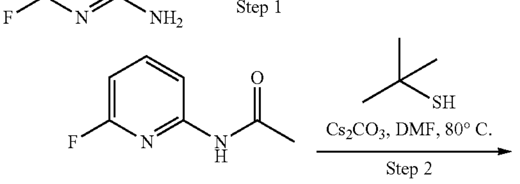

-continued

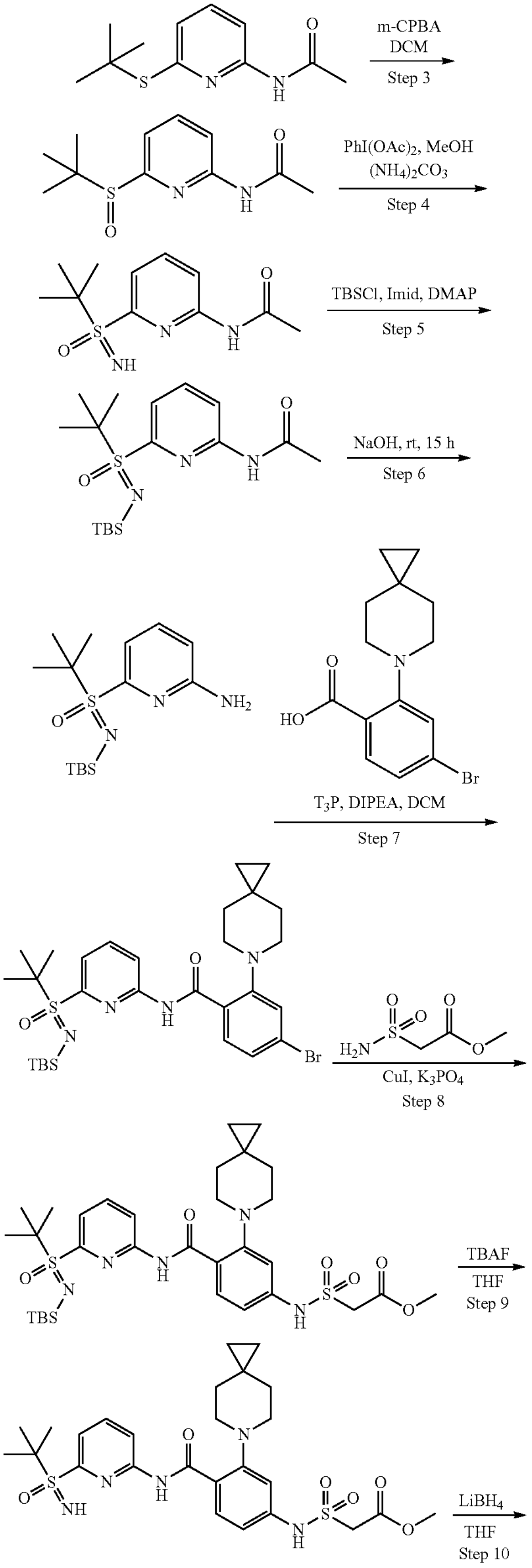

-continued

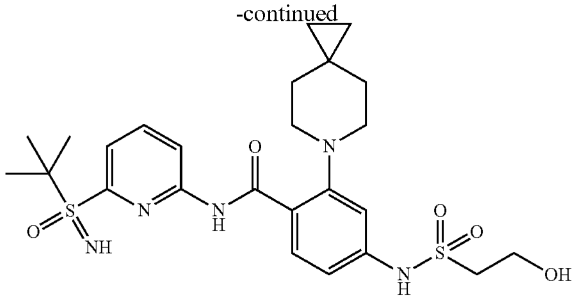

Step 1: To a solution of 6-fluoropyridin-2-amine (5.0 g, 45 mmol, Apollo scientific) in dichloromethane (100 mL) were added $Et_3N$ (15.54 mL, 112 mmol) and acetyl chloride (4.76 mL, 66.9 mmol) at 0° C. The reaction mixture was stirred at room temperature for 16 h before it was diluted with water and was extracted with dichloromethane. The organic extract was washed with brine, dried over $Na_2SO_4$, filtered, concentrated and purified by flash column chromatography, eluting with a gradient of 0% to 20% ethyl acetate in petroleum ether to provide N-(6-fluoropyridin-2-yl)acetamide (4.0 g, 26 mmol, 58% yield) as pale yellow solid. $^1H$ NMR (400 MHz, DMSO-$d_6$): δ ppm 10.65 (s, 1H), 7.93-8.01 (m, 2H), 6.29 (d, J=2.6 Hz, 1H), 2.09 (s, 3H). m/z (ESI): 155.1 $(M+H)^+$.

Step 2: A mixture of N-(6-fluoropyridin-2-yl)acetamide (4.0 g, 26 mmol), cesium carbonate (16.91 g, 51.9 mmol) and 2-methylpropane-2-thiol (3.51 g, 38.9 mmol) in DMF (60 mL) was stirred at 80° C. for 24 h. The reaction mixture was quenched with ice cold water and the precipitated solid was filtered, and dried to provide N-(6-(tert-butylthio)pyridin-2-yl)acetamide (4.0 g, 18 mmol, 69% yield) as off white solid. $^1H$ NMR (400 MHz, DMSO-$d_6$): δ ppm 10.34 (s, 1H), 7.86 (d, J=8.5 Hz, 1H), 7.61 (t, J=8.0 Hz, 1H), 7.02 (d, J=7.6 Hz, 1H), 2.11 (s, 3H), 1.48 (s, 9H). m/z (ESI): 225.1 $(M+H)^+$.

Step 3: To a solution of N-(6-(tert-butylthio)pyridin-2-yl) acetamide (3.5 g, 16 mmol) in dichloromethane (75 mL) was added m-CPBA (75%, 3.59 g, 15.6 mmol) at 0° C. and stirred at room temperature for 16 h. The reaction mixture was quenched with 10% sodium bicarbonate and was extracted with dichloromethane. The organic extract was washed with brine, dried over $Na_2SO_4$, filtered, concentrated and triturated with diethyl ether to provide N-(6-(tert-butylsulfinyl)pyridin-2-yl)acetamide (3.3 g, 13 mmol, 88% yield) as white solid. $^1H$ NMR (300 MHz, DMSO-$d_6$): δ ppm 10.68 (s, 1H), 8.18 (d, J=8.3 Hz, 1H), 8.03 (t, J=8.0 Hz, 1H), 7.52 (d, J=7.5 Hz, 1H), 2.12 (s, 3H), 1.15 (s, 9H). m/z (ESI): 241.1 $(M+H)^+$.

Step 4: A mixture of N-(6-(tert-butylsulfinyl)pyridin-2-yl)acetamide (3.3 g, 13 mmol), iodobenzene diacetate (17.69 g, 54.9 mmol) and ammonium carbonate (5.36 g, 68.7 mmol) in methanol (75 mL) was stirred at room temperature for 24 h. The reaction mixture was concentrated and the residue treated with water and extracted with ethyl acetate. The organic extract was washed with brine, dried over $Na_2SO_4$, filtered, concentrated, and triturated with diethyl ether to provide N-(6-(2-methylpropan-2-ylsulfonimidoyl) pyridin-2-yl)acetamide (2.1 g, 8.2 mmol, 60% yield) as off white solid. $^1H$ NMR (400 MHz, DMSO-$d_6$): δ ppm 10.82 (s, 1H), 8.29 (d, J=8.4 Hz, 1H), 8.03 (t, J=8.0 Hz, 1H), 7.75 (dd, J=7.6, 0.9 Hz, 1H), 4.11 (s, 1H), 2.14 (s, 3H), 1.29 (s, 9H).

Step 5: A solution of N-(6-(2-methylpropan-2-ylsulfonimidoyl)pyridin-2-yl)acetamide (2.24 g, 8.77 mmol) in $CH_2Cl_2$ (50 mL), imidazole (1.194 g, 17.55 mmol), DMAP (0.536 g, 4.39 mmol) and TBS-Cl (1.587 g, 10.53 mmol) was stirred at room temperature for 2.5 h. The reaction mixture was quenched with cold water and was extracted with $CH_2Cl_2$. The organic extract was washed with water, brine, dried over $Na_2SO_4$, filtered, and concentrated. The concentrate was purified by flash column chromatography using a gradient of 15% EtOAc in petroleum ether to afford N-(6-(N-(tert-butyldimethylsilyl)-2-methylpropan-2-ylsulfonimidoyl)pyridin-2-yl)acetamide (2.7 g, 7.3 mmol, 83% yield) as white solid. $^1$H NMR (400 MHz, DMSO-$d_6$): δ ppm 10.70 (s, 1H), 8.27 (d, J=8.4 Hz, 1H), 8.01-8.07 (m, 1H), 7.68 (d, J=7.6 Hz, 1H), 2.15 (s, 3H), 1.28 (s, 9H), 0.86 (s, 9H), −0.07 (d, 3H), −0.11 (d, 3H). m/z (ESI): 256 $(M-2^tBu)^+$.

Step 6: A mixture of N-(6-(N-(tert-butyldimethylsilyl)-2-methylpropan-2-ylsulfonimidoyl)pyridin-2-yl)acetamide (1.5 g, 4.1 mmol) and aqueous sodium hydroxide (2.5 M, 32.5 mL, 81 mmol) solution in methanol (30 mL) was stirred at room temperature for 15 h. The reaction mixture was concentrated, and the residue was treated with water. The precipitated solid was filtered, and dried to provide (6-aminopyridin-2-yl)(tert-butyl)((tert-butyldimethylsilyl)imino)-$\lambda^6$-sulfanone (1.2 g, 3.7 mmol, 90% yield) as white solid. $^1$H NMR (400 MHz, DMSO-$d_6$): δ ppm 7.58 (t, J=7.8 Hz, 1H), 7.09 (d, J=7.3 Hz, 1H), 6.60 (d, J=8.3 Hz, 1H), 6.35 (s, 2H), 1.26 (s, 9H), 0.85 (s, 9H), −0.07 (s, 3H), −0.13 (s, 3H). m/z (ESI): 214.1 $(M-2^tBu)^+$.

Step 7: A mixture of 4-bromo-2-(6-azaspiro[2.5]octan-6-yl)benzoic acid (0.50 g, 1.6 mmol, Intermediate 9-1), DIPEA (0.845 mL, 4.84 mmol), $T_3P$ (50% solution in ethyl acetate, 3.08 g, 4.84 mmol) and (6-aminopyridin-2-yl)(tert-butyl)((tert-butyldimethylsilyl)imino)-$\lambda^6$-sulfanone (0.634 g, 1.93 mmol) in dichloromethane (10 mL) was stirred at room temperature for 48 h. The reaction mixture was diluted with water and was extracted with dichloromethane. The organic extract was washed with brine, dried over $Na_2SO_4$, filtered, concentrated and purified by flash column chromatography, eluting with a gradient of 0% to 15% ethyl acetate in petroleum ether to provide 4-bromo-N-(6-(N-(tert-butyldimethylsilyl)-2-methylpropan-2-ylsulfonimidoyl)pyridin-2-yl)-2-(6-azaspiro[2.5]octan-6-yl)benzamide (0.20 g, 0.32 mmol, 20% yield) as pale yellow gum. $^1$H NMR (400 MHz, DMSO-$d_6$): δ ppm 12.86 (s, 1H), 8.51 (d, J=8.4 Hz, 1H), 8.13 (t, J=8.0 Hz, 1H), 8.00 (d, J=8.4 Hz, 1H), 7.77 (d, J=7.6 Hz, 1H), 7.68 (d, J=1.8 Hz, 1H), 7.55 (dd, J=8.5, 1.8 Hz, 1H), 2.97-3.10 (m, 4H), 1.60 (br s, 4H), 1.33 (s, 9H), 0.82 (s, 9H), 0.33 (s, 4H), −0.12 (s, 3H). −0.14 (s, 3H). m/z (ESI): 507.0 $(M-2^tBu)^+$.

Step 8: A mixture of 4-bromo-N-(6-(N-(tert-butyldimethylsilyl)-2-methylpropan-2-ylsulfonimidoyl)pyridin-2-yl)-2-(6-azaspiro[2.5]octan-6-yl)benzamide (0.20 g, 0.32 mmol), methyl 2-sulfamoylacetate (0.074 g, 0.48 mmol), potassium phosphate tribasic (0.137 g, 0.645 mmol), copper(I) iodide (0.061 g, 0.32 mmol) and (1R,2R)—N,N-dimethyl-1,2-cyclohexanediamine (0.023 g, 0.16 mmol) in DMF (4 mL) was stirred at 90° C. for 16 h. The reaction mixture was diluted with water and was extracted with ethyl acetate. The organic extract was washed with brine, dried over $Na_2SO_4$, filtered, and concentrated to provide methyl 2-(N-(4-((6-(N-(tert-butyldimethylsilyl)-2-methylpropan-2-ylsulfonimidoyl)pyridin-2-yl)carbamoyl)-3-(6-azaspiro[2.5]octan-6-yl)phenyl)sulfamoyl)acetate (0.18 g, 0.26 mmol, 81% yield) as pale yellow gum. m/z (ESI): 692.2 $(M+H)^+$.

Step 9: A mixture of methyl 2-(N-(4-((6-(N-(tert-butyldimethylsilyl)-2-methylpropan-2-ylsulfonimidoyl)pyridin-2-yl)carbamoyl)-3-(6-azaspiro[2.5]octan-6-yl)phenyl)sulfamoyl)acetate (0.18 g, 0.260 mmol) and tetrabutylammonium fluoride (1 M solution in THF, 0.390 mL, 0.390 mmol) in THF (4 mL) was stirred at room temperature for 3 h. The reaction mixture was quenched with a saturated aqueous ammonium chloride solution and was extracted with ethyl acetate. The organic extract was washed with brine, dried over $Na_2SO_4$, filtered, and concentrated to provide methyl 2-(N-(4-((6-(2-methylpropan-2-ylsulfonimidoyl)pyridin-2-yl)carbamoyl)-3-(6-azaspiro[2.5]octan-6-yl)phenyl)sulfamoyl)acetate (0.10 g, 0.17 mmol, 66% yield) as pale yellow gum. m/z (ESI): 578.1 $(M+H)^+$.

Step 10: To a solution of methyl 2-(N-(4-((6-(2-methylpropan-2-ylsulfonimidoyl)pyridin-2-yl)carbamoyl)-3-(6-azaspiro[2.5]octan-6-yl)phenyl)sulfamoyl)acetate (0.10 g, 0.17 mmol) in THF (3 mL) was added $LiBH_4$ (2.0 M solution in THF, 0.173 mL, 0.346 mmol) at 0° C. and stirred at room temperature for 1.5 h. The reaction mixture was quenched with a saturated aqueous ammonium chloride solution and was extracted with ethyl acetate. The organic extract was washed with brine, dried over $Na_2SO_4$, filtered, concentrated and purified by preparative HPLC to provide 4-((2-hydroxyethyl)sulfonamido)-N-(6-(2-methylpropan-2-ylsulfonimidoyl)pyridin-2-yl)-2-(6-azaspiro[2.5]octan-6-yl)benzamide (0.016 g, 0.029 mmol, 16% yield) as white solid. $^1$H NMR (400 MHz, DMSO-$d_6$): δ ppm 13.16 (s, 1H), 10.26 (s, 1H), 8.53 (d, J=8.4 Hz, 1H), 8.17-8.05 (m, 2H), 7.82 (dd, J=7.5, 0.9 Hz, 1H), 7.29 (d, J=2.2 Hz, 1H), 7.14 (dd, J=8.6, 2.1 Hz, 1H), 4.95 (br s, 1H), 4.04 (s, 1H), 3.76-3.80 (m, 2H), 3.37 (t, J=6.5 Hz, 2H), 2.99 (t, J=5.4 Hz, 4H), 1.60-1.70 (m, 3H), 1.35 (s, 9H), 0.36 (s, 4H). m/z (ESI): 550.2 $(M+H)^+$.

Example 27-1 and 27-2: 2-(6-Azaspiro[2.5]octan-6-yl)-4-(S-cyclopropylsulfonimidoyl)-N-(6-(3,3,3-trifluoropropoxy)-2-pyridinyl)benzamide and 2-(6-Azaspiro[2.5]octan-6-yl)-4-(R-cyclopropylsulfonimidoyl)-N-(6-(3,3,3-trifluoropropoxy)-2-pyridinyl)

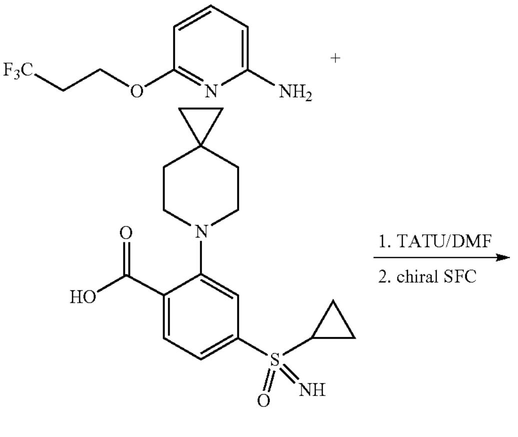

-continued

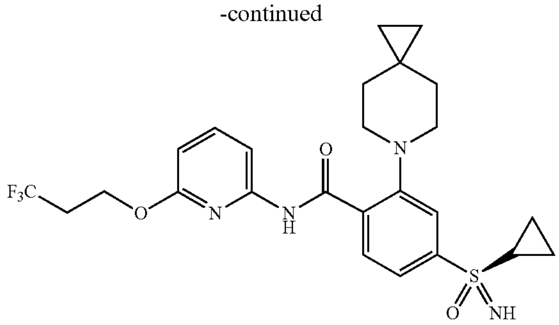

+

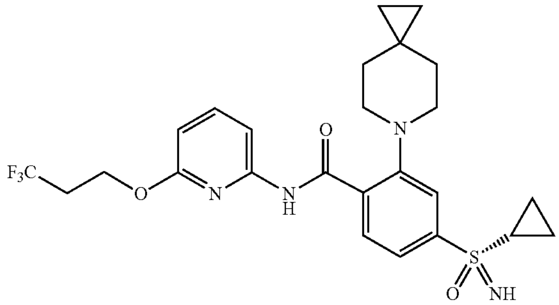

A mixture of 4-(cyclopropanesulfonimidoyl)-2-(6-azaspiro[2.5]octan-6-yl)benzoic acid (0.200 g, 0.598 mmol, Intermediate 16), 6-(3,3,3-trifluoropropoxy)pyridin-2-amine (0.160 g, 0.78 mmol, Intermediate 6), TATU (0.250 g, 0.776 mmol, Combi-Blocks), DMF (6 mL), and DIPEA (0.309 g, 0.426 mL, 2.39 mmol, Aldrich) was stirred at room temperature for 18 h. The mixture was diluted with saturated $Na_2CO_3$ and EtOAc. The organic phase was washed with $Na_2CO_3$, water and brine, dried over $Na_2SO_4$ and concentrated in vacuo. The crude was purified by silica gel chromatography: 0-100% EtOAc in heptane. The product was obtained as off-white solid. m/z (ESI): 523.1 $(M+H)^+$. The racemic mixture was purified by chiral SFC using an Regis (S,S) Whelk-01 (250×21 mm, 5 mm) with a mobile phase of 65% Liquid $CO_2$ and 35% MeOH using a flowrate of 80 mL/min to generate:

Example 27-1: 2-(6-Azaspiro[2.5]octan-6-yl)-4-(S-cyclopropylsulfonimidoyl)-N-(6-(3,3,3-trifluoropropoxy)-2-pyridinyl)benzamide. First eluting peak (68 mg, ee >99%). $^1$H NMR (400 MHz, CHLOROFORM-d) δ 12.92 (s, 1H), 8.45 (d, J=8.29 Hz, 1H), 8.00 (d, J=7.67 Hz, 1H), 7.95 (d, J=1.66 Hz, 1H), 7.85 (dd, J=1.76, 8.19 Hz, 1H), 7.66 (t, J=7.88 Hz, 1H), 6.55 (d, J=8.09 Hz, 1H), 4.54 (t, J=6.63 Hz, 2H), 3.15 (t, J=5.29 Hz, 4H), 2.55-2.72 (m, 3H), 1.66-1.98 (m, 5H), 1.46 (tdd, J=5.05, 6.87, 10.18 Hz, 1H), 1.24 (tdd, J=4.90, 6.95, 10.21 Hz, 1H), 1.13 (dq, J=5.18, 7.95 Hz, 1H), 0.94-1.04 (m, 1H), 0.42 (s, 4H). $^{19}$F NMR (377 MHz, CHLOROFORM-d) 6-64.71 (s, 3F).

Example 27-2:2-(6-Azaspiro[2.5]octan-6-yl)-4-(R-cyclopropylsulfonimidoyl)-N-(6-(3,3,3-trifluoropropoxy)-2-pyridinyl). Second eluting peak (67 mg, ee 99.3%). $^1$H NMR (400 MHz, CHLOROFORM-d) δ 12.92 (s, 1H), 8.45 (d, J=8.29 Hz, 1H), 8.00 (d, J=7.88 Hz, 1H), 7.95 (d, J=1.66 Hz, 1H), 7.85 (dd, J=1.66, 8.29 Hz, 1H), 7.66 (t, J=7.98 Hz, 1H), 6.55 (d, J=8.09 Hz, 1H), 4.54 (t, J=6.74 Hz, 2H), 3.15 (t, J=5.29 Hz, 4H), 2.54-2.73 (m, 3H), 1.69-1.80 (m, 4H), 1.41-1.49 (m, 1H), 1.19-1.29 (m, 2H), 1.08-1.17 (m, 1H), 0.98 (dq, J=5.29, 7.98 Hz, 1H), 0.42 (s, 4H). $^{19}$F NMR (376 MHz, CHLOROFORM-d) 6-64.70 (s, 3F).

The stereochemistry was arbitrarily assigned.

TABLE 16

Examples 18-1 to 18-3 were prepared following a similar procedure as described for Example 27-1 and 27-2

| Ex. # | Chemical Structure | Name | LRMS: (ESI + ve ion) m/z |
|---|---|---|---|
| 28-1 | 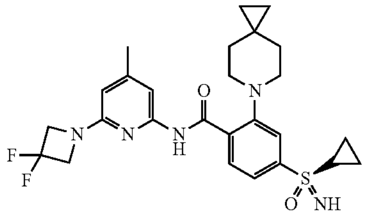 [SMILES: Cc1cc(NC(=O)c2ccc([S@](=N)(=O)C3CC3)cc2N2CCC3(CC2)CC3)nc(N2CC(F)(F)C2)c1] | 2-(6-Azaspiro[2.5]octan-6-yl)-4-(S-cyclopropylsulfonimidoyl)-N-(6-(3,3-difluoro-1-azetidinyl)-4-methyl-2-pyridinyl)benzamide | 516.2 |
| 28-2 | 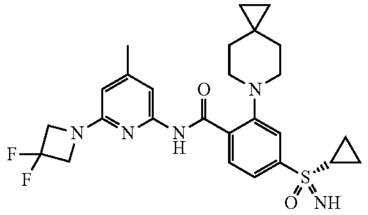 [SMILES: Cc1cc(NC(=O)c2ccc([S@@](=N)(=O)C3CC3)cc2N2CCC3(CC2)CC3)nc(N2CC(F)(F)C2)c1] | 2-(6-Azaspiro[2.5]octan-6-yl)-4-(R-cyclopropylsulfonimidoyl)-N-(6-(3,3-difluoro-1-azetidinyl)-4-methyl-2-pyridinyl)benzamide | 516.2 |

TABLE 16-continued

| Ex. # | Chemical Structure | Name | LRMS: (ESI + ve ion) m/z |
|---|---|---|---|
| Examples 18-1 to 18-3 were prepared following a similar procedure as described for Example 27-1 and 27-2 | | | |
| 29-1 | 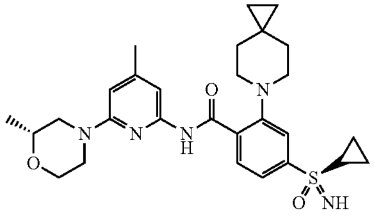 [SMILES: Cc1cc(NC(=O)c2ccc([S@](=N)(=O)C3CC3)cc2N2CCC3(CC2)CC3)nc(N2CCO[C@H](C)C2)c1] | 2-(6-Azaspiro[2.5]octan-6-yl)-4-(S-cyclopropylsulfonimidoyl)-N-(4-methyl-6-((2R)-2-methyl-4-morpholinyl)-2-pyridinyl)benzamide | 524.3 |
| 29-2 | 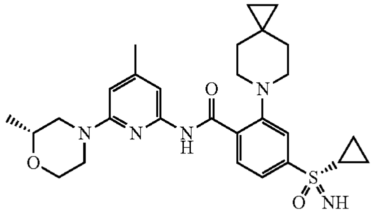 [SMILES: Cc1cc(NC(=O)c2ccc([S@@](=N)(=O)C3CC3)cc2N2CCC3(CC2)CC3)nc(N2CCO[C@H](C)C2)c1] | 2-(6-Azaspiro[2.5]octan-6-yl)-4-(R-cyclopropylsulfonimidoyl)-N-(4-methyl-6-((2R)-2-methyl-4-morpholinyl)-2-pyridinyl)benzamide | 524.3 |
| 30-1 | 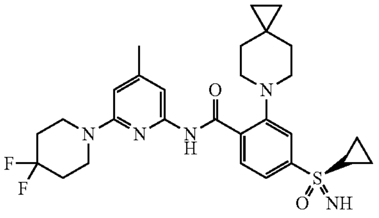 [SMILES: Cc1cc(NC(=O)c2ccc([S@](=N)(=O)C3CC3)cc2N2CCC3(CC2)CC3)nc(N2CCC(F)(F)CC2)c1] | 2-(6-Azaspiro[2.5]octan-6-yl)-4-(S-cyclopropylsulfonimidoyl)-N-(6-(4,4-difluoro-1-piperidinyl)-4-methyl-2-pyridinyl)benzamide | 544.3 |
| 30-2 | 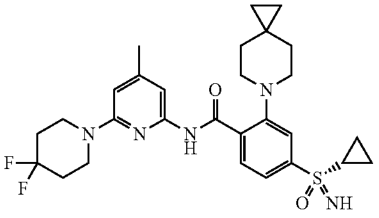 [SMILES: Cc1cc(NC(=O)c2ccc([S@@](=N)(=O)C3CC3)cc2N2CCC3(CC2)CC3)nc(N2CCC(F)(F)CC2)c1] | 2-(6-Azaspiro[2.5]octan-6-yl)-4-(R-cyclopropylsulfonimidoyl)-N-(6-(4,4-difluoro-1-piperidinyl)-4-methyl-2-pyridinyl)benzamide | 544.3 |

Example 31: 4-(Azetidin-3-ylsulfonyl)-2-(6-azaspiro[2.5]octan-6-yl)-N-(6-(3,3,3-trifluoropropoxy)pyridin-2-yl)benzamide trifluoroacetate

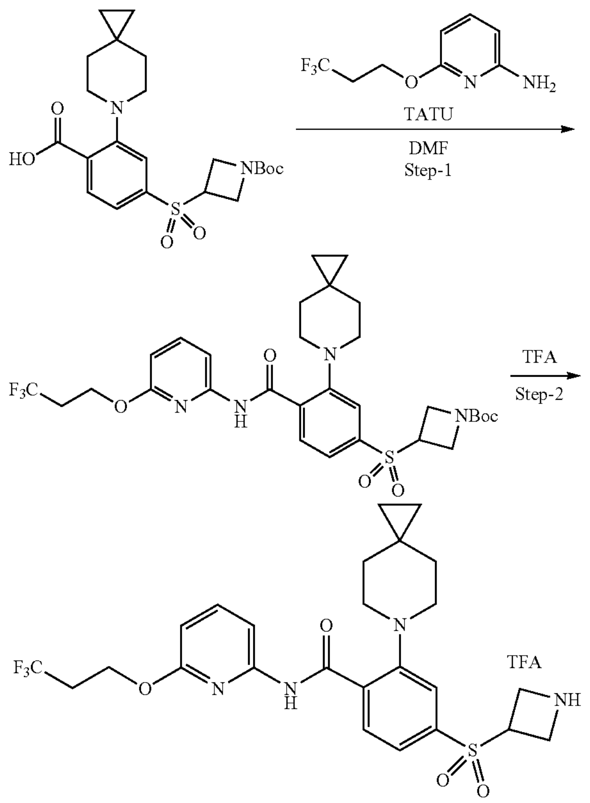

Step-1: A mixture of 4-((1-(tert-butoxycarbonyl)azetidin-3-yl)sulfonyl)-2-(6-azaspiro[2.5]octan-6-yl)benzoic acid (0.200 g, 0.444 mmol, Intermediate 15), 6-(3,3,3-trifluoropropoxy)pyridin-2-amine (0.119 g, 0.577 mmol, Intermediate 6), DMF (4 mL), Hunig's base (0.229 g, 0.316 mL, 1.78 mmol, Aldrich) and TATU (0.250 g, 0.776 mmol, Combi-Blocks) was stirred at room temperature overnight. The mixture was diluted with saturated $Na_2CO_3$ and EtOAc. The organic phase was taken and washed with $Na_2CO_3$, water and brine, dried over $Na_2SO_4$ and concentrated in vacuo. Purification by silica gel chromatography (0-100% EtOAc-heptane) gave tert-butyl 3-((3-(6-azaspiro[2.5]octan-6-yl)-4-((6-(3,3,3-trifluoropropoxy)pyridin-2-yl)carbamoyl)phenyl)sulfonyl)azetidine-1-carboxylate as an off-white solid. m/z (ESI): 639.2 $(M+H)^+$.

Step-2: tert-Butyl 3-((3-(6-azaspiro[2.5]octan-6-yl)-4-((6-(3,3,3-trifluoropropoxy)pyridin-2-yl)carbamoyl)phenyl)sulfonyl)azetidine-1-carboxylate (0.118 g, 0.184 mmol) was dissolved in DCM (8 mL) and TFA (4 mL). The reaction mixture was stirred at RT for 30 min and concentrated in vacuo. EtOAc was added to the TFA salt and evaporated. The product was obtained as off-white solid. $^1H$ NMR (400 MHz, METHANOL-$d_4$) δ 8.38 (d, J=8.09 Hz, 1H), 7.90-7.96 (m, 2H), 7.85 (dd, J=1.66, 8.29 Hz, 1H), 7.74 (t, J=7.98 Hz, 1H), 6.60 (d, J=8.09 Hz, 1H), 4.57 (t, J=6.32 Hz, 2H), 4.42 (d, J=7.46 Hz, 4H), 3.14-3.23 (m, 4H), 2.66-2.80 (m, 2H), 1.81 (br s, 4H), 0.44 (s, 4H). $^{19}F$ NMR (376 MHz, METHANOL-$d_4$) δ −66.16 (s, 3F), −76.96 (s, 3F). m/z (ESI): 539.2 $(M+H)^+$.

BIOLOGICAL EXAMPLES

The following assays were used in testing the exemplary compounds of the invention. Data for those examples tested in accordance with the procedures described below are presented in Table A below.

KIF18A Enzyme Assay: Microtubule-stimulated ATPase activity assay is used to measure KIF18A enzyme activity after treatment with compound. Compounds were 2-fold serially diluted in DMSO (Sigma Inc) over 22-point concentration range. Recombinant human KIF18A (1-467 His-tagged) protein was expressed using a baculovirus system and purified by affinity chromatography by Amgen Inc. Concentrations of KIF18A protein, microtubules (MT), and ATP in the reaction were optimized for standardized homogenous enzyme assay using ADP-Glo™ Kinase/ATPase Assay Kit (Promega Inc). The assay measures ADP formed from the ATPase reaction. Prepare reaction buffer [(15 mM Tris, pH 7.5 (Teknova Inc), 10 mM MgCl2 (JT Baker Inc), 0.01% Pluronic F-68 (Life Technologies Inc), 1 μM Taxol (Cytoskeleton Inc), and 30 μg/mL pig microtubules (Cytoskeleton Inc)]. Add compound and KIF18A protein (30 nM) to prepared reaction buffer and incubated for 15 minutes at room temperature, next add ATP (at $K_m$, 75 μM) to the reaction mixture and incubated for an additional 15 minutes at room temperature. Mix 5 μl of ADP-Glo™ Reagent and 2.5 μl of the reaction mixture and incubate for 40 minutes at room temperature. Add 10 μl ADP-Glo™ Detection Reagent and incubate for 40 minutes at room temperature. Read luminescence using EnVision microplate reader with ultra-luminescence module (Perkin Elmer Inc). Concentration-response curve-fitting and $IC_{50}$ determination was performed using Genedata Screener Software (Standard 15.0.1, Genedata Inc) with a four-parameter logistic regression fit model.

Table A provides data for compounds exemplified in the present application and priority document thereof, as representative compounds of the present invention, as follows: compound name and biological data. ($IC_{50}$ in uM, where available. Ex. # refers to Example No.)

TABLE A

BIOLOGICAL DATA

| Ex. # | Compound Name | KIF18A ATPase $IC_{50}$ (μM) |
|---|---|---|
| 1 | 4-(N-(2-Hydroxyethyl)sulfamoyl)-2-(6-azaspiro[2.5]octan-6-yl)-N-(6-(3,3,3-trifluoropropoxy)pyridin-2-yl)benzamide | 0.012 |
| 1-1 | (R)-4-(N-(2-Hydroxyethyl)sulfamoyl)-N-(6-(2-methylmorpholino)pyridin-2-yl)-2-(6-azaspiro[2.5]octan-6-yl)benzamide | 0.016 |
| 1-2 | N-(6-(4,4-Difluoropiperidin-1-yl)-4-methylpyridin-2-yl)-4-(N-(2-hydroxyethyl)sulfamoyl)-2-(6-azaspiro[2.5]octan-6-yl)benzamide | 0.032 |
| 1-3 | (R)-N-(6-(2-methylmorpholino)pyridin-2-yl)-4-(N-methylsulfamoyl)-2-(6-azaspiro[2.5]octan-6-yl)benzamide | 0.044 |
| 1-4 | (R)-4-(N-(1-Hydroxy-2-methylpropan-2-yl)sulfamoyl)-N-(6-(2-methylmorpholino)pyridin-2-yl)-2-(6-azaspiro[2.5]octan-6-yl)benzamide | 0.046 |
| 1-5 | 4-(N-(1-Hydroxypropan-2-yl)sulfamoyl)-N-(6-((R)-2-methylmorpholino)pyridin-2-yl)-2-(6-azaspiro[2.5]octan-6-yl)benzamide | 0.047 |
| 1-6 | (R)-4-(N-(tert-Butyl)sulfamoyl)-N-(6-(2-methylmorpholino)pyridin-2-yl)-2-(6-azaspiro[2.5]octan-6-yl)benzamide | 0.051 |

TABLE A-continued

| BIOLOGICAL DATA | | |
|---|---|---|
| Ex. # | Compound Name | KIF18A ATPase $IC_{50}$ (μM) |
| 1-7 | (R)-4-(Azetidin-1-ylsulfonyl)-N-(6-(2-methylmorpholino)pyridin-2-yl)-2-(6-azaspiro[2.5]octan-6-yl)benzamide | 0.067 |
| 1-8 | (R)-N-(4-Methyl-6-(2-methylmorpholino)pyridin-2-yl)-4-(N-(3-methyloxetan-3-yl)sulfamoyl)-2-(6-azaspiro[2.5]octan-6-yl)benzamide | 0.119 |
| 1-9 | 4-(N-(1-Hydroxybutan-2-yl)sulfamoyl)-N-(6-((R)-2-methylmorpholino)pyridin-2-yl)-2-(6-azaspiro[2.5]octan-6-yl)benzamide | 0.120 |
| 1-10 | 4-(N-(tert-Butyl)sulfamoyl)-N-(4-methyl-6-morpholinopyridin-2-yl)-2-(6-azaspiro[2.5]octan-6-yl)benzamide | 0.222 |
| 1-11 | (R)-4-((3,3-Dimethylazetidin-1-yl)sulfonyl)-N-(6-(2-methylmorpholino)pyridin-2-yl)-2-(6-azaspiro[2.5]octan-6-yl)benzamide | 0.566 |
| 1-12 | (R)-4-((3-Cyano-3-methylazetidin-1-yl)sulfonyl)-N-(6-(2-methylmorpholino)pyridin-2-yl)-2-(6-azaspiro[2.5]octan-6-yl)benzamide | 0.458 |
| 1-13 | (R)-4-((3-Cyanoazetidin-1-yl)sulfonyl)-N-(6-(2-methylmorpholino)pyridin-2-yl)-2-(6-azaspiro[2.5]octan-6-yl)benzamide | 0.209 |
| 2 | (R)-4-(Isopropylsulfonyl)-N-(6-(2-methylmorpholino)pyridin-2-yl)-2-(6-azaspiro[2.5]octan-6-yl)benzamide | 0.034 |
| 2-1 | (R)-4-((2-Hydroxyethyl)sulfonyl)-N-(6-(2-methylmorpholino)pyridin-2-yl)-2-(6-azaspiro[2.5]octan-6-yl)benzamide | 0.032 |
| 2-2 | (R)-4-(tert-Butylsulfonyl)-N-(6-(2-methylmorpholino)pyridin-2-yl)-2-(6-azaspiro[2.5]octan-6-yl)benzamide | 0.078 |
| 2-3 | (R)-N-(6-(2-Methylmorpholino)pyridin-2-yl)-4-((3-methyloxetan-3-yl)sulfonyl)-2-(6-azaspiro[2.5]octan-6-yl)benzamide | 0.141 |
| 2-4 | (R)-N-(6-(2-methylmorpholino)pyridin-2-yl)-4-(oxetan-3-ylsulfonyl)-2-(6-azaspiro[2.5]octan-6-yl)benzamide | 0.038 |
| 2-5 | (R)-4-((1-hydroxy-2-methylpropan-2-yl)sulfonyl)-N-(6-(2-methylmorpholino)pyridin-2-yl)-2-(6-azaspiro[2.5]octan-6-yl)benzamide | 0.051 |
| 2-6 | (R)-4-((2-Hydroxy-2-methylpropyl)sulfonyl)-N-(6-(2-methylmorpholino)pyridin-2-yl)-2-(6-azaspiro[2.5]octan-6-yl)benzamide | 0.110 |
| 2-7 | (R)-4-((2-Hydroxyethyl)sulfonyl)-N-(4-methyl-6-(2-methylmorpholino)pyridin-2-yl)-2-(6-azaspiro[2.5]octan-6-yl)benzamide | 0.103 |
| 3 | (R)-N-(6-(3-Hydroxypiperidin-1-yl)pyridin-2-yl)-4-((1-methylcyclopropane)-1-sulfonamido)-2-(6-azaspiro[2.5]octan-6-yl)benzamide | 0.046 |
| 3-1 | (S)-N-(6-(3-Hydroxypiperidin-1-yl)pyridin-2-yl)-4-((1-methylcyclopropane)-1-sulfonamido)-2-(6-azaspiro[2.5]octan-6-yl)benzamide | 0.056 |
| 3-2 | N-(6-(3-Hydroxy-3-methylpyrrolidin-1-yl)pyridin-2-yl)-4-((1-methylcyclopropane)-1-sulfonamido)-2-(6-azaspiro[2.5]octan-6-yl)benzamide | 0.359 |
| 3-3 | (S)-4-(N-(tert-Butyl)sulfamoyl)-N-(6-(3-hydroxypiperidin-1-yl)pyridin-2-yl)-2-(6-azaspiro[2.5]octan-6-yl)benzamide | 0.096 |
| 3-4 | 4-(N-(tert-Butyl)sulfamoyl)-N-(6-((3-(hydroxymethyl)oxetan-3-yl)amino)pyridin-2-yl)-2-(6-azaspiro[2.5]octan-6-yl)benzamide | 0.149 |
| 3-5 | N-(6-(3,3-Difluoropyrrolidin-1-yl)pyridin-2-yl)-4-((1-methylcyclopropane)-1-sulfonamido)-2-(6-azaspiro[2.5]octan-6-yl)benzamide | 0.045 |
| 3-6 | (R)-N-(6-(3-(Hydroxymethyl)piperidin-1-yl)pyridin-2-yl)-4-((1-methylcyclopropane)-1-sulfonamido)-2-(6-azaspiro[2.5]octan-6-yl) benzamide | 0.086 |
| 3-7 | (S)-N-(6-(3-(Hydroxymethyl)piperidin-1-yl)pyridin-2-yl)-4-((1-methylcyclopropane)-1-sulfonamido)-2-(6-azaspiro[2.5]octan-6-yl)benzamide | 0.065 |
| 3-8 | N-(6-(4-Hydroxy-4-methylpiperidin-1-yl)pyridin-2-yl)-4-((1-methylcyclopropane)-1-sulfonamido)-2-(6-azaspiro[2.5]octan-6-yl)benzamide | 0.243 |
| 3-9 | (S)-N-(6-(3-Hydroxy-3-methylpiperidin-1-yl)pyridin-2-yl)-4-((1-methylcyclopropane)-1-sulfonamido)-2-(6-azaspiro[2.5]octan-6-yl) benzamide | 0.175 |
| 3-10 | (R)-N-(6-(3-Hydroxy-3-methylpiperidin-1-yl)pyridin-2-yl)-4-((1-methylcyclopropane)-1-sulfonamido)-2-(6-azaspiro[2.5]octan-6-yl)benzamide | 0.143 |
| 3-11 | (R)-N-(6-(2-(Hydroxymethyl)morpholino)pyridin-2-yl)-4-((1-methylcyclopropane)-1-sulfonamido)-2-(6-azaspiro[2.5]octan-6-yl)benzamide | 0.073 |
| 3-12 | (S)-N-(6-(2-(Hydroxymethyl)morpholino)pyridin-2-yl)-4-((1-methylcyclopropane)-1-sulfonamido)-2-(6-azaspiro[2.5]octan-6-yl)benzamide | 0.081 |
| 3-13 | N-(6-(4-Fluoro-4-methylpiperidin-1-yl)pyridin-2-yl)-4-((1-methylcyclopropane)-1-sulfonamido)-2-(6-azaspiro[2.5]octan-6-yl)benzamide | 0.373 |
| 3-14 | N-(6-(3,3-Difluoropiperidin-1-yl)pyridin-2-yl)-4-((1-methylcyclopropane)-1-sulfonamido)-2-(6-azaspiro[2.5]octan-6-yl)benzamide | 0.038 |
| 3-15 | N-(6-(5-Chloroindolin-1-yl)pyridin-2-yl)-4-((1-methylcyclopropane)-1-sulfonamido)-2-(6-azaspiro[2.5]octan-6-yl)benzamide | 0.033 |
| 3-16 | N-(6-(3-Fluoroazetidin-1-yl)pyridin-2-yl)-4-((1-methylcyclopropane)-1-sulfonamido)-2-(6-azaspiro[2.5]octan-6-yl)benzamide | 0.058 |
| 3-17 | 4-((1-Methylcyclopropane)-1-sulfonamido)-N-(6-(piperidin-1-yl)pyridin-2-yl)-2-(6-azaspiro[2.5]octan-6-yl)benzamide | 0.034 |
| 3-18 | N-(6-(3,3-Difluoroazetidin-1-yl)pyridin-2-yl)-4-((1-methylcyclopropane)-1-sulfonamido)-2-(6-azaspiro[2.5]octan-6-yl)benzamide | 0.048 |
| 3-19 | N-(6-(3,3-Difluoroazetidin-1-yl)-4-methylpyridin-2-yl)-4-((1-methylcyclopropane)-1-sulfonamido)-2-(6-azaspiro[2.5]octan-6-yl)benzamide | 0.103 |
| 3-20 | N-(6-(5-Azaspiro[2.4]heptan-5-yl)pyridin-2-yl)-4-((1-methylcyclopropane)-1-sulfonamido)-2-(6-azaspiro[2.5]octan-6-yl)benzamide | 0.050 |
| 3-21 | N-(6-(4-Cyanopiperidin-1-yl)pyridin-2-yl)-4-((1-methylcyclopropane)-1-sulfonamido)-2-(6-azaspiro[2.5]octan-6-yl)benzamide | 0.091 |
| 3-22 | N-(6-(3-Cyanopiperidin-1-yl)pyridin-2-yl)-4-((1-methylcyclopropane)-1-sulfonamido)-2-(6-azaspiro[2.5]octan-6-yl)benzamide | 0.086 |
| 3-2 | N-(6-(4-Fluoropiperidin-1-yl)pyridin-2-yl)-4-((1-methylcyclopropane)-1-sulfonamido)-2-(6-azaspiro[2.5]octan-6-yl)benzamide | 0.044 |
| 4 | (R)-N-(6-(3-hydroxypiperidin-1-yl)pyridin-2-yl)-4-((methylsulfonyl)methyl)-2-(6-azaspiro[2.5]octan-6-yl)benzamide | 0.094 |
| 4-1 | N-(6-(2-Hydroxypropan-2-yl)pyridin-2-yl)-4-((1-methylcyclopropane)-1-sulfonamido)-2-(6-azaspiro[2.5]octan-6-yl)benzamide | 0.128 |
| 4-2 | N-(6-(2-Hydroxypropan-2-yl)pyridin-2-yl)-4-(N-(3-methyloxetan-3-yl)sulfamoyl)-2-(6-azaspiro[2.5]octan-6-yl)benzamide | 0.080 |
| 4-3 | (S)-4-(N-(tert-Butyl)sulfamoyl)-N-(6-(2-(hydroxymethyl)morpholino)pyridin-2-yl)-2-(6-azaspiro[2.5]octan-6-yl)benzamide | 0.086 |
| 4-4 | N-(6-Cyclopropylpyridin-2-yl)-4-(methylsulfonyl)-2-(6-azaspiro[2.5]octan-6-yl) benzamide | 0.180 |
| 4-5 | N-(6-Isopropylpyridin-2-yl)-4-(methylsulfonyl)-2-(6-azaspiro[2.5]octan-6-yl)benzamide | 0.179 |
| 4-6 | N-(6-(tert-Butyl)pyridin-2-yl)-4-(methylsulfonyl)-2-(6-azaspiro[2.5]octan-6-yl)benzamide | 0.166 |
| 4-7 | N-(6-(2-Hydroxypropan-2-yl)pyridin-2-yl)-4-(methylsulfonyl)-2-(6-azaspiro[2.5]octan-6-yl)benzamide | 0.315 |
| 4-8 | N-(6-(N-(tert-Butyl)sulfamoyl)pyridin-2-yl)-4-(methylsulfonyl)-2-(6-azaspiro[2.5]octan-6-yl) benzamide | 0.076 |

TABLE A-continued

BIOLOGICAL DATA

| Ex. # | Compound Name | KIF18A ATPase $IC_{50}$ (μM) |
|---|---|---|
| 4-9 | N-(6-(4,4-Difluoropiperidin-1-yl)pyridin-2-yl)-4-((1-methylcyclopropane)-1-sulfonamido)-2-(6-azaspiro[2.5]octan-6-yl)benzamide | 0.046 |
| 4-10 | N-(6-(4,4-Difluoropiperidin-1-yl)-4-methylpyridin-2-yl)-4-((1-methylcyclopropane)-1-sulfonamido)-2-(6-azaspiro[2.5]octan-6-yl) benzamide | 0.095 |
| 4-11 | (R)-N-(6-(2-Methylmorpholino)pyridin-2-yl)-4-(N-(3-methyloxetan-3-yl)sulfamoyl)-2-(6-azaspiro[2.5]octan-6-yl)benzamide | 0.043 |
| 4-12 | 4-(Methylsulfonyl)-N-(6-morpholinopyridin-2-yl)-2-(6-azaspiro[2.5]octan-6-yl)benzamide | 0.118 |
| 4-13 | (R)-N-(6-(2-Methylmorpholino)pyridin-2-yl)-4-(methylsulfonyl)-2-(6-azaspiro[2.5]octan-6-yl)benzamide | 0.069 |
| 4-14 | (R)-4-((1-Methylcyclopropane)-1-sulfonamido)-N-(6-(2-methylmorpholino)pyridin-2-yl)-2-(6-azaspiro[2.5]octan-6-yl)benzamide | 0.066 |
| 4-15 | (R)-N-(6-(2-Methylmorpholino)pyridin-2-yl)-4-((methylsulfonyl)methyl)-2-(6-azaspiro[2.5]octan-6-yl)benzamide | 0.085 |
| 4-16 | N-(4-Methyl-6-morpholinopyridin-2-yl)-4-((methylsulfonyl)methyl)-2-(6-azaspiro[2.5]octan-6-yl)benzamide | 0.145 |
| 4-17 | N-(6-(2-Hydroxypropan-2-yl)-4-methylpyridin-2-yl)-4-((1-methylcyclopropane)-1-sulfonamido)-2-(6-azaspiro[2.5]octan-6-yl)benzamide | 0.163 |
| 4-18 | N-(6-(2-Hydroxypropan-2-yl)-4-methylpyridin-2-yl)-4-(N-(3-methyloxetan-3-yl)sulfamoyl)-2-(6-azaspiro[2.5]octan-6-yl)benzamide | 0.089 |
| 4-1 | (R)-4-(N-(tert-Butyl)sulfamoyl)-N-(6-(3-hydroxypiperidin-1-yl)-4-methylpyridin-2-yl)-2-(6-azaspiro[2.5]octan-6-yl)benzamide | 0.115 |
| 5 | 4-((2-Hydroxyethyl)sulfonamido)-2-(6-azaspiro[2.5]octan-6-yl)-N-(6-(3,3,3-trifluoropropoxy)pyridin-2-yl)benzamide | 0.025 |
| 6 | N-(6-(4,4-difluoropiperidin-1-yl)-4-methylpyridin-2-yl)-4-((2-hydroxyethyl)sulfonamido)-2-(6-azaspiro[2.5]octan-6-yl)benzamide | 0.047 |
| 7-1 | N-(6-(3,3-Difluorocyclobutyl)-4-methylpyridin-2-yl)-4-((2-hydroxyethyl)sulfonamido)-2-(6-azaspiro[2.5]octan-6-yl)benzamide | 0.045 |
| 7-2 | (R)-N-(6-(2-Methylmorpholino)pyridin-2-yl)-4-(methylsulfonamido)-2-(6-azaspiro[2.5]octan-6-yl)benzamide | 0.039 |
| 7-3 | (R)-4-(1,1-Dioxidoisothiazolidin-2-yl)-N-(6-(2-methylmorpholino)pyridin-2-yl)-2-(6-azaspiro[2.5]octan-6-yl)benzamide | 0.076 |
| 7-4 | (R)-4-(1,1-Dioxido-1,2,5-thiadiazolidin-2-yl)-N-(6-(2-methylmorpholino)pyridin-2-yl)-2-(6-azaspiro[2.5]octan-6-yl)benzamide | 0.287 |
| 7-5 | (R)-4-((N,N-Dimethylsulfamoyl)amino)-N-(6-(2-methylmorpholino)pyridin-2-yl)-2-(6-azaspiro[2.5]octan-6-yl)benzamide | 0.055 |
| 7-6 | (R)-4-(1,1-Dioxido-1,2-thiazetidin-2-yl)-N-(6-(2-methylmorpholino)pyridin-2-yl)-2-(6-azaspiro[2.5]octan-6-yl)benzamide | 0.098 |
| 7-7 | (R)-4-((Difluoromethyl)sulfonamido)-N-(6-(2-methylmorpholino)pyridin-2-yl)-2-(6-azaspiro[2.5]octan-6-yl)benzamide | 0.049 |
| 7-8 | (R)-4-(Ethylsulfonamido)-N-(4-methyl-6-(2-methylmorpholino)pyridin-2-yl)-2-(6-azaspiro[2.5]octan-6-yl)benzamide | 0.072 |
| 7-9 | (R)-4-(Cyclobutanesulfonamido)-N-(6-(2-methylmorpholino)pyridin-2-yl)-2-(6-azaspiro[2.5]octan-6-yl)benzamide | 0.062 |
| 7-10 | (R)-N-(6-(2-Methylmorpholino)pyridin-2-yl)-4-(oxetane-3-sulfonamido)-2-(6-azaspiro[2.5]octan-6-yl)benzamide | 0.063 |
| 7-11 | N-(6-(4,4-Difluoropiperidin-1-yl)-4-methylpyridin-2-yl)-4-(oxetane-3-sulfonamido)-2-(6-azaspiro[2.5]octan-6-yl)benzamide | 0.081 |
| 7-12 | (R)-4-((2-Hydroxyethyl)sulfonamido)-N-(6-(2-methylmorpholino)pyridin-2-yl)-2-(6-azaspiro[2.5]octan-6-yl)benzamide | 0.030 |
| 7-13 | (S)-4-((2-Hydroxyethyl)sulfonamido)-N-(6-(2-methylmorpholino)pyridin-2-yl)-2-(6-azaspiro[2.5]octan-6-yl)benzamide | 0.046 |
| 7-14 | (R)-N-(6-(2-Methylmorpholino)pyridin-2-yl)-2-(6-azaspiro[2.5]octan-6-yl)-4-((3,3,3-trifluoropropyl)sulfonamido)benzamide | 0.343 |
| 7-15 | (R)-4-((1-Fluorocyclopropane)-1-sulfonamido)-N-(6-(2-methylmorpholino)pyridin-2-yl)-2-(6-azaspiro[2.5]octan-6-yl)benzamide | 0.090 |
| 7-16 | (R)-4-((1,1-Dimethylethyl)sulfonamido)-N-(6-(2-methylmorpholino)pyridin-2-yl)-2-(6-azaspiro[2.5]octan-6-yl)benzamide | 0.067 |
| 7-17 | 4-((2-Hydroxyethyl)sulfonamido)-N-(4-methyl-6-morpholinopyridin-2-yl)-2-(6-azaspiro[2.5]octan-6-yl)benzamide | 0.0170 |
| 7-18 | (R)-4-((2-Hydroxyethyl)sulfonamido)-N-(4-methyl-6-(2-methylmorpholino)pyridin-2-yl)-2-(6-azaspiro[2.5]octan-6-yl)benzamide | 0.074 |
| 7-19 | (S)-4-((2-Hydroxyethyl)sulfonamido)-N-(4-methyl-6-(2-methylmorpholino)pyridin-2-yl)-2-(6-azaspiro[2.5]octan-6-yl)benzamide | 0.049 |
| 7-20 | 4-((2-Hydroxyethyl)sulfonamido)-N-(6-morpholinopyridin-2-yl)-2-(6-azaspiro[2.5]octan-6-yl)benzamide | 0.036 |
| 7-21 | N-(6-(4,4-Difluoropiperidin-1-yl)-4-methylpyridin-2-yl)-4-(methylsulfonamido)-2-(6-azaspiro[2.5]octan-6-yl)benzamide | 0.049 |
| 7-22 | N-(6-(4,4-Difluoropiperidin-1-yl)-4-methylpyridin-2-yl)-4-((1,1-dimethylethyl)sulfonamido)-2-(6-azaspiro[2.5]octan-6-yl)benzamide | 0.103 |
| 7-23 | 4-(Cyclobutanesulfonamido)-N-(6-(4,4-difluoropiperidin-1-yl)-4-methylpyridin-2-yl)-2-(6-azaspiro[2.5]octan-6-yl)benzamide | 0.110 |
| 7-24 | 4-((Cyclopropylmethyl)sulfonamido)-N-(6-(4,4-difluoropiperidin-1-yl)-4-methylpyridin-2-yl)-2-(6-azaspiro[2.5]octan-6-yl)benzamide | 0.186 |
| 7-25 | 4-(Cyclopropanesulfonamido)-N-(6-(4,4-difluoropiperidin-1-yl)-4-methylpyridin-2-yl)-2-(6-azaspiro[2.5]octan-6-yl)benzamide | 0.039 |
| 7-26 | N-(6-(4,4-Difluoropiperidin-1-yl)pyridin-2-yl)-4-((2-hydroxyethyl)sulfonamido)-2-(6-azaspiro[2.5]octan-6-yl)benzamide | 0.023 |
| 7-27 | N-(6-(3,3-Difluoroazetidin-1-yl)-4-methylpyridin-2-yl)-4-(methylsulfonamido)-2-(6-azaspiro[2.5]octan-6-yl)benzamide | 0.014 |
| 7-28 | N-(6-(3,3-Difluoroazetidin-1-yl)-4-methylpyridin-2-yl)-4-((1-methylethyl)sulfonamido)-2-(6-azaspiro[2.5]octan-6-yl) benzamide | 0.068 |
| 7-29 | N-(6-(3,3-Difluoroazetidin-1-yl)-4-methylpyridin-2-yl)-4-((1,1-dimethylethyl)sulfonamido)-2-(6-azaspiro[2.5]octan-6-yl)benzamide | 0.134 |
| 7-30 | 4-(Cyclobutanesulfonamido)-N-(6-(3,3-difluoroazetidin-1-yl)-4-methylpyridin-2-yl)-2-(6-azaspiro[2.5]octan-6-yl)benzamide | 0.078 |
| 7-31 | 4-((Cyclopropylmethyl)sulfonamido)-N-(6-(3,3-difluoroazetidin-1-yl)-4-methylpyridin-2-yl)-2-(6-azaspiro[2.5]octan-6-yl)benzamide | 0.059 |
| 7-32 | N-(6-(3,3-Difluoroazetidin-1-yl)-4-methylpyridin-2-yl)-4-(oxetane-3-sulfonamido)-2-(6-azaspiro[2.5]octan-6-yl)benzamide | 0.025 |
| 7-33 | N-(6-(3,3-Difluoroazetidin-1-yl)-4-methylpyridin-2-yl)-4-((2-hydroxyethyl)sulfonamido)-2-(6-azaspiro[2.5]octan-6-yl)benzamide | 0.024 |
| 7-34 | 4-(Cyclopropanesulfonamido)-N-(6-(3,3-difluoroazetidin-1-yl)-4-methylpyridin-2-yl)-2-(6-azaspiro[2.5]octan-6-yl)benzamide | 0.041 |
| 7-35 | (R)-4-((2-Fluoroethyl)sulfonamido)-N-(6-(2-methylmorpholino)pyridin-2-yl)-2-(6-azaspiro[2.5]octan-6-yl)benzamide | 0.024 |

TABLE A-continued

BIOLOGICAL DATA

| Ex. # | Compound Name | KIF18A ATPase $IC_{50}$ (μM) |
|---|---|---|
| 7-36 | (R)-4-((Fluoromethyl)sulfonamido)-N-(4-methyl-6-(2-methylmorpholino)pyridin-2-yl)-2-(6-azaspiro[2.5]octan-6-yl)benzamide | 0.062 |
| 7-37 | (R)-4-(Ethylsulfonamido)-N-(6-(2-methylmorpholino)pyridin-2-yl)-2-(6-azaspiro[2.5]octan-6-yl)benzamide | 0.050 |
| 7-38 | (R)-4-((Fluoromethyl)sulfonamido)-N-(6-(2-methylmorpholino)pyridin-2-yl)-2-(6-azaspiro[2.5]octan-6-yl)benzamide | 0.048 |
| 7-39 | (R)-N-(6-(2-methylmorpholino)pyridin-2-yl)-2-(6-azaspiro[2.5]octan-6-yl)-4-((2,2,2-trifluoroethyl)sulfonamido)benzamide | 0.135 |
| 7-40 | (R)-4-((2,2-Difluoroethyl)sulfonamido)-N-(6-(2-methylmorpholino)pyridin-2-yl)-2-(6-azaspiro[2.5]octan-6-yl)benzamide | 0.067 |
| 7-41 | (R)-N-(6-(2-Methylmorpholino)pyridin-2-yl)-2-(6-azaspiro[2.5]octan-6-yl)-4-((trifluoromethyl)sulfonamido)benzamide | 0.207 |
| 7-42 | (R)-4-((2-Hydroxy-2-methylpropyl)sulfonamido)-N-(6-(2-methylmorpholino)pyridin-2-yl)-2-(6-azaspiro[2.5]octan-6-yl)benzamide | 0.111 |
| 7-43 | N-(6-(N-(tert-Butyl)sulfamoyl)pyridin-2-yl)-4-(methylsulfonamido)-2-(6-azaspiro[2.5]octan-6-yl)benzamide | 0.055 |
| 7-44 | N-(6-(4,4-Difluoropiperidin-1-yl)pyrazin-2-yl)-4-((2-hydroxyethyl)sulfonamido)-2-(6-azaspiro[2.5]octan-6-yl)benzamide | 0.016 |
| 8-1 | (R)-4-((2-Hydroxy-1-methylethyl)sulfonamido)-2-(6-azaspiro[2.5]octan-6-yl)-N-(6-(3,3,3-trifluoropropoxy)pyridin-2-yl)benzamide | 0.016 |
| 8-2 | (S)-4-((2-hydroxy-1-methylethyl)sulfonamido)-2-(6-azaspiro[2.5]octan-6-yl)-N-(6-(3,3,3-trifluoropropoxy)pyridin-2-yl)benzamide | 0.014 |
| 9-1 | (R)-N-(6-(3-Fluoroazetidin-1-yl)pyridin-2-yl)-4-((2-hydroxy-1-methylethyl)sulfonamido)-2-(6-azaspiro[2.5]octan-6-yl)benzamide | 0.033 |
| 9-2 | (S)-N-(6-(3-Fluoroazetidin-1-yl)pyridin-2-yl)-4-((2-hydroxy-1-methylethyl)sulfonamido)-2-(6-azaspiro[2.5]octan-6-yl)benzamide | 0.0472 |
| 9-3 | (R)-N-(6-(3,3-Difluoroazetidin-1-yl)pyridin-2-yl)-4-((2-hydroxy-1-methylethyl)sulfonamido)-2-(6-azaspiro[2.5]octan-6-yl)benzamide | 0.025 |
| 9-4 | (S)-N-(6-(3,3-Difluoroazetidin-1-yl)pyridin-2-yl)-4-((2-hydroxy-1-methylethyl)sulfonamido)-2-(6-azaspiro[2.5]octan-6-yl)benzamide | 0.068 |
| 9-5 | (R)-N-(6-(3,3-Difluoroazetidin-1-yl)-4-methylpyridin-2-yl)-4-((2-hydroxy-1-methylethyl)sulfonamido)-2-(6-azaspiro[2.5]octan-6-yl)benzamide | 0.017 |
| 9-6 | (S)-N-(6-(3,3-Difluoroazetidin-1-yl)-4-methylpyridin-2-yl)-4-((2-hydroxy-1-methylethyl)sulfonamido)-2-(6-azaspiro[2.5]octan-6-yl)benzamide | 0.057 |
| 9-7 | (S)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide | 0.027 |
| 9-8 | (R)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide | 0.038 |
| 9-9 | (S)-N-(6-(4,4-Difluoropiperidin-1-yl)pyridin-2-yl)-4-((2-hydroxy-1-methylethyl)sulfonamido)-2-(6-azaspiro[2.5]octan-6-yl)benzamide | 0.041 |
| 9-10 | (R)-N-(6-(4,4-Difluoropiperidin-1-yl)pyridin-2-yl)-4-((2-hydroxy-1-methylethyl)sulfonamido)-2-(6-azaspiro[2.5]octan-6-yl)benzamide | 0.037 |
| 9-11 | 4-(((R)-2-Hydroxy-1-methylethyl)sulfonamido)-N-(4-methyl-6-((R)-2-methylmorpholino)pyridin-2-yl)-2-(6-azaspiro[2.5]octan-6-yl)benzamide | 0.038 |
| 9-12 | 4-(((S)-2-Hydroxy-1-methylethyl)sulfonamido)-N-(4-methyl-6-((R)-2-methylmorpholino)pyridin-2-yl)-2-(6-azaspiro[2.5]octan-6-yl)benzamide | 0.039 |
| 9-13 | (R)-4-((2-Hydroxy-1-methylethyl)sulfonamido)-N-(4-methyl-6-morpholinopyridin-2-yl)-2-(6-azaspiro[2.5]octan-6-yl)benzamide | 0.018 |
| 9-14 | (S)-4-((2-Hydroxy-1-methylethyl)sulfonamido)-N-(4-methyl-6-morpholinopyridin-2-yl)-2-(6-azaspiro[2.5]octan-6-yl)benzamide | 0.018 |
| 9-15 | 4-(((R)-2-Hydroxy-1-methylethyl)sulfonamido)-N-(6-((R)-2-methylmorpholino)pyridin-2-yl)-2-(6-azaspiro[2.5]octan-6-yl)benzamide | 0.037 |
| 9-16 | 4-(((S)-2-Hydroxy-1-methylethyl)sulfonamido)-N-(6-((R)-2-methylmorpholino)pyridin-2-yl)-2-(6-azaspiro[2.5]octan-6-yl)benzamide | 0.048 |
| 9-17 | 4-(((R)-2-Hydroxy-1-methylethyl)sulfonamido)-N-(6-((S)-2-methylmorpholino)pyridin-2-yl)-2-(6-azaspiro[2.5]octan-6-yl)benzamide | 0.024 |
| 9-18 | 4-(((S)-2-Hydroxy-1-methylethyl)sulfonamido)-N-(6-((S)-2-methylmorpholino)pyridin-2-yl)-2-(6-azaspiro[2.5]octan-6-yl)benzamide | 0.036 |
| 10 | N-(6-(4,4-Difluoropiperidin-1-yl)-4-methylpyridin-2-yl)-4-((1-(hydroxymethyl)cyclopropane)-1-sulfonamido)-2-(6-azaspiro[2.5]octan-6-yl)benzamide | 0.122 |
| 10-1 | (R)-4-((1-(Hydroxymethyl)cyclopropane)-1-sulfonamido)-N-(6-(2-methylmorpholino)pyridin-2-yl)-2-(6-azaspiro[2.5]octan-6-yl)benzamide | 0.057 |
| 10-2 | N-(6-(3,3-Difluoroazetidin-1-yl)-4-methylpyridin-2-yl)-4-((1-(hydroxymethyl)cyclopropane)-1-sulfonamido)-2-(6-azaspiro[2.5]octan-6-yl)benzamide | 0.076 |
| 11 | N-(6-(3,3-difluoroazetidin-1-yl)-4-methylpyridin-2-yl)-4-((2-hydroxyethyl)sulfonamido)-2-(6-azaspiro[2.5]octan-6-yl)benzamide | 0.031 |
| 12-1 | 2-(6-Azaspiro[2.5]octan-6-yl)-4-(S-cyclopropylsulfonimidoyl)-N-(6-((2R)-2-methyl-4-morpholinyl)-2-pyridinyl)benzamide | 0.085 |
| 12-2 | 2-(6-Azaspiro[2.5]octan-6-yl)-4-(R-cyclopropylsulfonimidoyl)-N-(6-((2R)-2-methyl-4-morpholinyl)-2-pyridinyl)benzamide | 0.043 |
| 13-1 | N-(6-((R)-2-Methylmorpholino)pyridin-2-yl)-4-((R)-2-methylpropan-2-ylsulfonimidoyl)-2-(6-azaspiro[2.5]octan-6-yl)benzamide | 0.199 |
| 13-2 | N-(6-((R)-2-Methylmorpholino)pyridin-2-yl)-4-((S)-2-methylpropan-2-ylsulfonimidoyl)-2-(6-azaspiro[2.5]octan-6-yl)benzamide | 0.182 |
| 13-3 | 2-(6-Azaspiro[2.5]octan-6-yl)-N-(6-((2R)-2-methyl-4-morpholinyl)-2-pyridinyl)-4-(S-methylsulfonimidoyl)benzamide | 0.418 |
| 13-4 | 2-(6-Azaspiro[2.5]octan-6-yl)-N-(6-((2R)-2-methyl-4-morpholinyl)-2-pyridinyl)-4-(R-methylsulfonimidoyl)benzamide | 0.154 |
| 14 | N-(6-(Cyclopropylmethoxy)pyridin-2-yl)-4-((1-methylcyclopropane)-1-sulfonamido)-2-(6-azaspiro[2.5]octan-6-yl)benzamide | 0.019 |
| 15 | N-(6-(Cyclopropylmethoxy)pyridin-2-yl)-4-((1-methylcyclopropane)-1-sulfonamido)-2-(6-azaspiro[2.5]octan-6-yl)benzamide | 0.045 |
| 16 | N-(6-(2-Hydroxy-2-methylpropoxy)pyridin-2-yl)-4-((2-hydroxyethyl)sulfonamido)-2-(6-azaspiro[2.5]octan-6-yl)benzamide | 0.080 |
| 16-1 | N-(6-(1-Cyclopropylethoxy)pyridin-2-yl)-4-((2-hydroxyethyl)sulfonamido)-2-(6-azaspiro[2.5]octan-6-yl)benzamide | 0.051 |
| 16-2 | 4-((2-Hydroxyethyl)sulfonamido)-N-(6-((3-methyloxetan-3-yl)methoxy)pyridin-2-yl)-2-(6-azaspiro[2.5]octan-6-yl)benzamide | 0.050 |
| 16-3 | 4-((2-Hydroxyethyl)sulfonamido)-N-(6-((1-methylazetidin-3-yl)methoxy)pyridin-2-yl)-2-(6-azaspiro[2.5]octan-6-yl)benzamide | 0.063 |
| 16-4 | 4-((2-Hydroxyethyl)sulfonamido)-N-(6-(2-hydroxypropoxy)pyridin-2-yl)-2-(6-azaspiro[2.5]octan-6-yl)benzamide | 0.115 |
| 16-5 | N-(6-(3-Hydroxy-3-methylbutoxy)pyridin-2-yl)-4-((2-hydroxyethyl)sulfonamido)-2-(6-azaspiro[2.5]octan-6-yl)benzamide | 0.084 |

TABLE A-continued

| BIOLOGICAL DATA | | |
|---|---|---|
| Ex. # | Compound Name | KIF18A ATPase $IC_{50}$ (μM) |
| 16-6 | 4-((2-Hydroxyethyl)sulfonamido)-2-(6-azaspiro[2.5]octan-6-yl)-N-(6-(4,4,4-trifluoro-3-hydroxybutoxy)pyridin-2-yl)benzamide | 0.081 |
| 16-7 | N-(6-(3-Hydroxybutoxy)pyridin-2-yl)-4-((2-hydroxyethyl)sulfonamido)-2-(6-azaspiro[2.5]octan-6-yl)benzamide | 0.031 |
| 16-8 | 4-((2-Hydroxyethyl)sulfonamido)-2-(6-azaspiro[2.5]octan-6-yl)-N-(6-(3,3,3-trifluoro-2-hydroxypropoxy)pyridin-2-yl)benzamide | 0.018 |
| 16-9 | N-(6-(3,3-Difluoropropoxy)pyridin-2-yl)-4-((2-hydroxyethyl)sulfonamido)-2-(6-azaspiro[2.5]octan-6-yl)benzamide | 0.051 |
| 17 | 4-((2-Hydroxyethyl)sulfonamido)-N-(4-methyl-6-(3,3,3-trifluoropropoxy)pyridin-2-yl)-2-(6-azaspiro[2.5]octan-6-yl)benzamide | 0.024 |
| 17-1 | 4-((2-Hydroxyethyl)sulfonamido)-N-(4-methyl-6-(3,3,3-trifluoro-2-hydroxypropoxy)pyridin-2-yl)-2-(6-azaspiro[2.5]octan-6-yl)benzamide | 0.068 |
| 17-2 | N-(6-(2-Hydroxy-2-methylpropoxy)-4-methylpyridin-2-yl)-4-((2-hydroxyethyl)sulfonamido)-2-(6-azaspiro[2.5]octan-6-yl)benzamide | 0.059 |
| 17-3 | 4-((2-Hydroxyethyl)sulfonamido)-N-(4-methyl-6-(4,4,4-trifluorobutoxy)pyridin-2-yl)-2-(6-azaspiro[2.5]octan-6-yl)benzamide | 0.184 |
| 18 | 4-((2-Hydroxyethyl)sulfonamido)-N-(5-methyl-6-morpholinopyridin-2-yl)-2-(6-azaspiro[2.5]octan-6-yl)benzamide | 0.012 |
| 19 | (R)-N-(4-cyclopropyl-6-(2-methylmorpholino)pyridin-2-yl)-4-((2-hydroxyethyl)sulfonamido)-2-(6-azaspiro[2.5]octan-6-yl)benzamide | 0.087 |
| 20 | (R)-4-((2-Hydroxyethyl)sulfonamido)-N-(6-(2-methylmorpholino)-4-(trifluoromethyl)pyridin-2-yl)-2-(6-azaspiro[2.5]octan-6-yl)benzamide | 0.093 |
| 21 | N-(5-Cyano-6-(4,4-difluoropiperidin-1-yl)pyridin-2-yl)-4-((2-hydroxyethyl)sulfonamido)-2-(6-azaspiro[2.5]octan-6-yl)benzamide | 0.025 |
| 22 | N-(6-(4,4-Difluoropiperidin-1-yl)-5-methylpyridin-2-yl)-4-((2-hydroxyethyl)sulfonamido)-2-(6-azaspiro[2.5]octan-6-yl)benzamide | 0.041 |
| 23 | N-(6-(4,4-difluorocyclohexyl)-4-methylpyridin-2-yl)-4-((2-hydroxyethyl)sulfonamido)-2-(6-azaspiro[2.5]octan-6-yl)benzamide | 0.041 |
| 24 | (R)-N-(5-fluoro-6-(2-methylmorpholino)pyridin-2-yl)-4-((2-hydroxyethyl)sulfonamido)-2-(6-azaspiro[2.5]octan-6-yl)benzamide | 0.033 |
| 25 | (R)-N-(4-Cyano-6-(2-methylmorpholino)pyridin-2-yl)-4-((2-hydroxyethyl)sulfonamido)-2-(6-azaspiro[2.5]octan-6-yl)benzamide | 0.041 |
| 26 | 4-((2-Hydroxyethyl)sulfonamido)-N-(6-(2-methylpropan-2-ylsulfonimidoyl)pyridin-2-yl)-2-(6-azaspiro[2.5]octan-6-yl)benzamide | 0.363 |
| 27-1 | 2-(6-Azaspiro[2.5]octan-6-yl)-4-(S-cyclopropylsulfonimidoyl)-N-(6-(3,3,3-trifluoropropoxy)-2-pyridinyl)benzamide | 0.022 |
| 27-2 | 2-(6-Azaspiro[2.5]octan-6-yl)-4-(R-cyclopropylsulfonimidoyl)-N-(6-(3,3,3-trifluoropropoxy)-2-pyridinyl)benzamide | 0.016 |
| 28-1 | 2-(6-Azaspiro[2.5]octan-6-yl)-4-(S-cyclopropylsulfonimidoyl)-N-(6-(3,3-difluoro-1-azetidinyl)-4-methyl-2-pyridinyl)benzamide | 0.071 |
| 28-2 | 2-(6-Azaspiro[2.5]octan-6-yl)-4-(R-cyclopropylsulfonimidoyl)-N-(6-(3,3-difluoro-1-azetidinyl)-4-methyl-2-pyridinyl)benzamide | 0.037 |
| 29-1 | 2-(6-Azaspiro[2.5]octan-6-yl)-4-(S-cyclopropylsulfonimidoyl)-N-(4-methyl-6-((2R)-2-methyl-4-morpholinyl)-2-pyridinyl)benzamide | 0.165 |
| 29-2 | 2-(6-Azaspiro[2.5]octan-6-yl)-4-(R-cyclopropylsulfonimidoyl)-N-(4-methyl-6-((2R)-2-methyl-4-morpholinyl)-2-pyridinyl)benzamide | 0.059 |
| 30-1 | 2-(6-Azaspiro[2.5]octan-6-yl)-4-(S-cyclopropylsulfonimidoyl)-N-(6-(4,4-difluoro-1-piperidinyl)-4-methyl-2-pyridinyl)benzamide | 0.081 |
| 30-2 | 2-(6-Azaspiro[2.5]octan-6-yl)-4-(R-cyclopropylsulfonimidoyl)-N-(6-(4,4-difluoro-1-piperidinyl)-4-methyl-2-pyridinyl)benzamide | 0.042 |
| 31 | 4-(Azetidin-3-ylsulfonyl)-2-(6-azaspiro[2.5]octan-6-yl)-N-(6-(3,3,3-trifluoropropoxy)pyridin-2-yl)benzamide trifluoroacetate | 0.055 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

We claim:

1. A compound of formula I:

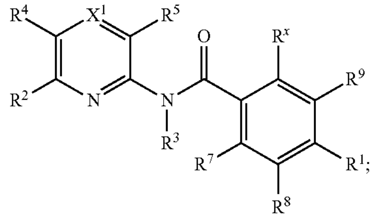

(I)

or any pharmaceutically-acceptable salt thereof, wherein:

$X^1$ is N or —$CR^6$;

$R^1$ is a group —Z—$R^{12}$ wherein Z is —$C_{0-4}$alk-, —$NR^{11}$—, —$NR^{11}SO_2$—$C_{0-4}$alk-, —$SO_2NR^{11}$—$C_{0-4}$alk-, —$NR^{11}SO_2NR^{11}$—, —$NR^{11}SO_2NR^{11}$—C(═O)—O—, —$C_{0-4}$alk-S(═O)(═NH)—, $C_{0-4}$alk-$NR^{11}$—S(═O)(═NH), —$C_{0-4}$alk-S—, —$C_{0-4}$alk-S(═O)—, —$C_{0-4}$alk-$SO_2$—, $C_{0-4}$alk-O—, —P—, —P(═O), —P(═O)$_2$, —(C═O)—, —(C═O)$NR^{11}$—, —C═N(OH)—, or —$NR^{11}$(C═O); or the group —Z—$R^{12}$ is —N═S(═O)—$(R^{12})_2$, wherein the two $R^{12}$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S;

$R^2$ is halo or a group —Y—$R^{13}$, wherein Y is —$C_{0-4}$alk-, —$N(C_{0-1}alk)$-$C_{0-4}$alk-, —O—$C_{0-4}$alk-, —S—, —S═O, —S(═O)$_2$—, —$SO_2N(C_{0-1}alk)$-$C_{0-4}$alk-, —$N(C_{0-1}alk)$-$SO_2$—$C_{0-4}$alk-, —$C_{0-4}$alk-S(═O)(═NH)—, —(C═O)—, —$C_{0-4}$alk-(C═O)—O—; or the group $—Y—R^{13}$ is $—N{=}S({=}O)—(R^{13})_2$, wherein the two $R^{13}$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S;

$R^3$ is H, methyl, or ethyl;

$R^4$ is H, halo, CN, $C_{1-4}$alk, or $C_{1-4}$haloalk;

$R^5$ is H, halo, $C_{1-8}$alk, or $C_{1-4}$haloalk;

$R^6$ is H, halo, CN, $C_{1-5}$alk, $C_{1-4}$haloalk, or $R^{6a}$;

$R^7$ is H, halo, $C_{1-5}$alk, or $C_{1-4}$haloalk;

$R^8$ is H, halo, $C_{1-5}$alk, or $C_{1-4}$haloalk;

$R^9$ is H, halo, $C_{1-8}$alk, or $C_{1-4}$haloalk;

$R^x$ is selected from the group consisting of

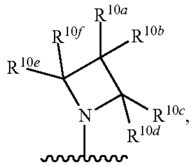

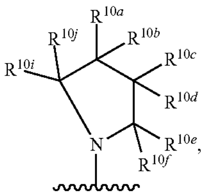

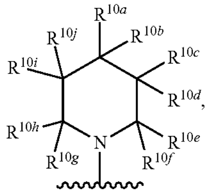

and

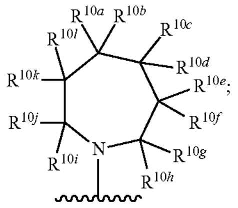

Each of $R^{10a}$, $R^{10b}$, $R^{10c}$, $R^{10d}$, $R^{10e}$, $R^{10f}$, $R^{10g}$, $R^{10h}$, $R^{10i}$, and $R^{10j}$ is H, halo, $R^{10k}$, or $R^{10l}$;

or alternatively, each of $R^{10a}$ and $R^{10b}$ pair, $R^{10c}$ and $R^{10d}$ pair, $R^{10e}$ and $R^{10f}$ pair, $R^{10g}$ and $R^{10h}$ pair, or $R^{10i}$ and $R^{10j}$ pair, independently, can combine with the carbon atom attached to each of them to form a saturated or partially-saturated 3-, 4-, 5-, 6-membered monocyclic ring spiro to the R ring; wherein said 3-, 4-, 5-, 6-membered monocyclic ring contains 0, 1, 2 or 3 N atoms and 0, 1, or 2 atoms selected from O and S, and further wherein said 3-, 4-, 5-, 6-membered monocyclic ring is substituted by 0, 1, 2 or 3 group(s) selected from F, Cl, Br, $C_{1-6}$alk, $C_{1-4}$haloalk, $—OR^a$, $—OC_{1-4}$haloalk, CN, $—NR^aR^a$, or oxo;

$R^{11}$ is H or $C_{1-8}$alk;

$R^{12}$ is H, $R^{12a}$, or $R^{12b}$;

$R^{13}$ is $R^{13a}$ or $R^{13b}$;

$R^{6a}$, $R^{10k}$, $R^{12a}$, and $R^{13a}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from O and S, which is substituted by 0, 1, 2 or 3 group(s) selected from F, Cl, Br, $C_{1-6}$alk, $C_{1-4}$haloalk, $—OR^a$, $—OC_{1-4}$haloalk, CN, $—C({=}O)R$, $—C({=}O)OR^a$, $—C({=}O)NR^aR^a$, $—C({=}NR^a)NR^aR^a$, $—OC({=}O)R$, $—OC({=}O)NR^aR^a$, $—OC_{2-6}alkNR^aR^a$, $—OC_{2-6}alkOR^a$, $—SR^a$, $—S({=}O)R$, $—S({=}O)_2R$, $—S({=}O)_2NR^aR^a$, $—NR^aR^a$, $—N(R^a)C({=}O)R$, $—N(R^a)C({=}O)OR$, $—N(R^a)C({=}O)NR^aR^a$, $—N(R^a)C({=}NR^a)NR^aR^a$, $—N(R^a)S({=}O)_2R$, $—N(R^a)S({=}O)_2NR^aR^a$, $—NR^aC_{2-6}alkNR^aR^a$, $—NR^aC_{2-6}alkOR^a$, $—C_{1-6}alkNR^aR^a$, $—C_{1-6}alkOR^a$, $—C_{1-6}alkN(R^a)C({=}O)R$, $—C_{1-6}alkOC({=}O)R$, $—C_{1-6}alkC({=}O)NR^aR^a$, $—C_{1-6}alkC({=}O)OR^a$, $R^{14}$, and oxo;

$R^{10l}$, $R^{12b}$, and $R^{13b}$ is independently, at each instance, selected from the group consisting of $C_{1-6}$alk substituted by 0, 1, 2, 3, 4, or 5 group(s) selected from F, Cl, Br, $—C({=}O)OR^a$, $—OR^a$, $—C_{1-2}$haloalk, $—OC_{1-4}$haloalk, CN, $NH_2$, $NH(CH_3)$, or $N(CH_3)_2$;

$R^{14}$ is independently, at each instance, selected from the group consisting of a saturated, partially-saturated or unsaturated 3-, 4-, 5-, 6-, or 7-membered monocyclic or 4-, 5-, 6-, 7-, 8-, 9-, 10-, 11-, or 12-membered bicyclic ring containing 0, 1, 2 or 3 N atoms and 0, 1, or 2 atoms selected from O and S, which is substituted by 0, 1, 2 or 3 group(s) selected from F, Cl, Br, $C_{1-6}$alk, $C_{1-4}$haloalk, $—OR^a$, $—OC_{1-4}$haloalk, CN, $—C({=}O)R$, $—C({=}O)OR^a$, $—C({=}O)NR^aR^a$, $—C({=}NR^a)NR^aR^a$, $—OC({=}O)R$, $—OC({=}O)NR^aR^a$, $—OC_{2-6}alkNR^aR^a$, $—OC_{2-6}alkOR^a$, $—SR$, $—S({=}O)R$, $—S({=}O)_2R$, $—S({=}O)_2NR^aR^a$, $—NR^aR^a$, $—N(R^a)C({=}O)R$, $—N(R^a)C({=}O)OR$, $—N(R^a)C({=}O)NR^aR^a$, $—N(R^a)C({=}NR^a)NR^aR^a$, $—N(R^a)S({=}O)_2R$, $—N(R^a)S({=}O)_2\ NR^aR^a$, $—NR^aC_{2-6}alkNR^aR^a$, $—NR^aC_{2-6}alkOR^a$, $—C_{1-6}alkNR^aR^a$, $—C_{1-6}alkOR^a$, $—C_{1-6}alkN(R^a)C({=}O)R$, $—C_{1-6}alkOC({=}O)R$, $—C_{1-6}alkC({=}O)NR^aR^a$, $—C_{1-6}alkC({=}O)OR^a$, and oxo;

$R^a$ is independently, at each instance, H or $R^b$; and $R^b$ is independently, at each instance, $C_{1-6}$alk, phenyl, or benzyl, wherein the $C_{1-6}$alk is being substituted by 0, 1, 2 or 3 substituents selected from halo, —OH, $—OC_{1-4}$alk, $—NH_2$, $—NHC_{1-4}$alk, $—OC({=}O)C_{1-4}$alk, or $—N(C_{1-4}alk)C_{1-4}$alk; and the phenyl or benzyl is being substituted by 0, 1, 2 or 3 substituents selected from halo, $C_{1-4}$alk, $C_{1-3}$haloalk, —OH, $—OC_{1-4}$alk, $—NH_2$, $—NHC_{1-4}$alk, $—OC({=}O)C_{1-4}$alk, or $—N(C_{1-4}alk)C_{1-4}$alk.

2. The compound of claim 1 wherein $R^x$ is

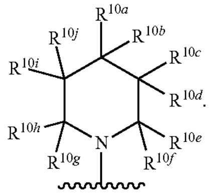

3. The compound according to claim 1 wherein $X^1$ is $—CR^6$; having the formula (Ia):

(Ia)

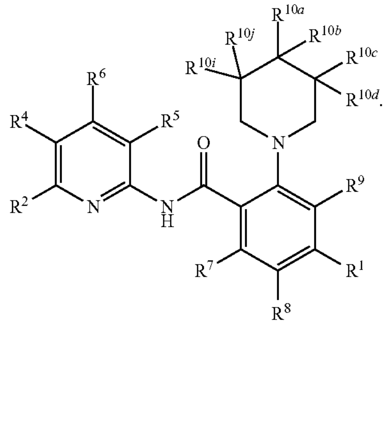

4. The compound according to claim 1 wherein $X^1$ is N; having the formula (Ib):

(Ib)

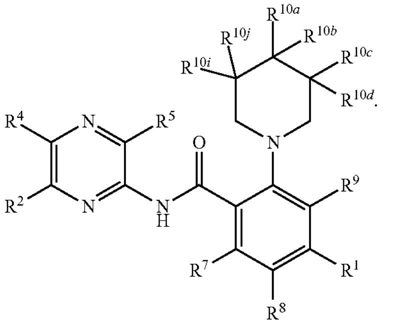

5. The compound according to claim 1 wherein $R^3$ is H or methyl.

6. The compound according to claim 1 wherein each of $R^{10c}$, $R^{10d}$, $R^{10e}$, $R^{10f}$, $R^{10g}$, $R^{10h}$, $R^{10i}$, and $R^{10j}$ is H, halo, $C_{1-6}$alk, or $C_{1-4}$haloalk; and each of $R^{10a}$ and $R^{10b}$ pair combine with the carbon atom attached to each of them form a saturated 3-, 4-, or 5-membered monocyclic ring spiro to the $R^x$ ring; wherein said ring contains 0, 1, 2 or 3 N atoms and 0 or 1 atoms selected from O and S.

7. The compound according to claim 1 wherein each of $R^{10c}$, $R^{10d}$, $R^{10e}$, $R^{10f}$, $R^{10g}$, $R^{10h}$, $R^{10i}$, and $R^{10j}$ is H, methyl, or ethyl; and each of $R^{10a}$ and $R^{10b}$ pair combine with the carbon atom attached to each of them form a cyclopropyl, cyclobutyl, or cyclopentyl ring spiro to the R ring.

8. The compound according to claim 1 wherein R is selected from:

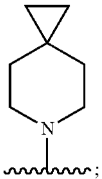;
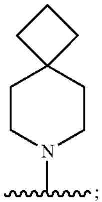;
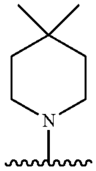; or
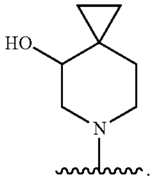.

9. The compound according to claim 1 wherein $R^x$ is

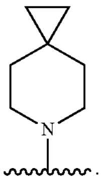 [SMILES: *N1CCC2(CC1)CC2].

10. The compound according to claim 1 wherein Z is absent, NH—, —$NHSO_2$—$(CH_2)_{0-4}$—, —$N(CH_3)$—$SO_2$—$(CH_2)_{0-4}$—, —$NCH_3SO_2NH$, —$NHSO_2NH$—C(═O)—O—, —$SO_2NH$—$(CH_2)_{0-4}$—, —$(CH_2)_{0-2}$—S(═O)(═NH)—, —$(CH_2)_{0-2}$—S—, —$(CH_2)_{0-2}$—S(═O)—, $(CH_3CH)$—S(═O)—, —$(CH_2)_{0-2}$—$SO_2$—, —O—, —P(═O), —(C═O)—, or —NH(C═O).

11. The compound according to claim 1 wherein the group —Z—$R^{12}$ is —N═S(═O)—$(R^{12})_2$, wherein the two $R^{12}$ pair can alternatively combine with the sulfur atom attached to each of them to form a saturated or partially-saturated 3-, 4-, 5-, or 6-membered monocyclic ring containing 0, 1, 2 or 3 N atoms and 0, 1, or 2 atoms selected from O and S; which is selected from:

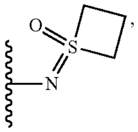,
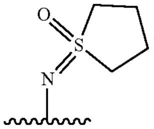, or
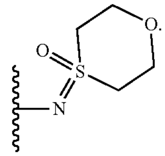.

12. The compound according to claim 1 wherein $R^1$ is a group —Z—$R^{12}$ wherein Z is —$NHSO_2$— or —$SO_2NH$—; and $R^{12}$ is oxetanyl, cyclopropyl, or $R^{12}$ is $C_{1-6}$alk substituted by 0, 1, 2 or 3 OH group(s).

13. The compound according to claim 1 wherein $R^1$ is a group —Z—$R^{12}$ wherein Z is —$NHSO_2$— and $R^{12}$ is —$CH_2$—$CH_2$—OH.

14. The compound according to claim 1 wherein $R^2$ is halo or a group —Y—$R^{13}$, wherein Y is absent, —$SO_2NH$—$(CH_2)_{0-4}$—, NH—, —O—$(CH_2)_{0-4}$, —O—$(CH(CH_3))$—, —$(CH_2)_{0-4}$—S(═O)(═NH)—, —(C═O)—, —$(CH_2)_{0-4}$—(C═O)—O—, or —$(CH_2)_{1-4}$;

$R^{13}$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 group(s) selected from F, Cl, Br, $C_{1-6}$alk, $C_{1-4}$haloalk, —OH, —$OC_{1-4}$haloalk, CN, $R^{14}$, and oxo; or;

$R^{13}$ is $C_{1-6}$alk substituted by 0, 1, 2, 3, 4, or 5 group(s) selected from F, Cl, Br, —OH, —$OC_{1-4}$haloalk, or CN.

15. The compound according to claim 1 wherein $R^2$ is a saturated 5- or 6-membered monocyclic ring wherein each said ring contains 0, 1, or 2 N atoms and 0 or 1 O atom, and wherein each said ring is substituted by 0, 1, 2 or 3 group(s) selected from F, Cl, Br, $C_{1-6}$alk, $C_{1-4}$haloalk, —OH, —$OCH_3$, —$OC_{1-4}$haloalk, CN, $R^{14}$, and oxo.

16. The compound according to claim 1 wherein $R^2$ is:

(a) F, Br;

(b) a group —Y—$R^{13}$, wherein Y is absent; and $R^{13}$ is morpholinyl, piperidinyl, azetidinyl, pyrrolidinyl, cyclopropyl, cyclobutyl, cyclopentyl, cyclohexyl, piperazinyl, tetrahydrofuranyl, tetrahydropyranyl, pyridinyl, pyrimidinyl, 3,6-dihydro-2H-pyranyl,

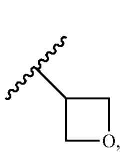,
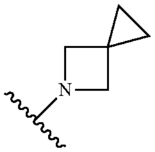,
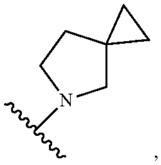,
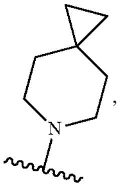,
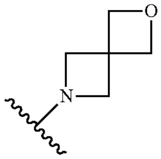,
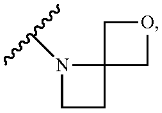,

-continued

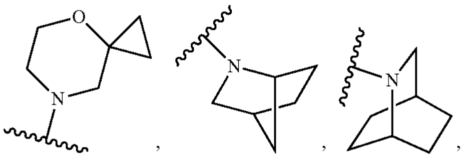
, , ,

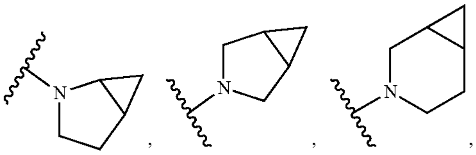
, , ,

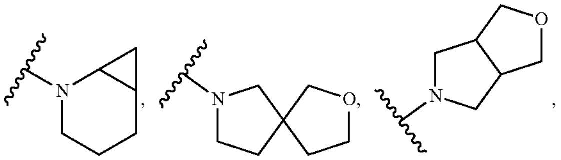
, , ,

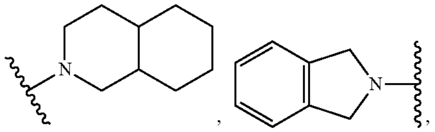
, ,

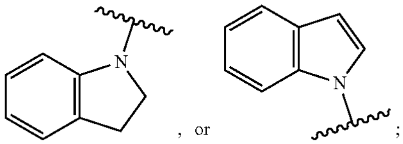
, or ;

wherein each said ring is substituted by 0, 1, 2 or 3 group(s) selected from F, Cl, Br, methyl, $CF_3$, $CH_2OH$, $CH(CH_3)OH$, $C(CH_3)_2OH$, —OH, —$OCHF_2$, CN, oxo, or cyclopropyl; or (c) a group —Y—$R^{13}$, wherein Y is absent, —$SO_2NH$—, NH, —O—, S(═O)(═NH)—, —O—($CH_2$), —O—($CH(CH_3)$)—, C(═O)—, C(═O)—O—, —$CH_2C$(═O)—O—, or —$CH_2$—; and wherein $R^{13}$ is

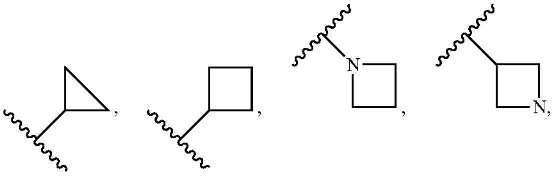
, , , N,

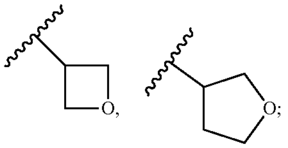
O, O;

wherein each ring is substituted by 0, 1, 2, 3, 4, or 5 group(s) selected from F, Cl, Br, methyl, $CF_3$, —OH, or CN;

or $R^{13}$ is H or $C_{1-6}$alk substituted by 0, 1, 2, 3, 4, or 5 group(s) selected from F, Cl, Br, methyl, $CF_3$, —OH, or CN.

17. The compound according to claim 1 wherein $R^2$ is (a) halo; (b) a group —Y—$R^{13}$, wherein Y is absent; and $R^{13}$ is morpholinyl, piperidinyl, azetidinyl, pyrrolidinyl, cyclopropyl, cyclobutyl, cyclopentyl, cyclohexyl, piperazinyl, tetrahydrofuranyl,

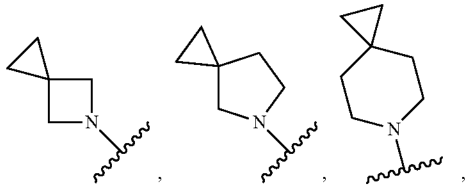
, , ,

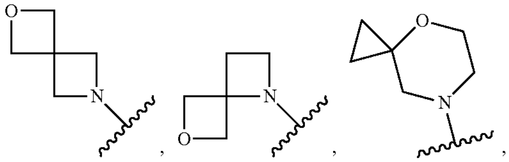
, , ,

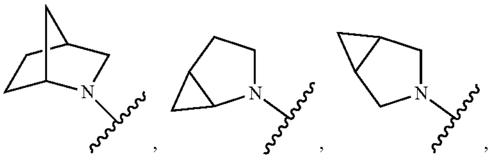
, , ,

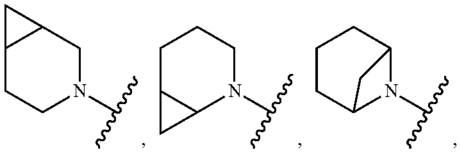
, , ,

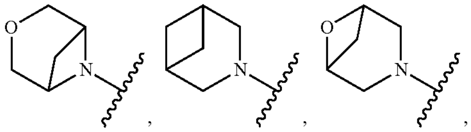
, , ,

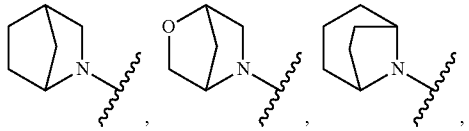
, , ,

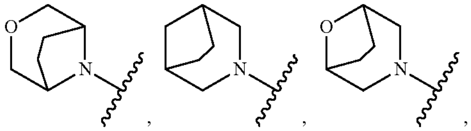
, , ,

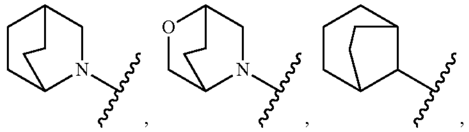
, , ,

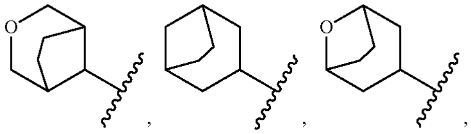
, , ,

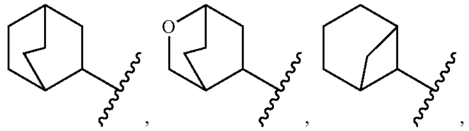
, , ,

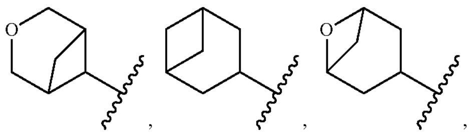
, , ,

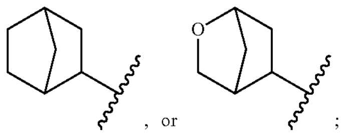
, or ;

wherein each said ring is substituted by 0, 1, 2 or 3 group(s) selected from F, Cl, Br, methyl, $CF_3$, —OH, —$OCHF_2$, CN, and oxo; or (c) a group —Y—$R^{13}$, wherein Y is NH, —O—, —O—($CH_2$)—, —O—($CH_2$)—($CH_2$)—, or —O—($CH_2$)—($CH_2$)—($CH_2$)—, and wherein $R^{13}$ is

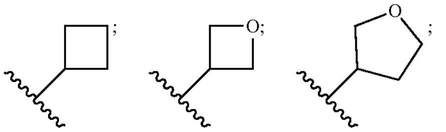 [SMILES: *C1CCC1 ; *C1COC1 ; *C1CCOC1]

or $R^{13}$ is $C_{1-6}$alk substituted by 0, 1, 2, 3, 4, or 5 group(s) selected from F, Cl, Br, methyl, $CF_3$, —OH, or CN.

18. The compound according to claim 1 wherein $R^2$ is

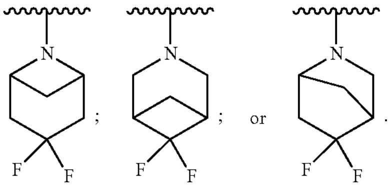

19. The compound according to claim 1 wherein $R^2$ is morpholinyl or piperdinyl substituted by 0, 1, 2 or 3 group(s) selected from F, Cl, Br, methyl, $CF_3$, —OH, —$OCHF_2$, CN, or oxo.

20. The compound according to claim 1 $R^2$ is morpholinyl substituted by 1, 2 or 3 methyl group(s).

21. The compound according to claim 1 wherein $R^4$ is selected from H, F, methyl, CN, or Br.

22. The compound according to claim 1 wherein $R^4$ is H.

23. The compound according to claim 1 wherein $R^5$ is H.

24. The compound according to claim 1 wherein $R^6$ is H, methyl, cyclopropyl, CN, $CF_3$, or azetidinyl.

25. The compound according to claim 1 wherein $R^7$ is H.

26. The compound according to claim 1 wherein $R^8$ is H or F.

27. The compound according to claim 1 wherein $R^9$ is H or F.

28. The compound of claim 1, selected from the group consisting of:

| Ex. # | Chemical Structure | Name |
|---|---|---|
| 1 | 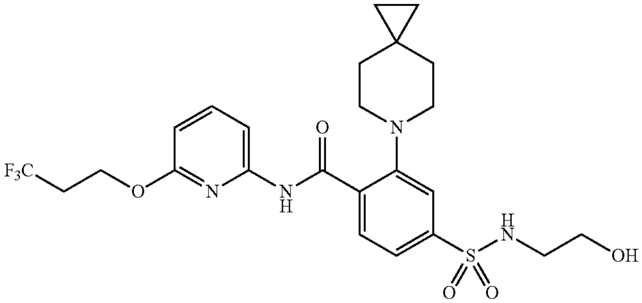 [SMILES: O=C(Nc1cccc(OCCC(F)(F)F)n1)c1ccc(S(=O)(=O)NCCO)cc1N1CCC2(CC1)CC2] | 4-(N-(2-Hydroxyethyl)sulfamoyl)-2-(6-azaspiro[2.5]octan-6-yl)-N-(6-(3,3,3-trifluoropropoxy)pyridin-2-yl)benzamide |
| 1-1 | 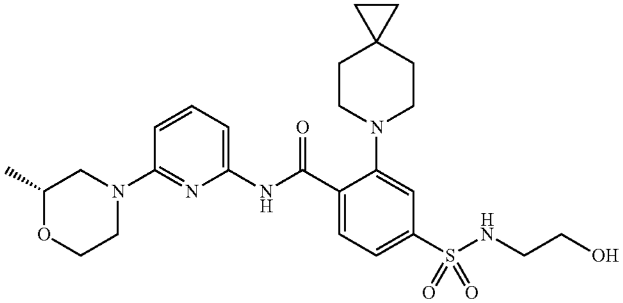 [SMILES: C[C@@H]1CN(c2cccc(NC(=O)c3ccc(S(=O)(=O)NCCO)cc3N3CCC4(CC3)CC4)n2)CCO1] | (R)-4-(N-(2-Hydroxyethyl)sulfamoyl)-N-(6-(2-methylmorpholino)pyridin-2-yl)-2-(6-azaspiro[2.5]octan-6-yl)benzamide |
| 1-2 | 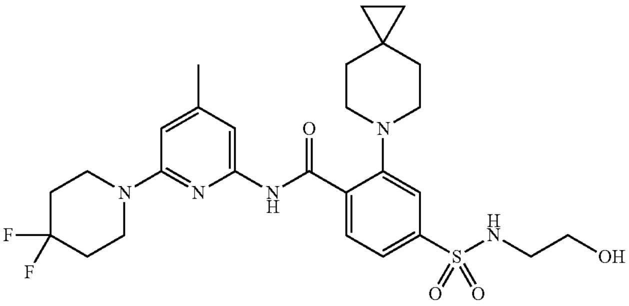 [SMILES: Cc1cc(NC(=O)c2ccc(S(=O)(=O)NCCO)cc2N2CCC3(CC2)CC3)nc(N2CCC(F)(F)CC2)c1] | N-(6-(4,4-Difluoropiperidin-1-yl)-4-methylpyridin-2-yl)-4-(N-(2-hydroxyethyl)sulfamoyl)-2-(6-azaspiro[2.5]octan-6-yl)benzamide |

-continued

| Ex. # | Chemical Structure | Name |
|---|---|---|
| 2 | 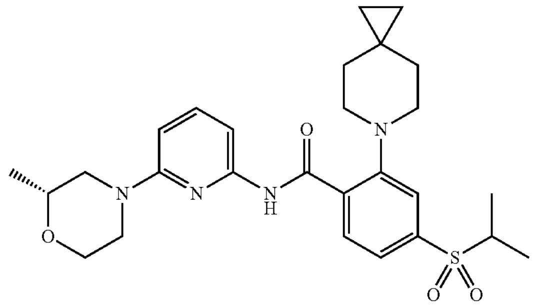 [SMILES: CC(C)S(=O)(=O)c1ccc(C(=O)Nc2cccc(N3CCO[C@H](C)C3)n2)c(N2CCC3(CC2)CC3)c1] | (R)-4-(Isopropylsulfonyl)-N-(6-(2-methylmorpholino)pyridin-2-yl)-2-(6-azaspiro[2.5]octan-6-yl)benzamide |
| 2-7 | 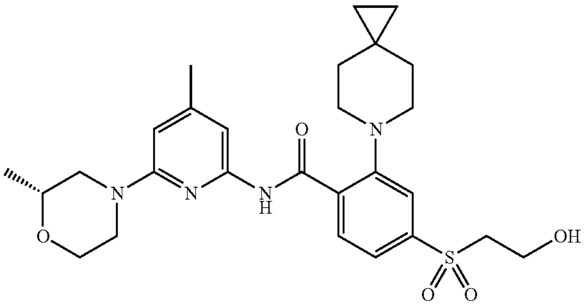 [SMILES: Cc1cc(NC(=O)c2ccc(S(=O)(=O)CCO)cc2N2CCC3(CC2)CC3)nc(N2CCO[C@H](C)C2)c1] | (R)-4-((2-Hydroxyethyl)sulfonyl)-N-(4-methyl-6-(2-methylmorpholino)pyridin-2-yl)-2-(6-azaspiro[2.5]octan-6-yl)benzamide |
| 3 | 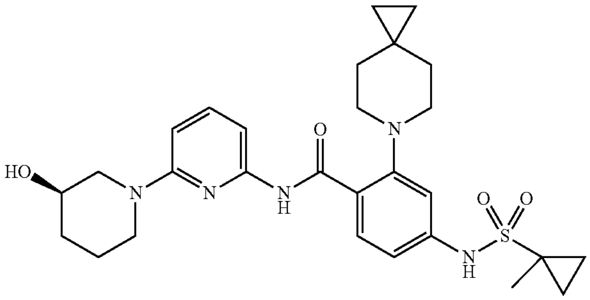 [SMILES: CC1(S(=O)(=O)Nc2ccc(C(=O)Nc3cccc(N4CCC[C@@H](O)C4)n3)c(N3CCC4(CC3)CC4)c2)CC1] | (R)-N-(6-(3-Hydroxypiperidin-1-yl)pyridin-2-yl)-4-((1-methylcyclopropane)-1-sulfonamido)-2-(6-azaspiro[2.5]octan-6-yl)benzamide |
| 4 | 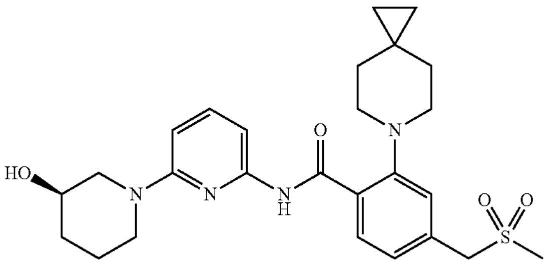 [SMILES: CS(=O)(=O)Cc1ccc(C(=O)Nc2cccc(N3CCC[C@@H](O)C3)n2)c(N2CCC3(CC2)CC3)c1] | (R)-N-(6-(3-hydroxypiperidin-1-yl)pyridin-2-yl)-4-((methylsulfonyl)methyl)-2-(6-azaspiro[2.5]octan-6-yl)benzamide |
| 5 | 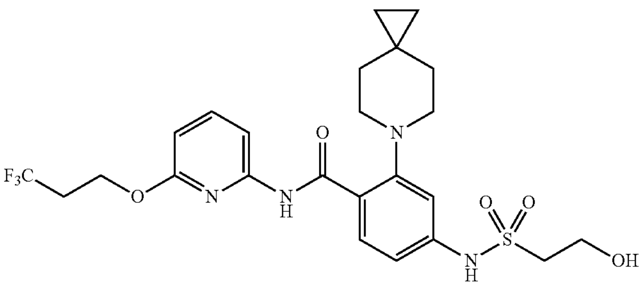 [SMILES: O=C(Nc1cccc(OCCC(F)(F)F)n1)c1ccc(NS(=O)(=O)CCO)cc1N1CCC2(CC1)CC2] | 4-((2-Hydroxyethyl)sulfonamido)-2-(6-azaspiro[2.5]octan-6-yl)-N-(6-(3,3,3-trifluoropropoxy)pyridin-2-yl)benzamide |

-continued

| Ex. # | Chemical Structure | Name |
| --- | --- | --- |
| 6 | 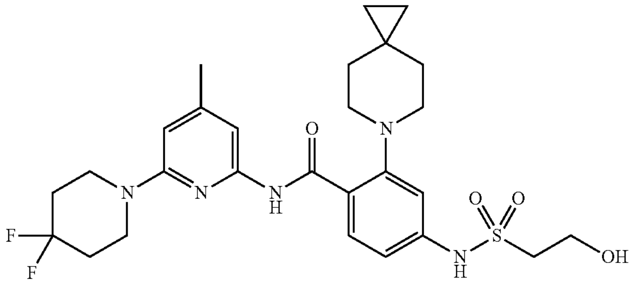 | N-(6-(4,4-Difluoropiperidin-1-yl)-4-methylpyridin-2-yl)-4-((2-hydroxyethyl)sulfonamido)-2-(6-azaspiro[2.5]octan-6-yl)benzamide |
| 7-1 | 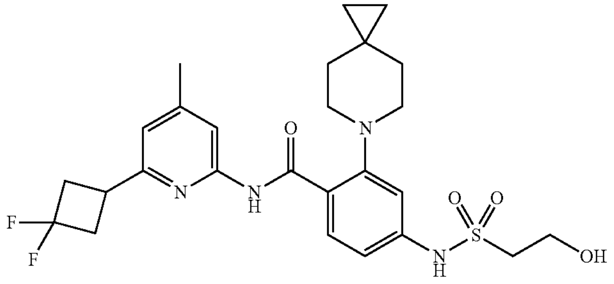 [SMILES: Cc1cc(NC(=O)c2ccc(NS(=O)(=O)CCO)cc2N2CCC3(CC2)CC3)nc(C2CC(F)(F)C2)c1] | N-(6-(3,3-Difluorocyclobutyl)-4-methylpyridin-2-yl)-4-((2-hydroxyethyl)sulfonamido)-2-(6-azaspiro[2.5]octan-6-yl)benzamide |
| 7-12 | 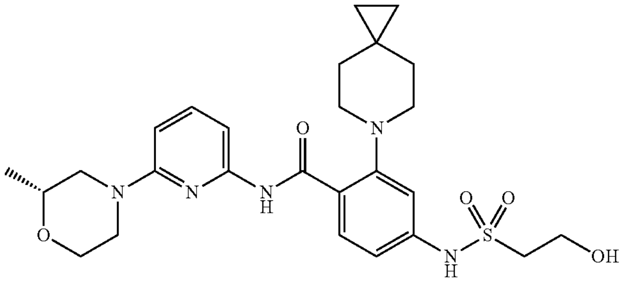 [SMILES: C[C@@H]1CN(c2cccc(NC(=O)c3ccc(NS(=O)(=O)CCO)cc3N3CCC4(CC3)CC4)n2)CCO1] | (R)-4-((2-Hydroxyethyl)sulfonamido)-N-(6-(2-methylmorpholino)pyridin-2-yl)-2-(6-azaspiro[2.5]octan-6-yl)benzamide |
| 7-33 | 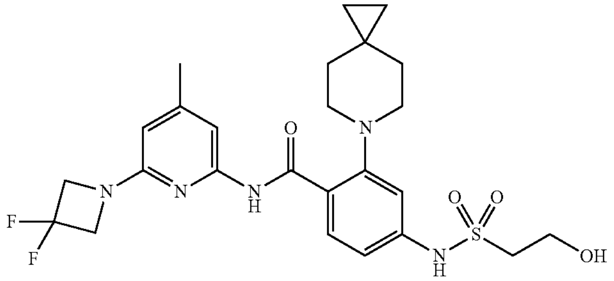 | N-(6-(3,3-Difluoroazetidin-1-yl)-4-methylpyridin-2-yl)-4-((2-hydroxyethyl)sulfonamido)-2-(6-azaspiro[2.5]octan-6-yl)benzamide |
| 7-44 | 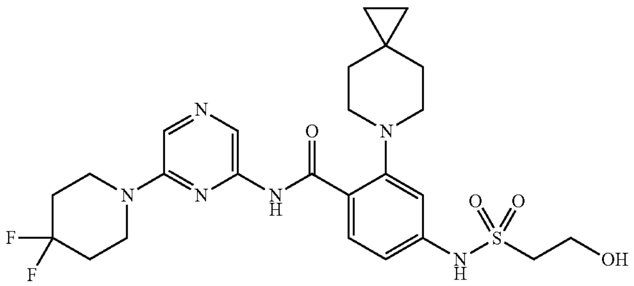 | N-(6-(4,4-Difluoropiperidin-1-yl)pyrazin-2-yl)-4-((2-hydroxyethyl)sulfonamido)-2-(6-azaspiro[2.5]octan-6-yl)benzamide |

-continued

| Ex. # | Chemical Structure | Name |
|---|---|---|
| 8-1 | 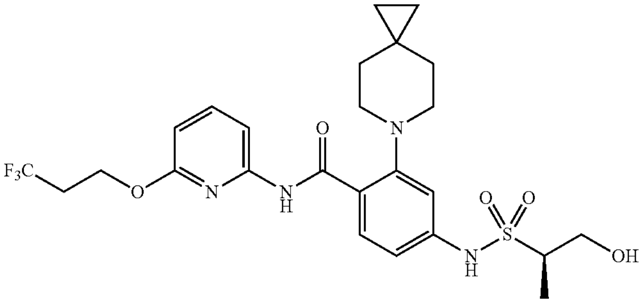 [SMILES: C[C@H](CO)S(=O)(=O)Nc1ccc(C(=O)Nc2cccc(OCCC(F)(F)F)n2)c(N2CCC3(CC2)CC3)c1] | (R)-4-((2-Hydroxy-1-methylethyl)sulfonamido)-2-(6-azaspiro[2.5]octan-6-yl)-N-(6-(3,3,3-trifluoropropoxy)pyridin-2-yl)benzamide |
| 8-2 | 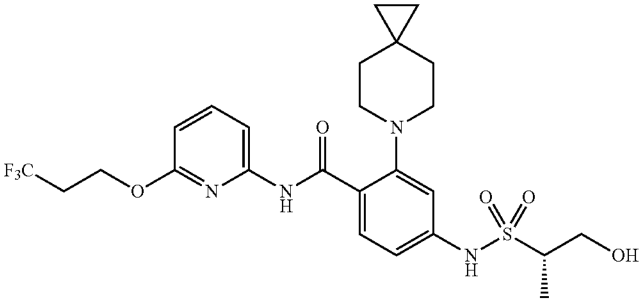 [SMILES: C[C@@H](CO)S(=O)(=O)Nc1ccc(C(=O)Nc2cccc(OCCC(F)(F)F)n2)c(N2CCC3(CC2)CC3)c1] | (S)-4-((2-Hydroxy-1-methylethyl)sulfonamido)-2-(6-azaspiro[2.5]octan-6-yl)-N-(6-(3,3,3-trifluoropropoxy)pyridin-2-yl)benzamide |
| 9-7 | 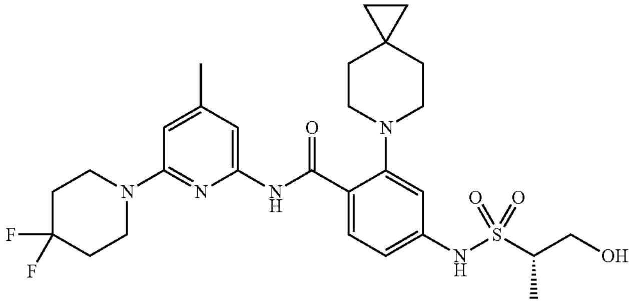 [SMILES: Cc1cc(NC(=O)c2ccc(NS(=O)(=O)[C@@H](C)CO)cc2N2CCC3(CC2)CC3)nc(N2CCC(F)(F)CC2)c1] | (S)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide |
| 9-8 | 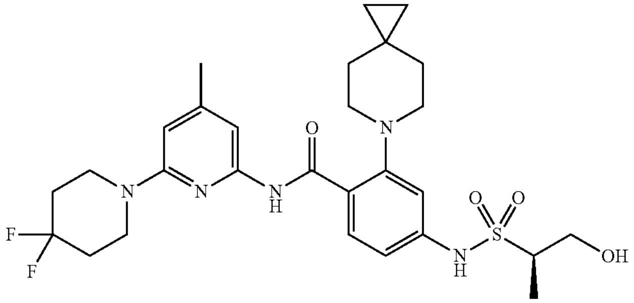 [SMILES: Cc1cc(NC(=O)c2ccc(NS(=O)(=O)[C@H](C)CO)cc2N2CCC3(CC2)CC3)nc(N2CCC(F)(F)CC2)c1] | (R)-N-(6-(4,4-Difluoropiperidin-1-yl)-4-methylpyridin-2-yl)-4-((2-hydroxy-1-methylethyl)sulfonamido)-2-(6-azaspiro[2.5]octan-6-yl)benzamide |
| 10 | 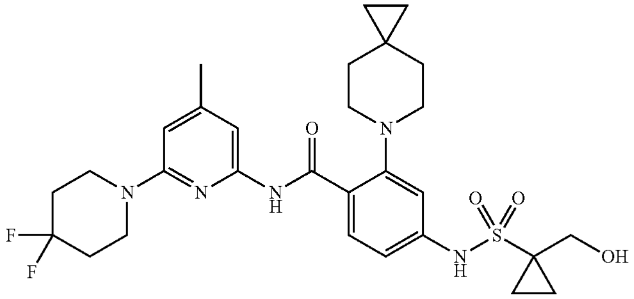 [SMILES: Cc1cc(NC(=O)c2ccc(NS(=O)(=O)C3(CO)CC3)cc2N2CCC3(CC2)CC3)nc(N2CCC(F)(F)CC2)c1] | N-(6-(4,4-Difluoropiperidin-1-yl)-4-methylpyridin-2-yl)-4-((1-(hydroxymethyl)cyclopropane)-1-sulfonamido)-2-(6-azaspiro[2.5]octan-6-yl)benzamide |

-continued

| Ex. # | Chemical Structure | Name |
|---|---|---|
| 11 | 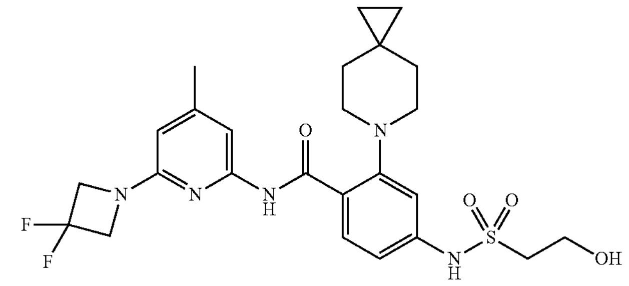 [SMILES: Cc1cc(NC(=O)c2ccc(NS(=O)(=O)CCO)cc2N2CCC3(CC2)CC3)nc(N2CC(F)(F)C2)c1] | N-(6-(3,3-Difluoroazetidin-1-yl)-4-methylpyridin-2-yl)-4-((2-hydroxyethyl)sulfonamido)-2-(6-azaspiro[2.5]octan-6-yl)benzamide |
| 14 | 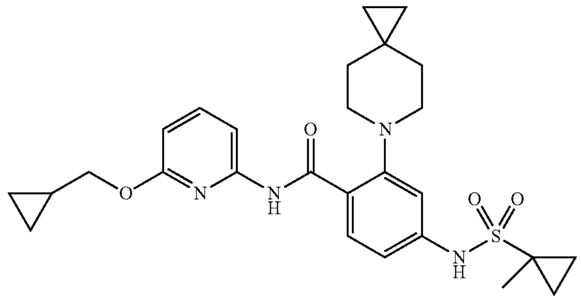 [SMILES: CC1(S(=O)(=O)Nc2ccc(C(=O)Nc3cccc(OCC4CC4)n3)c(N3CCC4(CC3)CC4)c2)CC1] | N-(6-(Cyclopropylmethoxy)pyridin-2-yl)-4-((1-methylcyclopropane)-1-sulfonamido)-2-(6-azaspiro[2.5]octan-6-yl)benzamide |
| 16 | 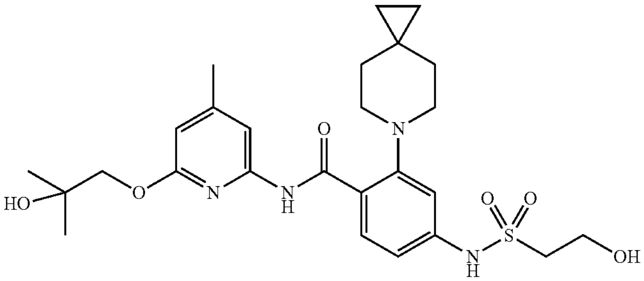 [SMILES: Cc1cc(NC(=O)c2ccc(NS(=O)(=O)CCO)cc2N2CCC3(CC2)CC3)nc(OCC(C)(C)O)c1] | N-(6-(2-Hydroxy-2-methylpropoxy)-4-methylpyridin-2-yl)-4-((2-hydroxyethyl)sulfonamido)-2-(6-azaspiro[2.5]octan-6-yl)benzamide |
| 17 | 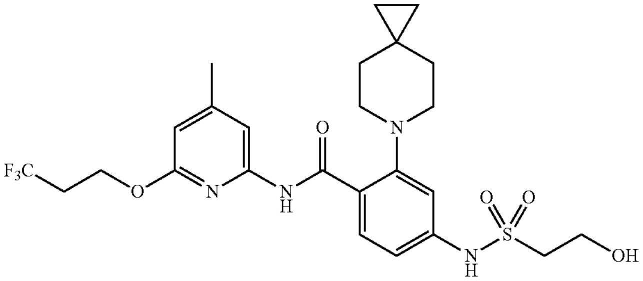 | 4-((2-Hydroxyethyl)sulfonamido)-N-(4-methyl-6-(3,3,3-trifluoropropoxy)pyridin-2-yl)-2-(6-azaspiro[2.5]octan-6-yl)benzamide |
| 21 | 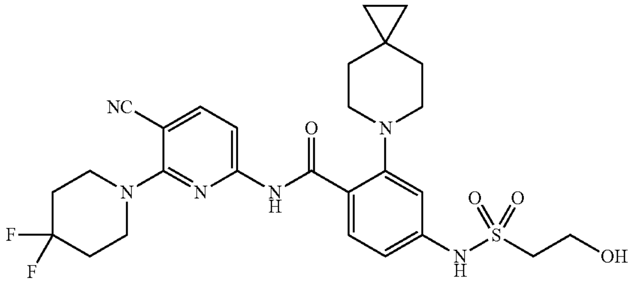 [SMILES: N#Cc1ccc(NC(=O)c2ccc(NS(=O)(=O)CCO)cc2N2CCC3(CC2)CC3)nc1N1CCC(F)(F)CC1] | N-(5-Cyano-6-(4,4-difluoropiperidin-1-yl)pyridin-2-yl)-4-((2-hydroxyethyl)sulfonamido)-2-(6-azaspiro[2.5]octan-6-yl)benzamide |

-continued

| Ex. # | Chemical Structure | Name |
|---|---|---|
| 22 | 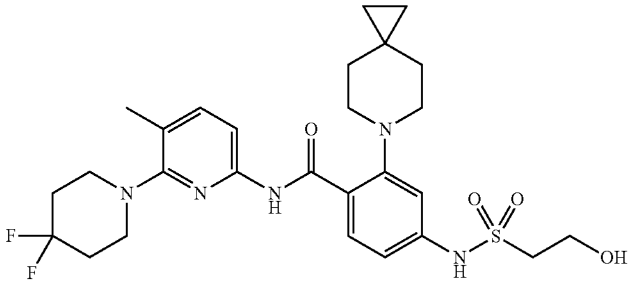 [SMILES: Cc1ccc(NC(=O)c2ccc(NS(=O)(=O)CCO)cc2N2CCC3(CC2)CC3)nc1N1CCC(F)(F)CC1] | N-(6-(4,4-Difluoropiperidin-1-yl)-5-methylpyridin-2-yl)-4-((2-hydroxyethyl)sulfonamido)-2-(6-azaspiro[2.5]octan-6-yl)benzamide |
| 23 | 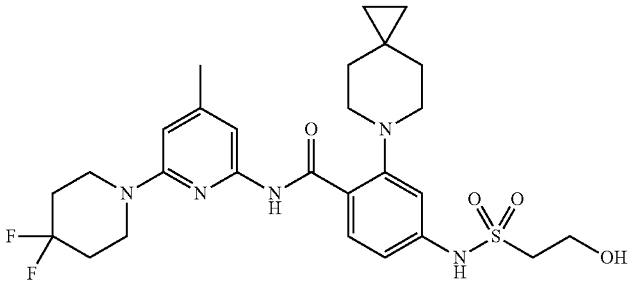 [SMILES: Cc1cc(NC(=O)c2ccc(NS(=O)(=O)CCO)cc2N2CCC3(CC2)CC3)nc(N2CCC(F)(F)CC2)c1] | N-(6-(4,4-difluorocyclohexyl)-4-methylpyridin-2-yl)-4-((2-hydroxyethyl)sulfonamido)-2-(6-azaspiro[2.5]octan-6-yl)benzamide |
| 24 | 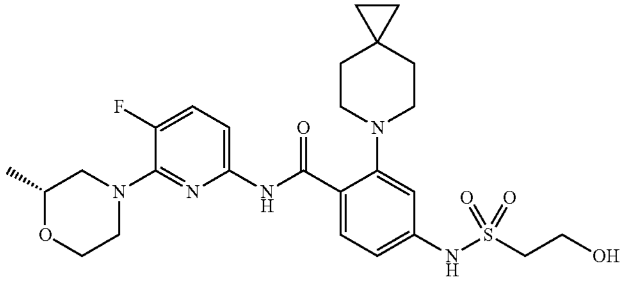 [SMILES: C[C@@H]1CN(c2nc(NC(=O)c3ccc(NS(=O)(=O)CCO)cc3N3CCC4(CC3)CC4)ccc2F)CCO1] | (R)-N-(5-Fluoro-6-(2-methylmorpholino)pyridin-2-yl)-4-((2-hydroxyethyl)sulfonamido)-2-(6-azaspiro[2.5]octan-6-yl)benzamide |
| 25 | 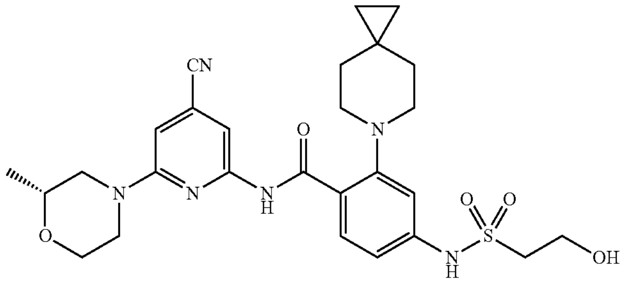 [SMILES: C[C@@H]1CN(c2cc(C#N)cc(NC(=O)c3ccc(NS(=O)(=O)CCO)cc3N3CCC4(CC3)CC4)n2)CCO1] | (R)-N-(4-Cyano-6-(2-methylmorpholino)pyridin-2-yl)-4-((2-hydroxyethyl)sulfonamido)-2-(6-azaspiro[2.5]octan-6-yl)benzamide |
| 27-1 | 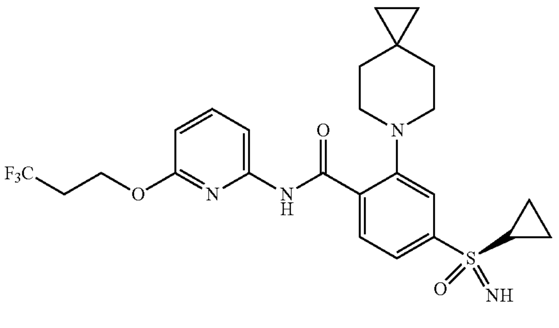 [SMILES: N=[S@](=O)(c1ccc(C(=O)Nc2cccc(OCCC(F)(F)F)n2)c(N2CCC3(CC2)CC3)c1)C1CC1] | 2-(6-Azaspiro[2.5]octan-6-yl)-4-(S-cyclopropylsulfonimidoyl)-N-(6-(3,3,3-trifluoropropoxy)-2-pyridinyl)benzamide |

-continued

| Ex. # | Chemical Structure | Name |
|---|---|---|
| 27-2 | 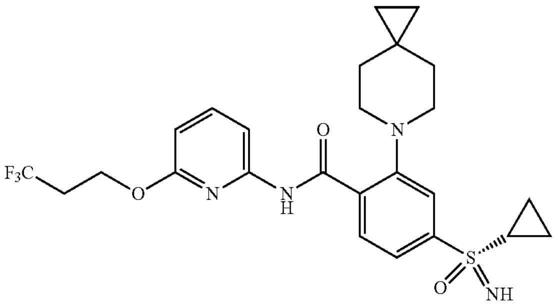 [SMILES: N=[S@@](=O)(c1ccc(C(=O)Nc2cccc(OCCC(F)(F)F)n2)c(N2CCC3(CC2)CC3)c1)C1CC1] | 2-(6-Azaspiro[2.5]octan-6-yl)-4-(R-cyclopropylsulfonimidoyl)-N-(6-(3,3,3-trifluoropropoxy)-2-pyridinyl)benzamide; |

or any pharmaceutically-acceptable salt thereof.

29. A pharmaceutical composition comprising the compound according to claim 1 or the pharmaceutically acceptable salt thereof, and a pharmaceutically-acceptable diluent or carrier.

30. A method of treating a condition that may be treated with KIF18a inhibitors, the method comprising administering to a patient in need thereof a therapeutically effective amount of the compound according to claim 1, or the pharmaceutically-acceptable salt thereof.

31. The method of claim 30 wherein said condition is cancer selected from the group consisting of (a) a solid or hematologically derived tumor selected from cancer of the cancer of the bladder, endometrial, lung squamous cell, breast, colon, kidney, liver, lung, small cell lung cancer, esophagus, gall-bladder, brain, head and neck, ovary, pancreas, stomach, cervix, thyroid, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, or (f) a melanoma, seminoma, teratocarcinoma, osteosarcoma, xenoderoma pigmentosum, keratoctanthoma, thyroid follicular cancer or Kaposi's sarcoma.

32. A method of reducing the size of a solid tumor in a subject, the method comprising administering to the subject in need thereof a therapeutically effective amount of the compound according to claim 1, or the pharmaceutically-acceptable salt thereof.

33. A method of treating a cell proliferation disorder in a subject, the method comprising administering to the subject in need thereof a therapeutically effective amount of the compound according to claim 1, or the pharmaceutically-acceptable salt thereof.

34. A method of inhibiting KIF18A in a cell, comprising contacting the cell with the compound according to claim 1, or the pharmaceutically acceptable salt thereof.

* * * * *